US008828908B2

(12) United States Patent
Mathews et al.

(10) Patent No.: US 8,828,908 B2
(45) Date of Patent: Sep. 9, 2014

(54) HERBICIDALLY ACTIVE BICYCLIC 1,3-DIONE COMPOUNDS

(75) Inventors: Christopher John Mathews, Bracknell (GB); Matthew Brian Hotson, Bracknell (GB); Alan John Dowling, Bracknell (GB); James Nicholas Scutt, Bracknell (GB); Mangala Govenkar, Ilhas Goa (IN); Lee Challinor, Bracknell (GB)

(73) Assignee: Syngenta Limited, Guildford, Surrey (GB)

( * ) Notice: Subject to any disclaimer, the term of this patent is extended or adjusted under 35 U.S.C. 154(b) by 296 days.

(21) Appl. No.: 12/601,619

(22) PCT Filed: May 27, 2008

(86) PCT No.: PCT/EP2008/004195
§ 371 (c)(1),
(2), (4) Date: May 11, 2010

(87) PCT Pub. No.: WO2008/145336
PCT Pub. Date: Dec. 4, 2008

(65) Prior Publication Data
US 2010/0216638 A1 Aug. 26, 2010

(30) Foreign Application Priority Data

May 29, 2007 (GB) .................................. 0710223.9

(51) Int. Cl.
| | |
|---|---|
| A01N 25/00 | (2006.01) |
| A01N 25/26 | (2006.01) |
| A01N 25/32 | (2006.01) |
| A01N 63/00 | (2006.01) |
| A01N 43/00 | (2006.01) |
| A01N 57/00 | (2006.01) |
| C07C 69/74 | (2006.01) |
| C07C 69/76 | (2006.01) |
| C07C 69/95 | (2006.01) |
| C07C 49/00 | (2006.01) |
| C07C 45/00 | (2006.01) |

(52) U.S. Cl.
USPC ........ 504/116.1; 504/100; 504/103; 504/118; 504/129; 504/194; 504/209; 514/227; 514/241; 514/247; 514/252.1; 514/252.11; 514/256; 514/362; 514/363; 514/364; 514/365; 514/372; 514/374; 514/376; 514/378; 514/380; 514/381; 514/383; 514/396; 514/406; 514/408; 514/439; 514/461; 514/471; 544/180; 544/238; 544/242; 544/336; 546/127; 546/128; 546/131; 546/134; 546/136; 548/146; 548/206; 548/215; 548/240; 548/250; 549/29; 549/200; 568/303; 568/308; 568/315; 568/316; 568/322; 568/323; 568/325; 568/327

(58) Field of Classification Search
USPC ............. 504/116.1, 100, 103, 118, 129, 194, 504/209; 560/1, 8, 51, 52, 55; 568/303, 568/308, 312, 315, 323, 325, 327, 330, 381
See application file for complete search history.

(56) References Cited

U.S. PATENT DOCUMENTS

| | | | |
|---|---|---|---|
| 4,175,135 A | 11/1979 | Haines et al. | |
| 4,209,532 A | 6/1980 | Wheeler et al. | |
| 4,409,153 A | 10/1983 | Hodakowski et al. | |
| 4,489,012 A | 12/1984 | Hodakowski | |
| 4,526,723 A * | 7/1985 | Wheeler et al. | 554/229 |
| 4,659,372 A * | 4/1987 | Wheeler | 504/313 |
| 5,801,120 A | 9/1998 | Lee et al. | |
| 6,458,965 B1 | 10/2002 | Lieb et al. | |
| 6,642,180 B1 * | 11/2003 | Fischer et al. | 504/246 |
| 6,894,005 B1 | 5/2005 | Maetzke et al. | |
| 8,058,210 B2 | 11/2011 | Lieb et al. | |
| 8,084,649 B2 | 12/2011 | Muehlebach et al. | |
| 2003/0216260 A1 | 11/2003 | Ruther et al. | |
| 2005/0164883 A1 | 7/2005 | Maetzke et al. | |
| 2006/0166829 A1 | 7/2006 | Fischer et al. | |
| 2010/0113270 A1 | 5/2010 | Mathews et al. | |
| 2010/0210466 A1 | 8/2010 | Muehlebach et al. | |
| 2012/0040826 A1 | 2/2012 | Jeanmart et al. | |

FOREIGN PATENT DOCUMENTS

| | | |
|---|---|---|
| CA | 2322158 | 8/2000 |
| CA | 2325526 | 9/2000 |
| CA | 2382432 | 2/2002 |
| CA | 2382435 | 2/2002 |

(Continued)

OTHER PUBLICATIONS

Jiang et al., "An efficient and mild CuI/L-proline-catalyzed arylation of acetylacetone or ethyl cyanoacetate," Synlett, 2005, No. 18, pp. 2731-2734.*

Muehlebach, M., et al., "Discovery and SAR of pinoxaden: a new broad spectrum, postemergence cereal herbicide," in Pesticide Chemistry, Crop Protection, Public Health, Environmental Safety, ed. H. Ohkawa et al., Jun. 2007, pp. 101-110.

Wenger, J., and Nidermann, T., "Chapter 9: Acetyl-CoA Carboxylase Inhibitors", in Modern Crop Protection Compounds, ed. W. Kraemer et al., Wiley-VCH Verlag, Weinheim, 2007, pp. 335-357.

(Continued)

*Primary Examiner* — Jane C Oswecki
(74) *Attorney, Agent, or Firm* — R. Kody Jones

(57) ABSTRACT

Bicyclic dione compounds of formula (I), and derivatives thereof, which are suitable for use as herbicides.

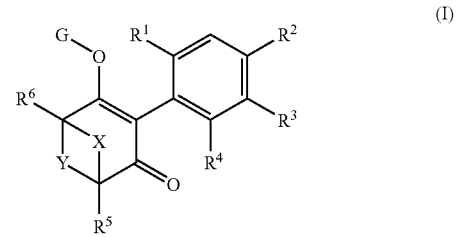

53 Claims, No Drawings

(56) References Cited

FOREIGN PATENT DOCUMENTS

| | | | |
|---|---|---|---|
| CA | 2456776 | 2/2004 | |
| DE | 2813341 | 4/1983 | |
| WO | 99/43649 | 9/1999 | |
| WO | 99/47525 | 9/1999 | |
| WO | 99/48869 | 9/1999 | |
| WO | 9943649 A | 9/1999 | |
| WO | 0015615 | 3/2000 | |
| WO | WO0015615 * | 3/2000 | ........... C07D 213/61 |
| WO | 00/37437 | 6/2000 | |
| WO | 0109092 | 2/2001 | |
| WO | WO0109092 A1 * | 2/2001 | ........... C07D 207/40 |
| WO | 01/17972 | 3/2001 | |
| WO | 01/17973 | 3/2001 | |
| WO | 01/74770 | 10/2001 | |
| WO | 0194339 | 12/2001 | |
| WO | WO0194339 A1 * | 12/2001 | ........... C07D 401/06 |
| WO | 03/013249 | 2/2003 | |
| WO | 2004058712 | 7/2004 | |
| WO | WO2004058712 A2 * | 7/2004 | ........... C07D 213/00 |
| WO | 2004111042 | 12/2004 | |
| WO | 2005105717 | 11/2005 | |
| WO | WO2005105717 A1 * | 11/2005 | .............. C07C 45/43 |
| WO | 2005/123667 | 12/2005 | |
| WO | 2005123667 A | 12/2005 | |
| WO | 2006034315 | 3/2006 | |
| WO | 2006034446 | 3/2006 | |
| WO | 2008/071405 | 6/2008 | |
| WO | 2008071405 A | 6/2008 | |
| WO | 2009015877 | 7/2008 | |
| WO | 2008/110307 | 9/2008 | |
| WO | 2008/110308 | 9/2008 | |
| WO | WO2008110308 A2 * | 9/2008 | ............ C07C 271/34 |
| WO | WO2009015877 A1 * | 2/2009 | ............ C07D 213/24 |

OTHER PUBLICATIONS

Wenger, et al.: "Chapter 11: Acetyl-CoA Carboxylase Inhibitors", in Modern Crop Protection Compounds, Second Edition, Jan. 2012, pp. 447-477.

Jiang, Y. et al., "An efficient and mild CuI/L-proline-catalysed arylation of acetylacetone or ethyl cyanoacetate", Synlett, 2005, No. 18, pp. 2731-2734.

* cited by examiner

HERBICIDALLY ACTIVE BICYCLIC 1,3-DIONE COMPOUNDS

This application is a 371 of International Application No. PCT/EP2008/004195 filed May 27, 2008, which claims priority to GB 0710223.9 filed May 29, 2007, the contents of which are incorporated herein by reference.

The present invention relates to novel, herbicidally active cyclic diones, and derivatives thereof, to processes for their preparation, to compositions comprising those compounds, and to their use in controlling weeds, especially in crops of useful plants, or in inhibiting plant growth.

Cyclic diones having herbicidal action are described, for example, in U.S. Pat. No. 4,175,135 and U.S. Pat. No. 4,209,532.

Novel bicyclic diones, and derivatives thereof, having herbicidal and growth-inhibiting properties have now been found.

The present invention accordingly relates to compounds of formula I

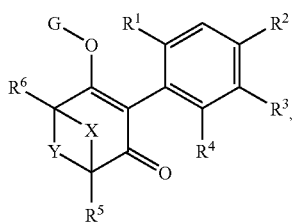

wherein
$R^1$ is methyl, ethyl, n-propyl, iso-propyl, cyclopropyl, halomethyl, haloethyl, halogen, vinyl, ethynyl, methoxy, ethoxy, halomethoxy or haloethoxy,
$R^2$ and $R^3$ are independently hydrogen, halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$haloalkenyl, $C_2$-$C_6$alkynyl, $C_3$-$C_6$alkenyloxy, $C_3$-$C_6$haloalkenyloxy, $C_3$-$C_6$alkynyloxy, $C_3$-$C_6$cycloalkyl, $C_1$-$C_6$alkylthio, $C_1$-$C_6$alkylsulfinyl, $C_1$-$C_6$alkylsulfonyl, $C_1$-$C_6$alkylsulfonyloxy, $C_1$-$C_6$haloalkylsulfonyloxy, cyano, nitro, optionally substituted phenyl or optionally substituted heteroaryl, where at least one of $R^2$ and $R^3$ is optionally substituted phenyl or optionally substituted heteroaryl,
$R^4$ is hydrogen, methyl, ethyl, n-propyl, iso-propyl, halomethyl, haloethyl, halogen, vinyl, ethynyl, methoxy, ethoxy, halomethoxy or haloethoxy,
$R^5$ and $R^6$ are independently hydrogen, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_1$-$C_6$alkoxy, $C_3$-$C_6$alkenyloxy, $C_3$-$C_6$haloalkenyloxy, $C_3$-$C_6$alkynyloxy, $C_1$-$C_4$alkoxy$C_1$-$C_4$alkyl, $C_1$-$C_4$alkoxy$C_1$-$C_4$alkoxy, $C_1$-$C_4$alkoxy$C_1$-$C_4$alkoxy$C_1$-$C_4$alkyl, $C_1$-$C_6$alkylthio, $C_1$-$C_4$alkylthio$C_1$-$C_4$alkyl, $C_1$-$C_4$alkylsulfinyl, $C_1$-$C_4$alkylsulfinyl$C_1$-$C_4$alkyl, $C_1$-$C_4$alkylsulfonyl, $C_1$-$C_4$alkylsulfonyl$C_1$-$C_4$alkyl, hydroxy-$C_1$-$C_4$alkyl, $C_1$-$C_6$haloalkoxy$C_1$-$C_4$alkyl, $C_3$-$C_6$alkenyloxy$C_1$-$C_4$alkyl, $C_3$-$C_6$haloalkenyloxy$C_1$-$C_4$alkyl, $C_3$-$C_6$alkynyloxy$C_1$-$C_4$alkyl, $C_1$-$C_6$cyanoalkyl, $C_1$-$C_6$cyanoalkoxy, $C_1$-$C_4$cyanoalkoxy$C_1$-$C_4$alkyl, hydroxy, $C_1$-$C_6$alkylcarbonyl, carboxy, $C_1$-$C_6$alkoxycarbonyl, $C_1$-$C_6$alkylaminocarbonyl, di-$C_1$-$C_6$alkylcarbonyl, tri($C_1$-$C_4$alkyl)silyl or tri($C_1$-$C_4$alkyl)silyloxy,
X is optionally substituted $C_1$-$C_3$alkylene,
Y is optionally substituted $C_1$-$C_3$alkylene or optionally substituted $C_2$-$C_3$alkenylene and
G is hydrogen, an alkali metal, alkaline earth metal, sulfonium, ammonium, $C_1$-$C_6$ alkyl, $C_3$-$C_6$ alkenyl, $C_3$-$C_6$alkynyl, or a latentiating group.

In the substituent definitions of the compounds of the formula I, the alkyl radicals and alkyl moieties of alkoxy, alkylsulfonyl etc. having 1 to 6 carbon atoms are preferably methyl, ethyl as well as propyl, butyl, pentyl and hexyl, in form of their straight and branched isomers.

The alkenyl and alkynyl radicals having 2 to 6 carbon atoms can be straight or branched and can contain more than 1 double or triple bond. Examples are vinyl, allyl, propargyl, butenyl, butynyl, pentenyl and pentynyl.

Suitable cycloalkyl groups contain 3 to 6 carbon atoms and are for example cyclopropyl, cyclobutyl, cyclopentyl and cyclohexyl. Cyclopropyl, cyclopentyl and cyclohexyl are preferred.

Preferred halogens are fluorine, chlorine and bromine.

Substituted $C_1$-$C_3$alkylene and substituted $C_2$-$C_3$alkenylene units represent saturated and unsaturated carbon chains which may be substituted once or more than once by substituents such as $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_3$-$C_7$cycloalkyl, $C_3$-$C_7$cycloalkyl$C_1$-$C_4$alkyl, $C_5$-$C_7$cycloalkenyl, $C_5$-$C_7$cycloalkenyl$C_1$-$C_4$alkyl, phenyl$C_1$-$C_4$alkyl, substituted phenyl$C_1$-$C_4$alkyl, heteroaryl$C_1$-$C_4$alkyl and substituted heteroaryl$C_1$-$C_4$alkyl, heterocyclyl$C_1$-$C_4$alkyl and substituted heterocyclyl$C_1$-$C_4$alkyl, $C_1$-$C_6$alkoxy, $C_1$-$C_6$haloalkoxy, $C_1$-$C_4$alkoxy$C_1$-$C_4$alkyl, $C_1$-$C_4$alkoxy$C_1$-$C_4$alkoxy, $C_1$-$C_4$alkoxy$C_1$-$C_4$alkoxy$C_1$-$C_4$alkyl, $C_1$-$C_6$alkylthio, $C_1$-$C_4$alkylthio$C_1$-$C_4$alkyl, $C_1$-$C_4$alkylsulfinyl, $C_1$-$C_4$alkylsulfinyl$C_1$-$C_4$alkyl, $C_{1-4}$alkylsulfonyl, $C_1$-$C_4$alkylsulfonyl$C_1$-$C_4$alkyl, halo, cyano, $C_1$-$C_6$cyanoalkyl, $C_1$-$C_6$cyanoalkoxy, hydroxy, $C_3$-$C_6$alkenyloxy, $C_3$-$C_6$haloalkenyloxy, $C_3$-$C_6$alkynyloxy, phenoxy, substituted phenoxy, heteroaryloxy, substituted heteroaryloxy, heterocyclyloxy, substituted heterocyclyloxy, phenyl$C_1$-$C_4$alkoxy, substituted phenyl$C_1$-$C_4$alkoxy, heteroaryl$C_1$-$C_4$alkoxy, substituted heteroaryl$C_1$-$C_4$alkoxy, heterocyclyl$C_1$-$C_4$alkoxy, substituted heterocyclyl$C_1$-$C_4$alkoxy, hydroxy-$C_1$-$C_4$alkyl, $C_1$-$C_6$haloalkoxy$C_1$-$C_4$alkyl, $C_3$-$C_6$alkenyloxy$C_1$-$C_4$alkyl, $C_3$-$C_6$haloalkenyloxy$C_1$-$C_4$alkyl, $C_3$-$C_6$alkynyloxy$C_1$-$C_4$alkyl, $C_1$-$C_4$alkylcarbonyloxy$C_1$-$C_4$alkyl, $C_1$-$C_4$alkoxycarbonyl$C_1$-$C_4$alkyl, $C_1$-$C_4$alkylaminocarbonyloxy$C_1$-$C_4$alkyl, di-$C_1$-$C_4$alkylaminocarbonyloxy$C_1$-$C_4$alkyl, phenoxy$C_1$-$C_4$alkyl, substituted phenoxy$C_1$-$C_4$alkyl, heteroaryloxy$C_1$-$C_4$alkyl, substituted heteroaryloxy$C_1$-$C_4$alkyl, heterocyclyloxy$C_1$-$C_4$alkyl, substituted heterocyclyloxy$C_1$-$C_4$alkyl, phenyl$C_1$-$C_4$alkoxy$C_1$-$C_4$alkyl, substituted phenyl$C_1$-$C_4$alkoxy$C_1$-$C_4$alkyl, heteroaryl$C_1$-$C_4$alkoxy$C_1$-$C_4$alkyl, substituted heteroaryl$C_1$-$C_4$alkoxy$C_1$-$C_4$alkyl, heterocyclyl$C_1$-$C_4$alkoxy$C_1$-$C_4$alkyl, substituted heterocyclyl$C_1$-$C_4$alkoxy$C_1$-$C_4$alkyl, $C_1$-$C_6$cyanoalkoxy$C_1$-$C_4$alkyl, tri($C_1$-$C_4$alkyl)silyloxy$C_1$-$C_4$alkyl, carboxy, $C_1$-$C_4$alkylcarbonyl, $C_1$-$C_4$alkoxycarbonyl, amidocarbonyl, $C_1$-$C_4$alkylaminocarbonyl, di-$C_1$-$C_4$alkylaminocarbonyl, phenylaminocarbonyl, substituted phenylaminocarbonyl, heteroarylaminocarbonyl, substituted heteroarylcarbonyl, $C_1$-$C_4$alkylcarbonyloxy, $C_1$-$C_4$alkoxycarbonyloxy, $C_1$-$C_6$alkylaminocarbonyloxy, di$C_1$-$C_4$alkylaminocarbonyloxy, $C_1$-$C_6$alkylaminothiocarbonyloxy, phenylcarbonyloxy, substituted phenylcarbonyloxy, heteroarylcarbonyloxy, substituted heteroarylcarbonyloxy, heterocyclylcarbonyloxy, substituted heterocyclylcarbonyloxy, amino, $C_1$-$C_4$alkylcarbonylamino, $C_1$-$C_4$alkoxycarbonylamino, ($C_1$-$C_4$alkylthio)carbonylamino, $C_1$-$C_4$alkoxythiocarbonylamino, $C_1$-$C_4$alkyl(thiocarbonyl)amino, $C_1$-$C_4$alkylaminocarbonylamino, di-$C_1$-$C_4$alkylaminocarbonylamino, phenylcarbonylamino, substituted phenylcarbonylamino, heteroarylcarbonylamino, substituted heteroarylcarbonylamino, phenoxycarbonylamino, substituted phenoxycarbonylamino, phenylaminocarbonylamino, substituted phenylaminocarbonylamino, $C_1$-$C_4$alkylsulfonylamino, $C_1$-$C_4$haloalkylsulfonylamino, phenylsulfonylamino, substituted phenylsulfonylamino, $C_1$-$C_4$alkylcarbonylamino$C_1$-$C_4$alkyl, $C_1$-$C_4$alkoxycarbonylamino$C_1$-$C_4$alkyl, ($C_1$-$C_4$alkylthio)carbonylamino$C_1$-$C_4$alkyl, $C_1$-$C_4$alkoxythiocarbonylamino$C_1$-$C_4$alkyl, $C_1$-$C_4$alkyl(thiocarbonyl)amino$C_1$-$C_4$alkyl, $C_1$-$C_4$alkylaminocarbonylamino$C_1$-$C_4$alkyl, di-$C_1$-$C_4$alkylaminocarbonylamino$C_1$-$C_4$alkyl, phenylcarbonylamino$C_1$-$C_4$alkyl, substituted phenylcarbonylamino$C_1$-$C_4$alkyl, heteroarylcarbonylamino$C_1$-$C_4$alkyl, substituted heteroarylcarbonylamino$C_1$-$C_4$alkyl, phenoxycarbonylamino$C_1$-$C_4$alkyl, substituted phenoxycarbonylamino$C_1$-$C_4$alkyl, phenylaminocarbonylamino$C_1$-$C_4$alkyl, substituted phenylaminocarbonylamino$C_1$-$C_4$alkyl, $C_1$-$C_4$alkylsulfonylamino$C_1$-$C_4$alkyl, $C_1$-$C_4$haloalkylsulfonylamino$C_1$-$C_4$alkyl, phenylsulfonylamino$C_1$-$C_4$alkyl, substituted phenylsulfonylamino$C_1$-$C_4$alkyl, tri($C_1$-$C_4$alkyl)silyl, tri($C_1$-$C_4$alkyl)silyloxy, phenyl and substituted phenyl, heteroaryl and substituted heteroaryl, heterocyclyl and substituted heterocyclyl. Preferably, the $C_1$-$C_3$alkylene and $C_2$-$C_3$alkenylene groups X and Y are unsubstituted, or are substituted once or twice by $C_1$-$C_4$alkyl, $C_1$-$C_4$alkoxy, $C_1$-$C_4$alkoxy$C_1$-$C_4$alkyl, halogen or hydroxy.

Where two preferably adjacent substituents are present on the $C_1$-$C_3$alkylene and $C_2$-$C_3$alkenylene groups these substituents may additionally join together to form a 3-7 membered saturated ring, which may optionally contain one or more heteroatoms selected from oxygen, sulfur or nitrogen, or may form a 5-7 membered unsaturated ring, which may optionally contain one or more heteroatoms which are selected from oxygen, sulfur or nitrogen. Preferred rings which are formed are dioxolane rings, optionally substituted once or twice by $C_1$-$C_3$alkyl.

Preferred examples of heteroaryls are thienyl, furyl, pyrrolyl, isoxazolyl, oxazolyl, isothiazolyl, thiazolyl, pyrazolyl, imidazolyl, triazolyl, tetrazolyl, pyridyl, pyrimidinyl, pyrazinyl, pyridazinyl, triazinyl, oxadiazolyl and thiadiazolyl, and, where appropriate, N-oxides and salts thereof.

These heteroaryls as well as the phenyl rings can be substituted by one or more substituents, where preferred substituents may be selected from $C_1$-$C_4$alkyl, $C_2$-$C_4$alkenyl, $C_2$-$C_4$alkynyl, $C_1$-$C_4$haloalkyl, $C_3$-$C_7$cycloalkyl, $C_5$-$C_7$cycloalkenyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$haloalkylsulfinyl, $C_1$-$C_4$alkylsulfonyl, $C_1$-$C_4$haloalkylsulfonyl, fluoro, chloro, bromo, iodo, cyano, nitro, hydroxy-$C_1$-$C_4$alkyl, formyl, carboxy, $C_1$-$C_4$alkylcarbonyl, $C_1$-$C_4$alkoxycarbonyl, amidocarbonyl, $C_1$-$C_4$alkylaminocarbonyl, di-$C_1$-$C_4$alkylaminocarbonyl, amino, $C_1$-$C_4$alkylcarbonylamino, $C_1$-$C_4$alkoxycarbonylamino, $C_1$-$C_4$alkylaminocarbonylamino, di$C_1$-$C_4$alkylaminocarbonylamino, $C_1$-$C_4$alkylsulfonylamino, $C_1$-$C_4$haloalkylsulfonylamino, $C_1$-$C_4$alkylsulfonyloxy and $C_1$-$C_4$haloalkylsulfonyloxy and are preferably selected from $C_1$-$C_4$alkyl, $C_1$-$C_4$alkoxy, $C_1$-$C_4$haloalkoxy, halo, cyano and nitro, especially $C_1$-$C_2$alkyl, $C_1$-$C_2$alkoxy, $C_1$-$C_2$haloalkoxy, fluoro, chloro and cyano.

The group G denotes hydrogen, an alkali metal cation such as sodium or potassium, alkaline earth metal cation such as calcium, sulfonium cation (preferably —S($C_1$-$C_6$alkyl$_3$)$^+$) or ammonium cation (preferably —NH$_4^+$ or —N($C_1$-$C_6$alkyl)$_4^+$), or $C_1$-$C_6$alkyl, $C_3$-$C_6$alkenyl or $C_3$-$C_6$alkynyl or a latentiating group.

The latentiating group G is preferably selected from $C_1$-$C_8$alkyl, $C_2$-$C_8$ haloalkyl, phenyl$C_1$-$C_6$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_8$ alkenyl, $C_3$-$C_8$ haloalkenyl, $C_3$-$C_8$ alkynyl, C($X^a$)—$R^a$, C($X^b$)—$X^c$—$R^b$, C($X^d$)—N($R^c$)—$R^d$, —SC$_2$—$R^e$, —P($X^e$)($R^f$)—$R^g$ or CH$_2$—$X^f$—$R^h$ wherein $X^a$, $X^b$, $X^c$, $X^d$, $X^e$ and $X^f$ are independently of each other oxygen or sulfur;

$R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$-aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_8$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro, $R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro, $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_5$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_5$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_5$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, amino, $C_1$-$C_3$alkylamino, $C_1$-$C_3$dialkylamino, $C_1$-$C_3$alkoxy or $C_3$-$C_7$cycloalkylamino, di-$C_3$-$C_7$cycloalkylamino or $C_3$-$C_7$cycloalkoxy or $R^c$ and $R^d$ may join together to form a 3-7 membered ring, optionally containing one heteroatom selected from O or S and optionally substituted by 1 or 2 $C_1$-$C_3$alkyl groups.

$R^e$ is $C_1$-$C_{10}$alkyl, $C_2$-$C_{10}$alkenyl, $C_2$-$C_{10}$alkynyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_5$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_5$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_5$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano, amino or by nitro, heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano, nitro, amino, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino $R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, amino, hydroxyl, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$haloalkoxy, $C_1$-$C_5$alkylamino or $C_2$-$C_8$dialkylamino, benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro, and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_5$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro, or heteroaryl, or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro.

In particular, the latentiating group G is a group —C($X^a$)—$R^a$ or —C($X^b$)—$X^c$—$R^b$, and the meanings of $X^a$, $R^a$, $X^b$, $X^c$ and $R^b$ are as defined above.

Preferably, G denotes hydrogen, an alkali metal or alkaline earth metal, where hydrogen is particularly preferred.

The latentiating groups G are selected to allow its removal by one or a combination of biochemical, chemical or physical processes to afford compounds of formula I where G is H before, during or following application to the treated area or plants. Examples of these processes include enzymatic cleavage, chemical hydrolysis and photolysis. Compounds bearing such groups G may offer certain advantages, such as improved penetration of the cuticula of the plants treated, increased tolerance of crops, improved compatibility or stability in formulated mixtures containing other herbicides, herbicide safeners, plant growth regulators, fungicides or insecticides, or reduced leaching in soils.

In a preferred group of compounds of the formula I, $R^1$ is methyl, ethyl, halogen, halomethyl, vinyl, ethynyl or halomethoxy. More preferably, $R^1$ is methyl or ethyl, especially ethyl.

It is also preferred that $R^1$ is —OCHF$_2$ or —CF$_3$.

Preferably, $R^2$ and $R^3$ are independently hydrogen, optionally substituted phenyl or optionally substituted heteroaryl.

More preferably, $R^2$ and $R^3$ are independently hydrogen, phenyl or phenyl substituted by $C_1$-$C_2$alkyl, $C_1$-$C_2$haloalkyl, $C_1$-$C_2$alkoxy, $C_1$-$C_2$haloalkoxy, fluoro, chloro, bromo or cyano, heteroaryl or heteroaryl substituted by $C_1$-$C_2$alkyl, $C_1$-$C_2$haloalkyl, $C_1$-$C_2$alkoxy, $C_1$-$C_2$haloalkoxy, fluoro, chloro, bromo or cyano.

Preferred heteroaryls are thienyl, pyridyl, pyrimidinyl, pyrazolyl and thiazolyl.

It is particularly preferred, that $R^2$ is hydrogen and $R^3$ is phenyl or phenyl substituted by $C_1$-$C_2$alkyl, $C_1$-$C_2$haloalkyl, $C_1$-$C_2$alkoxy, $C_1$-$C_2$haloalkoxy, fluoro, chloro, bromo or cyano.

Preferably, $R^4$ is hydrogen, methyl, ethyl, vinyl or ethynyl and, more preferably, $R^4$ is hydrogen, methyl or ethyl.

Preferably, $R^5$ is hydrogen, $C_1$-$C_4$ alkyl, $C_1$-$C_4$alkoxy or $C_1$-$C_4$alkoxy$C_1$-$C_4$alkyl and, more preferably, $R^5$ is hydrogen or methyl, especially hydrogen.

Preferably, $R^6$ is hydrogen or methyl and, more preferably, $R^6$ is hydrogen.

Preferably, X is optionally substituted $C_1$-$C_2$alkylene.

More preferably X is methylene, ethylene, methylene substituted by $C_1$-$C_3$ alkyl, $C_1$-$C_3$alkoxy or $C_1$-$C_3$alkoxy$C_1$-$C_3$alkyl or ethylene substituted by $C_1$-$C_3$ alkyl, $C_1$-$C_3$alkoxy or $C_1$-$C_3$alkoxy$C_1$-$C_3$alkyl.

Most preferably, X is methylene or ethylene.

Preferably, Y is optionally substituted $C_1$-$C_2$alkylene or optionally substituted $C_2$alkenylene.

More preferably, Y is $C_1$-$C_2$alkylene or $C_1$-$C_2$alkylene substituted by halogen, hydroxyl, cyano, $C_1$-$C_3$alkyl, $C_1$-$C_3$alkoxy or $C_1$-$C_3$alkoxy$C_1$-$C_3$alkyl, $C_2$alkenylene or $C_2$alkenylene substituted by halogen, hydroxyl, cyano, $C_1$-$C_3$alkyl, $C_1$-$C_3$alkoxy or $C_1$-$C_3$alkoxy$C_1$-$C_3$alkyl, in particular ethylene or ethenylene.

In a very preferred group of compounds of the formula I, $R^1$ is methyl or ethyl,
$R^2$ is hydrogen, $R^3$ is phenyl or phenyl substituted by $C_1$-$C_2$alkyl, $C_1$-$C_2$alkoxy, $C_1$-$C_2$haloalkyl, $C_1$-$C_2$haloalkoxy, fluoro, chloro, bromo or cyano, $R^4$ is hydrogen, $R^5$ is hydrogen, $R^6$ is hydrogen, X is methylene, Y is ethylene and G is hydrogen.

The invention relates also to the salts which the compounds of formula I are able to form with amines, alkali metal and alkaline earth metal bases or quaternary ammonium bases. Among the alkali metal and alkaline earth metal hydroxides as salt formers, special mention should be made of the hydroxides of lithium, sodium, potassium, magnesium and calcium, but especially the hydroxides of sodium and potassium. The compounds of formula I according to the invention also include hydrates which may be formed during the salt formation.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$-alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and diisopropylamine.

Preferred quaternary ammonium bases suitable for salt formation correspond, for example, to the formula $[N(R_aR_b R_cR_d)]OH$ wherein $R_a$, $R_b$, $R_c$ and $R_d$ are each independently of the others $C_1$-$C_4$alkyl. Further suitable tetraalkylammonium bases with other anions can be obtained, for example, by anion exchange reactions.

Depending on the nature of the substituents, compounds of formula I may exist in different isomeric forms. When G is hydrogen, for example, compounds of formula I may exist in different tautomeric forms.

wherein $X^a$ is oxygen, or an isocyanate, $R^cN=C=O$, or a carbamoyl chloride, $Cl-C(X^d)-N(R^c)-R^d$ (wherein $X^d$ is oxygen and with the proviso that neither $R^c$ or $R^d$ is hydrogen), or a thiocarbamoyl $(X^d)-N(R^c)-R^d$ (wherein $X^d$ is sulfur and with the proviso that neither $R^c$ or $R^d$ is hydrogen) or a chloroformate, $Cl-C(X^b)-X^c-R^b$, (wherein $X^b$ and $X^c$ are oxygen), or a chlorothioformate $Cl-C(X^b)-X^c-R^b$ (wherein $X^b$ is oxygen and $X^c$ is sulfur), or a chlorodithioformate $Cl-C(X^b)-X^c-R^b$, (wherein $X^b$ and $X^c$ are sulfur), or an isothiocyanate, $R^cN=C=S$, or by sequential treatment with carbon disulfide and an alkylating agent, or with a phosphorylating agent such as a phosphoryl chloride, $Cl-P(X^e)(R^f)-R^g$ or with a sulfonylating agent such as a sulfonyl chloride $Cl-SO_2-R^e$, preferably in the presence of at least one equivalent of base. Those skilled in the art will recognise that in certain circumstances, for example when $R^5$ is different from $R^6$, these reactions may produce, in addition to a compound of formula I, a second compound of formula IA. This invention covers both a compound of formula I and a compound of formula IA, together with mixtures of these compounds in any ratio.

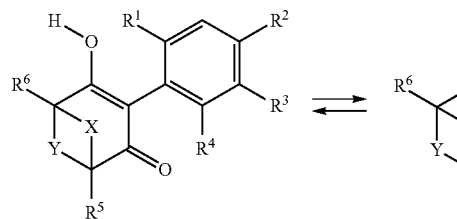 ⇌ 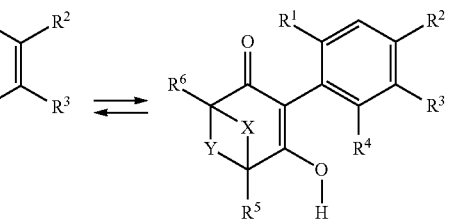 ⇌ 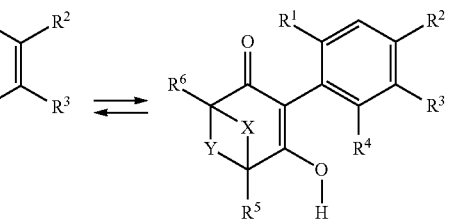

This invention covers all such isomers and tautomers and mixtures thereof in all proportions. Also, when substituents contain double bonds, cis- and trans-isomers can exist. These isomers, too, are within the scope of the claimed compounds of the formula I.

A compound of formula I wherein G is $C_1$-$C_8$ alkyl, $C_2$-$C_8$ haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$ alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$ alkylsulfonyl, halogen, cyano or by nitro), $C_3$-$C_8$ alkenyl, $C_3$-$C_8$ haloalkenyl, $C_3$-$C_8$ alkynyl, $C(X^a)-R^a$, $C(X^b)-X^c-R^b$, $C(X^d)-N(R^c)-R^d$, $-SO_2-R^e$, $-P(X^e)(R^f)-R^g$ or $CH_2-X^f-R^h$ where $X^a$, $X^b$, $X^c$, $X^d$, $X^e$, $X^f$, $R^a$, $R^b$, $R^c$, $R^d$, $R^e$, $R^f$, $R^g$ and $R^h$ are as defined above may be prepared by treating a compound of formula (A), which is a compound of formula I wherein G is H, with a reagent G-Z, wherein G-Z is alkylating agent such as an alkyl halide (the definition of alkyl halides includes simple $C_1$-$C_8$ alkyl halides such as methyl iodide and ethyl iodide, substituted alkyl halides such as chloromethyl alkyl ethers, $Cl-CH_2-X^f-R^h$, wherein $X^f$ is oxygen, and chloromethyl alkyl sulfides $Cl-CH_2-X^f-R^h$, wherein $X^f$ is sulfur), a $C_1$-$C_8$ alkyl sulfonate, or a di-$C_1$-$C_8$-alkyl sulfate, or with a $C_3$-$C_8$ alkenyl halide, or with a $C_3$-$C_8$ alkynyl halide, or with an acylating agent such as a carboxylic acid, $HO-C(X^a)R^a$, wherein $X^a$ is oxygen, an acid chloride, $Cl-C(X^a)R^a$, wherein $X^a$ is oxygen, or acid anhydride, $[R^aC(X^a)]_2O$,

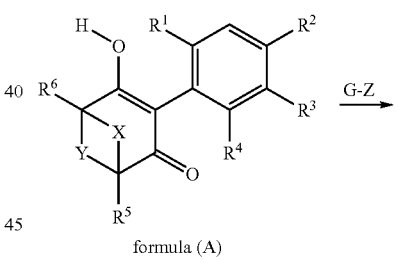

formula (A)

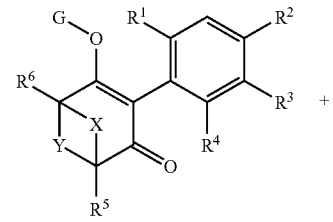

formula (I)

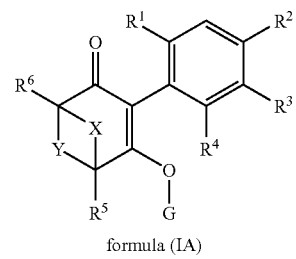

formula (IA)

The O-alkylation of cyclic 1,3-diones is known; suitable methods are described, for example, by T. Wheeler U.S. Pat. No. 4,436,666. Alternative procedures have been reported by M. Pizzorno and S. Albonico, Chem. Ind. (London), (1972), 425; H. Born et al., J. Chem. Soc., (1953), 1779; M. Constantino et al., Synth. Commun., (1992), 22 (19), 2859; Y. Tian et al., Synth. Commun., (1997), 27 (9), 1577, S. Chandra Roy et al., Chem. Letters, 2006, 35, (No 1) 16, and P. Zubaidha et al., Tetrahedron Lett., (2004), 45, 7187.

The O-acylation of cyclic 1,3-diones may be effected by procedures similar to those described, for example, by R. Haines, U.S. Pat. No. 4,175,135, and by T. Wheeler, U.S. Pat. No. 4,422,870, U.S. Pat. No. 4,659,372 and U.S. Pat. No. 4,436,666. Typically diones of formula (A) may be treated with the acylating agent in the presence of at least one equivalent of a suitable base, optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide, sodium hydride, and suitable organic bases include trialkylamines, such as trimethylamine and triethylamine, pyridines or other amine bases such as 1,4-diazobicyclo[2.2.2]octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. For cases where the acylating agent is a carboxylic acid, acylation is preferably effected in the presence of a coupling agent such as 2-chloro-1-methylpyridinium iodide, N,N'-dicyclohexylcarbodiimide, 1-(3-dimethylaminopropyl)-3-ethylcarbodiimide and N,N-carbodiimidazole, and a base such as triethylamine or pyridine in a suitable solvent such as tetrahydrofuran, dichloromethane or acetonitrile. Suitable procedures are described, for example, by W. Zhang and G. Pugh, Tetrahedron Lett., (1999), 40 (43), 7595-7598 and T. Isobe and T. Ishikawa, J. Org. Chem., (1999), 64 (19), 6984.

Phosphorylation of cyclic 1,3-diones may be effected using a phosphoryl halide or thiophosphoryl halide and a base by procedures analogous to those described by L. Hodakowski, U.S. Pat. No. 4,409,153.

Sulfonylation of a compound of formula (A) may be achieved using an alkyl or aryl sulfonyl halide, preferably in the presence of at least one equivalent of base, for example by the procedure of C. Kowalski and K. Fields, J. Org. Chem., (1981), 46, 197.

Compounds of formula (A) may be prepared via the cyclisation of compounds of formula (B), preferably in the presence of an acid or base, and optionally in the presence of a suitable solvent, by analogous methods to those described by T. Wheeler, U.S. Pat. No. 4,209,532. Compounds of formula (B) wherein R is hydrogen may be cyclised under acidic conditions, preferably in the presence of a strong acid such as sulfuric acid, polyphosphoric acid or Eaton's reagent, optionally in the presence of a suitable solvent such as acetic acid, toluene or dichloromethane.

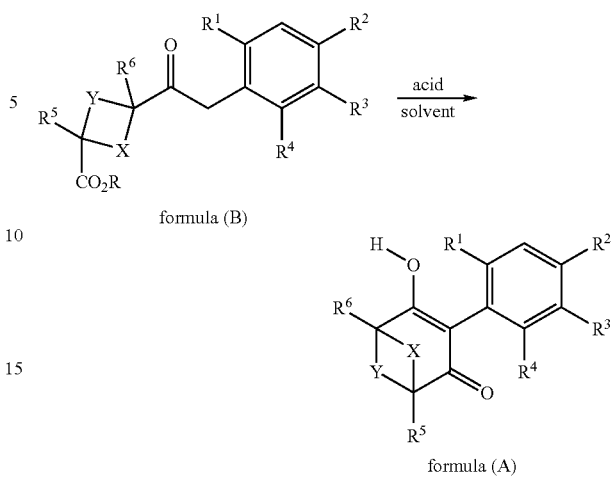

formula (B)

formula (A)

Compounds of formula (B) wherein R is alkyl (preferably methyl or ethyl) may be cyclised under basic conditions, preferably in the presence of at least one equivalent of a strong base such as potassium tert-butoxide, lithium diisopropylamide or sodium hydride and in a solvent such as tetrahydrofuran, toluene, dimethylsulfoxide or N,N-dimethylformamide.

Compounds of formula (B), wherein R is H may be prepared by saponification of compounds of formula (C) wherein R' is alkyl (preferably methyl or ethyl) under standard conditions, followed by acidification of the reaction mixture to effect decarboxylation, by similar processes to those described, for example, by T. Wheeler, U.S. Pat. No. 4,209,532:

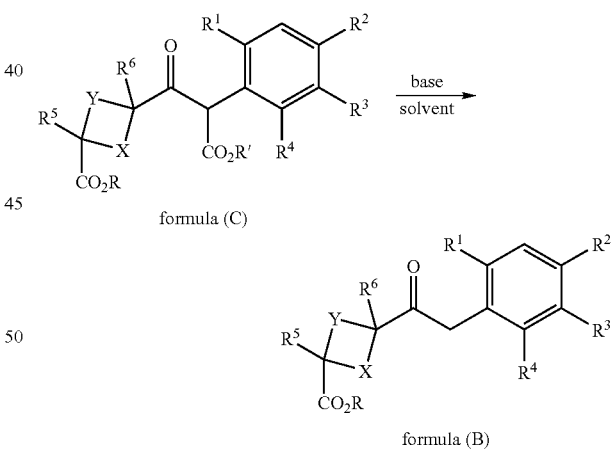

formula (C)

formula (B)

Compounds of formula (B), wherein R is H may be esterified to compounds of formula (B), wherein R is alkyl, under standard conditions.

Compounds of formula (C) wherein R is alkyl may be prepared by treating compounds of formula (D) with suitable carboxylic acid chlorides of formula (E) wherein R is alkyl under basic conditions. Suitable bases include potassium tert-butoxide, sodium bis(trimethylsilyl)amide and lithium diisopropylamide and the reaction is preferably conducted in a suitable solvent (such as tetrahydrofuran or toluene) at a temperature of between −80° C. and 30° C.:

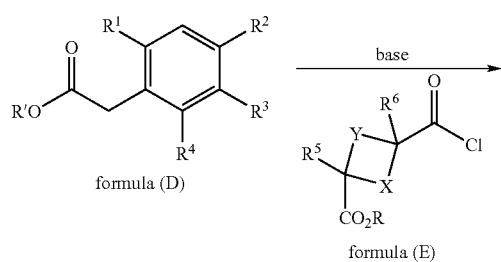

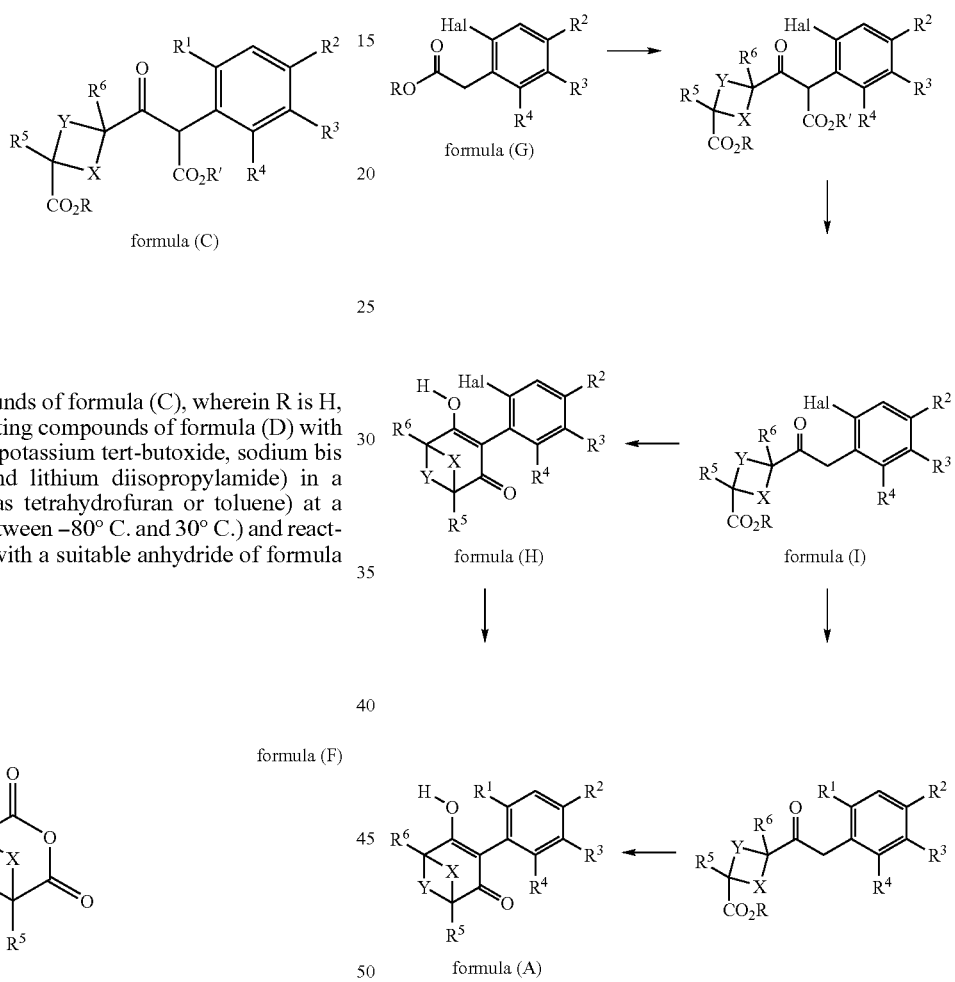

Alternatively, compounds of formula (C), wherein R is H, may be prepared by treating compounds of formula (D) with a suitable base (such as potassium tert-butoxide, sodium bis (trimethylsilyl)amide and lithium diisopropylamide) in a suitable solvent (such as tetrahydrofuran or toluene) at a suitable temperature (between −80° C. and 30° C.) and reacting the resulting anion with a suitable anhydride of formula (F):

Compounds of formula (E) and formula (F) are known (see, for example, K. Crowley, J. Am. Chem. Soc., (1964), Vol. 86, No. 24, 5692-5693; E. Bercot and T. Rovis, J. Am. Chem. Soc., (2005), 127, 247-254; R. McDonald and R. Reitz, J. Am. Chem. Soc., (1976), Vol. 98, No. 25, 8144-8155; A. Smith III et al., J. Org. Chem., (1974), Vol. 39, No. 12, 1607-1612; J. Baldwin and M. Lusch, J. Org. Chem., (1979), Vol. 44, No. 12, 1923-1927; R. Carlson and K. May, Tetrahedron Lett., (1975), Vol. 16, No. 11, 947-950; A. Börner et al., Tetrahedron Asymmetry (2002), 13, 1615-1620) or may be made by similar methods from commercially available starting materials.

Using similar procedures to those outlined above, and starting from halogenated phenyl acetic acid esters of formula (G) (wherein Hal is chlorine, bromine or iodine), compounds of formula (H) may be prepared. Compounds of formula (H) are compounds of formula (A) wherein $R^1$ is chlorine, bromine or iodine. In turn, compounds of formula (H) may be converted into additional compounds of formula (A) by reaction with suitable coupling partners under conditions described in the literature for Suzuki-Miyaura, Sonogashira, Stille and related reactions.

For example, a compound of formula (H) may be treated with an alkyl- or alkenylboronic acid, $R^1$—$B(OH)_2$, boronate ester thereof, $R^1$—$B(OR'')_2$ (preferably an ester wherein the fragment —$B(OR'')_2$ represents a cyclic boronate ester derived from a 1,2- or a 1,3-alkanediol, such as pinacol, 2,2-dimethyl-1,3-propanediol and 2-methyl-2,4-pentanediol), or a metal (especially potassium) alkyl-, alkenyl- and alkynyltrifluororoborate salt, $R_1$—$BF_3^-M^+$ in the presence of a suitable palladium catalyst, a suitable ligand and a suitable base in the presence of a suitable solvent, under Suzuki-Miyaura conditions (see, for example I. Kondolff, H.

Doucet and M, Santelli, Tetrahedron, (2004), 60, 3813-3818; F. Bellina, A. Carpita and R. Rossi, Synthesis (2004), 15, 2419-2440; G. Molander and C-S Yun, Tetrahedron, (2002), 58, 1465-1470; G. Zou, Y. Reddy and J. Falck, Tetrahedron Lett., (2001), 42, 4213-7215; A. Suzuki, Journal of Organometallic Chemistry, (2002), 653, 83; H. Stefani, R. Cella and A. Vieira, Tetrahedron, (2007), 62, 3623-3658; G. Molander, C-S Yun, M. Ribagorda and B. Biolatto, J. Org. Chem., (2003), 68, 5534-5539; S. Darses, G. Michaud and J-P, Genêt, Eur. J. Org. Chem., (1999), 1877-1883).

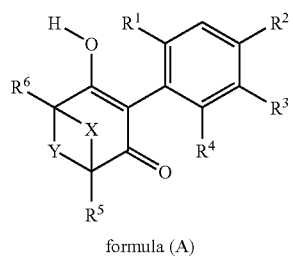

formula (A)

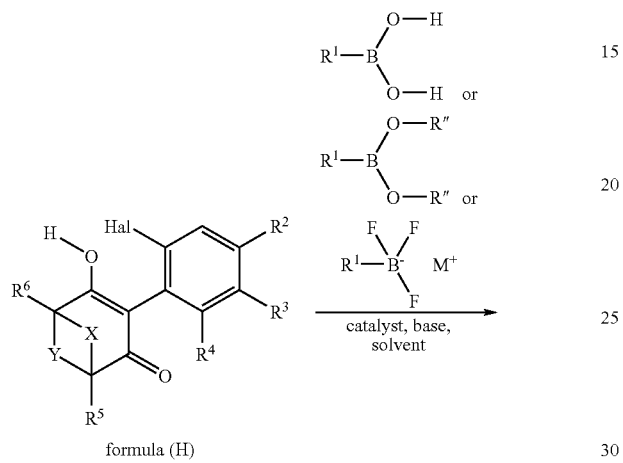

formula (H)

Alternatively, a compound of formula (A) wherein $R^1$ is ethynyl may be prepared from a compound of formula (H) by treatment with acetylene, or trimethylsilylacetylene, in the presence of a suitable palladium catalyst, a suitable ligand, and a suitable base, optionally in the presence of a suitable copper co-catalyst and a suitable solvent, as described, for example by K. Sonogashira, J. Organomet. Chem., (2002), 653, 46-49 and by N. Leadbeater and B. Tominack, Tetrahedron Lett., (2003), 8653-8656. Those skilled in the art will appreciate that a reaction involving trimethylsilylacetylene will require a further hydrolysis step using well-known conditions (see, for example, S. Coutts et al., Tetrahedron Lett., (1994), Vol. 35, No. 29, 5109-5112; C. Hutton et al., Tetrahedron Lett., (2004), 45, 6657-6660).

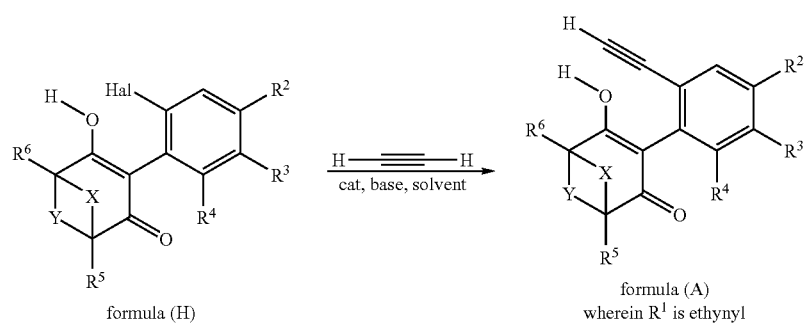

formula (H)         formula (A)
                    wherein $R^1$ is ethynyl

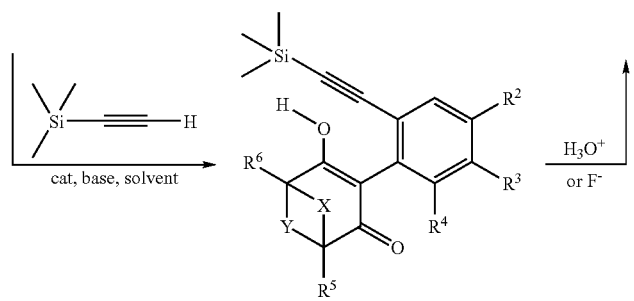

A compound of formula (A) wherein $R^1$ is ethynyl may be reduced to a compound of formula (A) wherein $R^1$ is ethyl under standard conditions (for example by catalytic hydrogenation).

In a further approach to a compound of formula (A) wherein $R^1$ is alkenyl or alkynyl, a compound of formula (H) may be coupled with an alkenyl- or alkynylstannane under conditions reported in the literature for effecting the Stille reaction (for a review of the Stille reaction, see V. Farina, V. Krishnamurthy and W. Scott, Org. React., (1997), 50, 1-652). Preferably the alkenyl- or alkynylstannane is a tributylstannane, ($Bu_3Sn$—$R^1$), and the reaction is carried out in the presence of a suitable palladium catalyst, a suitable ligand, and optionally in the presence of a copper co-catalyst and additive as described, for example, by S. Mee, V. Lee and J. Baldwin, Angew. Chem. Int. Ed., (2004), 1132-1136.

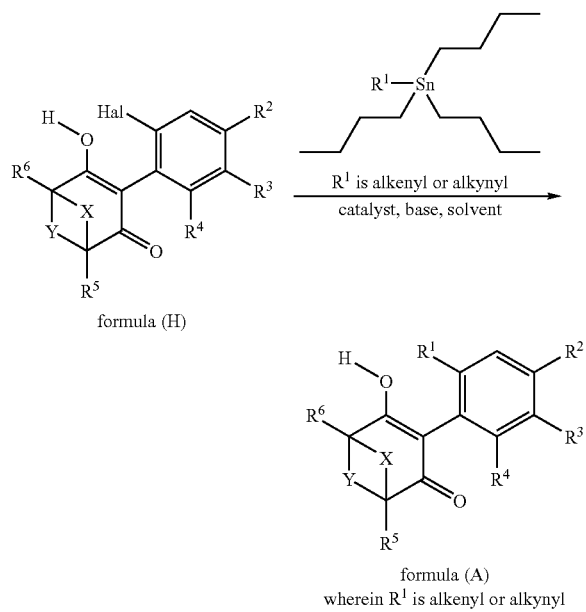

As before, a compound of formula (A) wherein $R^1$ is alkenyl or alkynyl, may be reduced to a compound of formula (A) wherein $R^1$ is alkyl, by known conditions (for example by catalytic hydrogenation).

Those skilled in the art will recognise that the above cross-couplings instead may be carried out under similar conditions on a compound of formula I; subsequent cyclisation under conditions previously described for a compound of formula (B) will also afford compounds of formula (A). Furthermore, those skilled in the art will also appreciate that additional compounds of formula (A) may be prepared from intermediates $G_a$, $G_b$ and $G_c$ under similar conditions using appropriate reagents.

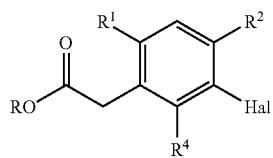

formula ($G_a$)

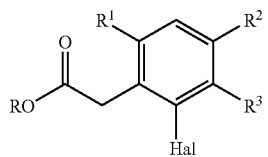

formula ($G_b$)

formula ($G_c$)

For example, compounds of formula ($G_b$) may be converted into compounds of formula (D) wherein $R^3$ is optionally substituted aryl or optionally substituted heteroaryl by reaction with a suitable aryl- or heteroarylboronic acid, $R^3$—$B(OH)_2$, or suitable ester thereof, or with a metal (especially potassium) aryl- or heteroaryltrifluoroborate salt, in the presence of a suitable palladium catalyst under known Suzuki-Miyaura conditions (see, for example, S-D Cho et al., Tetrahedron, (2007), 63, 1345-1352; M. Lysèn and K. Köhler, Synthesis, (2006), 4, 692-698; G. Zhang, Synthesis, (2005), 4, 537-542; F. Bellina, A. Carpita and R. Rossi, Synthesis (2004), 15, 2419-2440; S. Walker, T. Barder, J. Martinelli and S. Buchwald, Angew. Chem. Int. Ed., (2004), 43, 1871-1876; Y. Wang and D. Sauer, Org. Lett., (2004), 6 (16), 2793-2796; T. Barder and S. Buchwald, Org. Lett., (2004), 6 (16), 2649-2652; A. Bouillon et al., Tetrahedron, (2003), 59, 10043-10049; A. Littke and G. Fu, Angew. Chem. Int. Ed., (2002), 41, 4176-4211; F. Lieb et al., WO99/48869). These compounds of formula (D) may be converted into compounds of formula (A) by methods previously described.

In a further approach, a compound of formula (A) may be prepared by reaction of a compound of formula (J) with a phenyllead tricarboxylate, preferably a phenyllead triacetate of formula (K), in the presence of a suitable ligand (for example 4-dimethylaminopyridine, pyridine, imidazole, bipyridine, and 1,10-phenanthroline, preferably one to ten equivalents of 4-dimethylaminopyridine with respect to compound (J)) in a suitable solvent (for example chloroform, dichloromethane and toluene, preferably chloroform and optionally in the presence of a co-solvent such as toluene) at 25° C. to 100° C. (preferably 60-90° C.). Similar reactions are described in the literature (for example see, J. Pinhey, B. Rowe, Aust. J. Chem., (1979), 32, 1561-1566; J. Morgan, J. Pinhey, J. Chem. Soc. Perkin Trans. 1; (1990), 3, 715-720.)

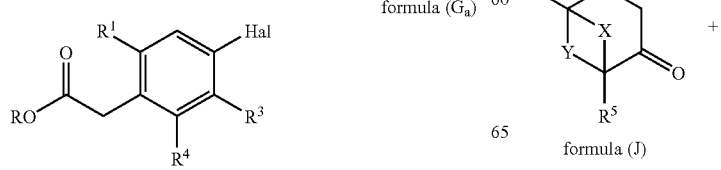

formula (J)

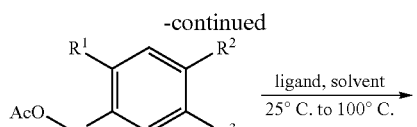

formula (K)

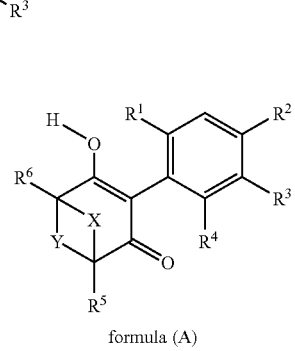

formula (A)

Compounds of formula (J) are known compounds or may be prepared by routes analogous to those described in the literature (see, for example, S. Spessard and B. Stoltz, Organic Letters, (2002), Vol. 4, No. 11, 1943-1946; F. Effenberger et al., Chem. Ber., (1984), 117, 3280-3296; W. Childers et al., Tetrahedron Lett., (2006), 2217-2218; W. Childers et al., US2006/0004108; H. *Schneider and C. Luethy, EP*1352890; D. Jackson, A. Edmunds, M. Bowden and B. Brockbank, WO2005/105745 and WO2005/105717; R. Beaudegnies, C. Luethy, A. Edmunds, J. Schaetzer and S. Wendeborn, WO2005/123667; J-C. Beloeil, J-Y. Lallemand, T. Prange, Tetrahedron, (1986), Vol. 42. No. 13, 3491-3502; H. Favre et al., Can. J. Chem. (1956), 34 1329-39).

A compound of formula (K) may be prepared from a compound of formula (L) by treatment with lead tetraacetate in a suitable solvent (for example chloroform) at 25° C. to 100° C. (preferably 25-50° C.), optionally in the presence of a catalyst such as mercury diacetate according to procedures described in the literature (for example see, K. Shimi, G. Boyer, J-P. Finet and J-P. Galy, Letters in Organic Chemistry, (2005), 2, 407-409; J. Morgan and J. Pinhey, J. Chem. Soc. Perkin Trans. 1, (1990), 3, 715-720).

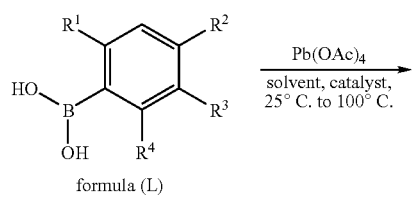

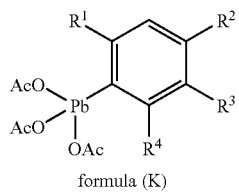

formula (K)

An aryl boronic acid of formula (L), or ester thereof, may be prepared from an aryl halide of formula (M), wherein Hal is Br or I by known methods (see, for example, M. Murata et al., Synthesis, (2007), 3, 351-354; T. Ishiyama, M. Murata and N. Miyaura, J. Org. Chem., (1995), 60, 7508-7510; W. J. Thompson and J. Gaudino, J. Org. Chem., (1984), 49, 5237 and R. T. Hawkins et al., J. Am. Chem. Soc., (1960), 82, 3053). For example, a phenyl halide of formula (M) may be treated with an alkyllithium or alkyl magnesium halide at low temperature, and the aryl magnesium or aryl lithium reagent obtained may then be allowed to react with a trialkylborate to give an aryl dialkylboronate which may be hydrolysed to an arylboronic acid of formula (L) under acidic, or other known, conditions:

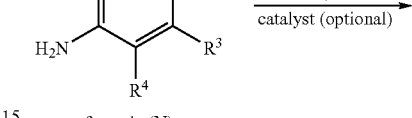

formula (N)

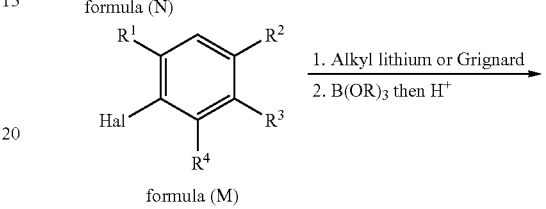

formula (M)

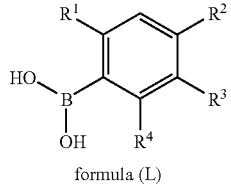

formula (L)

A phenyl halide of formula (M) may be prepared from an aniline of formula (N) by known methods, for example the Sandmeyer reaction, via the corresponding diazonium salt (see, for example, J. March, Advanced Organic Chemistry, $3^{rd}$ Edition, John Wiley and Sons, pages 647-648 and references therein. For additional examples see also W. Denney et al., J. Med. Chem., (1991), 34, 217-222; P. Knochel et al., Synthesis, (2007), No. 1, 81-84). Alternatively, an aniline of formula (N) may be diazotised, the diazonium salt treated with a borylating agent such as bis(pinacolato)diboron under conditions described, for example, by D. Willis and R. Strongin, Tetrahedron Lett., (2000), 41, 8683-8686, and the resulting boronate ester hydrolysed as before to give an additional arylboronic acid of formula (L).

Anilines of formula (N) are known compounds, or may be prepared from known compounds by known methods.

In a further approach, a compound of formula (A) may be prepared from a compound of formula (O) by reaction with a phenyl Iboronic acid of formula (L) in the presence of a suitable palladium catalyst and a base, preferably in a suitable solvent. Suitable palladium catalysts are generally palladium (II) or palladium(0) complexes, for example palladium(II) dihalides, palladium(II) acetate, palladium(II) sulfate, bis (triphenylphosphine)palladium(II) dichloride, bis(tricyclopentyl-phosphine)palladium(II) dichloride, bis(tricyclohexylphosphine)palladium(II) dichloride, bis (dibenzylideneacetone)palladium(0) or tetrakis (triphenylphosphine)palladium(0). The palladium catalyst can also be prepared "in situ" from palladium(II) or palladium(0) compounds by complexing with the desired ligands, by, for example, combining the palladium(II) salt to be complexed, for example palladium(II) dichloride ($PdCl_2$) or palladium(II) acetate ($Pd(OAc)_2$), together with the desired ligand, for example triphenylphosphine ($PPh_3$), tricyclopentylphosphine or tricyclohexylphosphine and the selected solvent, with a compound of formula (O), a compound of formula (L) and a base. Also suitable are bidendate ligands, for example 1,1'-bis(diphenyl-phosphino)ferrocene or 1,2-bis(diphenylphosphino)ethane. By heating the reaction medium, the palladium(II) complex or palladium(0) complex desired for the C—C coupling reaction is thus formed "in situ", and then initiates the C—C coupling reaction.

The palladium catalysts are used in an amount of from 0.001 to 50 mol %, preferably in an amount of from 0.1 to 15 mol %, based on the compound of formula (O). More preferably the palladium source is palladium acetate, the base is lithium hydroxide and the solvent is a mixture of 1,2-dimethoxyethane and water in a ratio of 4:1 to 1:4. The reaction may also be carried out in the presence of other additives, such as tetralkylammonium salts, for example, tetrabutylammonium bromide:

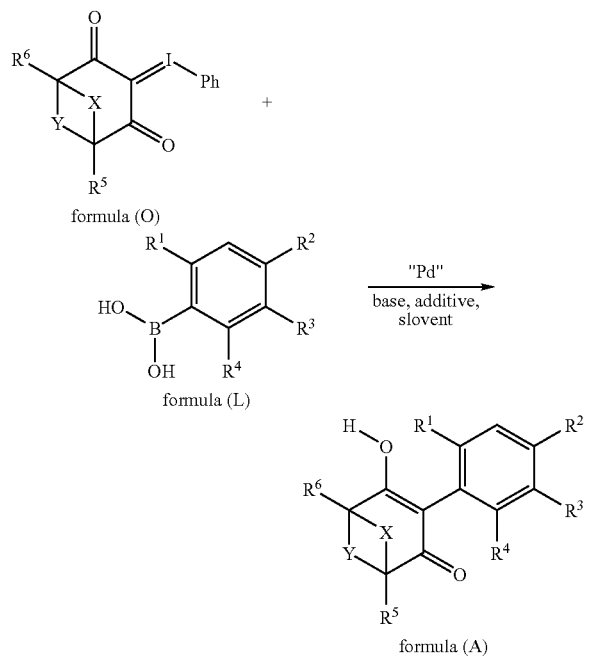

A compound of formula (O) may be prepared from a compound of formula (J) by treatment with (diacetoxy)iodobenzene according to the procedures of K. Schank and C. Lick, Synthesis, (1983), 392, or of Z Yang et al., Org. Lett., (2002), 4 (no 19), 3333:

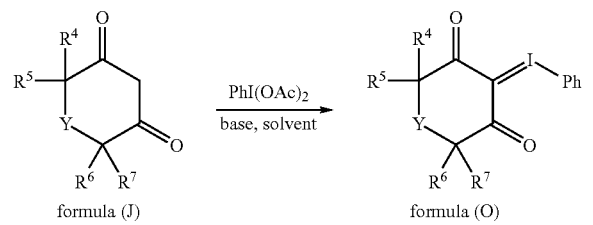

In a further approach, a compound of formula (A) may be prepared from a compound of formula I, wherein G is $C_1$-$C_4$alkyl, by hydrolysis, preferably in the presence of an acid catalyst such as hydrochloric acid and optionally in the presence of a suitable solvent such as tetrahydrofuran. A compound of formula I, wherein G is $C_1$-$C_4$alkyl, may be prepared by reacting a compound of formula (P), wherein Hal is a halogen (preferably bromine or iodine), with a phenyl boronic acid of formula (L) in the presence of a suitable palladium catalyst (for example 0.001-50% palladium(II) acetate with respect to compound (P)) and a base (for example 1 to 10 equivalents potassium phosphate with respect to compound (P)) and preferably in the presence of a suitable ligand (for example 0.001-50% (2-dicyclohexylphosphino)-2',6'-dimethoxybiphenyl with respect to compound (P)), and in a suitable solvent (for example toluene), preferably between 25° C. and 200° C. Similar couplings are known in the literature (see for example, Y. Song, B. Kim and J.-N. Heo, Tetrahedron Letters, (2005), 46(36), 5987-5990).

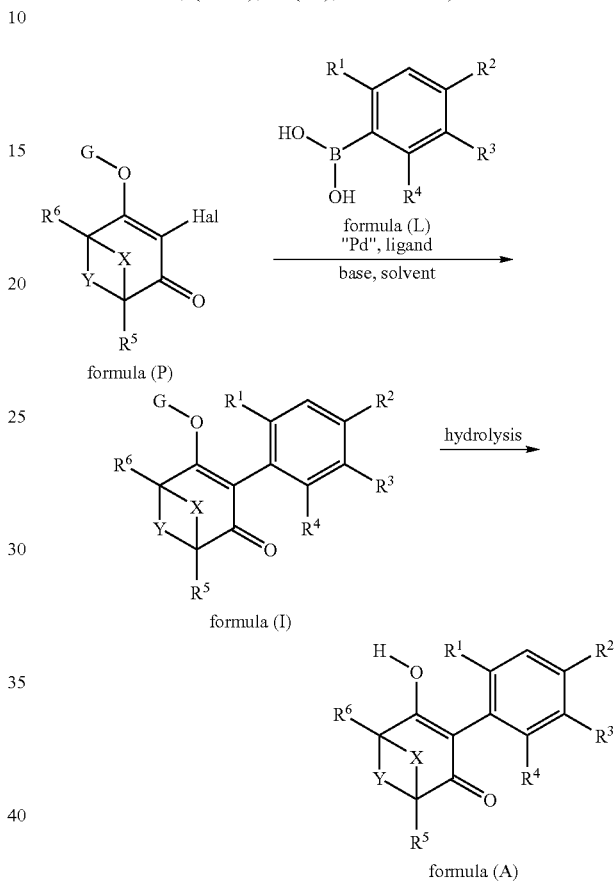

A compound of formula (P), wherein G is $C_1$-$C_4$ alkyl, may be prepared by halogenating a compound of formula (J), followed by alkylation of the resulting halide of formula (O) with a $C_1$-$C_4$ alkyl halide or tri-$C_1$-$C_4$alkylorthoformate under known conditions, for example by the procedures of R. Shepherd and A. White (J. Chem. Soc. Perkin Trans. 1 (1987), 2153) and Y.-L. Lin et al. (Bioorg. Med. Chem. 10 (2002) 685-690). Alternatively, a compound of formula (P) may be prepared by alkylating a compound of formula (J) with a $C_1$-$C_4$ alkyl halide or a tri-$C_1$-$C_4$alkylorthoformate, and halogenating the resulting enone of formula (R) under known conditions (see for example Y. Song, B. Kim and J.-N. Heo, Tetrahedron Letters (2005), 46(36), 5987-5990).

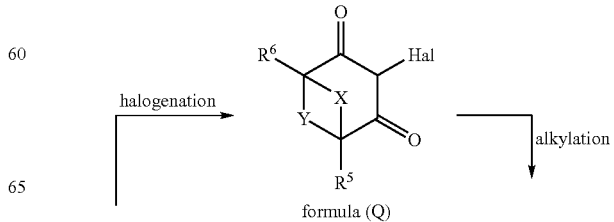

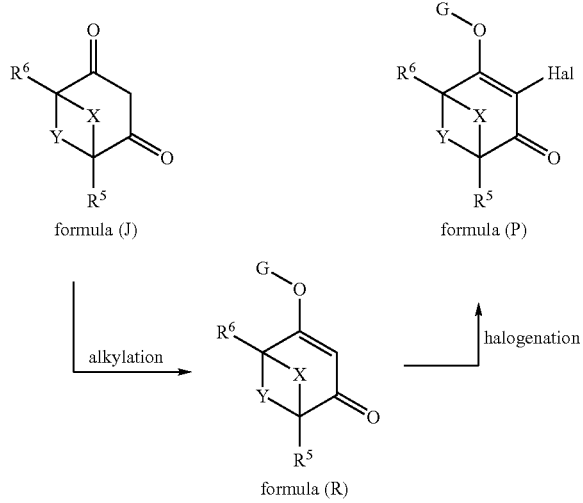

formula (J)  formula (P)

alkylation → formula (R) ← halogenation

In a further approach, a compound of formula (A) may be prepared by reacting a compound of formula (J) with a compound of formula (M) in the presence of a suitable palladium catalyst, a base, preferably in the presence of a suitable ligand and in a suitable solvent, and optionally under microwave irradiation. Suitable palladium catalysts are generally palladium(II) or palladium(0) complexes, for example palladium (II) dihalides, palladium(II) acetate, palladium(II) sulfate, bis(triphenylphosphine)palladium(II) dichloride, bis(tricyclopentylphosphine)palladium(II) dichloride, bis(tricyclohexylphosphine)palladium(II) dichloride, bis(dibenzylideneacetone)-palladium(0) and tetrakis(triphenylphosphine) palladium(0). Suitable bases include alkali metal carbonates, phosphates, alkoxides and amides. Suitable ligands include phosphines, for example 2, 2'-bis(di-p-tolylphosphino)-1,1'-binaphthyl, 2,2'-bis(diphenylphosphino)-1,1'-binaphthyl, 1,1'-bis(di-o-tolylphosphino)ferrocene, Xantphos, (2-di-t-butylphosphino)-2'-methylbiphenyl, (2-dicyclohexylphosphino)-2'-methylbiphenyl, (2-dicyclohexylphosphino)-2',4', 6'-triisopropylbiphenyl and the like. Suitable solvents include tetrahydrofuran, 1,4-dioxane and 1,2-dimethoxyethane. The palladium catalysts are used in an amount of from 0.001 to 50 mol %, preferably in an amount of from 0.1 to 15 mol %, based on the compound of formula (J). Preferably the ligands are used in a 1:1 to 2:1 ratio with respect to the palladium catalyst. Preferably one to five equivalents of base (with respect to a compound of formula (J)) are used, more preferably two to three equivalents are used. Even more preferably the palladium source is palladium(II) acetate or bis(dibenzylideneacetone)palladium(0) (especially palladium (II) acetate), the ligand is (2-dicyclohexylphosphino)-2',4',6'-triisopropylbiphenyl, the base is potassium phosphate, and the solvent is 1,2-dimethoxyethane.

Similar conditions are reported in the literature for effecting the arylation of carbocyclic 1,3-diones (see for example, J. Fox, X. Huang, A. Chieffi, S. Buchwald, J. Am. Chem. Soc. (2000), 122, 1360-1370; B. Hong et al. WO 2005/000233).

Alternatively, a compound of formula (A) may be prepared by reacting a compound of formula (J) with a compound of formula (M) in the presence of a suitable copper catalyst (for example 0.001-50% copper(I) iodide with respect to compound (J)) and a base (for example 1 to 10 equivalents potassium carbonate with respect to compound (J)) and preferably in the presence of a suitable ligand (for example 0.001-50% L-proline with respect to compound (J)), and in a suitable solvent (for example dimethylsulfoxide), preferably between 25° C. and 200° C. Similar couplings are known in the literature (see for example, Y. Jiang, N. Wu, H. Wu, M. He, Synlett, (2005), 18, 2731-2734).

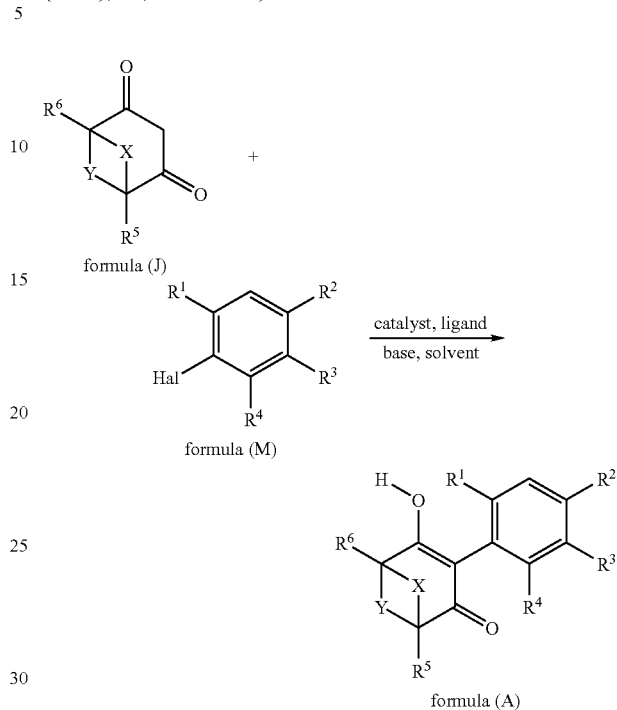

formula (J) + formula (M) → formula (A)

In a further approach, a compound of formula I may be prepared by reacting a compound of formula (T) with a phenyl- or heteroarylboronic acid of formula, $R^2$—$B(OH)_2$, or a suitable derivative, such as a metal (especially potassium) trifluororoborate or ester (such as those derived from a 1,2- or a 1,3-alkanediol, for example pinacol, 2,2-dimethyl-1,3-propanediol and 2-methyl-2,4-pentanediol), under Suzuki-Miyaura conditions.

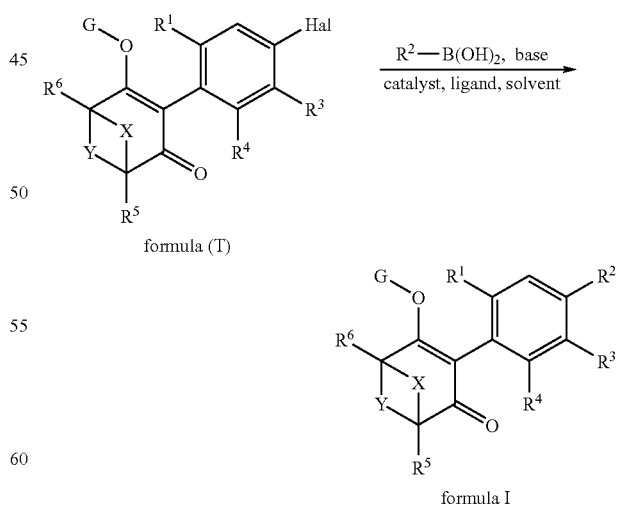

formula (T) → formula I

A compound of formula (T), wherein G is H, may be prepared by reacting a compound of formula (J) with a phenyllead tricarboxylate, preferably a phenyllead triacetate of formula (S) wherein Hal is chlorine or bromine, in the presence of a suitable ligand (for example 4-dimethylaminopyridine, pyridine, imidazole, bipyridine, and 1,10-phenanthroline, preferably one to ten equivalents of 4-dimethylaminopyridine with respect to compound (S)) in a suitable solvent (for example chloroform, dichloromethane and toluene, preferably chloroform and optionally in the presence of a co-solvent such as toluene) at 25° C. to 100° C. (preferably 60-90° C.).

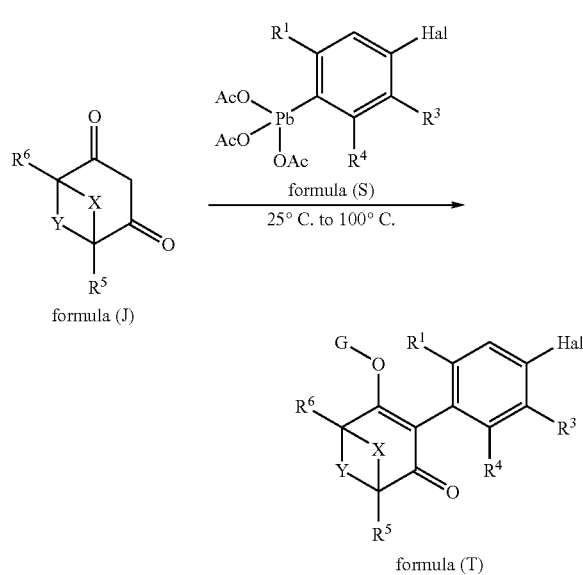

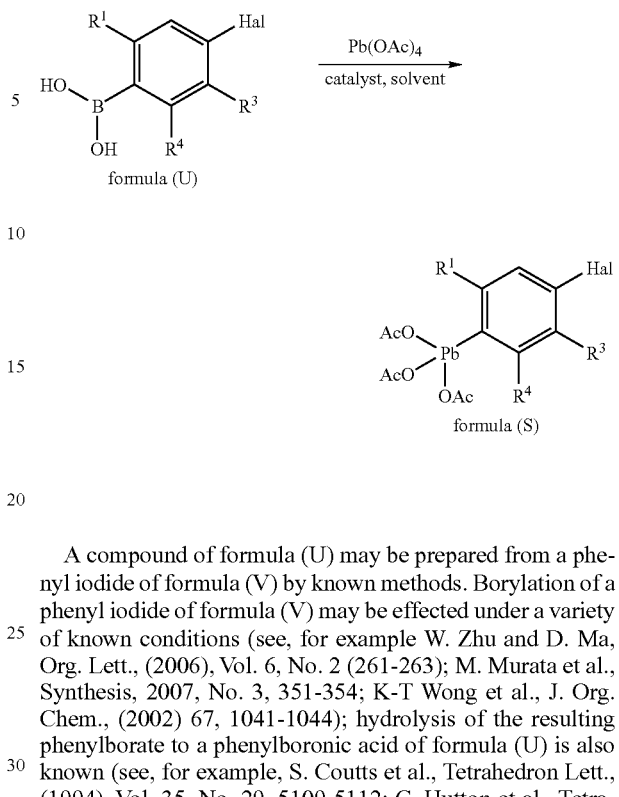

A compound of formula (S) may be prepared from a phenylboronic acid of formula (U) by similar conditions to those used to prepare a compound of formula (K) from a compound of formula (L).

A compound of formula (U) may be prepared from a phenyl iodide of formula (V) by known methods. Borylation of a phenyl iodide of formula (V) may be effected under a variety of known conditions (see, for example W. Zhu and D. Ma, Org. Lett., (2006), Vol. 6, No. 2 (261-263); M. Murata et al., Synthesis, 2007, No. 3, 351-354; K-T Wong et al., J. Org. Chem., (2002) 67, 1041-1044); hydrolysis of the resulting phenylborate to a phenylboronic acid of formula (U) is also known (see, for example, S. Coutts et al., Tetrahedron Lett., (1994), Vol. 35, No. 29, 5109-5112; C. Hutton et al., Tetrahedron Lett., (2004), 45, 6657-6660). A phenyl iodide of formula (V) may be prepared from an aniline of formula (W), using a variety of different reaction conditions (see, for example, P. Knochel et al., Synthesis, (2007), No. 1, 81-84 and references therein).

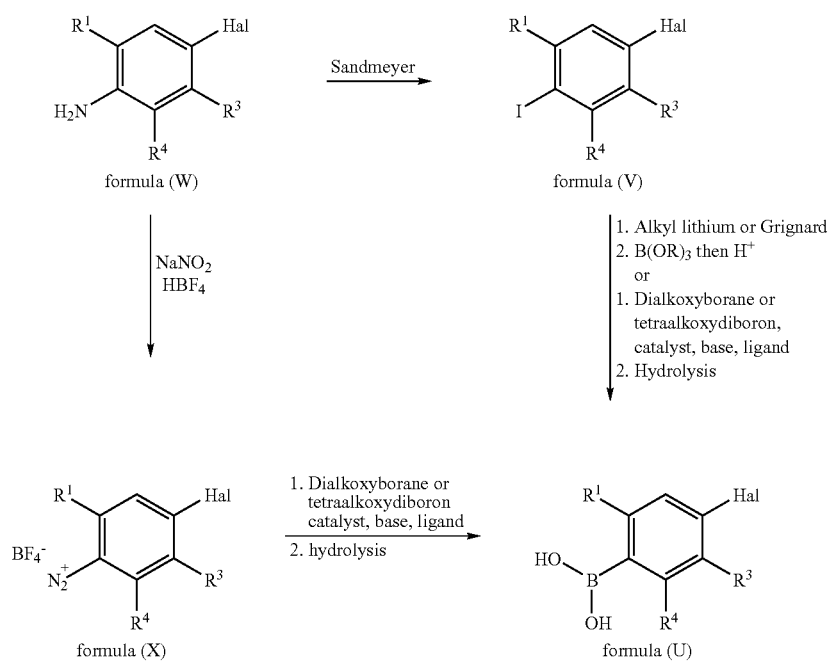

Alternatively a compound of formula (U) may be prepared from an aniline of formula (W) by diazotisation to give a phenyldiazonium salt of formula (X), followed by borylation of the resulting diazonium salt according to procedures described, for example by D. Willis and R. Strongin, (Tetrahedron Lett., (2000), 41, 8683-8686) and the resulting boronate ester may be converted to the boronic acid of formula (U) as before.

In a further approach, a compound of formula I may be prepared by reacting a compound of formula ($T_1$) with a phenyl- or heteroarylboronic acid of formula, $R^3$—$B(OH)_2$, or a suitable derivative, such as a metal (especially potassium) trifluororoborate or ester (such as those derived from a 1,2- or a 1,3-alkanediol, for example pinacol, 2,2-dimethyl-1,3-propanediol and 2-methyl-2,4-pentanediol), under Suzuki-Miyaura conditions.

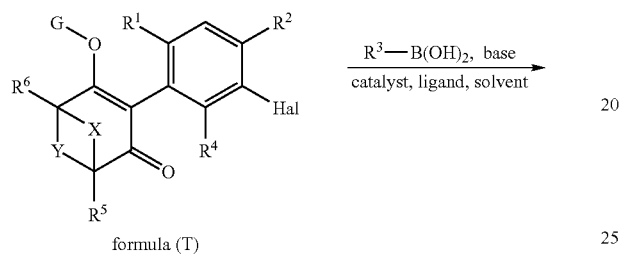

formula (T)

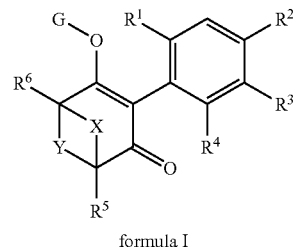

formula I

A compound of formula ($T_1$), wherein G is H, may be prepared from a compound of formula ($W_1$) by procedures analogous to those used in the preparation of a compound of formula (T) from a compound of formula (W):

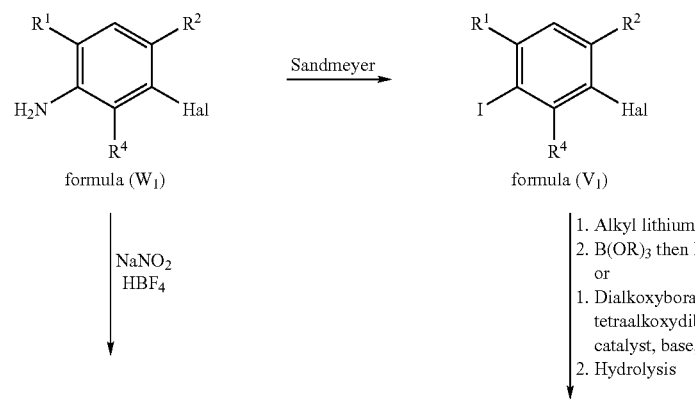

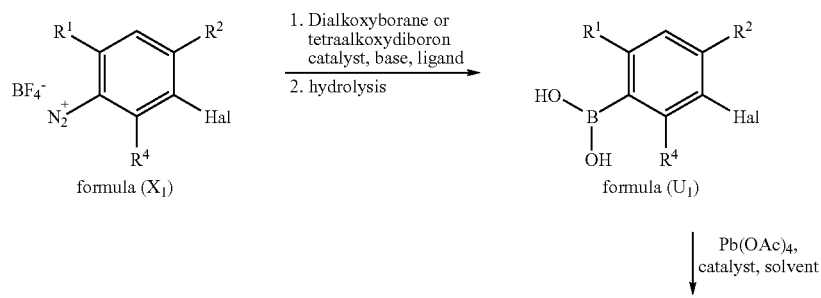

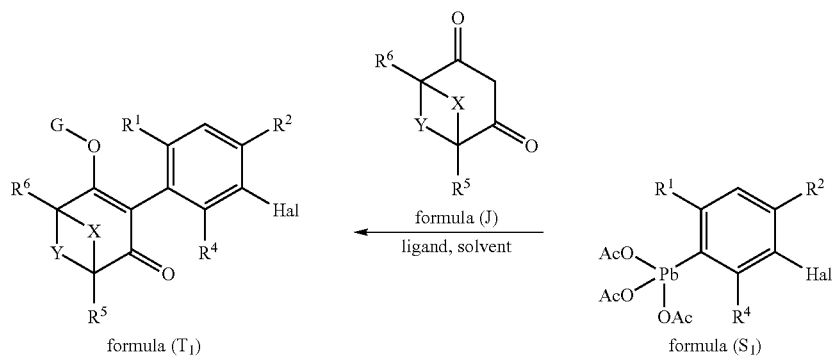

Anilines of formula (W) and formula (W₁) are known compounds, or may be made from known compounds by known methods.

The compounds of the formulae (T) and (T₁) have been particularly designed for the synthesis of the compounds of the formula I.

In a further approach, a compound of formula I may be prepared from a phenylboronic acid of formula (Y), or a suitable ester or salt thereof, by cross coupling with a phenyl- or heteroaryl-halide, R²-Hal, where Hal is preferably chlorine, bromine, iodine under Suzuki-Miyaura conditions.

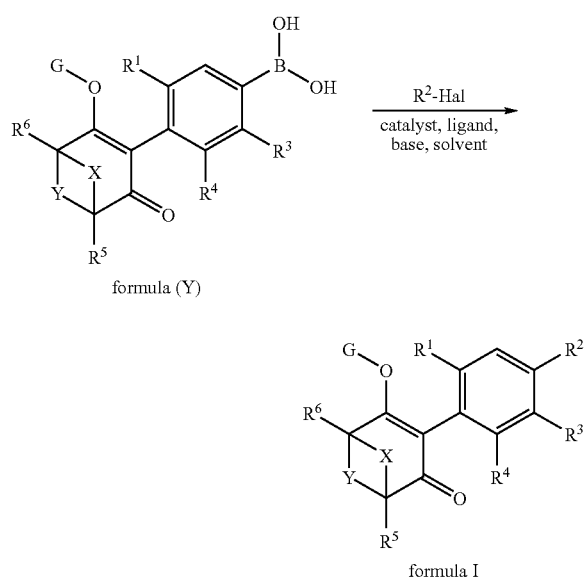

A compound of formula (Y) may be prepared from a compound of formula (T) by treatment with at least two equivalents of a suitable metallating agent such as an alkyl lithium or an alkyl magnesium halide in a solvent such as tetrahydrofuran or diethyl ether, or by treatment with at least one equivalent of a suitable base (such as sodium hydride) followed by treatment of the resulting anion with at least one equivalent of a suitable metallating agent in a suitable solvent such as tetrahydrofuran or diethyl ether, and reacting the resulting organometallic species with a suitable borylating agent such as trimethylborate, to give a phenylboronate of formula (Z) wherein R'" is an alkyl group, preferably methyl. A phenyl boronate of formula (Z) may be hydrolysed under acidic conditions to give a phenylboronic acid of formula (Y). Alternatively a compound of formula (T) may be reacted a borylating reagent, H—B(OR")₂, or (R"O)₂B—B(OR")₂, under known conditions (see, for example, M. Miruta et al., Synlett, (2006), 12, 1867-1870; N. Miyaura et al., J. Org. Chem., (1995), 60, 7508, and W. Zhu and D. Ma, Org. Lett., (2006), 8 (2), 261), to give a compound of formula (Z). Suitable borylating reagents include bis(pinacolato)diboron, bis(neopentyl glycolato)diboron, bis(hexylene glycolato)diboron and 4,4,5,5-tetramethyl-1,3,2-dioxaborolane. A compound of formula (Z), wherein the fragment —B(OR")₂ represents a suitable cyclic boronate ester, may be coupled with a phenyl or heteroaryl halide R³-Hal, under Suzuki-Miyaura conditions.

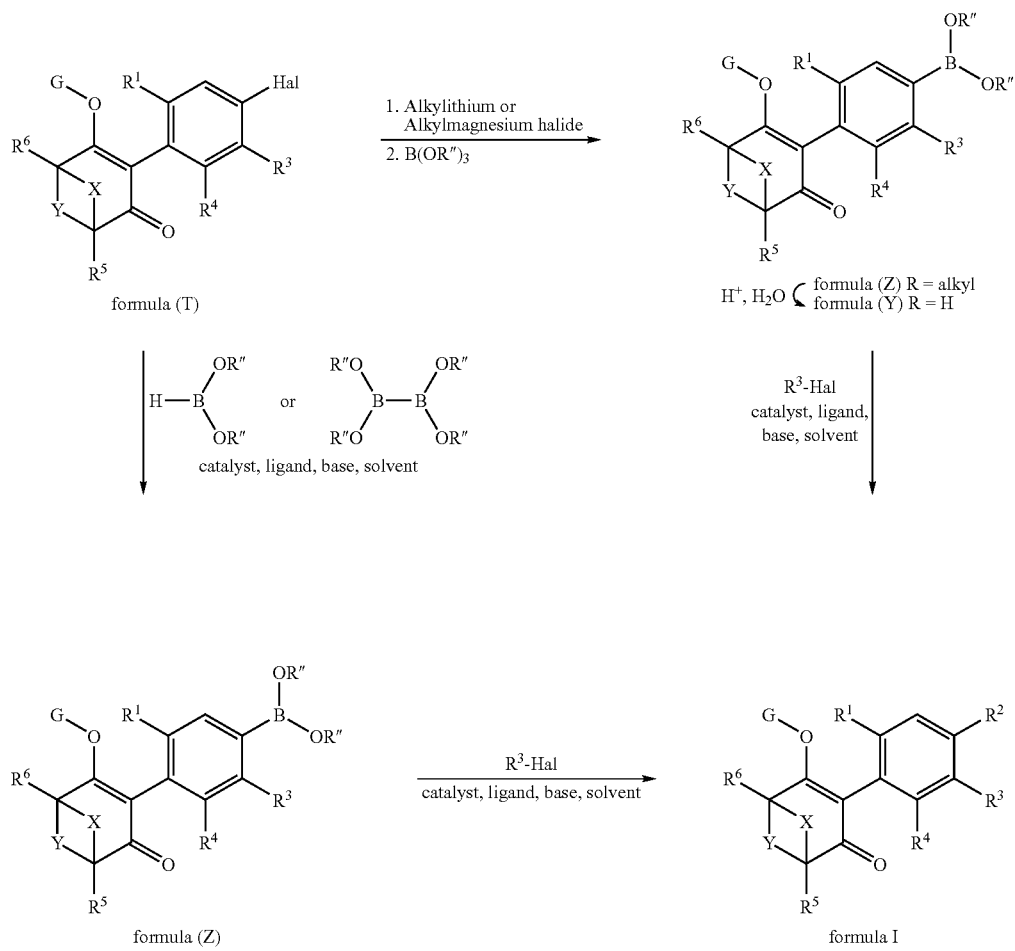

Alternatively, a compound of formula I may be prepared from a phenylboronic acid of formula ($Y_1$), or a suitable ester or salt thereof, by cross coupling with a phenyl- or heteroaryl-halide, $R^2$-Hal, where Hal is preferably chlorine, bromine, iodine under Suzuki-Miyaura conditions.

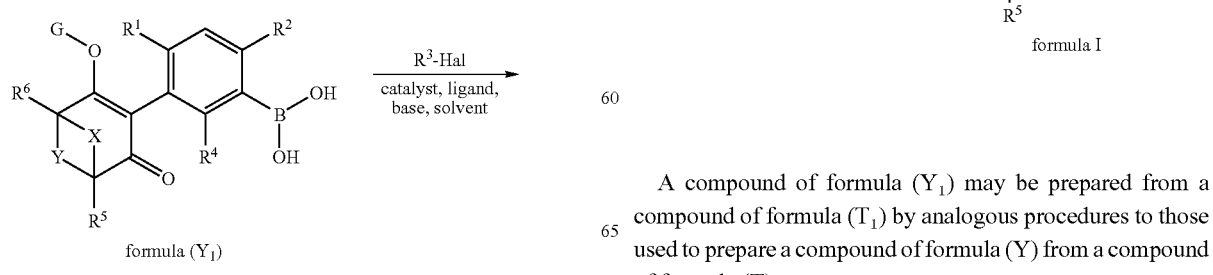

A compound of formula ($Y_1$) may be prepared from a compound of formula ($T_1$) by analogous procedures to those used to prepare a compound of formula (Y) from a compound of formula (T).

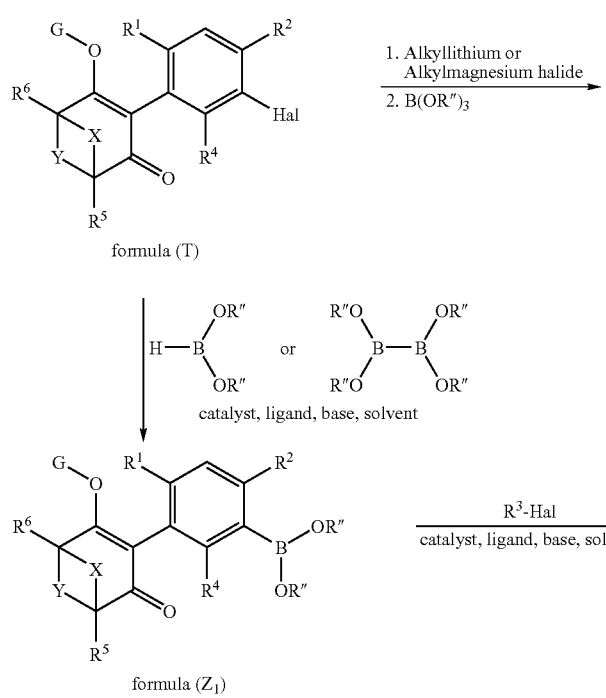

formula (T)

formula (Z₁)

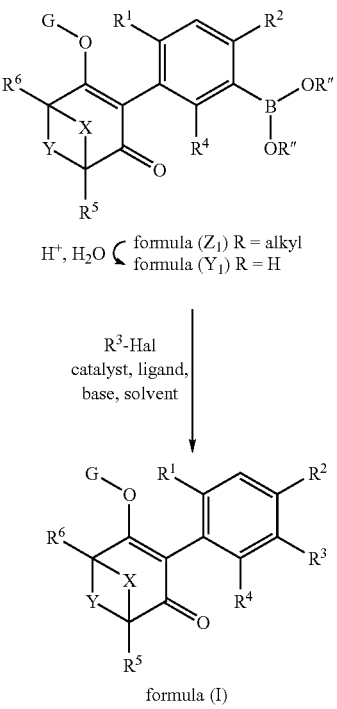

H⁺, H₂O ⊂ formula (Z₁) R = alkyl
         formula (Y₁) R = H formula (I)

The compounds of the formulae (Y) and (Y₁) have been particularly designed for the synthesis of the compounds of the formula I.

The compounds of formula I according to the invention can be used as herbicides in unmodified form, as obtained in the synthesis, but they are generally formulated into herbicidal compositions in a variety of ways using formulation adjuvants, such as carriers, solvents and surface-active substances. The formulations can be in various physical forms, for example in the form of dusting powders, gels, wettable powders, water-dispersible granules, water-dispersible tablets, effervescent compressed tablets, emulsifiable concentrates, microemulsifiable concentrates, oil-in-water emulsions, oil flowables, aqueous dispersions, oily dispersions, suspoemulsions, capsule suspensions, emulsifiable granules, soluble liquids, water-soluble concentrates (with water or a water-miscibie organic solvent as carrier), impregnated polymer films or in other forms known, for example, from the Manual on Development and Use of FAO Specifications for Plant Protection Products, 5th Edition, 1999. Such formulations can either be used directly or are diluted prior to use. Diluted formulations can be prepared, for example, with water, liquid fertilisers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be formulated with other adjuvants, for example finely divided solids, mineral oils, vegetable oils, modified vegetable oils, organic solvents, water, surface-active substances or combinations thereof. The active ingredients can also be contained in very fine microcapsules consisting of a polymer. Microcapsules contain the active ingredients in a porous carrier. This enables the active ingredients to be released into their surroundings in controlled amounts (e.g. slow release). Microcapsules usually have a diameter of from 0.1 to 500 microns. They contain active ingredients in an amount of about from 25 to 95° A) by weight of the capsule weight. The active ingredients can be present in the form of a monolithic solid, in the form of fine particles in solid or liquid dispersion or in the form of a suitable solution. The encapsulating membranes comprise, for example, natural and synthetic gums, cellulose, styrene-butadiene copolymers, polyacrylonitrile, polyacrylate, polyester, polyamides, polyureas, polyurethane or chemically modified polymers and starch xanthates or other polymers that are known to the person skilled in the art in this connection. Alternatively it is possible for very fine microcapsules to be formed wherein the active ingredient is present in the form of finely divided particles in a solid matrix of a base substance, but in that case the microcapsule is not encapsulated.

The formulation adjuvants suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylenes carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethyl hexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG 400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and higher molecular weight alcohols, such as amyl alcohol, tetrahydrofurfuryl alcohol, hexanol, octanol, ethylene glycol, propylene glycol, glycerol, N-methyl-2-pyrrolidone and the like. Water is generally the carrier of choice for the dilution of the concentrates. Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheatmeal, soybean flour, pumice, wood flour, ground walnut shells, lignin and similar materials, as described, for example, in CFR 180.1001. (c) & (d).

A large number of surface-active substances can advantageously be used both in solid and in liquid formulations, especially in those formulations which can be diluted with a carrier prior to use. Surface-active substances may be anionic, cationic, non-ionic or polymeric and they may be used as emulsifying, wetting or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol-alkylene oxide addition products, such as nonylphenol ethoxylate; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further adjuvants which can usually be used in pesticidal formulations include crystallisation inhibitors, viscosity-modifying substances, suspending agents, dyes, anti-oxidants, foaming agents, light absorbers, mixing aids, anti-foams, complexing agents, neutralising or pH-modifying substances and buffers, corrosion-inhibitors, fragrances, wetting agents, absorption improvers, micronutrients, plasticisers, glidants, lubricants, dispersants, thickeners, anti-freezes, microbiocides, and also liquid and solid fertilisers.

The formulations may also comprise additional active substances, for example further herbicides, herbicide safeners, plant growth regulators, fungicides or insecticides.

The compositions according to the invention can additionally include an additive comprising an oil of vegetable or animal origin, a mineral oil, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhone-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000. Another preferred adjuvant is Adigor® (Syngenta AG) which is a methylated rapeseed oil-based adjuvant.

The application and action of the oil additives can be further improved by combining them with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltrisiloxanes, which are commercially available e.g. as Silwet L-77®, and also perfluorinated surfactants. The concentration of surface-active substances in relation to the total additive is generally from 1 to 30% by weight. Examples of oil additives that consist of mixtures of oils or mineral oils or derivatives thereof with surfactants are Edenor ME SU®, Turbocharge® (Syngenta AG, CH) and Actipron® (BP Oil UK Limited, GB).

The said surface-active substances may also be used in the formulations alone, that is to say without oil additives.

Furthermore, the addition of an organic solvent to the oil additive/surfactant mixture can contribute to a further enhancement of action. Suitable solvents are, for example, Solvesso® (ESSO) and Aromatic Solvent® (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada.)

In addition to the oil additives listed above, in order to enhance the activity of the compositions according to the invention it is also possible for formulations of alkylpyrrolidones, (e.g. Agrimax®) to be added to the spray mixture. Formulations of synthetic lattices, such as, for example, polyacrylamide, polyvinyl compounds or poly-1-p-menthene (e.g. Bond®, Courier® or Emerald®) can also be used. Solutions that contain propionic acid, for example Eurogkem Pene-trate®, can also be mixed into the spray mixture as activity-enhancing agents.

The herbicidal formulations generally contain from 0.1 to 99% by weight, especially from 0.1 to 95% by weight, of a compound of formula I and from 1 to 99.9% by weight of a formulation adjuvant, which preferably includes from 0 to 25% by weight of a surface-active substance. Whereas commercial products will preferably be formulated as concentrates, the end user will normally employ dilute formulations.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied at a rate of 1 to 4000 g/ha, especially from 5 to 1000 g/ha. Preferred formulations have especially the following compositions:

| (% = percent by weight): | |
|---|---|
| Emulsifiable concentrates: | |
| active ingredient: | 1 to 95%, preferably 60 to 90% |
| surface-active agent: | 1 to 30%, preferably 5 to 20% |
| liquid carrier: | 1 to 80%, preferably 1 to 35% |
| Dusts: | |
| active ingredient: | 0.1 to 10%, preferably 0.1 to 5% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surface-active agent: | 1 to 40%, preferably 2 to 30% |
| Wettable powders: | |
| active ingredient: | 0.5 to 90%, preferably 1 to 80% |
| surface-active agent: | 0.5 to 20%, preferably 1 to 15% |
| solid carrier: | 5 to 95%, preferably 15 to 90% |
| Granules: | |
| active ingredient: | 0.1 to 30%, preferably 0.1 to 15% |
| solid carrier: | 99.5 to 70%, preferably 97 to 85% |

The following Examples further illustrate, but do not limit, the invention.

| F1. Emulsifiable concentrates | a) | b) | c) | d) |
|---|---|---|---|---|
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | — | 10% | 20% |
| arom. hydrocarbon mixture $C_9$-$C_{12}$ | 85% | 78% | 55% | 16% |

Emulsions of any desired concentration can be prepared from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)-propane | — | 20% | 20% | — |
| polyethylene glycol MW 400 | 20% | 10% | — | — |
| NMP | — | — | 30% | 10% |
| arom. hydrocarbon mixture $C_9$-$C_{12}$ | 75% | 60% | — | — |

The solutions are suitable for application in the form of microdrops.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly disperse silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

| F4. Coated granules | a) | b) | c) |
|---|---|---|---|
| active ingredient | 0.1% | 5% | 15% |
| highly disperse silicic acid | 0.9% | 2% | 2% |
| inorg. carrier (diameter 0.1-1 mm) e.g. $CaCO_3$ or $SiO_2$ | 99.0% | 93% | 83% |

The active ingredient is dissolved in methylene chloride, the solution is sprayed onto the carrier and the solvent is subsequently evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly disperse silicic acid | 0.9% | 1% | 2% |
| inorg. carrier (diameter 0.1-1 mm) e.g. $CaCO_3$ or $SiO_2$ | 98.0% | 92% | 80% |

The finely ground active ingredient is applied uniformly, in a mixer, to the carrier moistened with polyethylene glycol. Non-dusty coated granules are obtained in this manner.

| F6. Extruder granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

| F7. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, yielding a suspension concentrate from which suspensions of any desired concentration can be prepared by dilution with water.

The invention relates also to a method for the selective control of grasses and weeds in crops of useful plants, which comprises treating the useful plants or the area under cultivation or the locus thereof with a compound of formula I.

Crops of useful plants in which the compositions according to the invention can be used include especially cereals, cotton, soybeans, sugar beet, sugar cane, plantation crops, rape, maize and rice, and for non-selective weed control. The term "crops" is to be understood as also including crops that have been rendered tolerant to herbicides or classes of herbicides (for example ALS, GS, EPSPS, PPO, ACCase and HPPD inhibitors) as a result of conventional methods of breeding or genetic engineering. An example of a crop that has been rendered tolerant e.g. to imidazolinones, such as imazamox, by conventional methods of breeding is Clearfield® summer rape (Canola). Examples of crops that have been rendered tolerant to herbicides by genetic engineering methods include e.g. glyphosate- and glufosinate-resistant maize varieties commercially available under the trade names RoundupReady® and LibertyLink®.

The weeds to be controlled may be both monocotyledonous and dicotyledonous weeds, such as, for example, *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum, Rottboellia, Cyperus, Abutilon, Sida, Xanthium, Amaranthus, Chenopodium, Ipomoea, Chrysanthemum, Galium, Viola* and *Veronica*.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

Areas under cultivation are to be understood as including land where the crop plants are already growing as well as land intended for the cultivation of those crop plants.

The compounds of formula I according to the invention can also be used in combination with other herbicides. The following mixtures of the compound of formula I are especially important.

Preferably, in these mixtures, the compound of the formula I is one of those compounds listed in Tables 1 to 35 below:

compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atrazine, formula I+aviglycine, formula I+azafenidin, compound of formula I+azimsulfuron, compound of formula I+BCPC, compound of formula I+beflubutamid, compound of formula I+benazolin, formula I+bencarbazone, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, formula I+bromophenoxim, compound of formula I+bromoxynil, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, formula I+desmetryn, compound of formula I+dicamba, compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, formula I+dipropetryn, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, formula I+ethephon, compound of formula I+ethofumesate, compound of formula I+ethoxyfen, compound of formula I+ethoxysulfuron, compound of formula I+etobenzanid, compound of formula I+fenoxaprop-P, compound of formula I+fenoxaprop-P-ethyl, compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, formula I+fluazolate, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, formula I+flumetralin, compound of formula I+flumetsulam, compound of formula I+flumiclorac, compound of formula I+flumiclorac-pentyl, compound of formula I+flumioxazin, formula I+flumipropin, compound of formula I+fluometuron, compound of formula I+fluoroglycofen, compound of formula I+fluoroglycofen-ethyl, formula I+fluoxaprop, formula I+flupoxam, formula I+flupropacil, compound of formula I+flupropanate, compound of formula I+flupyrsulfuron, compound of formula I+flupyrsulfuron-methyl-sodium, compound of formula I+flurenol, compound of formula I+fluridone, compound of formula I+fluorochloridone, compound of formula I+fluoroxypyr, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glyphosate, compound of formula I+halosulfuron, compound of formula I+halosulfuron-methyl, compound of formula I+haloxyfop, compound of formula I+haloxyfop-P, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+isoproturon, compound of formula I+isouron, compound of formula I+isoxaben, compound of formula I+isoxachlortole, compound of formula I+isoxaflutole, formula I+isoxapyrifop, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+methabenzthiazuron, formula I+methazole, compound of formula I+methylarsonic acid, compound of formula I+methyldymron, compound of formula I+methyl isothiocyanate, compound of formula I+metobenzuron, formula I+metobromuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, formula I+NDA-402989, compound of formula I+neburon, compound of formula I+nicosulfuron, formula I+nipyraclofen, formula I+n-methyl glyphosate, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, formula I+prohexadione-calcium, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyzamide, compound of formula I+prosulfocarb, compound of formula I+prosulfuron, compound of formula I+pyraclonil, compound of formula I+pyraflufen, compound of formula I+pyraflufen-ethyl, formula I+pyrasulfotole, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula f+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, formula I+pyroxasulfone, formula I+pyroxulam, compound of formula I+quinclorac, compound of formula I+quinmerac, compound of formula I+quinoclamine, compound of formula I+quizalofop, compound of formula I+quizalofop-P, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, formula I+tebutam, compound of formula I+tebuthiuron, formula I+tefuryltrione, compound of formula 1+tembotrione, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazafluoron, compound of formula I+thiazopyr, compound of formula I+thifensulfuron, compound of formula I+thiencarbazone, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+trinexapac-ethyl, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), compound of formula I+4-hydroxy-3-[[2-[(2-methoxyethoxy)methyl]-6-(trifluoromethyl)-3-pyridinyl]carbonyl]-bicyclo[3.2.1]oct-3-en-2-one (CAS RN 352010-68-5), and compound of formula I+4-hydroxy-3-[[2-(3-methoxypropyl)-6-(difluoromethyl)-3-pyridinyl]carbonyl]bicyclo[3.2.1]oct-3-en-2-one.

The mixing partners of the compound of formula I may also be in the form of esters or salts, as mentioned e.g. in The Pesticide Manual, Twelfth Edition, British Crop Protection Council, 2000.

The mixing ratio of the compound of formula I to the mixing partner is preferably from 1:100 to 1000:1.

The mixtures can advantageously be used in the above-mentioned formulations (in which case "active ingredient" relates to the respective mixture of compound of formula I with the mixing partner).

The compounds of formula I according to the invention can also be used in combination with safeners. Preferably, in these mixtures, the compound of the formula I is one of those compounds listed in Tables 1 to 35 below. The following mixtures with safeners, especially, come into consideration: compound of formula I+cloquintocet-mexyl, compound of formula I+cloquintocet acid and salts thereof, compound of formula I+fenchlorazole-ethyl, compound of formula I+fenchiorazole acid and salts thereof, compound of formula I+mefenpyr-diethyl, compound of formula I+mefenpyr diacid, compound of formula I+isoxadifen-ethyl, compound of formula I+isoxadifen acid, compound of formula I+furilazole, compound of formula I+furilazole R isomer, compound of formula I+benoxacor, compound of formula I+dichlormid, compound of formula I+AD-67, compound of formula I+oxabetrinil, compound of formula I+cyometrinil, compound of formula I+cyometrinil Z-isomer, compound of formula I+fenclorim, compound of formula I+cyprosulfamide, compound of formula I+naphthalic anhydride, compound of formula I+flurazole, compound of formula I+N-(2-methoxybenzoyl)-4-[(methylaminocarbonyl)amino]-benzenesulfonamide, compound of formula I+CL 304,415, compound of formula I+dicyclonon, compound of formula I+fluxofenim, compound of formula I+DKA-24, compound of formula I+R-29148 and compound of formula I+PPG-1292. A safening effect can also be observed for the mixtures compound of the formula I+dymron, compound of the formula I+MCPA, compound of the formula I+mecopropand compound of the formula I+mecoprop-P.

The above-mentioned safeners and herbicides are described, for example, in the Pesticide Manual, Twelfth Edition, British Crop Protection Council, 2000. R-29148 is described, for example by P. B. Goldsbrough et al., Plant Physiology, (2002), Vol. 130 pp. 1497-1505 and references therein, PPG-1292 is known from WO09211761, and N-(2-methoxybenzoyl)-4-[(methylaminocarbonyl)amino]benzenesulfonamide is known from EP365484.

The rate of application of safener relative to the herbicide is largely dependent upon the mode of application. In the case of field treatment, generally from 0.001 to 5.0 kg of safener/ha, preferably from 0.001 to 0.5 kg of safener/ha, and generally from 0.001 to 2 kg of herbicide/ha, but preferably from 0.005 to 1 kg/ha, are applied.

The herbicidal compositions according to the invention are suitable for all methods of application customary in agriculture, such as, for example, pre-emergence application, post-emergence application and seed dressing. Depending upon the intended use, the safeners can be used for pretreating the seed material of the crop plant (dressing the seed or seedlings) or introduced into the soil before or after sowing, followed by the application of the (unsafened) compound of the formula I, optionally in combination with a co-herbicide. It can, however, also be applied alone or together with the herbicide before or after emergence of the plants. The treatment of the plants or the seed material with the safener can therefore take place in principle independently of the time of application of the herbicide. The treatment of the plant by simultaneous application of herbicide and safener (e.g. in the form of a tank mixture) is generally preferred. The rate of application of safener relative to herbicide is largely dependent upon the mode of application. In the case of field treatment, generally from 0.001 to 5.0 kg of safener/ha, preferably from 0.001 to 0.5 kg of safener/ha are applied. In the case of seed dressing, generally from 0.001 to 10 g of safener/kg of seed, preferably from 0.05 to 2 g of safener/kg of seed, are applied. When the safener is applied in liquid form, with seed soaking, shortly before sowing, it is advantageous to use safener solutions which contain the active ingredient in a concentration of from 1 to 10 000 ppm, preferably from 100 to 1000 ppm.

The mixtures can advantageously be used in the above-mentioned formulations (in which case "active ingredient" relates to the respective mixture of compound of formula I with the mixing partner).

The following Examples illustrate the invention further but do not limit the invention.

PREPARATION EXAMPLES

Example 1

Preparation of 3-(4'-chloro-4-methylbiphen-3-yl)bicyclo[3.2.1]octane-2,4-dione

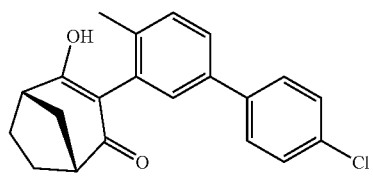 [SMILES: Cc1ccc(-c2ccc(Cl)cc2)cc1C1=C(O)[C@H]2CC[C@H](C2)C1=O]

Step 1: Preparation of 3-amino-4'-chloro-4-methylbiphenyl

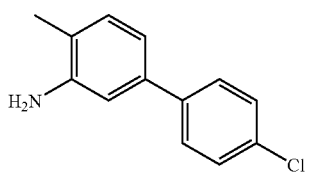

Tetrakis(triphenylphosphine)palladium (0) (3.7 g, 0.003 mol) and 4-chlorophenylboronic acid (20.2 g, 0.13 mol) are added to a solution of 5-bromo-2-methylaniline (20 g, 0.1 mol) in 1,2-dimethoxyethane (200 ml). After stirring the reaction mixture for 15 minutes at 20° C., a solution of 20% aqueous sodium carbonate (300 ml) is added to the mixture, and the resulting mixture is heated at reflux for 24 hours. The reaction mixture is cooled to room temperature, diluted with water (600 ml) and extracted using ethyl acetate. The combined organic extracts are dried over anhydrous sodium sulfate, filtered and the filtrate evaporated in vacuo. The residue is further purified by column chromatography on silica gel, eluting with 7% ethyl acetate in hexane to give 3-amino-4'-chloro-4-methylbiphenyl (21.0 g).

Step 2: Preparation of 3-bromo-4'-chloro-4-methylbiphenyl

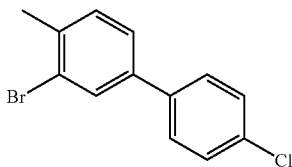

Hydrobromic acid (48% wt. in water, 120 ml) is added dropwise to a suspension of 3-amino-4'-chloro-4-methylbiphenyl (21 g, 0.09 mol) in water (80 ml), and the mixture stirred until the solid is dissolved. The mixture is cooled to −5° C. and a solution of sodium nitrite (10.12 g, 0.14 mol) in water (50 ml) is added dropwise, maintaining the temperature at 0-5° C. The reaction mixture is stirred for 1 hour, then added to a pre-cooled solution of cuprous bromide (17.9 g, 0.12 mol) in hydrobromic acid (48% wt. in water, 120 ml) at 0° C. The reaction mixture is stirred and allowed to warm to room temperature overnight. The mixture is extracted with ethyl acetate, and the organic extracts are combined, dried over anhydrous sodium sulfate, filtered and the filtrate concentrated in vacuo. The residue is further purified by column chromatography on silica gel, eluting with 2% ethyl acetate in hexane to give 3-bromo-4'-chloro-4-methylbiphenyl (15.0 g).

Step 3: Preparation of 4'-chloro-4-methylbiphen-3-ylboronic acid

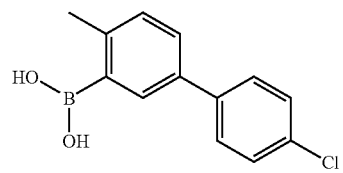 [SMILES: Cc1ccc(-c2ccc(Cl)cc2)cc1B(O)O]

3-Bromo-4'-chloro-4-methylbiphenyl (5.0 g, 0.02 mol) is dissolved in anhydrous tetrahydrofuran (125 ml), and the mixture is cooed to −78° C. n-Butyllithium (1.33 molar solution in hexanes, 17.3 ml) is added dropwise over 30 minutes, maintaining the temperature at approximately −78° C. The reaction mixture is stirred for one and a half hours at −78° C., then trimethylborate (2.58 g, 0.024 mol) is added dropwise and the reaction mixture stirred for three and a half hours, allowing it to warm to 0° C. A solution of 2N aqueous hydrochloric acid (50 ml) is then added dropwise, and once the addition is complete the mixture is stirred for 2 hours. The mixture is concentrated in vacuo to remove most of the tetrahydrofuran, then diluted with water (~80 ml) and extracted with diethyl ether. The organic extracts are combined, dried over anhydrous sodium sulfate, filtered and the filtrate evaporated in vacuo. The residue is further purified by flash column chromatography on silica gel, eluting with 7% ethyl acetate in hexane to give 4'-chloro-4-methylbiphen-3-ylboronic acid (2.5 g).

Step 4: Preparation of 3-(4'-chloro-4-methylbiphen-3-yl)bicyclo[3.2.1]octane-2,4-dione

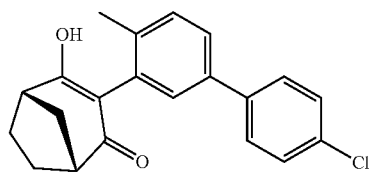 [SMILES: Cc1ccc(-c2ccc(Cl)cc2)cc1C1=C(O)[C@H]2CC[C@H](C2)C1=O]

Step 4a: (Diacetoxy)iodobenzene (1.17 g, 3.62 mmol) and sodium carbonate (0.384 g, 3.62 mmol) are suspended in water (10 ml) and the mixture is stirred at room temperature for 15 minutes. A solution of bicyclo[3.2.1]octane-2,4-dione (0.500 g, 3.62 mmol), prepared by the method of R. Beaudegnies et al., WO2005/123667, and sodium carbonate (0.384 g, 3.62 mmol) in water (10 ml) is added dropwise over 2 minutes, and once the addition is complete the reaction mixture is stirred for 2.5 hours at room temperature. The reaction mixture is poured into a separating funnel and extracted with chloroform (3×20 ml). The organic extracts are combined, dried over anhydrous magnesium sulfate, filtered and the filtrate is evaporated in vacuo to give the iodonium ylide (1.19 g) as a white solid.

Step 4b: A mixture of the iodonium ylide (0.600 g, 1.76 mmol) prepared in Step 4a, 5-(4-chlorophenyl)-2-methylphenylboronic acid (0.522 g, 2.12 mmol), palladium(II) acetate (0.020 g, 0.09 mmol), tetra-n-butylammonium bromide (0.283 g, 0.88 mmol) and lithium hydroxide monohydrate (0.222 g, 5.28 mmol) are stirred together in a mixture of 1,2-dimethoxyethane (12 ml) and water (3 ml) under an atmosphere of nitrogen. The reaction mixture is heated to 50° C., held at 50° C. for 2 hours then allowed to cool to room temperature. The reaction mixture is filtered through diatomaceous earth, washing with 2M aqueous hydrochloric acid (40 ml) and ethyl acetate (20 ml), then the filtrate is poured into a separating tunnel and the organic phase collected. The aqueous phase is extracted with ethyl acetate (2×20 ml) and the organic extracts are combined, dried over anhydrous magnesium sulfate, filtered and the filtrate evaporated in vacuo. The residue is partially purified by column chromatography on silica gel, eluting with a mixture of ethyl acetate and hexane (gradient elution, 100% hexane to 70% ethyl acetate/30% hexane) to give a partially purified sample of the desired product. Further purification is achieved by dissolving the product in ethyl acetate (20 ml) and extracting with 0.5M aqueous potassium carbonate (×2, 20 ml). The aqueous extracts are collected, acidified combined to pH 2 by addition of concentrated hydrochloric acid and the product is extracted into ethyl acetate (2×20 ml). The organic extracts are combined, dried over anhydrous magnesium sulfate, filtered and concentrated under reduced pressure to give 3-(4'-chloro-4-methylbiphen-3-yl)bicyclo[3.2.1]octane-2,4-dione.

Example 2

Preparation of 3-(4'-chloro-4-ethylbiphen-3-yl)bicyclo[3.2.1]octane-2,4-dione

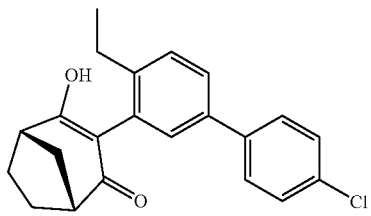 [SMILES: CCc1ccc(-c2ccc(Cl)cc2)cc1C1=C(O)[C@H]2CC[C@H](C2)C1=O]

Step 1: Preparation of 4-ethyl-3-nitroaniline

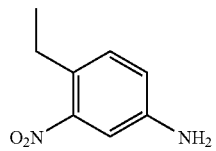

Ammonium nitrate (39.6 g, 0.49 mol) is added portionwise to a chilled (ice-bath) solution of 4-ethylaniline (20 g, 0.16 mol) in concentrated sulfuric acid (100 ml), maintaining the temperature at −10° to 0° C. by external cooling. The reaction mixture is stirred for two hours, then poured onto crushed ice, and the precipitate is collected by filtration. The solid is taken up in water, the solution made neutral by addition of dilute aqueous sodium hydroxide solution and extracted with ethyl acetate. The organic extracts are combined, dried over anhydrous sodium sulfate, filtered and the filtrate is evaporated in vacuo to give 4-ethyl-3-nitroaniline (20 g).

Step 2: Preparation of 4-bromo-1-ethyl-2-nitrobenzene

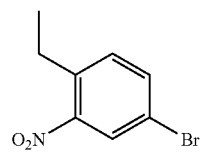

Hydrobromic acid (48% wt. in water, 240 ml) is added dropwise to a suspension of 4-ethyl-3-nitroaniline (20 g, 0.12 mol) in water (80 ml), and the mixture is stirred until the solid dissolves. The mixture is cooled to −5° C. and a solution of sodium nitrite (19.8 g, 0.28 mol) in water (100 ml) is added dropwise, maintaining the temperature at 0-5° C. Once the addition is complete, the cooling bath is removed and the reaction mixture is stirred for one hour at room temperature. The mixture is added dropwise to a pre-cooled solution of cuprous bromide (22.4 g, 0.16 mol) in hydrobromic acid (48% wt. in water) at 0° C. The reaction mixture is stirred and allowed to warm to room temperature over three hours. The mixture is extracted with diethyl ether, and the organic extracts are combined, dried over anhydrous sodium sulfate, filtered and the filtrate is concentrated in vacuo. The residue is further purified by column chromatography on silica gel, eluting with hexane to give 4-bromo-1-ethyl-2-nitrobenzene (18 g)

Step 3: Preparation of 4'-chloro-4-ethyl-3-nitrobiphenyl

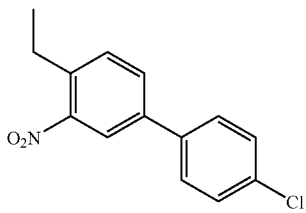 [SMILES: CCc1ccc(-c2ccc(Cl)cc2)cc1[N+](=O)[O-]]

To 4-bromo-1-ethyl-2-nitrobenzene (20.0 g, 0.087 mol) in 150 ml 1,2-dimethoxyethane is added, at room temperature, 4-chlorophenylboronic acid (14.98 g, 0.096 mol) and tetrakis(triphenylphosphine)palladium(0) (2.0 g, 0.00174 mol) and nitrogen gas is bubbled through the mixture. After stirring for 10 minutes at 20° C., a solution of sodium carbonate (73.8 g, 0.696 mol) in water (350 ml) is added and mixture is heated at reflux for 16 hours. The reaction mixture is cooled to room temperature, filtered through diatomaceous earth, washing with 200 ml of ethyl acetate. The mixture is poured into a separating funnel and the two phases are separated. The aqueous phase is extracted with ethyl acetate. The organic extracts are combined, dried over anhydrous magnesium sulfate, filtered and the filtrate is evaporated in vacuo to give 4'-chloro-4-ethyl-3-nitrobiphenyl (23.84 g) as a brown oil used without further purification in the next step.

Step 4: Preparation of 3-amino-4'-chloro-4-ethylbiphenyl

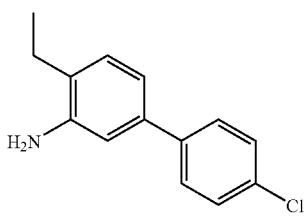

4'-Chloro-4-ethyl-3-nitrobiphenyl (22.6 g, 0.086 mol) is suspended in methanol (250 ml) and the reaction mixture is stirred at room temperature. Distilled water (100 ml) is added, followed by zinc dust (39.0 g, 0.60 mol) and ammonium chloride (13.8 g, 0.26 mol) and the mixture is heated to reflux for 1 hour. The reaction mixture is cooled to room temperature, filtered through diatomaceous earth and the filtrate is evaporated in vacuo to remove most of the methanol. The residue is partitioned between ethyl acetate (200 ml) and water and the aqueous phase is re-extracted with ethyl acetate (200 ml). The organic extracts are combined, washed with water and brine, dried over anhydrous magnesium sulfate, filtered and the filtrate is evaporated in vacuo to give 3-amino-4'-chloro-4-ethylbiphenyl (15.0 g) as a colourless solid. The product is used directly without further purification in Step 5.

Step 5: Preparation of 3-bromo-4'-chloro-4-ethylbiphenyl

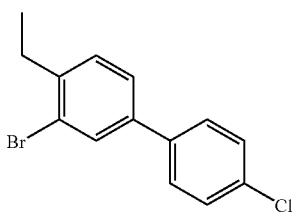 [SMILES: CCc1ccc(-c2ccc(Cl)cc2)cc1Br]

Step 5a: 3-Amino-4'-chloro-4-ethylbiphenyl (60.0 g, 0.26 mol) is added portionwise to a mixture of hydrobromic acid (48% wt. in water, 350 ml) and water (250 ml), and once the addition is complete the mixture is heated to 40° C. and stirred for 20 minutes, before being cooled to 5° C. in an ice bath. A solution of sodium nitrite (20.65 g, 0.30 mol) in water (100 ml) is added dropwise over 45 minutes, and once the addition is complete the mixture is stirred at 5° C. for a further 45 minutes.

Step 5b: Meanwhile, hydrobromic acid (48% wt. in water, 400 ml) is heated and stirred at 70° C. and copper sulfate pentahydrate (74.75 g, 0.30 mol) is added in one portion and the mixture is stirred at 70° C. for two minutes to give a dark purple solution, and then copper powder (26.44 g, 0.42 mol) is added in one portion, resulting in a pink suspension.

Step 5c: The mixture containing the diazonium salt (prepared in step 5a) is added portionwise over 70 minutes to the stirred mixture prepared in Step 5b at 70° C. (in between additions the mixture containing the diazonium salt is kept cold in an ice bath). Once the addition is complete the mixture is stirred at 70° C. for a further 30 minutes and then allowed to cool to room temperature, and extracted with ethyl acetate (3×500 ml). The organic extracts are combined, washed with water and brine, dried over anhydrous magnesium sulfate, filtered and the filtrate is evaporated in vacuo. Purification by column chromatography on silica gel affords 3-bromo-4'-chloro-4-ethylbiphenyl (52.1 g) as a yellow oil

Step 6: Preparation of 3-(4'-chloro-4-ethylbiphen-3-yl)bicyclo[3.2.1]octane-2,4-dione

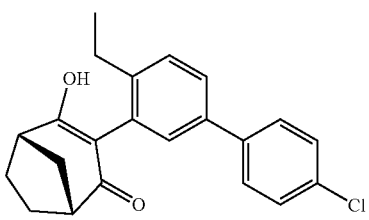

To a microwave vial containing bicyclo[3.2.1]octane-2,4-dione (0.112 g, 0.812 mmol), palladium (II) acetate (7.6 mg, 0.034 mmol), 2-dicyclohexylphosphino-2',4',6'-tri-iso-propyl-1,1'-biphenyl (24.2 mg, 0.051 mmol), and finely ground potassium phosphate (0.316 g, 1.49 mmol) is added degassed dimethoxyethane (2 ml), then 3-bromo-4'-chloro-4-ethylbiphenyl (0.200 g, 0.667 mmol). This reaction mixture is then heated at 160° C. under microwave irradiation for 60 minutes, then cooled to room temperature and washed with 2M hydrochloric acid (2 ml) and extracted with ethyl acetate (3×3 ml). The organic phase is dried over magnesium sulfate, filtered, and the filtrate concentrated in vacuo. The crude mixture is purified by flash column chromatography on silica gel (30%

Example 3

Preparation of 3-(4'-chloro-4-ethylbiphen-3-yl)bicyclo[3.2.1]oct-6-ene-2,4-dione

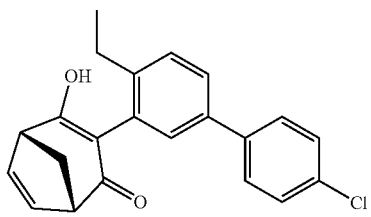 [SMILES: CCc1ccc(-c2ccc(Cl)cc2)cc1C1=C(O)[C@H]2C=C[C@H](C2)C1=O]

Step 1: Preparation of 4'-chloro-4-ethylbiphen-3-ylboronic acid

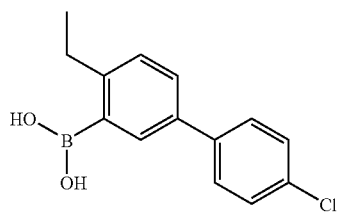 [SMILES: CCc1ccc(-c2ccc(Cl)cc2)cc1B(O)O]

3-Bromo-4'-chloro-4-ethylbiphenyl (10 g, 0.03 mol) is dissolved in tetrahydrofuran (250 ml), and the temperature is cooled to −78° C. n-Butyllithium (1.33 molar solution in hexanes, 34.6 ml) is added dropwise over 30 minutes, maintaining the temperature at around −78° C. The reaction mixture is stirred for one and a half hours, then trimethylborate (4.9 g, 0.05 mole) is added dropwise and the reaction mixture is stirred for two hours. A solution of 2N aqueous hydrochloric acid (100 ml) is added dropwise, and once the addition is complete the mixture is stirred for two hours. The mixture is concentrated to remove most of the tetrahydrofuran, then diluted with water and extracted with diethyl ether. The organic extracts are washed with water and brine, combined, dried over anhydrous sodium sulfate, filtered and the filtrate is evaporated in vacuo. The residue is further purified by flash column chromatography on silica gel, eluting with 7% ethyl acetate in hexane to give 4'-chloro-4-ethylbiphen-3-ylboronic acid (5.4 g).

Step 2: Preparation of 4'-chloro-4-ethylbiphen-3-yllead triacetate

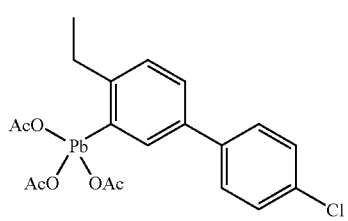

Step 2a: To a mixture of lead tetraacetate (2.15 g, 4.85 mmol) and mercuric diacetate (0.15 g, 0.47 mmol), thoroughly flushed with nitrogen, is added anhydrous chloroform (6 ml). This mixture is warmed to 40° C., and 4'-chloro-4-ethylbiphen-3-ylboronic acid (1.17 g, 4.50 mmol) is added in one portion and the suspension is heated at this temperature for 5 hours. The mixture is than cooled to room temperature, concentrated to a small volume and triturated with hexanes and filtered to yield crude 4'-chloro-4-ethylbiphen-3-yllead triacetate (2.70 g).

Step 2b: Crude 4'-chloro-4-ethylbiphen-3-yllead triacetate (1.50 g) is dissolved in anhydrous chloroform (20 ml), to which is added powdered anhydrous potassium carbonate (0.58 g, 4.16 mmol) followed by rapid stirring for 5 minutes. Solids are removed by filtration, and the organic solution is concentrated to afford pure 4'-chloro-4-ethylbiphen-3-yllead triacetate (1.176 g) as a bright orange solid.

Step 3: Preparation of 3-(4'-chloro-4-ethylbiphen-3-yl)bicyclo[3.2.1]oct-6-ene-2,4-dione

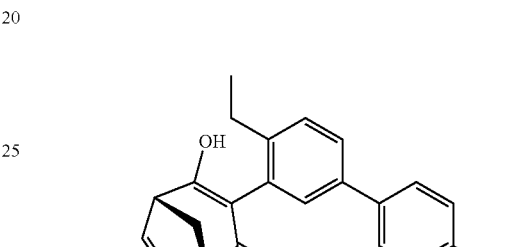

To a solution of 4'-chloro-4-ethylbiphen-3-yllead triacetate (0.478 g, 0.80 mmol) in chloroform (5 ml) is added bicyclo[3.2.1]oct-6-ene-2,4-dione (0.097 g, 0.72 mmol) (preparation described by R. Beaudegnies et al., WO2005/123667) and 4-dimethylaminopyridine (0.36 g, 2.86 mmol), and the reaction mixture is stirred at room temperature for 5 minutes. Next toluene (1 ml) is added, and the mixture is stirred at 80° C. for 2 hours (pre-heated oil bath). The reaction mixture is allowed to cool to room temperature, quenched with 2M hydrochloric acid and the inorganic precipitate removed by filtration. The organic phase is separated, and the aqueous phase is further washed with dichloromethane (×2), and again the phases are separated. All organics are combined then evaporated under reduced pressure to give a brown gum. This crude product is first purified by preparative reverse-phase HPLC, then also by flash column chromatography on silica gel (20% to 100% ethyl acetate/hexane eluant ratio) to afford 3-(4'-chloro-4-ethylbiphen-3-yl)bicyclo[3.2.1]oct-6-ene-2,4-dione.

Example 4

Preparation of 3-(4-methyl-3',4'-difluorobiphen-3-yl)bicyclo[3.2.1]octane-2,4-dione

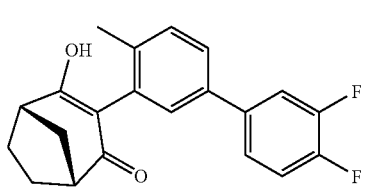 [SMILES: Cc1ccc(-c2ccc(F)c(F)c2)cc1C1=C(O)[C@H]2CC[C@H](C2)C1=O]

Step 1: Preparation of 5-chloro-2-methylphenyllead triacetate

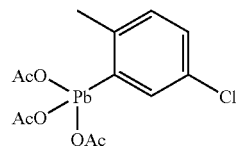

To a mixture of lead tetraacetate (2.15 g, 4.85 mmol) and mercuric diacetate (0.15 g, 0.47 mmol), thoroughly flushed with nitrogen, is added anhydrous chloroform (6 ml). This mixture is warmed to 40° C., and 5-chloro-2-methylphenylboronic acid (0.76 g, 4.46 mmol) is added in one portion, and the suspension is heated at this temperature for 5 hours. After cooling to room temperature the mixture is concentrated to a small volume then triturated with hexanes and filtered to yield crude 5-chloro-2-methylphenyllead triacetate (2.27 g).

Step 2: Preparation of 3-(5-chloro-2-methylphenyl)bicyclo[3.2.1]octane-2,4-dione

To a solution of 5-chloro-2-methylphenyllead triacetate (0.41 g, 0.80 mmol) in chloroform (4 ml) is added bicyclo[3.2.1]octane-2,4-dione (0.10 g, 0.72 mmol) and 4-dimethylaminopyridine (0.46 g, 3.62 mmol), and the reaction mixture is stirred at room temperature for 5 minutes. Next toluene (1 ml) is added, and the mixture is stirred at 80° C. for 1 hour (pre-heated oil bath). The reaction mixture is allowed to cool to room temperature, quenched with 1M hydrochloric acid, and the organic phase separated. The aqueous phase is further washed with dichloromethane (×2), and again the phases are separated. All organics are combined then evaporated under reduced pressure to give a crude oil. Purification by preparative reverse-phase HPLC furnishes 3-(5-chloro-2-methylphenyl)bicyclo[3.2.1]octane-2,4-dione (0.063 g, 33%) as a colourless gum.

Step 3: Preparation of 3-(3',4'-difluoro-4-methylbiphen-3-yl)bicyclo[3.2.1]octane-2,4-dione

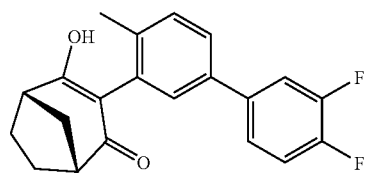 [SMILES: Cc1ccc(-c2ccc(F)c(F)c2)cc1C1=C(O)[C@H]2CC[C@H](C2)C1=O]

To a microwave vial is added 3-(5-chloro-2-methylphenyl)bicyclo[3.2.1]octane-2,4-dione (0.10 g, 0.38 mmol), 3,4-dichlorofluorophenylboronic acid (0.120 g, 0.76 mmol), palladium (II) acetate (1.7 mg, 0.008 mmol), sodium S-phos-3'-sulphonate (7.8 mg, 0.015 mmol), and potassium phosphate (0.404 g, 1.90 mmol). Degassed water (0.8 ml) is next added (washing down any solids from the slides of the vial), followed by purging with nitrogen then stirring at room temperature for 5 minutes. The mixture is then heated at 160° C. under microwave irradiation for 15 minutes, cooled to room temperature, and partitioned between 2M hydrochloric acid and dichloromethane. The organic layer is separated, concentrated in vacuo, then purified by preparative reserve phase HPLC to afford 3-(3',4'-difluoro-4-methylbiphen-3-yl)bicyclo[3.2.1]octane-2,4-dione.

Example 5

Preparation of 3-(2',4'-dichloro-4-ethylbiphen-3-yl)bicyclo[3.2.1]octane-2,4-dione

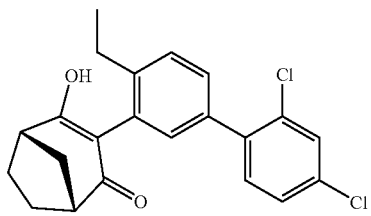 [SMILES: CCc1ccc(-c2ccc(Cl)cc2Cl)cc1C1=C(O)[C@H]2CC[C@H](C2)C1=O]

Step 1: Preparation of 5-bromo-2-ethylaniline

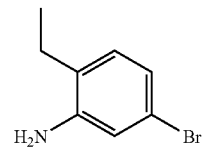

To a solution of 2-ethyl-5-bromo nitrobenzene (9.71 g, 230 mmol) in ethanol (125 ml) is added tin(II) chloride dihydrate (35.72 g, 225.71 mmol), followed by heating at 70° C. for 2 hours. After cooling to room temperature the solution is poured into crushed ice (1 liter) then diluted with ethyl acetate (200 ml). Solid sodium carbonate is cautiously added until pH 7 is achieved, at which stage the viscous mixture is filtered through diatomaceous earth (further washing with ethyl acetate/aqueous sodium carbonate) and the phases separated. After additional extraction of the aqueous phase, all organic phases are combined, dried over anhydrous magnesium sulfate then concentrated in vacuo. The crude oil is purified by flash column chromatography on silica gel (hexane/ethyl acetate 8:2 ratio) to afford 5-bromo-2-ethylaniline (7.89 g) as a brown oil.

Step 2: Preparation of 4-bromo-1-ethyl-2-iodobenzene

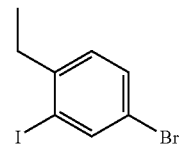

To a stirred mixture of 5-bromo-2-ethylaniline (3.39 g, 200 mmol) in distilled water (110 ml) is added concentrated sulfuric acid (5.60 ml), followed by brief heating at reflux until dissolution. The mixture is allowed to cool to room temperature, producing a fine precipitate, then further cooled to approximately 0° C. in an ice/salt bath. To this slurry is added an aqueous solution of sodium nitrite (1.17 g, 16.94 mmol) in distilled water (10 ml) dropwise over 15 minutes, maintaining a temperature below 5° C., followed by additional stirring for 30 minutes. The reaction mixture is next filtered then added to a second solution of aqueous potassium iodide (8.44 g, 50.83 mmol) in distilled water (45 ml) dropwise at room temperature. After the addition is complete the solution is briefly heated to 80° C. then allowed to cool to room temperature again. The reaction mixture is extracted with ethyl acetate (3×50 ml), and the organic phase is washed with 1M aqueous hydrochloric acid (30 ml) and aqueous sodium thiosulfate (2×30 ml). After drying over anhydrous magnesium sulfate and concentration in vacuo 4-bromo-1-ethyl-2-iodobenzene (4.90 g) is furnished as an orange liquid.

Step 3: Preparation of 5-bromo-2-ethylphenylboronic acid

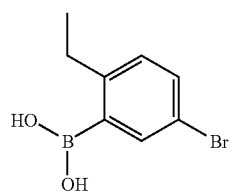

To a solution of 4-bromo-1-ethyl-2-iodobenzene (10.00 g, 32.20 mmol) in anhydrous tetrahydrofuran (60 ml) at −78° C. is added a solution of isopropylmagnesium chloride (16.90 ml, 33.80 mmol, 2M solution in tetrahydrofuran) dropwise, maintaining a temperature below −60° C. After stirring for 20 minutes the reaction mixture is allowed to slowly warm to room temperature followed by an additional hour of stirring. The solution is re-cooled to −78° C. and trimethylborate (7.18 ml, 64.32 mmol) is added dropwise, after which the mixture is again allowed to warm to room temperature with further stirring for 2 hours. Dilute aqueous hydrochloric acid (30 ml) is added, and the crude product is extracted into ethyl acetate (100 ml). The aqueous phase is washed with ethyl acetate (2×100 ml), and all organics are combined, dried over anhydrous magnesium sulfate then concentrated in vacuo to give a light brown solid which is triturated with hexanes to afford 5-bromo-2-ethylphenylboronic acid (6.46 g) as a cream powder.

Step 4: Preparation of 5-bromo-2-ethylphenyllead triacetate

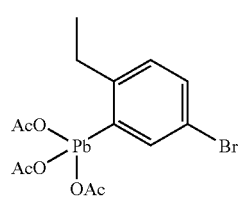

To a mixture of lead tetraacetate (13.7 g, 31.00 mmol) and mercuric diacetate (0.47 g, 1.50 mmol), thoroughly flushed with nitrogen, is added anhydrous chloroform (42 ml). This mixture is warmed to 40° C., and 5-bromo-2-ethylphenylboronic acid (6.50 g, 28.00 mmol) is added in one portion and the suspension is heated at this temperature for 5 hours. The mixture is then allowed to cool to room temperature, followed by further cooling to 0° C. then addition of powdered anhydrous potassium carbonate (3.22 g) with rapid stirring for 5 minutes then filtration. The filtrate is concentrated to half its volume, followed by the addition of hexanes to induce precipitation. This mixture is further concentrated, the solvent decanted, and the solid washed with hexanes to afford 5-bromo-2-ethylphenyllead triacetate (10.69 g) as a sandy coloured solid.

Step 5: Preparation of 3-(5-bromo-2-ethylphenyl)bicyclo[3.2.1]octane-2,4-dione

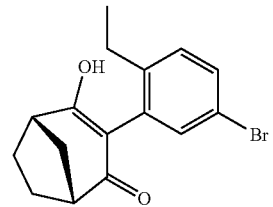 [SMILES: CCc1ccc(Br)cc1C1=C(O)[C@H]2CC[C@H](C2)C1=O]

To a solution of 5-bromo-2-ethylphenyllead triacetate (16.34 g, 28.80 mmol) in chloroform (160 ml) is added bicyclo[3.2.1]octane-2,4-dione (3.61 g, 26.10 mmol) and 4-dimethylaminopyridine (16.63 g, 131 mmol), and the reaction mixture is stirred at room temperature for 5 minutes. Next toluene (40 ml) is added, and the mixture is stirred at 80° C. for 1 hour (pre-heated oil bath). The reaction mixture is allowed to cool to room temperature, quenched with 1M hydrochloric acid, and the organic phase separated. The aqueous phase is further washed with dichloromethane (×2), and again the phases are separated. All organics are combined then evaporated under reduced pressure to give a crude oil, which is purified by flash column chromatography on silica gel (30% to 50% ethyl acetate/iso-hexane eluant ratio, then 10% methanol/dichloromethane eluant ratio). The resulting gum is then recrystalised from dichloromethane/hexane to afford 3-(5-bromo-2-ethylphenyl)bicyclo[3.2.1]octane-2,4-dione (4.62 g, 55%) as a cream coloured solid.

Step 6: Preparation of 3-(2',4'-dichloro-4-ethylbiphen-3-yl)bicyclo[3.2.1]octane-2,4-dione

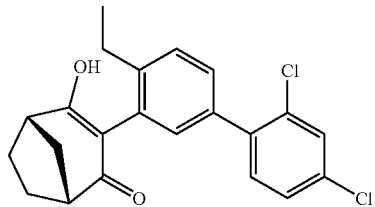 [SMILES: CCc1ccc(-c2ccc(Cl)cc2Cl)cc1C1=C(O)[C@H]2CC[C@H](C2)C1=O]

To a microwave vial is added 3-(5-bromo-2-ethylphenyl)bicyclo[3.2.1]octane-2,4-dione (0.200 g, 0.623 mmol), 2,4-dichlorophenyl boronic acid (0.167 g, 0.87 mmol), [1,1'-bis(diphenylphosphino)ferrocene]dichloropalladium(II) (0.040 g, 0.05 mmol) and cesium fluoride (0.284 g, 1.87 mmol). Degassed dimethoxyethane is next added (washing down any solids from the slides of the vial), followed by purging with nitrogen then stirring at room temperature for 5 minutes. The mixture is heated at 160° C. under microwave irradiation for 15 minutes, cooled to room temperature, then partitioned between 2M hydrochloric acid and dichloromethane. After separation of the organic layer the aqueous phase is again washed with dichloromethane, then all organic fractions are combined and concentrated in vacuo to afford a crude gum. This crude product is purified by flash column chromatography on silica gel (30% to 100% ethyl acetate/iso-hexane eluant ratio) to afford 3-(2',4'-dichloro-4-ethylbiphen-3-yl)bicyclo[3.2.1]octane-2,4-dione.

Example 6

Preparation of 3-(4'-chloro-4-ethyl-3'-methylbiphen-3-yl)bicyclo[3.2.1]octane-2,4-dione

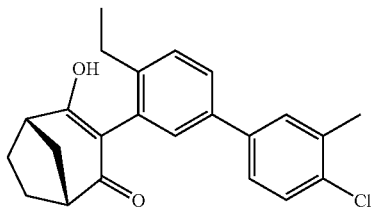 [SMILES: CCc1ccc(-c2ccc(Cl)c(C)c2)cc1C1=C(O)[C@H]2CC[C@H](C2)C1=O]

To a microwave vial is added palladium(II) acetate (3.7 mg, 0.016 mmol), tris(3-sulfophenyl)phosphine trisodium salt (23 mg, 0.041 mmol), 4-chloro-3-methylphenyl boronic acid (0.167 g, 0.97 mmol), 3-(5-bromo-2-ethyl-phenyl)-bicyclo[3.2.1]octane-2,4-dione (0.209 g, 0.65 mmol) and potassium phosphate (0.691 g, 3.26 mmol). A degassed mixed solution of acetonitrile/distilled water (1.6 ml, 1:1 ratio) is next added (washing-down any solids from the slides of the vial), followed by stirring for 5 minutes and flushing with nitrogen. This mixture is then heated at 160° C. under microwave irradiation for 15 minutes. After cooling to room temperature the reaction mixture is diluted with N,N-dimethylformamide (1 ml), then partitioned between 2M hydrochloric acid and dichloromethane. After the organic phase is separated the aqueous phase is again washed with dichloromethane, then all organic fractions are combined and concentrated in vacuo to afford a crude gum. This crude product is then purified by preparative reverse-phase HPLC to afford 3-(4'-chloro-4-ethyl-3'-methylbiphen-3-yl)bicyclo[3.2.1]octane-2,4-dione.

Example 7

Preparation of 3-[5-(5-chloropyridin-2-yl)-2-ethylphenyl]bicyclo[3.2.1]octane-2,4-dione

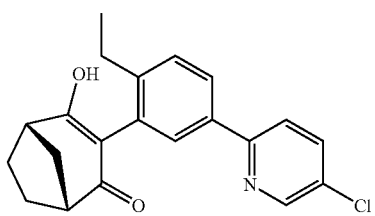 [SMILES: CCc1ccc(-c2ccc(Cl)cn2)cc1C1=C(O)[C@H]2CC[C@H](C2)C1=O]

Step 1: Preparation of 3-(2-ethyl-5-iodophenyl)bicyclo[3.2.1]octane-2,4-dione

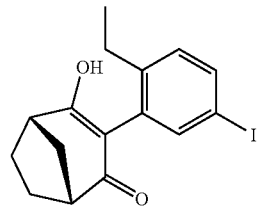 [SMILES: CCc1ccc(I)cc1C1=C(O)[C@H]2CC[C@H](C2)C1=O]

To a microwave vial is added 3-(5-bromo-2-ethylphenyl)bicyclo[3.2.1]octane-2,4-dione (1.00 g, 3.11 mmol), sodium iodide (0.93 g, 6.23 mmol), hexamethyldisilazane (0.45 g, 3.11 mmol), copper(I) iodide (0.03, 0.15 mmol), trans-N,N'-dimethylcyclohexane-1,2-diamine (0.044 g, 0.31 mmol) then degassed dioxane (5 ml). After purging with nitrogen the mixture is heated at 180° C. for 1 hour under microwave irradiation. The mixture is cooled to room temperature, quenched with 2M hydrochloric acid and extracted with dichloromethane (×2). Organic fractions are combined, washed with saturated aqueous sodium metabisulfite, dried over magnesium sulfate then filtered. The filtrate is concentrated in vacuo, then purified by flash column chromatography (20% to 100% ethyl acetate/hexane eluant ratio) to afford 3-(2-ethyl-5-iodophenyl)bicyclo[3.2.1]-octane-2,4-dione (1.14 g, 100%) as a white solid.

Step 2: Preparation of 3-(2,4-dioxobicyclo[3.2.1]oct-3-yl)-4-ethylphenylboronic acid

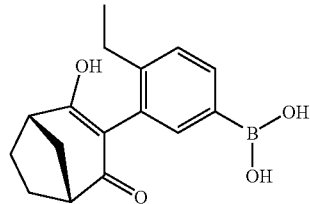 [SMILES: CCc1ccc(B(O)O)cc1C1=C(O)[C@H]2CC[C@H](C2)C1=O]

To a solution of 3-(2-ethyl-5-iodophenyl)bicyclo[3.2.1]octane-2,4-dione (0.65 g, 1.77 mmol) in anhydrous tetrahydrofuran (15 ml) at −10° C. is added iso-propyl magnesium chloride lithium chloride complex (10.6 ml, 10.6 mmol, 1M in tetrahydrofuran) dropwise over 10 minutes. The reaction mixture is stirred at this temperature for 1.5 hours, then cooled to −78° C., at which point trimethyl borate (1.39 ml, 12.4 mmol) is added dropwise to maintain a temperature below −60° C. After re-cooling to −78° C. the mixture is further stirred for 5 minutes, then additionally at room temperature for 1 hour. The solution is quenched with 2M hydrochloric acid and extracted with ethyl acetate (×3). All organic fractions are combined, dried over magnesium sulfate, filtered and the filtrate concentrated in vacuo to give an orange-coloured gum. This crude product is dissolved in a minimum amount of dichloromethane then precipitated with iso-hexane to afford 3-(2,4-dioxo-bicyclo[3.2.1]oct-3-yl)-4-ethylphenylboronic acid (0.46 g, 90%) as a cream-coloured solid.

Step 3: Preparation of 3-[5-(5-chloropyridin-2-yl)-2-ethylphenyl]bicyclo[3.2.1]octane-2,4-dione

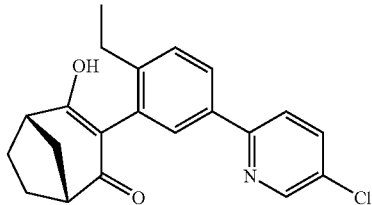 [SMILES: CCc1ccc(-c2ccc(Cl)cn2)cc1C1=C(O)[C@H]2CC[C@H](C2)C1=O]

To a microwave vial containing 3-(2,4-dioxobicyclo[3.2.1]oct-3-yl)-4-ethylphenylboronic acid (0.15 g, 0.52 mmol) and potassium phosphate (0.667 g, 3.15 mmol) is added 2-bromo-5-chloropyridine (0.121 g, 0.63 mmol), palladium acetate (4.0 mg, 0.016 mmol) and tris(3-sulfophenyl)phosphine trisodium salt (21 mg, 0.038 mmol). A degassed solvent mixture of water/acetonitrile (1.6 ml, 2:1 ratio) is then added, followed by flushing with nitrogen, then stirring at ambient temperature for 5 minutes before heating at 160° C. under microwave irradiation for 15 minutes. After cooling to room temperature the reaction is partitioned between 2M aqueous hydrochloric acid and dichloromethane, and the organic phase is separated. The aqueous phase is further extracted with dichloromethane and all organic fractions are combined then evaporated. The residue is purified by preparative reverse-phase HPLC to give 3-[5-(5-chloropyridin-2-yl)-2-ethylphenyl]bicyclo[3.2.1]octane-2,4-dione.

Example 8

Preparation of 3-[2-ethyl-5-(4-methylthiazol-2-yl)phenyl]bicyclo[3.2.1]octane-2,4-dione

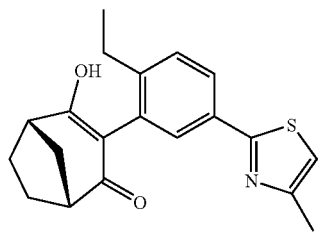 [SMILES: CCc1ccc(-c2nc(C)cs2)cc1C1=C(O)[C@H]2CC[C@H](C2)C1=O]

3-(5-Bromo-2-ethylphenyl)bicyclo[3.2.1]octane-2,4-dione (200 mg, 0.62 mmol), 4-methylthiazole (74 mg, 0.75 mmol), silver carbonate (860 mg, 3.1 mmol), triphenylphosphine (16.3 mg, 62.2 umol) and [1,1-bis(diphenylphosphino)ferrocene]palladium(II)chloride (26 mg, 31.1 umol) are added to a scintillation vial and shaken with a degassed solvent mixture of acetonitrile:water 1:1 (1.5 ml) at 65° C. for 22 hours. The mixture is concentrated under reduced pressure, taken up in DMSO (1.5 ml), filtered and purified by preparative reverse-phase HPLC to give 3-[2-ethyl-5-(4-methyl-thiazol-2-yl)phenyl]bicyclo[3.2.1]octane-2,4-dione.

Example 9

Preparation of 3-[2-ethyl-5-(1-oxypyridin-2-yl)phenyl]bicyclo[3.2.1]octane-2,4-dione

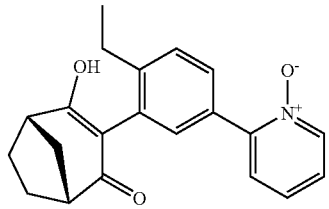 [SMILES: CCc1ccc(-c2cccc[n+]2[O-])cc1C1=C(O)[C@H]2CC[C@H](C2)C1=O]

3-(5-Bromo-2-ethylphenyl)bicyclo[3.2.1]octane-2,4-dione (100 mg, 0.31 mmol), pyridine-N-oxide (118 mg, 1.25 mmol), palladium (II) acetate (3.5 mg, 15.5 umol), potassium carbonate (86 mg, 0.62 mmol) and tri-tert-butylphosphonium tetrafluoroborate (13.5 mg, 46 umol) are added to a scintillation vial and shaken in degassed toluene at 110° C. for 22 hours. The mixture is concentrated under reduced pressure, taken up in DMSO (1.5 ml), filtered and purified by preparative reverse-phase HPLC to give 3-[2-ethyl-5-(1-oxypyridin-2-yl)phenyl]-bicyclo[3.2.1]octane-2,4-dione.

Example 10

Preparation of 3-[2-ethyl-5-(4-methylpyrazol-1-yl)-phenyl]bicyclo[3.2.1]octane-2,4-dione

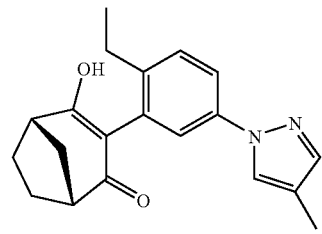 [SMILES: CCc1ccc(-n2cc(C)cn2)cc1C1=C(O)[C@H]2CC[C@H](C2)C1=O]

3-(5-Bromo-2-ethylphenyl)bicyclo[3.2.1]octane-2,4-dione (100 mg, 0.31 mmol), 4-methylpyrazole (38 mg, 0.46 mmol), potassium phosphate (264 mg, 1.24 mmol), L-proline (36 mg, 0.31 mmol) and copper (I) iodide (60 mg, 0.31 mmol) are combined in a microwave vial, suspended in DMSO and heated under microwave irradiation at 160° C. for 45 minutes. The mixture is filtered and purified by preparative reverse-phase HPLC to give 3-[2-ethyl-5-(4-methylpyrazol-1-yl)phenyl]bicyclo-[3.2.1]octane-2,4-dione.

Example 11

Preparation of 3-[5-(4-chloroimidazol-1-yl)-2-ethylphenyl]bicyclo[3.2.1]octane-2,4-dione and 3-[5-(5-chloroimidazol-1-yl)-2-ethylphenyl]bicyclo[3.2.1]octane-2,4-dione

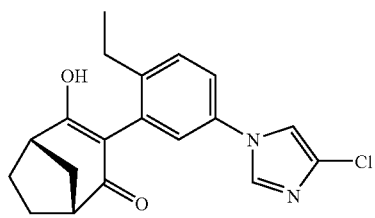

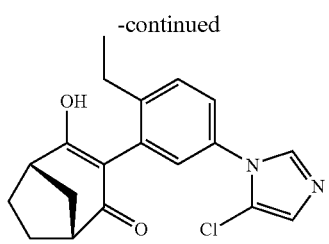

3-(5-Bromo-2-ethylphenyl)bicyclo[3.2.1]octane-2,4-dione (100 mg, 0.31 mmol), 4-chloroimidazole (47 mg, 0.46 mmol), potassium phosphate (264 mg, 1.24 mmol), L-proline (36 mg, 0.31 mmol) and copper (I) iodide (60 mg, 0.31 mmol) are combined in a microwave vial, suspended in DMSO and heated under microwave irradiation at 160° C. for 45 minutes. The mixture is filtered and purified by preparative reverse-phase HPLC to give a mixture of 3-[5-(4-chloroimidazol-1-yl)-2-ethylphenyl]bicyclo[3.2.1]octane-2,4-dione and 3-[5-(5-chloroimidazol-1-yl)-2-ethylphenyl]-bicyclo[3.2.1]octane-2,4-dione.

Example 12

Preparation of 3-(2'-fluoro-4,4'-dichlorobiphen-3-yl)bicyclo[3.2.1]octane-2,4-dione

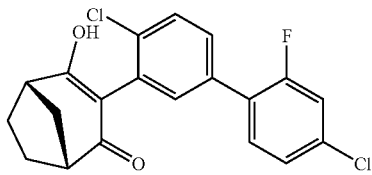

Step 1: Preparation of 4-bromo-1-chloro-2-iodobenzene

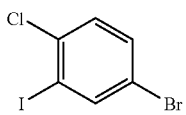

tert-Butyl nitrite (11.1 ml, 93.3 mmol) is added to a suspension of copper(II) chloride (10.04 g, 75 mmol) in acetonitrile (224 ml) and the mixture is heated with stirring to 60° C. A solution of 4-bromo-2-iodoaniline (18.54 g, 62 mmol) in acetonitrile (56 ml) is added dropwise over about an hour, and once the addition is complete the mixture is stirred at 60° C. for 2 hours. The mixture is cooled to room temperature, poured into 20% aqueous hydrochloric acid (1.3 liters) and extracted with diethyl ether (1.5 liters). The organic extract is separated and the aqueous re-extracted with ether (1 liter). The organic extracts are combined and dried over anhydrous magnesium sulfate, filtered and the filtrate evaporated in vacuo. The residue is further purified by column chromatography on silica gel to give 4-bromo-1-chloro-2-iodobenzene (8.62 g) as an oil.

Step 2: Preparation of 5-bromo-2-chlorophenylboronic acid

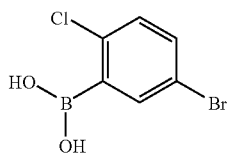

4-Bromo-1-chloro-2-iodobenzene (10.35 g, 33 mmol) is dissolved in anhydrous tetrahydrofuran (60 ml) and the solution is cooled to −75° C. under an atmosphere of argon. Isopropylmagnesium chloride (17.1 ml, 34 mmol, 2M solution in tetrahydrofuran) is added dropwise over 30 minutes, maintaining the internal temperature below −70° C. by external cooling. Once the addition is complete, the reaction mixture is stirred at approximately −70° C. for 30 minutes and then allowed to warm to room temperature and stirred for 1 hour. The reaction mixture is then cooled to −78° C. and trimethyl borate (7.3 ml, 65 mmol) is added dropwise. The mixture is stirred at −78° C. for 30 minutes and then the cooling bath is removed and the mixture is stirred at room temperature for 1.5 hours. 2M Aqueous hydrochloric acid (30 ml) is added, and the crude product is extracted with ethyl acetate. The organic phase is washed with water and brine, dried over anhydrous magnesium sulfate, filtered and the filtrate evaporated in vacuo. Trituration with hexane gives 5-bromo-2-chlorophenylboronic acid (6.16 g) as an off-white solid.

Step 3: Preparation of 5-bromo-2-chlorophenyllead triacetate

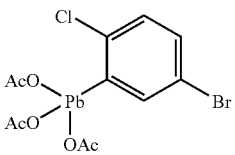

To a mixture of lead tetraacetate (26.83 g, 61 mmol) and mercuric diacetate (0.77 g, 2.4 mmol), thoroughly flushed with nitrogen, is added anhydrous chloroform (50 ml) and the reaction mixture is stirred and heated to 40° C. 5-Bromo-2-chlorophenylboronic acid (11.39 g, 48 mmol) is added in one portion, and the reaction mixture is stirred at 40° C. for 4 hours. After cooling to room temperature potassium carbonate (3.34 g) is added, the mixture stirred vigorously for 5 minutes and then filtered. The filtrate is concentrated in vacuo to give 5-bromo-2-chlorophenyllead triacetate (25.33 g), used without further purification in the next step.

Step 4: Preparation of 3-(5-bromo-2-chlorophenyl)bicyclo[3.2.1]octane-2,4-dione

To a mixture of bicyclo[3.2.1]octane-2,4-dione (6.82 g, 4.0 mmol) and 4-dimethylaminopyridine (24.5 g, 0.2 mol) is added anhydrous chloroform (300 ml) and the mixture is stirred. To this solution is added anhydrous toluene (75 ml), followed by 5-bromo-2-chlorophenyllead triacetate (25.33 g, 4.4 mmol) in one portion and the reaction mixture is heated at 80° C. overnight. The mixture is allowed to cool to room temperature, then diluted with dichloromethane (300 ml) and 2M aqueous hydrochloric acid (600 ml), and filtered through diatomaceous earth to remove inorganic residues. The filter cake is washed with dichloromethane, and all organic fractions are combined, washed with 2M aqueous hydrochloric acid, water and brine, dried over anhydrous magnesium sulfate then concentrated in vacuo. The residue is further purified by flash column chromatography on silica gel to afford 4-(5-bromo-2-chlorophenyl)bicyclo[3.2.1]octane-2,4-dione (1.02 g) of sufficient purity to be used in the next step.

Step 5: Preparation of 3-(2'-fluoro-4,4'-dichlorobiphen-3-yl)bicyclo[3.2.1]octane-2,4-dione

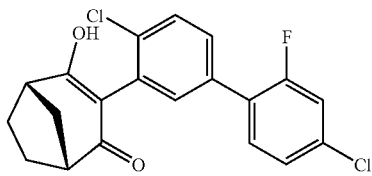

A mixture of 4-(5-bromo-2-chlorophenyl)bicyclo[3.2.1]octane-2,4-dione (0.15 g, 0.5 mmol), 2-fluoro-4-chlorophenylboronic acid (0.12 g, 0.7 mmol), and cesium fluoride (0.209 g, 1.4 mmol) are stirred together in 1,2-dimethoxyethane (2 ml) under an atmosphere of nitrogen at room temperature for 30 minutes. [1,1'-bis(diphenyl-phosphino)ferrocene]dichloropalladium(II) (60 mg, 0.7 mmol) is added and the reaction mixture is heated at 80° C. overnight. The reaction mixture is filtered through diatomaceous earth, washing the filter cake with dichloromethane (10 ml) and water (5 ml). The mixture is acidified to pH1 by addition of 2M aqueous hydrochloric acid, and the organic phase is separated. The aqueous phase is extracted with dichloromethane, and all organic extracts are combined, dried over anhydrous magnesium sulfate, filtered through a short plug of silica, and the filtrate is evaporated. The residue is dissolved in N,N-dimethylformamide (approximately 1 ml) and purified by preparative reverse-phase HPLC to give 3-(2'-fluoro-4,4'-dichlorobiphen-3-yl)bicyclo[3.2.1]octane-2,4-dione.

Example 13

Preparation of 3-(4'-chloro-4-ethylbiphen-3-yl)bicyclo[3.2.2]nonane-2,4-dione

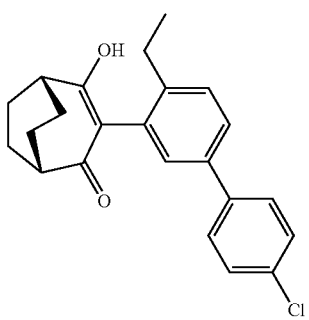 [SMILES: CCc1ccc(-c2ccc(Cl)cc2)cc1C1=C(O)[C@H]2CC[C@H](CC2)C1=O]

Step 1: Preparation of 3-(5-bromo-2-ethylphenyl)bicyclo[3.2.2]nonane-2,4-dione

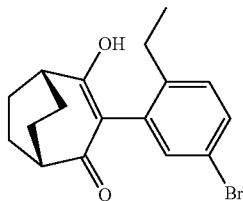 [SMILES: CCc1ccc(Br)cc1C1=C(O)[C@H]2CC[C@H](CC2)C1=O]

A solution of bicyclo[3.2.2]nonane-2,4-dione (0.12 g, 0.79 mmol), prepared by the method of W. Childers et al., US2006/0004108, in dry chloroform (4 ml) is stirred at room temperature then thoroughly flushed with nitrogen. To this mixture is then added 4-dimethylaminopyridine (0.482 g, 3.95 mmol) and anhydrous toluene (1 ml), followed by heating to 80° C. 5-Bromo-2-ethylphenyllead triacetate (0.673 g, 1.18 mmol) is added in one portion, and the mixture is further heated at this temperature for a further 4 hours then left to stand overnight. Dichloromethane (10 ml) and 2M hydrochloric acid (10 ml) are added, and the resulting biphasic mixture is filtered to remove any inorganic salts (washing with additional dichloromethane, 10 ml). The organic phase separated, and the aqueous phase is extracted again with dichloromethane (10 ml×2). All organic fractions are combined, dried over magnesium sulfate, filtered and the filtrate concentrated under reduced pressure to give a yellow gum. This crude product is purified by flash column chromatography on silica gel (100% to 40% hexane/ethyl acetate eluant ratio) to afford 3-(5-bromo-2-ethylphenyl)-bicyclo[3.2.2]nonane-2,4-dione (0.130 g, 49%) as a yellow solid.

Step 2: Preparation of 3-(4'-chloro-4-ethylbiphen-3-yl)bicyclo[3.2.2]nonane-2,4-dione

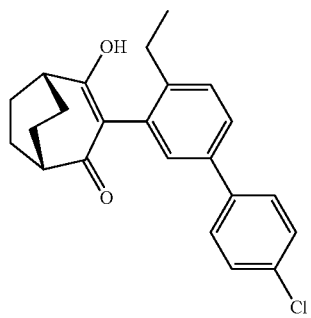 [SMILES: CCc1ccc(-c2ccc(Cl)cc2)cc1C1=C(O)[C@H]2CC[C@H](CC2)C1=O]

A solution of 3-(5-bromo-2-ethylphenyl)bicyclo[3.2.2]nonane-2,4-dione (0.13 g, 0.39 mmol) and 4-chlorophenylboronic acid (0.087 g, 0.55 mmol) in anhydrous dimethoxyethane (5 ml) is stirred at room temperature under an atmosphere of nitrogen. The reaction mixture is then evacuated and flushed with nitrogen (degassing cycle repeated 4 times). Cesium fluoride (0.178 g, 1.17 mmol) is added, and the suspension is stirred at room temperature for 45 minutes. Next [1,1'-bis(diphenylphosphino)ferrocene]dichloropalladium(II) (0.048 g, 0.06 mmol) is added in one portion, and the reaction mixture is heated at 80° C. for 23 hours. After cooling to room temperature the suspension is filtered through diatomaceous earth, then washed with 2M hydrochloric acid (20 ml) and dichloromethane (20 ml). The organic phase is separated, and the aqueous phase is extracted with dichloromethane (10 ml×2). All organics are combined, dried over magnesium sulfate, filtered and the filtrate concentrated under reduced pressure to give a brown gum. The crude product is purified by flash column chromatography on silica gel (100% to 40% hexane/ethyl acetate eluant ratio), then further purified by preparative reverse-phase HPLC to afford to afford 3-(4'-chloro-4-ethylbiphen-3-yl)bicyclo[3.2.2]nonane-2,4-dione.

Example 14

Preparation of 3-(4'-chloro-4-ethyl-2'-fluorobiphen-3-yl)bicyclo[3.2.2]non-6-ene-2,4-dione

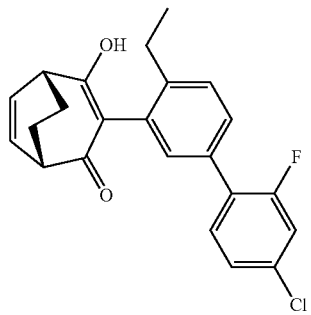 [SMILES: CCc1ccc(-c2ccc(Cl)cc2F)cc1C1=C(O)[C@H]2C=C[C@H](CC2)C1=O]

Step 1: Preparation of 3-(5-bromo-2-ethylphenyl)bicyclo[3.2.2]non-6-ene-2,4-dione

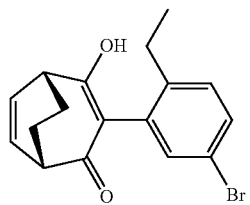 [SMILES: CCc1ccc(Br)cc1C1=C(O)[C@H]2C=C[C@H](CC2)C1=O]

A solution of bicyclo[3.2.2]non-6-ene-2,4-dione (0.835 g, 5.58 mmol), prepared by the method of R. Beaudegnies et al., WO2005/123667, in dry chloroform (30 ml) is stirred at room temperature then thoroughly flushed with nitrogen. To this mixture is added 4-dimethylaminopyridine (3.41 g, 28 mmol) and anhydrous toluene (5 ml), followed by heating to 80° C. 5-Bromo-2-ethylphenyllead triacetate (4.75 g, 8.36 mmol) is added portionwise over 20 minutes, and the mixture is further heated at this temperature for a further 4 hours then left to stand overnight. 2M hydrochloric acid (40 ml) is added, and the suspension is vigorously stirred for 30 minutes then filtered through diatomaceous earth (washing with additional dichloromethane, 40 ml). The organic phase is separated, and the aqueous phase is extracted with dichloromethane (40 ml×2). All organic fractions are combined, dried over magnesium sulfate, filtered and the filtrate concentrated under reduced pressure to give a brown oil. The crude product is purified by flash column chromatography on silica gel (100% to 40% hexane/ethyl acetate eluant ratio) to afford 3-(5-bromo-2-ethylphenyl)bicyclo[3.2.2]non-6-ene-2,4-dione (0.400 g, 22%) as a yellow gum.

Step 2: Preparation of 3-(4'-chloro-4-ethyl-2'-fluoro-biphen-3-yl)bicyclo[3.2.2]non-6-ene-2,4-dione

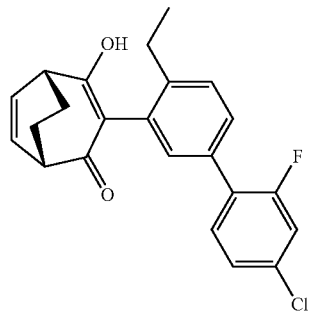 [SMILES: CCc1ccc(-c2ccc(Cl)cc2F)cc1C1=C(O)[C@H]2C=C[C@H](CC2)C1=O]

A solution of 3-(5-bromo-2-ethylphenyl)bicyclo[3.2.2]non-6-ene-2,4-dione (0.180 g, 0.54 mmol) and 4-chloro-2-fluorophenylboronic acid (0.133 g, 0.76 mmol) in anhydrous dimethoxyethane (5 ml) is stirred at room temperature under an atmosphere of nitrogen. The reaction mixture is then evacuated and flushed with nitrogen (degassing cycle repeated 4 times). Cesium fluoride (0.246 g, 1.62 mmol) is added, and the suspension is stirred at room temperature for 45 minutes. Next [1,1'-bis(diphenylphosphino)ferrocene]dichloro-palladium(II) (0.066 g, 0.081 mmol) is added in one portion, and the reaction mixture is heated at 80° C. for 21.5 hours. After cooling to room temperature the suspension is filtered through diatomaceous earth, then washed with 2M hydrochloric acid (20 ml) and dichloromethane (20 ml). The organic phase is separated, and the aqueous phase is extracted with dichloromethane (10 ml×2). All organics are combined, dried over magnesium sulfate, filtered and the filtrate concentrated under reduced pressure to give a brown gum. The crude product is purified by flash column chromatography on silica gel (100% to 0% hexane/ethyl acetate eluant ratio), then further purified by preparative reverse-phase HPLC to afford 3-(4'-chloro-4-ethyl-2'-fluorobiphen-3-yl)bicyclo[3.2.2]non-6-ene-2,4-dione.

Example 15

Preparation of 3-(4'-chloro-4-ethylbiphen-3-yl)-1-methoxybicyclo[3.2.2]non-6-ene-2,4-dione

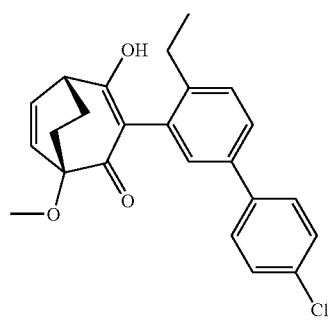 [SMILES: CCc1ccc(-c2ccc(Cl)cc2)cc1C1=C(O)[C@H]2C=C[C@](OC)(CC2)C1=O]

Step 1: Preparation of 3-chloro-1-methoxybicyclo[3.2.2]non-6-en-2,4-dione

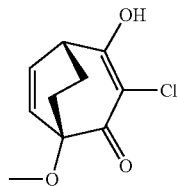

Step 1a: A solution of 1-methoxy-1,3-cyclohexadiene (5.2 g, 0.047 mol) in toluene (20 ml) is added dropwise to a solution of tetrachlorocyclopropene (4.21 g, 0.0236 mol) in 20 ml toluene at 70° C., and once the addition is complete the mixture is heated at 80° C. for 4 hours. The mixture is cooled to room temperature and the solvent is evaporated under reduced pressure. The residue (11.4 g) is used without further purification in the next step.

Step 1b: The residue produced in Step 1b is dissolved in 1,4-dioxane (50 ml), and water (50 ml) and lithium hydroxide monohydrate (5.0 g, 0.12 mol) are added. The mixture is stirred at 80° C. for 18 hours, then cooled to room temperature, diluted with water (200 ml) and extracted with ethyl acetate (3×100 ml). The organic extracts are discarded. The aqueous phase is acidified to pH 2 by addition of concentrated hydrochloric acid, and extracted with ethyl acetate (3×100 ml). The organic extracts are combined, dried over anhydrous magnesium sulfate, filtered and the filtrate is evaporated under reduced pressure. The residue is partially purified by column chromatography on silica gel, to give an impure sample of 3-chloro-1-methoxybicyclo[3.2.2]non-6-en-2,4-dione used without further purification in the next step.

Step 2: Preparation of 1-methoxybicyclo[3.2.2]non-6-en-2,4-dione

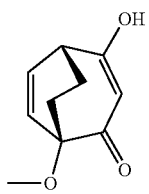

Zinc dust (1.53 g, 0.0233 mol) is added in one portion to a solution of 3-chloro-1-methoxybicyclo[3.2.2]non-6-en-2,4-dione, prepared in Step 1b, in glacial acetic acid (20 ml) and the mixture is heated to 95° C. for 1¾ hours. The mixture is cooled to room temperature, filtered through diatomaceous earth and the filtrate is concentrated under reduced pressure. The residue is partitioned between ethyl acetate and water, and the aqueous phase is extracted with ethyl acetate. The organic extracts are combined, dried over anhydrous magnesium sulfate, filtered and the filtrate is evaporated under reduced pressure. Purification by column chromatography on silica gel, and further purification by preparative reverse-phase HPLC, gives 1-methoxybicyclo[3.2.2]non-6-en-2,4-dione.

Step 3: Preparation of 3-(4'-chloro-4-ethylbiphen-3-yl)-1-methoxybicyclo[3.2.2]non-6-ene-2,4-dione

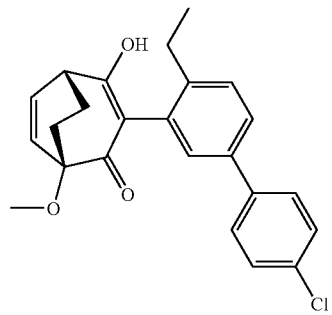 [SMILES: CCc1ccc(-c2ccc(Cl)cc2)cc1C1=C(O)[C@H]2C=C[C@](OC)(CC2)C1=O]

1-methoxybicyclo[3.2.2]non-6-en-2,4-dione (0.080 g, 0.044 mmol) stirred in dry chloroform (4 ml) under a nitrogen atmosphere. 4-Dimethylaminopyridine (0.268 g, 2.2 mmol) is added, followed by dry toluene (1 ml) and the mixture is heated to 80° C. To this reaction mixture is then added 4'-chloro-4-methylbiphen-3-yl-lead triacetate (0.400 g, 0.67 mmol) portionwise, over 4 minutes, and the mixture is held at 80° C. for 3¼ hour. The reaction mixture is cooled to room temperature, acidified with dilute aqueous hydrochloric acid (10 ml), stirred vigorously for 10 minutes, then filtered through diatomaceous earth and the filter cake is washed with dichloromethane (10 ml). The filtrate is poured into a separating funnel, the organic layer collected and the aqueous phase is extracted with dichloromethane (2×10 ml). The organic fractions are combined, dried over anhydrous magnesium sulfate, filtered and the filtrate is concentrated under vacuum. The residue is taken up in N,N-dimethylformamide (approximately 2 ml) and purified by preparative reverse-phase HPLC to give 3-(4'-chloro-4-ethylbiphen-3-yl)-1-methoxybicyclo[3.2.2]non-6-ene-2,4-dione.

Example 16

Preparation of 3-(3,5-dimethylbiphen-4-yl)bicyclo[3.2.1]-2,4-dione

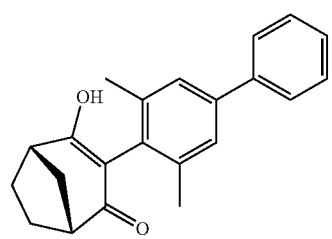 [SMILES: Cc1cc(-c2ccccc2)cc(C)c1C1=C(O)[C@H]2CC[C@H](C2)C1=O]

Step 1: Preparation of 3,5-dimethylbiphen-4-ylboronic acid

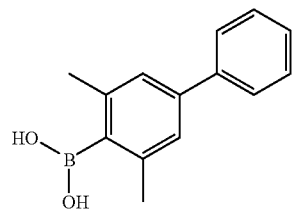 [SMILES: Cc1cc(-c2ccccc2)cc(C)c1B(O)O]

tert-Butyllithium (1.7 M solution in hexanes, 36.2 ml, 62.6 mmol) is added dropwise to a solution of 4-bromo-3,5-dimethylbiphenyl (7.27 g; 28 mmol) in dry tetrahydrofuran (150 ml) at −78° C. and stirred under an atmosphere of nitrogen for 30 minutes. Trimethylborate (9.54 ml; 84 mmol) is added and the resulting mixture is stirred at −78° C. for 30 min and then allowed to warm to room temperature. The reaction mixture is acidified with aqueous hydrochloric acid and extracted with ether (2×150 ml). The organic layers are combined, dried over anhydrous magnesium sulfate, filtered and the filtrate evaporated in vacuo to give a yellow solid. The crude product is triturated with iso-hexane and filtered to give 3,5-dimethyl-biphen-4-ylboronic acid (5.89 g) as a white powder.

Step 2: Preparation of 3,5-dimethylbiphen-4-yllead triacetate

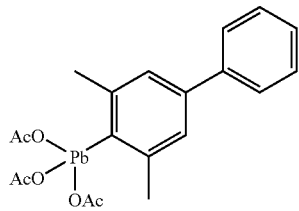

To a solution of lead tetraacetate (4.3 g, 9.7 mmol) in dry chloroform (15 ml) at 40° C. is added 3,5-dimethylbiphen-4-ylboronic acid (2.0 g; 8.8 mmol) in one portion under an atmosphere of nitrogen. The mixture is stirred at 40° C. for 4 hours, and then is cooled to room temperature. The precipitate is removed by filtration, and the filtrate is then passed through a plug of potassium carbonate supported on diatomaceous earth to remove acetic acid. The filtrate is evaporated in vacuo to afford 3,5-dimethylbiphen-4-yllead triacetate (3.37 g) as a brown oil.

Step 3: Preparation of 3-(3,5-dimethylbiphen-4-yl) bicyclo[3.2.1]-2,4-dione

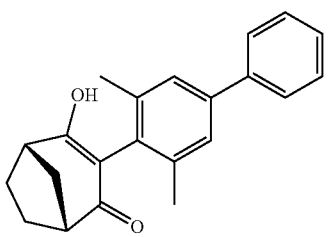 [SMILES: Cc1cc(-c2ccccc2)cc(C)c1C1=C(O)[C@H]2CC[C@H](C2)C1=O]

To a mixture of bicyclo[3.2.1]octane-2,4-dione (0.553 g, 4 mmol) in dry chloroform (12 ml) is added 4-dimethylaminopyridine (2.44 g, 20 mmol), and the mixture is stirred at room temperature until all the solid is dissolved. To this solution is then added dry toluene (8 ml), and 3,5-dimethyl-biphen-4-yllead triacetate (0.5 M solution in dry chloroform, 10 ml, 5 mmol), and the mixture is heated under reflux for 1 hour. The reaction mixture is cooled to room temperature, acidified to pH=1 with 2N aqueous hydrochloric acid, filtered and the filtrate is extracted with dichloromethane. The organic extracts are combined, dried over anhydrous magnesium sulfate, filtered and the filtrate evaporated in vacuo. The residue is further purified by column chromatography on silica gel to give 3-(3,5-dimethylbiphen-4-yl)bicyclo[3.2.1]octane-2,4-dione as a white powder.

Example 17

Preparation of 3-(4'-chloro-3,5-diethylbiphen-4-yl) bicyclo[3.2.1]octane-2,4-dione

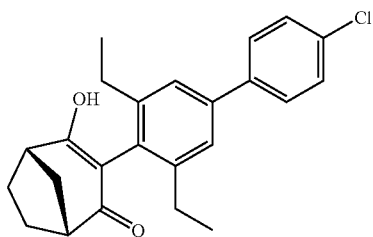 [SMILES: CCc1cc(-c2ccc(Cl)cc2)cc(CC)c1C1=C(O)[C@H]2CC[C@H](C2)C1=O]

Step 1: Preparation of (4-bromo-2,6-diethylphenyl)carbamic acid tert-butyl ester

Di-tert-butyl dicarbonate (106.13 g, 0.486 mol) is added to a solution of 2,6-diethyl-4-bromoaniline (74 g, 0.324 mol) in ethanol (500 ml) and the reaction mixture is stirred at room temperature for 50 hours. The solvent is evaporated under reduced pressure, the residue dissolved in ethyl acetate and washed with saturated aqueous sodium carbonate solution. The organic phase is dried over anhydrous sodium sulfate, filtered and the filtrate is concentrated under reduced pressure to give (4-bromo-2,6-diethylphenyl)carbamic acid tert-butyl ester (68 g).

Step 2: Preparation of (4'-chloro-3,5-diethylbiphen-4-yl)carbamic acid tert-butyl ester

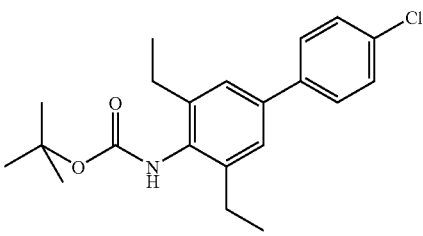 [SMILES: CCc1cc(-c2ccc(Cl)cc2)cc(CC)c1NC(=O)OC(C)(C)C]

A solution of cesium carbonate (89.12 g, 0.27 mol) in water (600 ml) is added to a degassed solution of (4-bromo-2,6-diethylphenyl)carbamic acid tert-butyl ester (30 g, 0.091 mol) and 4-chlorophenylboronic acid (21.54 g, 0.138 mol) in acetone (3 L), and the mixture is stirred at room temperature under an atmosphere of nitrogen. Palladium acetate (1.02 g, 0.004 mol) and 2-(dicyclohexylphosphino)-2',4',6'-tri-isopropyl-1,1'-biphenyl (4.33 g, 0.009 mol) are added and the reaction mixture is stirred at room temperature for 12 hours. The mixture is filtered through diatomaceous earth, and the filtrate is evaporated under reduced pressure to remove most of the acetone. The remaining solution is extracted with ethyl acetate (3×300 ml). The organic extracts are combined and concentrated under reduced pressure to give (4'-chloro-3,5-diethylbiphen-4-yl)carbamic acid tert-butyl ester (22 g).

Step 3: Preparation of
4'-chloro-3,5-diethylbiphen-4-ylamine

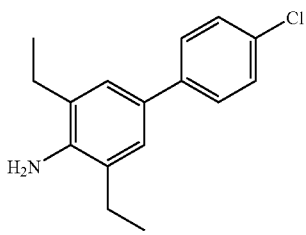 [SMILES: CCc1cc(-c2ccc(Cl)cc2)cc(CC)c1N]

Concentrated hydrochloric acid (22 ml) is added to a solution of (4'-chloro-3,5-diethylbiphen-4-yl)carbamic acid tert-butyl ester (22 g, 0.06 mol) in methanol (110 ml), and the reaction mixture is heated to 60° C. for 2 hours. The mixture is cooled to room temperature and most of the methanol is removed by evaporation under reduced pressure. The mixture is diluted with water, made basic by addition of 2N aqueous potassium hydroxide solution and extracted with ethyl acetate (3×200 ml). The organic extracts are combined and the solvents are removed under reduced pressure to give 4'-chloro-3,5-diethylbiphen-4-ylamine (9.6 g).

Step 4: Preparation of
4-bromo-4'-chloro-3,5-diethylbiphenyl

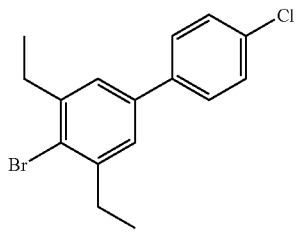 [SMILES: CCc1cc(-c2ccc(Cl)cc2)cc(CC)c1Br]

4'-Chloro-3,5-diethylbiphen-4-ylamine (9.6 g, 0.036 mol) is added to acetonitrile (95 ml) and stirred at room temperature until dissolution is complete. The reaction mixture is cooled to between −5° C. and 0° C., tert-butyl nitrite (5.7 ml, 0.044 mol) is added dropwise and the reaction mixture is maintained at between −5° C. and 0° C. for 30-40 minutes. The mixture is added slowly to a preheated (50° C.) suspension of copper (I) bromide (2.87 g, 0.02 mol) in hydrobromic acid (2.8 ml) and stirred at 50° C. for 10-15 minutes. The reaction mixture is cooled to room temperature, then poured into ice-cold water and extracted with ethyl acetate (3×250 ml). The organic extracts are washed with water, dried over anhydrous sodium sulfate and concentrated under reduced pressure. The residue is purified by column chromatography on silica gel to yield 4-bromo-4'-chloro-3,5-diethylbiphenyl (4.5 g).

Step 5: Preparation of
4'-chloro-3,5-diethylbiphen-4-ylboronic acid

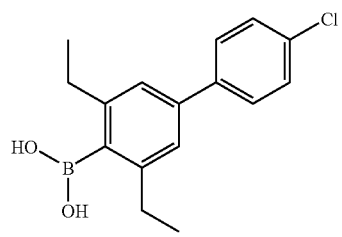 [SMILES: CCc1cc(-c2ccc(Cl)cc2)cc(CC)c1B(O)O]

tert-Butyllithium (1.6 M solution in hexane, 13 ml, 0.02 mol) is added dropwise to a solution of 4-bromo-4'-chloro-3,5-diethylbiphenyl (4.5 g, 0.0139 mol) in dry tetrahydrofuran (50 ml) at −78° C. under an atmosphere of nitrogen. The reaction mixture is stirred at −78° C. for 30 minutes, then trimethylborate (9.3 ml, 0.083 mol) is added. The resulting mixture is stirred at −78° C. for 1 hour and then allowed to warm to room temperature over 3 hours. The reaction mixture is acidified with 0.1 N aqueous hydrochloric acid solution and the mixture is stirred at room temperature overnight. The mixture is extracted with ethyl acetate (3×100 ml). The organic layers are combined, dried over anhydrous sodium sulfate, filtered and the filtrate is evaporated. The residue is purified by column chromatography on silica gel to give 4'-chloro-3,5-diethylbiphen-4-ylboronic acid as a white powder (1.8 g).

Step 6: Preparation of
4'-chloro-3,5-diethylbiphen-4-yllead triacetate

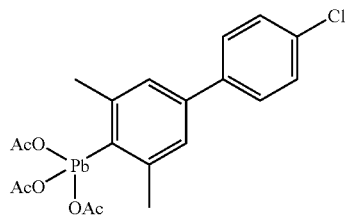

4'-Chloro-3,5-diethylbiphen-4-ylboronic (2.1 g, 0.007 mol) is added to a mixture of lead tetraacetate (3.67 g, 0.008 mol) and mercuric acetate (0.12 g, 5 mol %) in chloroform (15 ml) and the reaction mixture is stirred for 15 minutes at room temperate under an atmosphere of nitrogen, then stirred and heated at 40° C. for 4 hours. The reaction mixture is cooled to ambient temperature, filtered through a plug of diatomaceous earth and concentrated under reduced pressure to give an orange solid. Trituration with hexane (20 ml) affords a yellow solid which is dried under high vacuum. The solid is dissolved in chloroform (50 ml) and anhydrous potassium carbonate (11.6 g, 0.084 mol) is added. The suspension is stirred rapidly for 10 minutes, then filtered through plug of diatomaceous earth. The filtrate is concentrated under reduced pressure to give 4'-chloro-3,5-diethylbiphen-4-yllead triacetate (2.0 g) as a cream solid.

Step 7: Preparation of 3-(4'-chloro-3,5-diethylbiphen-4-yl)bicyclo[3.2.1]-2,4-dione

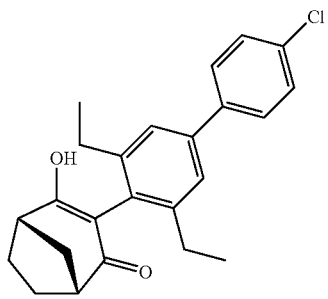 [SMILES: CCc1cc(-c2ccc(Cl)cc2)cc(CC)c1C1=C(O)[C@H]2CC[C@H](C2)C1=O]

Bicyclo[3.2.1]-2,4-dione (0.20 g, 1.44 mmol) and 4-dimethylaminopyridine (0.88 g, 7.21 mmol) are added to a mixture of chloroform (4 ml) and toluene (1 ml). The reaction mixture was flushed with nitrogen for 15 minutes at ambient temperature. 4'-Chloro-3,5-diethylbiphen-4-yllead triacetate (0.98 g, 1.58 mmol) is added in one portion and the reaction mixture is stirred and heated to 80° C. under an atmosphere of nitrogen for 1 hour. The reaction mixture is cooled to room temperature, acidified to pH 1 with 2N aqueous hydrochloric acid, filtered through a plug of diatomaceous earth and the two phases separated. The aqueous phase is extracted with dichloromethane (2×5 ml), the organic phases are combined, washed with water, and dried over anhydrous sodium sulfate. The mixture is filtered, and the filtrate is evaporated under reduced pressure. The residue is purified by column chromatography on silica gel to give 3-(4'-chloro-3,5-diethylbiphen-4-yl)bicyclo[3.2.1]-2,4-dione.

Example 18

Preparation of 3-(4'-chloro-3-ethylbiphen-4-yl)bicyclo[3.2.1]octane-2,4-dione

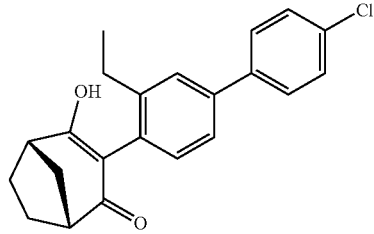

Step 1: Preparation of N-(4-bromo-2-ethylphenyl)acetamide

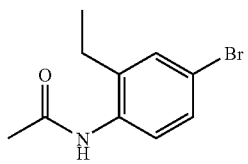

To a solution of 4-bromo-2-ethylaniline (50 g, 0.25 mol) in dichloromethane (250 ml) is added triethylamine (63.24 g, 0.62 mol) and the mixture is stirred at room temperature for 30 minutes. The reaction mixture is cooled to 0° C. and acetyl chloride (39.25 g, 0.5 mol) is added dropwise. The reaction mixture is stirred at 25-30° C. for 60 minutes, then poured into water, and the two phases separated. The organic phase is washed with water, dried over anhydrous sodium sulfate, filtered and the filtrate is evaporated under reduced pressure to yield N-(4-bromo-2-ethylphenyl)acetamide (40 g).

Step 2: Preparation of N-(4'-chloro-3-ethylbiphen-4-yl)acetamide

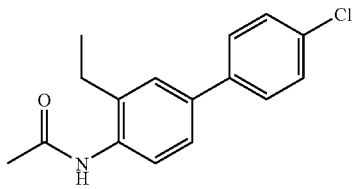 [SMILES: CCc1cc(-c2ccc(Cl)cc2)ccc1NC(C)=O]

To a degassed solution of N-(4-bromo-2-ethylphenyl)acetamide (20 g, 0.082 mol) in toluene (1200 ml) and ethanol (400 ml), 4-chlorobenzene boronic acid (15.5 g, 0.099 mol) is added under an atmosphere of nitrogen, and the reaction mixture is heated to 80° C. Tetrakis(triphenylphosphine)palladium(0) (2.0 g, 0.0017 mol) is added followed by 2M aqueous potassium carbonate solution (160 ml). The reaction mixture is heated at reflux for 4 hours then cooled to room temperature. The reaction mixture is filtered through diatomaceous earth, and the filtrate is evaporated under reduced pressure. The residue is partitioned between ethyl acetate and water. The aqueous phase is extracted with ethyl acetate (3×500 ml) and the organic solutions are combined and concentrated under reduced pressure to give N-(4'-chloro-3-ethylbiphen-4-yl)acetamide (20.5 g).

Step 3: Preparation of 4'-chloro-3-ethylbiphen-4-ylamine

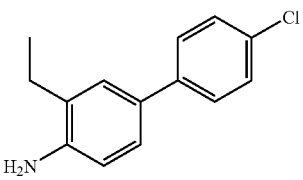 [SMILES: CCc1cc(-c2ccc(Cl)cc2)ccc1N]

To a solution of N-(4'-chloro-3-ethylbiphen-4-yl)acetamide (18 g, 0.06 mol) in dioxane (126 ml), is added concentrated hydrochloric acid (36 ml) and the reaction mixture is heated at reflux for 2 hours. The dioxane is evaporated under reduced pressure. The residue is diluted with water, the solution made basic by addition of 2N aqueous potassium hydroxide solution and extracted with ethyl acetate (3×500 ml). The organic extracts are combined and concentrated under reduced pressure to give 4'-chloro-3-ethylbiphen-4-ylamine (13.5 g).

Step 4: Preparation of 4-bromo-4'-chloro-3-ethylbiphenyl

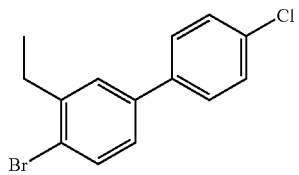 [SMILES: CCc1cc(-c2ccc(Cl)cc2)ccc1Br]

4'-Chloro-3-ethylbiphen-4-ylamine (14.3 g, 0.06 mol) is added to acetonitrile (143 ml) and stirred at room temperature until dissolution is complete. The reaction mixture is cooled to between −5° C. and 0° C., tert-butyl nitrite (90%, 9.8 ml, 0.074 mol) is added dropwise and the reaction mixture is maintained at between −5° C. and 0° C. for 30-40 minutes. The mixture is added slowly to a preheated (50° C.) suspension of copper (I) bromide (4.87 g, 0.034 mol) in hydrobromic acid (4.8 ml) and stirred at 50° C. for 10-15 minutes. The reaction mixture is cooled to room temperature, then poured into ice-cold water and extracted with ethyl acetate (3×500 ml). The organic extracts are washed with water, dried over anhydrous sodium sulfate and concentrated under reduced pressure. The residue is purified by column chromatography on silica gel to yield 4-bromo-4'-chloro-3-ethylbiphenyl (12 g).

Step 5: Preparation of 4'-chloro-3-ethylbiphen-4-ylboronic acid

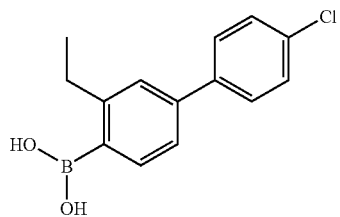 [SMILES: CCc1cc(-c2ccc(Cl)cc2)ccc1B(O)O]

A solution of n-butyl lithium in hexanes (1.6 M, 38.75 ml, 0.062 mol) is added dropwise to a solution of 4-bromo-4'-chloro-3-ethylbiphenyl (12.35 g, 0.041 mol) in tetrahydrofuran (125 ml) at −78° C., under an atmosphere of nitrogen, and the mixture is stirred at −78° C. for 30 minutes. Trimethyl borate (27.8 ml, 0.25 mol) is added slowly at −78° C. and the mixture is stirred for 1 hr. The reaction mixture is allowed to warm to room temperature over 2-3 hrs and then stirred at room temperature for 1 hr. 0.1N aqueous hydrochloric acid (343 ml) is added and the mixture is stirred at room temperature overnight. The reaction mixture is extracted with ethyl acetate (3×300 ml) and the organic extracts are combined, dried with anhydrous sodium sulfate, filtered and the filtrate is concentrated under reduced pressure. The residue is purified by column chromatography on silica gel to give 4'-chloro-3-ethylbiphen-4-ylboronic acid (4.5 g) as white solid.

Step 6: Preparation of 4'-chloro-3-ethylbiphen-4-yllead triacetate

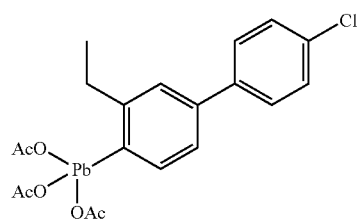

4'-Chloro-3-ethylbiphen-4-ylboronic acid (4.2 g, 0.016 mol) is added in one portion to a mixture of lead tetraacetate (7.86 g, 0.017 mol) and mercuric acetate (0.25 g, 5 mol %) in chloroform (23 ml) under an atmosphere of nitrogen. The reaction mixture is stirred at ambient temperature until dissolution is complete, and then heated at 40° C. for 4 hrs. The reaction mixture is cooled to ambient temperature, filtered through a plug of diatomaceous earth and the filtrate is concentrated under reduced pressure to give an orange colored solid. Trituration with hexanes (50 ml) affords a yellow solid which is dried under high vacuum. This solid is then dissolved in chloroform (100 ml), anhydrous potassium carbonate (26.7 g, 0.19 mol) is added and the suspension is stirred rapidly for 10 minutes. The mixture is filtered through a plug of diatomaceous earth, and the filtrate is concentrated under reduced pressure to give 4'-chloro-3-ethylbiphen-4-yllead triacetate (5.6 g) as a cream colored solid.

Step 7: Preparation of 3-(4'-chloro-3-ethylbiphen-4-yl)bicyclo[3.2.1]octane-2,4-dione

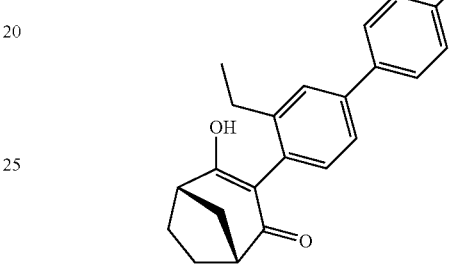

Bicyclo[3.2.1]-2,4-dione (0.20 g, 1.44 mmol) and 4-dimethylaminopyridine (0.88 g, 7.21_mmol) are added to a mixture of chloroform (4 ml) and toluene (1 ml), and the reaction mixture is flushed with nitrogen for 15 minutes at ambient temperature. 4'-Chloro-3-ethylbiphen-4-yllead triacetate (0.95 g, 1.58 mmol) is added in one portion and the reaction mixture is stirred and heated to 80° C. under an atmosphere of nitrogen for 1 hour. The reaction mixture is cooled to room temperature, acidified to pH 1 with 2N aqueous hydrochloric acid, filtered through a plug of diatomaceous earth and the two phases separated. The aqueous phase is extracted with dichloromethane (2×5 ml), the organic phases are combined, washed with water, and dried over anhydrous sodium sulfate. The mixture is filtered, and the filtrate is evaporated under reduced pressure. The residue is purified by column chromatography on silica gel to give 3-(4'-chloro-3-ethylbiphen-4-yl) bicyclo[3.2.1]octane-2,4-dione.

Example 19

Preparation of 3-(4'-chloro-3-methylbiphen-4-yl)bicyclo[3.2.1]octane-2,4-dione

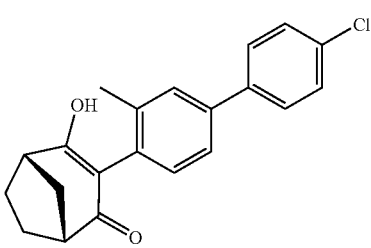 [SMILES: Cc1cc(-c2ccc(Cl)cc2)ccc1C1=C(O)[C@H]2CC[C@H](C2)C1=O]

Step 1: Preparation of 4'-chloro-3-methylbiphen-4-ylamine

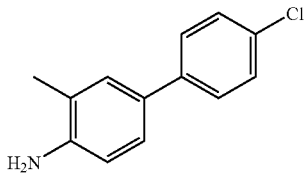

To a stirred, degassed solution of 4-bromo-2-methylaniline (20 g, 0.107 mol) in toluene (1200 ml) and ethanol (400 ml), under an atmosphere of nitrogen, is added 4-chlorophenylboronic acid (20.32 g, 0.13 mol) and the reaction mixture is stirred and heated to 80° C. Tetrakis(triphenylphosphine)palladium(0) (2.48 g, 0.002 mol) is added to the reaction mixture, and to this is added 2M aqueous potassium carbonate solution (160 ml). The reaction mixture is heated at reflux for 4 hours, then cooled to room temperature. The reaction mixture was filtered through diatomaceous earth, and the filtrate was evaporated under reduced pressure. The residue is partitioned between ethyl acetate and water. The aqueous phase is extracted with ethyl acetate (3×500 ml) and the organic extracts are combined and concentrated under reduced pressure to give 4'-chloro-3-methylbiphen-4-ylamine (16.5 g).

Step 2: Preparation of 4-bromo-4'-chloro-3-methylbiphenyl

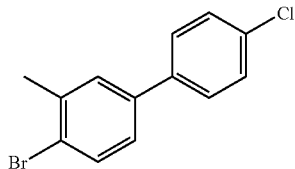

4'-Chloro-3-methylbiphen-4-ylamine (16.5 g, 0.077 mol) is added to acetonitrile (140 ml) and stirred at room temperature until dissolution is complete. The reaction mixture is cooled to between −5° C. and 0° C., tent-butyl nitrite (90%, 12.4 ml, 0.093 mol) is added dropwise and the reaction mixture is maintained at between −5 and 0° C. for 30-40 minutes. The mixture is added slowly to the preheated (50° C.) suspension of copper (I) bromide (5.8 g, 0.04 mol) in hydrobromic acid (5.8 ml) and stirred at 50° C. for 10-15 minutes. The reaction mixture is cooled to room temperature, then poured into ice-cold water and extracted with ethyl acetate (3×300 ml). The organic extracts are washed with water, dried over anhydrous sodium sulfate and concentrated under reduced pressure. The residue is purified by column chromatography on silica gel to yield 4-bromo-4'-chloro-3-methylbiphenyl (11.5 g).

Step 3: Preparation of 4'-chloro-3-methylbiphen-4-ylboronic acid

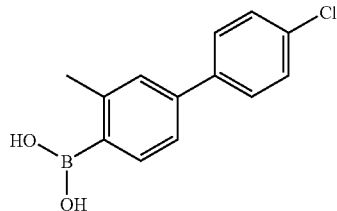 [SMILES: Cc1cc(-c2ccc(Cl)cc2)ccc1B(O)O]

A solution of n-butyl lithium in hexanes (1.6 M, 37.5 ml, 0.060 mol) is added dropwise to a solution of 4-bromo-4'-chloro-3-methylbiphenyl (11.5 g, 0.041 mol) in tetrahydrofuran (120 ml) at −78° C., under an atmosphere of nitrogen, and the mixture is stirred at −78° C. for 30 minutes. Trimethyl borate (27.4 ml, 0.245 mol) is added slowly at −78° C. and the mixture is stirred for 1 hr. The reaction mixture is allowed to warm to room temperature over 2-3 hrs and then stirred at room temperature for 1 hr. 0.1N aqueous hydrochloric acid (320 ml) is added and the mixture is stirred at room temperature overnight. The reaction mixture is extracted with ethyl acetate (3×300 ml) and the organic extracts are combined, dried with anhydrous sodium sulfate, filtered and the filtrate is concentrated under reduced pressure. The residue is purified by column chromatography on silica gel to give 4'-chloro-3-methylbiphen-4-ylboronic acid (6.0 g) as white solid.

Step 4: Preparation of 4'-chloro-3-methylbiphen-4-yllead triacetate

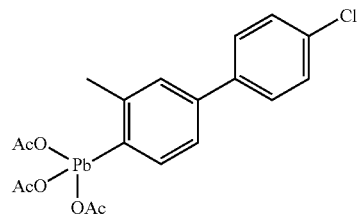

4'-Chloro-3-methylbiphen-4-ylboronic acid (6.0 g, 0.024 mol) is added in one portion to a mixture of lead tetraacetate (13.0 g, 0.029 mol) and mercuric acetate (0.38 g, 5 mol %) in chloroform (50 ml) under an atmosphere of nitrogen. The reaction mixture is stirred at ambient temperature until dissolution is complete, and then heated at 40° C. for 4 hrs. The reaction mixture is cooled to ambient temperature, filtered through a plug of diatomaceous earth and the filtrate is concentrated under reduced pressure to give an orange colored solid. Trituration with hexane (50 ml) to afford a yellow solid which was dried under high vacuum. This solid is then dissolved in chloroform (100 ml), anhydrous potassium carbonate (42.5 g, 0.3 mol) is added and the suspension is stirred rapidly for 10 minutes. The mixture is filtered through a plug of diatomaceous earth, and the filtrate is concentrated under reduced pressure to give 4'-chloro-3-methylbiphen-4-yllead triacetate (7.8 g) as a cream colored solid.

Step 5: Preparation of 3-(4'-chloro-3-methylbiphen-4-yl)bicyclo[3.2.1]octane-2,4-dione

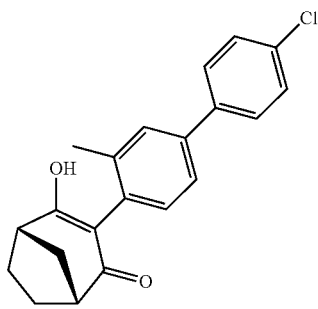 [SMILES: Cc1cc(-c2ccc(Cl)cc2)ccc1C1=C(O)[C@H]2CC[C@H](C2)C1=O]

Bicyclo[3.2.1]-2,4-dione (0.20 g, 1.44 mmol) and 4-dimethylaminopyridine (0.88 g, 7.21_mmol) are added to a mixture of chloroform (4 ml) and toluene (1 ml), and the reaction mixture is flushed with nitrogen for 15 minutes at ambient temperature. 4'-Chloro-3-methylbiphen-4-yllead triacetate (0.95 g, 1.6 mmol) is added in one portion and the reaction mixture is stirred and heated to 80° C. under an atmosphere of nitrogen for 1 hour. The reaction mixture is cooled to room temperature, acidified to pH 1 with 2N aqueous hydrochloric acid, filtered through a plug of diatomaceous earth and the two phases separated. The aqueous phase is extracted with dichloromethane (2×5 ml), the organic phases are combined, washed with water, and dried over anhydrous sodium sulfate. The mixture is filtered, and the filtrate is evaporated under reduced pressure. The residue is purified by column chromatography on silica gel to give 3-(4'-chloro-3-methylbiphen-4-yl)bicyclo[3.2.1]octane-2,4-dione.

Example 20

Preparation of 3-(4'-chloro-4-ethylbiphen-3-yl)-6,6-dimethylbicyclo[3.1.1]heptane-2,4-dione

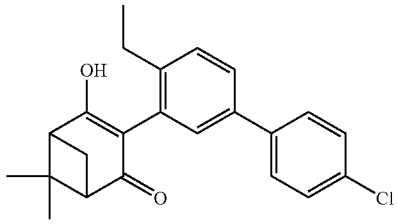

3-Bromo-4'-chloro-4-ethylbiphenyl (0.200 g, 0.68 mmol) is added to a mixture of 6,6-dimethylbicyclo[3.1.1]heptane-2,4-dione (0.124 g, 0.81 mmol), prepared by the method of W. Childers et al., US2006/0004108, powdered potassium phosphate (0.316 g, 1.49 mmol), palladium (II) acetate (0.008 g, 0.034 mmol) and (2-dicyclohexylphosphino)-2',4',6'-triisopropylbiphenyl (0.024 g, 0.051 mmol) in degassed 1,2-dimethoxyethane (2 ml) and the mixture is stirred and heated to 160° C. for 1 hour under microwave irradiation. The mixture is cooled to room temperature, diluted with ethyl acetate and washed with 2 M aqueous hydrochloric acid. The organic phase is washed with brine, dried over anhydrous magnesium sulfate, filtered and the filtrate is evaporated under reduced pressure. The residue is taken up in N,N-dimethylformamide (2 ml) and purified by preparative reverse-phase HPLC to give 3-(4'-chloro-4-ethylbiphen-3-yl)-6,6-dimethylbicyclo [3.1.1]heptane-2,4-dione.

Example 21

Preparation of 3-(4'-chloro-4-ethyl-2'-fluorobiphen-3-yl)-6,6-dimethyl-bicyclo[3.1.1]heptane-2,4-dione

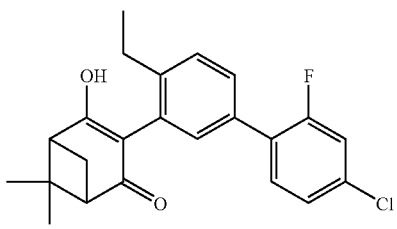

Step 1: Preparation of 4'-chloro-4-ethyl-2'-fluoro-3-nitrobiphenyl

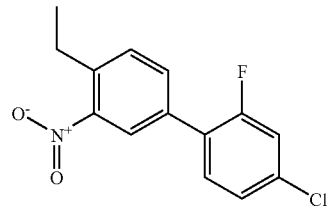 [SMILES: CCc1ccc(-c2ccc(Cl)cc2F)cc1[N+](=O)[O-]]

Tetrakis(triphenylphosphine)palladium(0) is added to a solution of 2-fluoro-4-chlorophenylboronic acid (1.25 g, 7.17 mmol) and 4-bromo-1-ethyl-2-nitrobenzene (1.50 g, 6.52 mmol) in 1,2-dimethoxyethane (12 ml) and the mixture is stirred at room temperature for 15 minutes. A solution of sodium carbonate (5.52 g, 52 mmol) in water (26 ml) is added and the mixture is heated to reflux for 17 hours. The reaction mixture is cooled to room temperature, diluted with ethyl acetate and the two phases separated. The organic phase is collected, the aqueous phase is extracted with ethyl acetate and the organic solutions are combined, dried over anhydrous magnesium sulfate, filtered and the filtrate is evaporated under reduced pressure to give 4'-chloro-4-ethyl-2'-fluoro-3-nitrobiphenyl (1.795 g), used without further purification in the next step.

Step 2: Preparation of 4'-chloro-4-ethyl-2'-fluorobiphen-3-ylamine

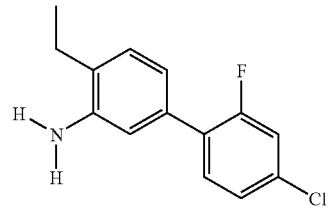 [SMILES: CCc1ccc(-c2ccc(Cl)cc2F)cc1N]

4'-chloro-4-ethyl-2'-fluoro-3-nitrobiphenyl (1.795 g, 6.45 mmol) is suspended in a mixture of methanol (20 ml) and water (4 ml). To this mixture is added zinc dust (2.95 g, 45 mmol) and a solution of ammonium chloride (1.04 g, 19 mmol) in water (4 ml), and once the addition is complete the mixture is heated at reflux for 3 hours. The mixture is cooled to room temperature, and filtered through a plug of diatomaceous earth. The filtrate is partitioned between ethyl acetate and water, and the organic extract is washed with brine, dried over anhydrous magnesium sulfate, filtered and the filtrate is evaporated under reduced pressure to give 4'-chloro-4-ethyl-2'-fluorobiphen-3-ylamine (1.546 g), used without further purification in the next step.

Step 3: Preparation of 3-bromo-4'-chloro-4-ethyl-2'-fluorobiphenyl

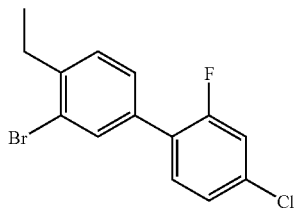 [SMILES: CCc1ccc(-c2ccc(Cl)cc2F)cc1Br]

Step 3a: 48% Aqueous hydrobromic acid (12.5 ml) is added dropwise to a suspension of 4'-chloro-4-ethyl-2'-fluorobiphen-3-ylamine (1.546 g, 6.22 mmol) in water (6 ml) and the mixture is stirred at 40° C. for 20 minutes and then cooled to 5° C. in an ice-bath. A solution of sodium nitrite (0.494 g, 7.16 mmol) in water (6.5 ml) is added dropwise, at such a rate that the temperature of the reaction may be maintained at around 5° C. by external cooling. The mixture is stirred at 5° C. for 3 hours and 30 minutes.

Step 3b: Copper (II) sulfate pentahydrate (1.79 g, 7.16 mmol) and copper powder (0.633 g, 9.96 mmol) are added to a 48% aqueous hydrobromic acid at 70° C., and the mixture is stirred for 10 minutes.

Step 3c: The mixture prepared in step 3a is added portionwise to the mixture prepared in step 3b, and once the addition is complete the mixture is stirred at 70° C. for 1 hour and 15 minutes. The mixture is cooled to room temperature, and then extracted with ethyl acetate. The organic extract is washed with brine, dried over anhydrous magnesium sulfate, filtered and the filtrate is evaporated under reduced pressure. The residue is purified by column chromatography on silica gel to give 3-bromo-4'-chloro-4-ethyl-2'-fluorobiphenyl (0.848 g) as a colourless oil.

Step 4: Preparation of 3-(4'-chloro-4-ethyl-2'-fluoro-biphen-3-yl)-6,6-dimethyl-bicyclo[3.1.1]heptane-2,4-dione

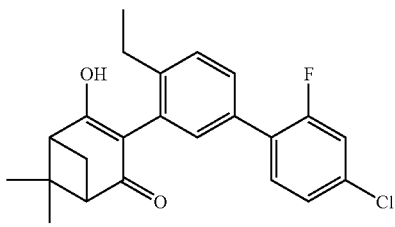

3-Bromo-4'-chloro-4-ethyl-2'-fluorobiphenyl (0.213 g, 0.68 mmol) is added to a mixture of 6,6-dimethylbicyclo[3.1.1]heptane-2,4-dione (0.124 g, 0.81 mmol), powdered potassium phosphate (0.316 g, 1.49 mmol), palladium (II) acetate (0.008 g, 0.034 mmol) and (2-dicyclohexylphosphino)-2',4',6'-triisopropylbiphenyl (0.024 g, 0.051 mmol) in degassed 1,2-(2.5 ml) and the mixture is stirred and heated to 160° C. for 1 hour under microwave irradiation. The mixture is cooled to room temperature, diluted with ethyl acetate and washed with 2 M aqueous hydrochloric acid. The organic phase is washed with brine, dried over anhydrous magnesium sulfate, filtered and the filtrate is evaporated under reduced pressure. The residue is taken up in N,N-dimethylformamide (2 ml) and purified by preparative reverse-phase HPLC. Fractions containing the desired product are taken up in ethyl acetate and washed with brine, dried over anhydrous magnesium sulfate, filtered and the fitrate is evaporated under reduced pressure to give 3-(4'-chloro-4-ethyl-2'-fluorobiphen-3-yl)-6,6-dimethylbicyclo[3.1.1]-heptane-2,4-dione.

Example 22

Preparation of 3-(4'-chloro-4-ethylbiphen-3-yl)-1,8,8-trimethylbicyclo[3.2.1]octane-2,4-dione

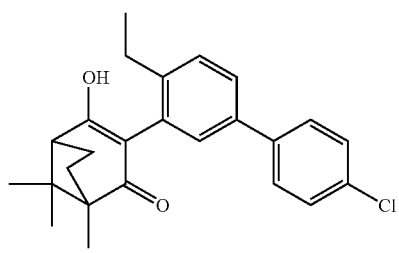 [SMILES: CCc1ccc(-c2ccc(Cl)cc2)cc1C1=C(O)C2CCC(C)(C1=O)C2(C)C]

Step 1: Preparation of 3-(5-bromo-2-ethylphenyl)-1,8,8-trimethylbicyclo[3.2.1]octane-2,4-dione

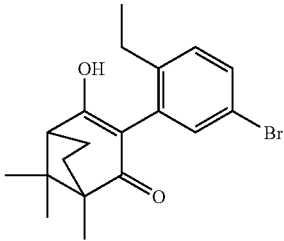 [SMILES: CCc1ccc(Br)cc1C1=C(O)C2CCC(C)(C1=O)C2(C)C]

A solution of 1,8,8-trimethylbicyclo[3.2.1]octane-2,4-dione (0.22 g, 1.22 mmol) (preparation described by H. Favre et al., Can. J. Chem. (1956), 34 1329-39) in dry chloroform (10 ml) is stirred at room temperature then thoroughly flushed with nitrogen. To this mixture is then added 4-dimethylaminopyridine (0.744 g, 6.15 mmol) and anhydrous toluene (3 ml), followed by heating to 80° C. 5-Bromo-2-ethylphenyl-lead triacetate (0.673 g, 1.18 mmol) is added portionwise over 10 minutes, and the mixture is further heated at this temperature for a further 4 hours then left to stand overnight. 2M hydrochloric acid (10 ml) is added, and the resulting biphasic mixture is filtered to remove any inorganic salts (washing with additional dichloromethane, 10 ml). The organic phase separated, and the aqueous phase is extracted again with dichloromethane (10 ml×2). All organic fractions are combined, dried over magnesium sulfate, filtered and the filtrate concentrated under reduced pressure to give an orange gum. This crude product is purified by flash column chromatography on silica gel (100% to 40% hexane/ethyl acetate eluant ratio) to afford 3-(5-bromo-2-ethylphenyl)-1,8,8-trimethylbicyclo[3.2.1]octane-2,4-dione (0.04 g, 9%) as a colourless gum.

Step 2: Preparation of 3-(4'-chloro-4-ethylbiphen-3-yl)-1,8,8-trimethylbicyclo[3.2.1]octane-2,4-dione

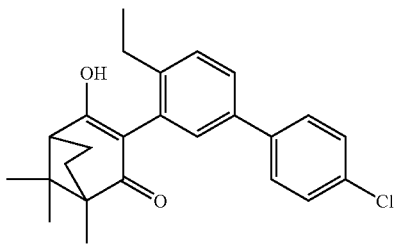 [SMILES: CCc1ccc(-c2ccc(Cl)cc2)cc1C1=C(O)C2CCC(C)(C1=O)C2(C)C]

A solution of 3-(5-bromo-2-ethyl-phenyl)-1,8,8-trimethylbicyclo[3.2.1]octane-2,4-dione (0.035 g, 0.1 mmol) and 4-chlorophenylboronic acid (0.022 g, 0.14 mmol) in anhydrous dimethoxyethane (2 ml) is stirred at room temperature under an atmosphere of nitrogen. The reaction mixture is then evacuated and flushed with nitrogen (degassing cycle repeated 4 times). Cesium fluoride (0.046 g, 0.30 mmol) is added, and the suspension is stirred at room temperature for 1 hour. Next [1,1'-bis(diphenylphosphino)ferrocene]dichloropalladium(II) (0.012 g, 0.015 mmol) is added in one portion, and the reaction mixture is heated at 80° C. for 5.5 hours. After cooling to room temperature the suspension is filtered through diatomaceous earth, then washed with 2M hydrochloric acid (5 ml) and dichloromethane (5 ml). The organic phase is separated, and the aqueous phase is extracted with dichloromethane (5 ml×2). All organics are combined, dried over magnesium sulfate, filtered and the filtrate concentrated under reduced pressure to give a brown gum. The crude product is purified by flash column chromatography on silica gel (100% to 40% hexane/ethyl acetate eluant ratio), then further purified by preparative reverse-phase HPLC to afford to afford 3-(4'-chloro-4-ethylbiphen-3-yl)bicyclo[3.2.2]nonane-2,4-dione.

Additional compounds in Table A were prepared by analogous procedures, from appropriate starting materials. It should be noted that certain compounds of the invention exist as a mixture of atropisomers, or other isomers noted above, under the conditions used to obtain the $^1$H nmr data. Where this has occurred, the characterising data are reported for individual isomers, isomer A and isomer B, which together represent the mixture of atropisomers, or other isomers, present at ambient temperature in the specified solvent. Unless otherwise stated, proton NMR spectra were recorded at ambient temperature. Compounds characterised by HPLC-MS were analysed using one of two methods described below.

Method A utilised a Waters 2795 HPLC equipped with a Waters Atlantis dC18 column (column length 20 mm, internal diameter of column 3 mm, particle size 3 micron, temperature 40° C.), Waters photodiode array and Micromass ZQ2000. The analysis was conducted using a three minute run time, according to the following gradient table:

| Time (minutes) | Solvent A (%) | Solvent B (%) | Flow (ml/minute) |
| --- | --- | --- | --- |
| 0.00 | 90.0 | 10.0 | 2.00 |
| 0.25 | 90.0 | 100 | 2.00 |
| 2.00 | 10.0 | 90.0 | 2.00 |
| 2.50 | 10.0 | 90.0 | 2.00 |
| 2.60 | 90.0 | 10.0 | 2.00 |
| 3.0 | 90.0 | 10.0 | 2.00 |

Solvent A: $H_2O$ containing 0.1% HCOOH
Solvent B: $CH_3CN$ containing 0.1% HCOOH Method B utilised an Waters 2777 injector with a 1525 micro pump HPLC equipped with a Waters Atlantis dC18 IS column (column length 20 mm, internal diameter of column 3 mm, particle size 3 micron), Waters 2996 photodiode array, Waters 2420 ELSD and Micromass ZQ2000. The analysis was conducted using a three minute run time, according to the following gradient table:

| Time (mins) | Solvent A (%) | Solvent B (%) | Flow (ml/mn) |
| --- | --- | --- | --- |
| 0.00 | 95.0 | 5 | 1.300 |
| 2.50 | 0.0 | 100 | 1.300 |
| 2.80 | 0.00 | 100 | 1.300 |
| 2.90 | 95.0 | 5 | 1.300 |

Solvent A: $H_2O$ with 0.05% TFA
Solvent B: $CH_3CN$ with 0.05% TFA

TABLE A

| Compound Number | Structure | $^1$H NMR (CDCl$_3$ unless stated) or other physical data |
| --- | --- | --- |
| T1 | 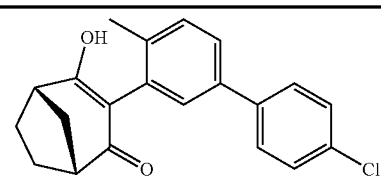 | δ 7.50-7.42 (m, 3H), 7.40-7.31 (m, 3H), 7.24 (dd, 0.6H isomer A), 7.14 (dd, 0.4H, isomer B), 5.87 (br.s, 0.4H, isomer B), 5.81 (br.s, 0.6H, isomer A), 3.01-3.11 (m, 2H), 2.30-1.65 (m, 6H), 2.18 (s, 1.2H, isomer B), 2.08 (s, 1.8H, isomer A) |
| T2 | 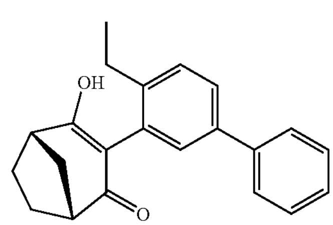 [SMILES: CCc1ccc(-c2ccccc2)cc1C1=C(O)[C@H]2CC[C@H](C2)C1=O] | δ 7.60-7.50 (m, 3H, isomers A and B), 7.44-7.36 (m, 3H, isomers A and B), 7.35-7.29 (m, 1H, isomers A and B), 7.14 (d, 0.48H, isomer A), 7.27 (d, 0.52H, isomer B), 5.80-5.70 (br s, 1H, isomers A and B), 3.10-3.00 (m, 2H, isomers A and B), 2.60-2.30 (m, 2H, isomers A and B), 2.30-2.10 (m, 3H, isomers A and B), 2.00-1.90 (m, 1H, isomers A and B), 1.85-1.80 (m, 1H, isomers A and B), 1.72-1.67 (m, 1H, isomers A and B), 1.11 (t, 1.44H, isomer A), 1.16 (t, 1.56H, isomer B). |

TABLE A-continued

| Compound Number | Structure | $^1$H NMR (CDCl$_3$ unless stated) or other physical data |
|---|---|---|
| T3 | 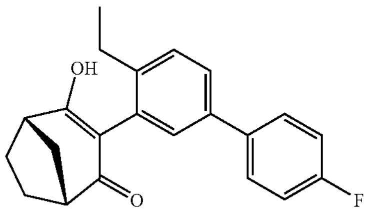 [SMILES: CCc1ccc(-c2ccc(F)cc2)cc1C1=C(O)[C@H]2CC[C@H](C2)C1=O] | δ 7.52-7.49 (m, 3H), 7.38 (t, 1H), 7.22 (d, 1H), 7.11-7.07 (m, 2H), 5.60 (br s, 1H), 3.08-3.05 (m, 2H), 2.60-2.30 (m, 2H), 2.30-2.10 (m, 3H), 2.10-1.90 (m, 1H), 1.90-1.75 (m, 1H), 1.75-1.60 (m, 1H), 1.10 (t, 3H). |
| T4 | 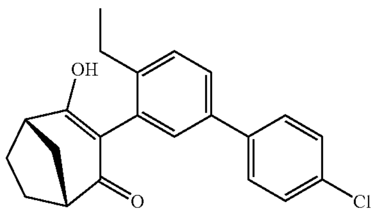 | δ 7.45-7.39 (m, 3H, isomers A and B), 7.33-7.3 (m, 3H, isomer A and B), 7.16 (d, 0.67H, isomer B), 7.04 (d, 0.33H, isomer A), 3.00-2.98 (m, 2H, isomers A and B), 2.50-2.40 (m, 1H, isomers A and B), 2.40-2.29 (m, 1H, isomers A and B), 2.29-2.05 (m, 3H, isomers A and B), 2.00-1.90 (m, 1H, isomers A and B), 1.80-1.70 (m, 1H, isomers A and B), 1.70-1.60 (m, 1H × 2, isomers A and B), 1.08 (t, 0.99H, isomer B), 1.04 (t, 2.01H, isomer A). |
| T5 | 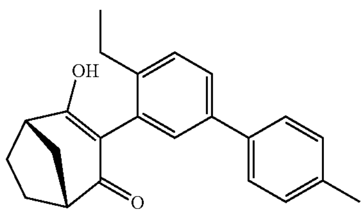 [SMILES: CCc1ccc(-c2ccc(C)cc2)cc1C1=C(O)[C@H]2CC[C@H](C2)C1=O] | δ 7.56-7.50 (1H, m), 7.47-7.42 (m, 2H), 7.38-7.34 (t, 1H), 7.24 (d, 1H), 7.22 (d, 2H), 5.70 (br s, 1H), 3.08-3.04 (m, 2H), 2.60-2.45 (m, 1H), 2.45-2.30 (m, 4H), 2.30-2.10 (m, 3H), 2.05-1.90 (m, 1H), 1.85-1.75 (m, 1H), 1.75-1.65 (m, 1H), 1.07 (t, 3H). |
| T6 | 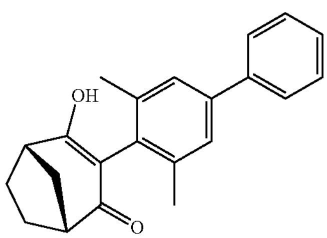 [SMILES: Cc1cc(-c2ccccc2)cc(C)c1C1=C(O)[C@H]2CC[C@H](C2)C1=O] | (d$_6$-DMSO) 7.62 (d, 2H), 7.44 (app t, 2H), 7.33 (m, 1H); 7.24 (d, 2H), 3.06-2.85 (m, 2H), 2.75-2.30 (m, 2H), 2.17-2.07 (m, 2H), 1.96 (s, 6H), 1.66-1.56 (m, 2H). |
| T7 | 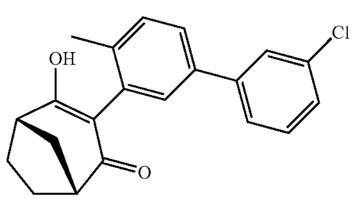 [SMILES: Cc1ccc(-c2cccc(Cl)c2)cc1C1=C(O)[C@H]2CC[C@H](C2)C1=O] | δ 7.54 (m, 1H, isomers A and B), 7.45 (m, 2H, isomers A and B), 7.30 (m, 3.6H, isomers A and B), 7.12 (d, 0.4H, isomer B), 3.09 (br. s, 2H, isomers A and B), 2.22 (m, 3H, isomers A and B), 2.20 (s, 1.2H, isomer B), 2.10 (s, 1.8H, isomer A), 2.00 (m, 1H, isomers A and B), 1.82 (m, 1H, isomers A and B), 1.70 (m, 1H, isomers A and B). |
| T8 | 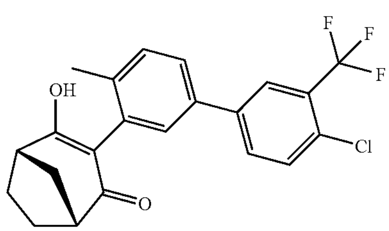 [SMILES: Cc1ccc(-c2ccc(Cl)c(C(F)(F)F)c2)cc1C1=C(O)[C@H]2CC[C@H](C2)C1=O] | δ 7.85 (m, 1H, isomers A and B), 7.65 (m, 1H, isomers A and B), 7.54 (d, 1H, isomers A and B), 7.47 (m, 1H, isomers A and B), 7.38 (m, 1H, isomers A and B), 7.25 (m, 0.6H, isomer A), 7.14 (d, 0.4H, isomer B) 3.10 (br. s, 2H, isomers A and B), 2.25 (m, 3H, isomers A and B), 2.20 (s, 1.2H, isomer B), 2.10 (s, 1.8H, isomer A), 2.00 (m, 1H, isomers A and B), 1.85 (m, 1H, isomers A and B), 1.70 (m, 1H, isomers A and B). |
| T9 | 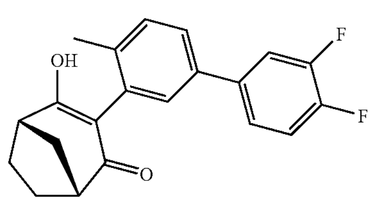 [SMILES: Cc1ccc(-c2ccc(F)c(F)c2)cc1C1=C(O)[C@H]2CC[C@H](C2)C1=O] | δ 7.40 (m, 1H, isomers A and B), 7.31 (m, 2H, isomers A and B), 7.22 (m, 1H, isomers A and B), 7.18 (m, 1.6H, isomers A and B), 7.08 (d, 0.4H, isomer B), 3.10 (m, 2H, isomers A and B), 2.21 (m, 3H, isomers A and B), 2.16 (s, 1.2H, isomer B), 2.05 (s, 1.8H, isomer A), 1.90 (m, 2H, isomers A and B), 1.70 (m, 1H, isomers A and B) |

TABLE A-continued

| Compound Number | Structure | ¹H NMR (CDCl₃ unless stated) or other physical data |
|---|---|---|
| T10 | 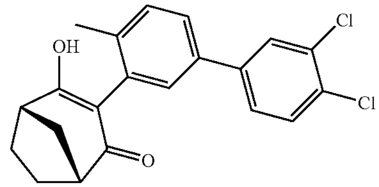 [SMILES: Cc1ccc(-c2ccc(Cl)c(Cl)c2)cc1C1=C(O)[C@H]2CC[C@H](C2)C1=O] | CD₃OD δ 7.77 (m, 1H, isomers A and B), 7.55 (m, 2H, isomers A and B), 7.45 (m, 1H, isomers A and B), 7.32 (m, 1H, isomers A and B), 7.22 (d, 0.6H, isomer A), 7.16 (d, 0.4H, isomer B), 3.05 (m, 2H, isomers A and B), 2.25 (m, 3H, isomers A and B), 2.20 (s, 1.2H, isomer B), 2.09 (s, 1.8H, isomer A), 1.90 (m, 2H, isomers A and B), 1.75 (m, 1H, isomers A and B) |
| T11 | 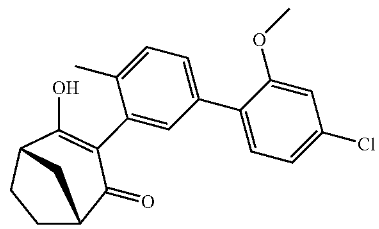 [SMILES: COc1cc(Cl)ccc1-c1ccc(C)c(C2=C(O)[C@H]3CC[C@H](C3)C2=O)c1] | CD₃OD δ 7.30 (m, 1H, isomers A and B), 7.21 (m, 2H, isomers A and B), 7.03 (m, 1.6H, isomers A and B), 6.96 (m, 1.4H, isomers A and B), 3.77 (m, 3H, isomers A and B), 3.00 (m, 2H, isomers A and B), 2.22 (m, 3H, isomers A and B), 2.15 (s, 1.2H, isomer B), 2.04 (s, 1.8H, isomer A), 1.82 (m, 2H, isomers A and B), 1.69 (m, 1H, isomers A and B) |
| T12 | 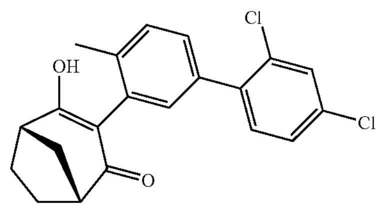 | CD₃OD δ 7.51 (m, 1H, isomers A and B), 7.35 (m, 2H, isomers A and B), 7.25 (m, 2H, isomers A and B), 7.00 (d, 0.6H, isomer A), 6.91 (d, 0.4H, isomer B), 3.00 (m, 2H, isomers A and B), 2.22 (m, 3H, isomers A and B), 2.19 (s, 1.2H, isomer B), 2.08 (s, 1.8H, isomer A), 1.85 (m, 2H, isomers A and B), 1.70 (m, 1H, isomers A and B) |
| T13 | 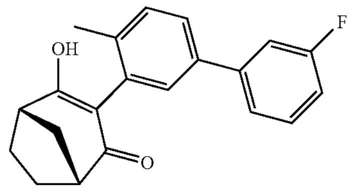 [SMILES: Cc1ccc(-c2cccc(F)c2)cc1C1=C(O)[C@H]2CC[C@H](C2)C1=O] | CD₃OD δ 7.42 (m, 3H, isomers A and B), 7.29 (m, 2H, isomers A and B), 7.20 (d, 0.6H, isomer A), 7.12 (d, 0.4H, isomer B), 7.00 (m, 1H, isomers A and B), 3.00 (m, 2H, isomers A and B), 2.24 (m, 3H, isomers A and B), 2.16 (s, 1.2H, isomer B), 2.05 (s, 1.8H, isomer A), 1.85 (m, 2H, isomers A and B), 1.70 (m, 1H, isomers A and B) |
| T14 | 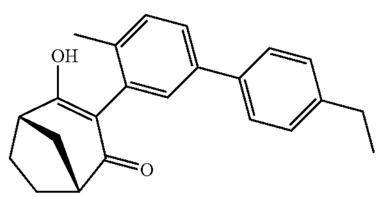 [SMILES: CCc1ccc(-c2ccc(C)c(C3=C(O)[C@H]4CC[C@H](C4)C3=O)c2)cc1] | CD₃OD δ 7.48 (m, 2H, isomers A and B), 7.40 (m, 1H, isomers A and B), 7.23 (m, 3H, isomers A and B), 7.18 (d, 0.6H, isomer A), 7.10 (d, 0.4H, isomer B), 3.00 (m, 2H, isomers A and B), 2.64 (q, 2H, isomers A and B), 2.22 (m, 3H, isomers A and B), 2.14 (s, 1.2H, isomer B), 2.03 (s, 1.8H, isomer A), 1.85 (m, 2H, isomers A and B), 1.70 (m, 1H, isomers A and B), 1.24 (t, 3H, isomers A and B). |
| T15 | 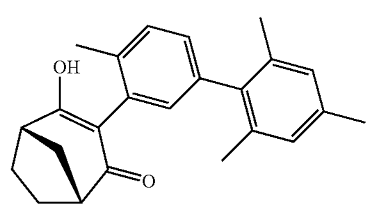 [SMILES: Cc1cc(C)c(-c2ccc(C)c(C3=C(O)[C@H]4CC[C@H](C4)C3=O)c2)c(C)c1] | CD₃OD δ 7.22 (dd, 1H, isomers A and B), 6.88 (m, 1H, isomers A and B), 6.85 (s, 2H, isomers A and B), 6.67 (d, 0.6H, isomer A), 6.60 (d, 0.4H, isomer B), 2.99 (m, 2H, isomers A and B), 2.25 (s, 3H, isomers A and B), 2.20 (m, 3H, isomers A and B), 2.16 (s, 1.2H, isomer B), 2.06 (s, 1.8H, isomer A), 1.98 (app. d, 6H, isomers A and B), 1.84 (m, 2H, isomers A and B), 1.67 (m, 1H, isomers A and B). |
| T16 | 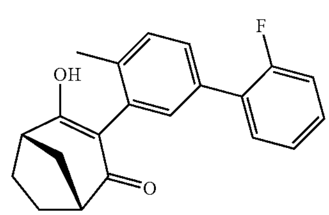 [SMILES: Cc1ccc(-c2ccccc2F)cc1C1=C(O)[C@H]2CC[C@H](C2)C1=O] | CD₃OD δ 7.45 (m, 1H, isomers A and B), 7.35 (m, 1H, isomers A and B), 7.30 (m, 2H, isomers A and B), 7.20 (m, 1H, isomers A and B), 7.15 (m, 1.6H, isomers A and B), 7.05 (d, 0.4H, isomer B), 3.00 (m, 2H, isomers A and B), 2.22 (m, 3H, isomers A and B), 2.16 (s, 1.2H, isomer B), 2.05 (s, 1.8H, isomer A), 1.85 (m, 2H, isomers A and B), 1.70 (m, 1H, isomers A and B). |

TABLE A-continued

| Compound Number | Structure | ¹H NMR (CDCl₃ unless stated) or other physical data |
|---|---|---|
| T17 | 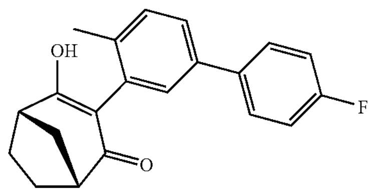 [SMILES: Cc1ccc(-c2ccc(F)cc2)cc1C1=C(O)[C@H]2CC[C@H](C2)C1=O] | CD₃OD δ 7.58 (m, 2H, isomers A and B), 7.38 (m, 1H, isomers A and B), 7.25 (m, 1H, isomers A and B), 7.10 (m, 3H, isomers A and B), 3.00 (m, 2H, isomers A and B), 2.22 (m, 3H, isomers A and B), 2.15 (s, 1.2H, isomer B), 2.04 (s, 1.8H, isomer A), 1.85 (m, 2H, isomers A and B), 1.70 (m, 1H, isomers A and B). |
| T18 | 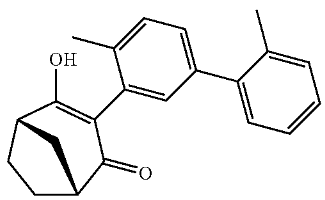 [SMILES: Cc1ccc(-c2ccccc2C)cc1C1=C(O)[C@H]2CC[C@H](C2)C1=O] | CD₃OD δ 7.22 (m, 2H, isomers A and B), 7.17 (m, 3H, isomers A and B), 7.10 (m, 1H, isomers A and B), 6.88 (d, 0.6H, isomer A), 6.81 (d, 0.4H, isomer B), 3.00 (m, 2H, isomers A and B), 2.25 (app. d, 3H, isomers A and B), 2.20 (m, 3H, isomers A and B), 2.16 (s, 1.2H, isomer B), 2.05 (s, 1.8H, isomer A), 1.85 (m, 2H, isomers A and B), 1.68 (m, 1H, isomers A and B). |
| T19 | 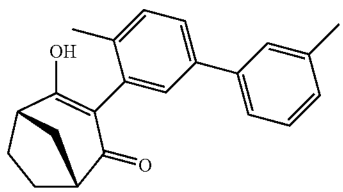 [SMILES: Cc1cccc(-c2ccc(C)c(C3=C(O)[C@H]4CC[C@H](C4)C3=O)c2)c1] | CD₃OD δ 7.39 (m, 3H, isomers A and B), 7.26 (m, 2H, isomers A and B), 7.18 (d, 0.6H, isomer A), 7.10 (m, 1.4H, isomers A and B), 3.00 (m, 2H, isomers A and B), 2.37 (s, 3H, isomers A and B), 2.22 (m, 3H, isomers A and B), 2.15 (s, 1.2H, isomer B), 2.04 (s, 1.8H, isomer A), 1.85 (m, 2H, isomers A and B), 1.70 (m, 1H, isomers A and B). |
| T20 | 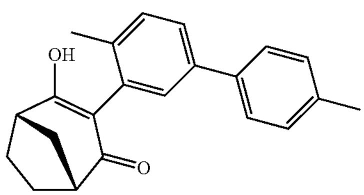 [SMILES: Cc1ccc(-c2ccc(C)c(C3=C(O)[C@H]4CC[C@H](C4)C3=O)c2)cc1] | CD₃OD δ 7.45 (m, 2H, isomers A and B), 7.40 (m, 1H, isomers A and B), 7.20 (m, 3.6H, isomers A and B), 7.10 (d, 0.4H, isomer B), 3.00 (m, 2H, isomers A and B), 2.34 (s, 3H, isomers A and B), 2.22 (m, 3H, isomers A and B), 2.14 (s, 1.2H, isomer B), 2.03 (s, 1.8H, isomer A), 1.85 (m, 2H, isomers A and B), 1.70 (m, 1H, isomers A and B). |
| T21 | 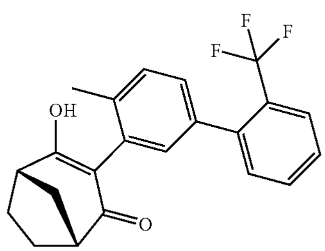 [SMILES: Cc1ccc(-c2ccccc2C(F)(F)F)cc1C1=C(O)[C@H]2CC[C@H](C2)C1=O] | CD₃OD δ 7.72 (d, 1H, isomers A and B), 7.59 (app. t, 1H, isomers A and B), 7.48 (m, 1H, isomers A and B), 7.37 (d, 1H, isomers A and B), 7.20 (m, 1H, isomers A and B), 7.10 (m, 1H, isomers A and B), 6.90 (d, 0.6H, isomer A), 6.82 (d, 0.4H, isomer B), 3.00 (m, 2H, isomers A and B), 2.22 (m, 3H, isomers A and B), 2.17 (s, 1.2H, isomer B), 2.06 (s, 1.8H, isomer A), 1.85 (m, 2H, isomers A and B), 1.68 (m, 1H, isomers A and B). |
| T22 | 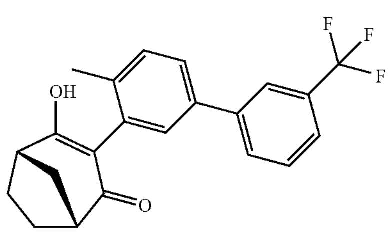 [SMILES: Cc1ccc(-c2cccc(C(F)(F)F)c2)cc1C1=C(O)[C@H]2CC[C@H](C2)C1=O] | CD₃OD δ 7.83 (m, 2H, isomers A and B), 7.60 (m, 2H, isomers A and B), 7.45 (m, 1H, isomers A and B), 7.31 (m, 1H, isomers A and B), 7.22 (d, 0.6H, isomer A), 7.16 (d, 0.4H, isomer B), 3.00 (m, 2H, isomers A and B), 2.24 (m, 3H, isomers A and B), 2.17 (s, 1.2H, isomer B), 2.06 (s, 1.8H, isomer A), 1.86 (m, 2H, isomers A and B), 1.70 (m, 1H, isomers A and B). |
| T23 | 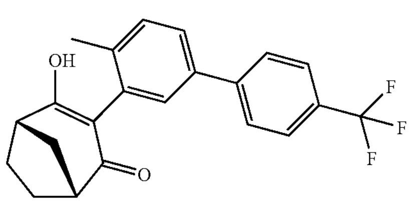 [SMILES: Cc1ccc(-c2ccc(C(F)(F)F)cc2)cc1C1=C(O)[C@H]2CC[C@H](C2)C1=O] | CD₃OD δ 7.76 (app. t, 2H, isomers A and B), 7.70 (m, 2H, isomers A and B), 7.48 (m, 1H, isomers A and B), 7.31 (m, 1H, isomers A and B), 7.26 (d, 0.6H, isomer A), 7.19 (d, 0.4H, isomer B), 3.00 (m, 2H, isomers A and B), 2.23 (m, 3H, isomers A and B), 2.17 (s, 1.2H, isomer B), 2.06 (s, 1.8H, isomer A), 1.85 (m, 2H, isomers A and B), 1.70 (m, 1H, isomers A and B). |

TABLE A-continued

| Compound Number | Structure | ¹H NMR (CDCl₃ unless stated) or other physical data |
|---|---|---|
| T24 | 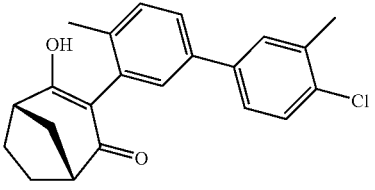 [SMILES: Cc1cc(-c2ccc(C)c(C3=C(O)[C@H]4CC[C@H](C4)C3=O)c2)ccc1Cl] | CD₃OD δ 7.50 (m, 1H, isomers A and B), 7.39 (m, 3H, isomers A and B), 7.25 (m, 1H, isomers A and B), 7.18 (d, 0.6H, isomer A), 7.10 (d, 0.4H, isomer B), 3.00 (m, 2H, isomers A and B), 2.40 (m, 3H, isomers A and B), 2.22 (m, 3H, isomers A and B), 2.15 (s, 1.2H, isomer B), 2.05 (s, 1.8H, isomer A), 1.85 (m, 2H, isomers A and B), 1.70 (m, 1H, isomers A and B). |
| T25 | 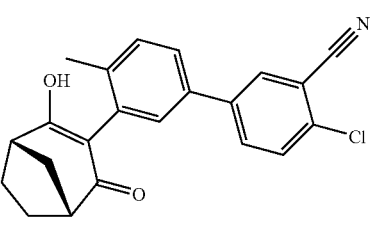 [SMILES: Cc1ccc(-c2ccc(Cl)c(C#N)c2)cc1C1=C(O)[C@H]2CC[C@H](C2)C1=O] | CD₃OD δ 8.01 (m, 1H, isomers A and B), 7.86 (m, 1H, isomers A and B), 7.65 (m, 1H, isomers A and B), 7.45 (m, 1H, isomers A and B), 7.30 (m, 1H, isomers A and B), 7.22 (d, 0.6H, isomer A), 7.18 (d, 0.4H, isomer B), 3.01 (m, 2H, isomers A and B), 2.22 (m, 3H, isomers A and B), 2.18 (s, 1.2H, isomer B), 2.06 (s, 1.8H, isomer A), 1.85 (m, 2H, isomers A and B), 1.70 (m, 1H, isomers A and B) |
| T26 | 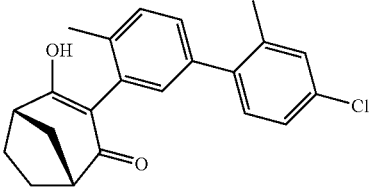 [SMILES: Cc1ccc(-c2ccc(Cl)cc2C)cc1C1=C(O)[C@H]2CC[C@H](C2)C1=O] | CD₃OD δ 7.25 (m, 2H, isomers A and B), 7.18 (m, 2H, isomers A and B), 7.09 (m, 1H, isomers A and B), 6.88 (d, 0.6H, isomer A), 6.80 (d, 0.4H, isomer B), 3.00 (m, 2H, isomers A and B), 2.25 (m, 6H, isomers A and B), 2.18 (s, 1.2H, isomer B), 2.06 (s, 1.8H, isomer A), 1.85 (m, 2H, isomers A and B), 1.69 (m, 1H, isomers A and B). |
| T27 | 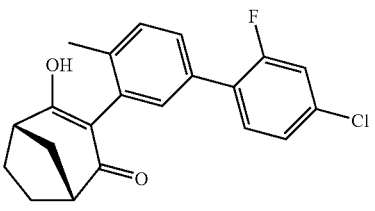 [SMILES: Cc1ccc(-c2ccc(Cl)cc2F)cc1C1=C(O)[C@H]2CC[C@H](C2)C1=O] | CD₃OD δ 7.45 (m, 1H, isomers A and B), 7.34 (m, 1H, isomers A and B), 7.25 (m, 3H, isomers A and B), 7.11 (d, 0.6H, isomer A), 7.02 (d, 0.4H, isomer B), 3.00 (m, 2H, isomers A and B), 2.22 (m, 3H, isomers A and B), 2.16 (s, 1.2H, isomer B), 2.05 (s, 1.8H, isomer A), 1.85 (m, 2H, isomers A and B), 1.70 (m, 1H, isomers A and B). |
| T28 | 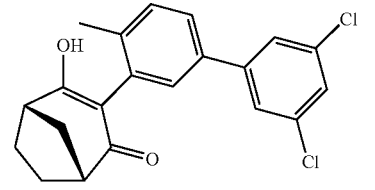 | CD₃OD δ 7.55 (m, 2H, isomers A and B), 7.45 (m, 1H, isomers A and B), 7.39 (m, 1H, isomers A and B), 7.32 (m, 1H, isomers A and B), 7.21 (d, 0.6H, isomer A), 7.12 (d, 0.4H, isomer B), 3.05 (m, 2H, isomers A and B), 2.25 (m, 3H, isomers A and B), 2.20 (s, 1.2H, isomer B), 2.10 (s, 1.8H, isomer A), 1.90 (m, 2H, isomers A and B), 1.75 (m, 1H, isomers A and B). |
| T29 | 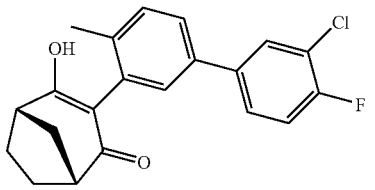 [SMILES: Cc1ccc(-c2ccc(F)c(Cl)c2)cc1C1=C(O)[C@H]2CC[C@H](C2)C1=O] | CD₃OD δ 7.65 (m, 1H, isomers A and B), 7.50 (m, 1H, isomers A and B), 7.38 (m, 1H, isomers A and B), 7.25 (m, 2H, isomers A and B), 7.15 (d, 0.6H, isomer A), 7.09 (d, 0.4H, isomer B), 3.00 (m, 2H, isomers A and B), 2.22 (m, 3H, isomers A and B), 2.16 (s, 1.2H, isomer B), 2.05 (s, 1.8H, isomer A), 1.85 (m, 2H, isomers A and B), 1.70 (m, 1H, isomers A and B). |
| T30 | 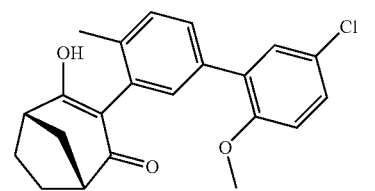 [SMILES: COc1ccc(Cl)cc1-c1ccc(C)c(C2=C(O)[C@H]3CC[C@H](C3)C2=O)c1] | CD₃OD δ 7.30 (m, 1H, isomers A and B), 7.22 (m, 3H, isomers A and B), 7.02 (m, 1.6H, isomers A and B), 6.95 (d, 0.4H, isomer B), 3.76 (s, 3H, isomers A and B), 3.00 (m, 2H, isomers A and B), 2.22 (m, 3H, isomers A and B), 2.15 (s, 1.2H, isomer B), 2.04 (s, 1.8H, isomer A), 1.85 (m, 2H, isomers A and B), 1.70 (m, 1H, isomers A and B). |

TABLE A-continued

| Compound Number | Structure | ¹H NMR (CDCl₃ unless stated) or other physical data |
|---|---|---|
| T31 | 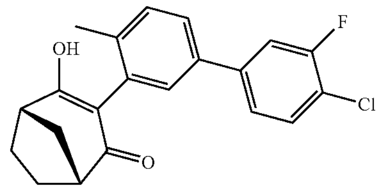 [SMILES: Cc1ccc(-c2ccc(Cl)c(F)c2)cc1C1=C(O)[C@H]2CC[C@H](C2)C1=O] | CD₃OD δ 7.45 (m, 4H, isomers A and B), 7.28 (m, 1H, isomers A and B), 7.20 (d, 0.6H, isomer A), 7.13 (d, 0.4H, isomer B) 3.00 (m, 2H, isomers A and B), 2.23 (m, 3H, isomers A and B), 2.16 (s, 1.2H, isomer B), 2.05 (s, 1.8H, isomer A), 1.85 (m, 2H, isomers A and B), 1.70 (m, 1H, isomers A and B). |
| T32 | 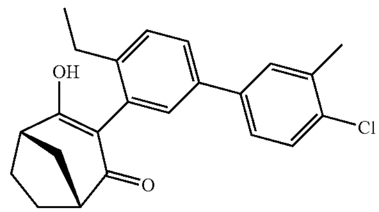 [SMILES: CCc1ccc(-c2ccc(Cl)c(C)c2)cc1C1=C(O)[C@H]2CC[C@H](C2)C1=O] | CD₃OD δ 7.50 (m, 1H, isomers A and B), 7.45 (m, 1H, isomers A and B), 7.36 (m, 2H, isomers A and B), 7.30 (m, 1H, isomers A and B), 7.15 (d, 0.6H, isomer A), 7.05 (d, 0.4H, isomer B) 3.00 (m, 2H, isomers A and B), 2.50 (q, 0.8, isomer B), 2.40 (s, 3H, isomers A and B), 2.35 (q, 1.2H, isomer A), 2.22 (m, 3H, isomers A and B), 1.85 (m, 2H, isomers A and B), 1.70 (m, 1H, isomers A and B), 1.10 (m, 3H, isomers A and B) |
| T33 | 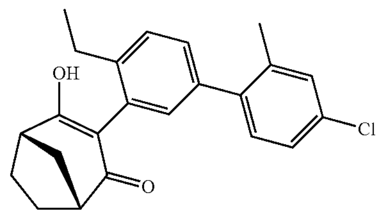 | CD₃OD δ 7.25 (m, 2H, isomers A and B), 7.15 (m, 3H, isomers A and B), 6.85 (d, 0.6H, isomer A), 6.76 (d, 0.4H, isomer B) 3.00 (m, 2H, isomers A and B), 2.50 (q, 0.8H, isomer B), 2.38 (q, 1.2H, isomer A), 2.28 (app. d, 3H, isomers A and B), 2.20 (m, 3H, isomers A and B), 1.85 (m, 2H, isomers A and B), 1.70 (m, 1H, isomers A and B), 1.11 (m, 3H, isomers A and B) |
| T34 | 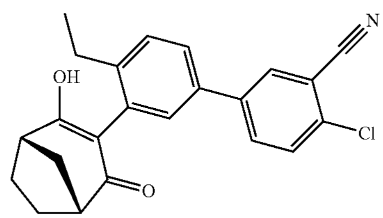 [SMILES: CCc1ccc(-c2ccc(Cl)c(C#N)c2)cc1C1=C(O)[C@H]2CC[C@H](C2)C1=O] | CD₃OD δ 8.01 (m, 1H, isomers A and B), 7.88 (m, 1H, isomers A and B), 7.65 (dd, 1H, isomers A and B), 7.50 (m, 1H, isomers A and B), 7.34 (m, 1H, isomers A and B), 7.21 (d, 0.6H, isomer A), 7.12 (d, 0.4H, isomer B), 3.00 (m, 2H, isomers A and B), 2.50 (q, 0.8H, isomer B), 2.40 (q, 1.2H, isomer A), 2.22 (m, 3H, isomers A and B), 1.85 (m, 2H, isomers A and B), 1.70 (m, 1H, isomers A and B), 1.12 (m, 3H, isomers A and B) |
| T35 | 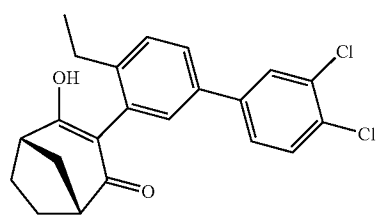 [SMILES: CCc1ccc(-c2ccc(Cl)c(Cl)c2)cc1C1=C(O)[C@H]2CC[C@H](C2)C1=O] | CD₃OD δ 7.72 (m, 1H, isomers A and B), 7.52 (m, 2H, isomers A and B), 7.48 (m, 1H, isomers A and B), 7.30 (m, 1H, isomers A and B), 7.18 (d, 0.6H, isomer A), 7.08 (d, 0.4H, isomer B), 3.00 (m, 2H, isomers A and B), 2.50 (q, 0.8H, isomer B), 2.39 (q, 1.2H, isomer A), 2.22 (m, 3H, isomers A and B), 1.85 (m, 2H, isomers A and B), 1.70 (m, 1H, isomers A and B), 1.12 (m, 3H, isomers A and B) |
| T36 | 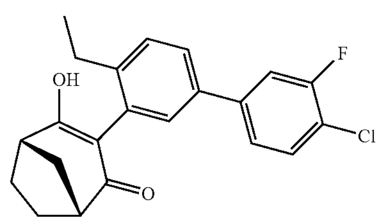 [SMILES: CCc1ccc(-c2ccc(Cl)c(F)c2)cc1C1=C(O)[C@H]2CC[C@H](C2)C1=O] | CD₃OD δ 7.48 (m, 3H, isomers A and B), 7.40 (m, 1H, isomers A and B), 7.30 (m, 1H, isomers A and B), 7.19 (d, 0.6H, isomer A), 7.09 (d, 0.4H, isomer B), 3.00 (m, 2H, isomers A and B), 2.50 (q, 0.8H, isomer B), 2.38 (q, 1.2H, isomer A), 2.22 (m, 3H, isomers A and B), 1.85 (m, 2H, isomers A and B), 1.70 (m, 1H, isomers A and B), 1.10 (m, 3H, isomers A and B) |
| T37 | 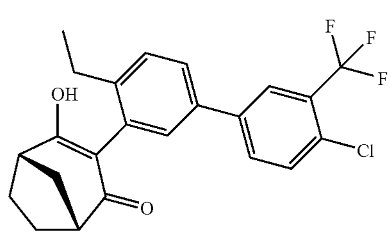 [SMILES: CCc1ccc(-c2ccc(Cl)c(C(F)(F)F)c2)cc1C1=C(O)[C@H]2CC[C@H](C2)C1=O] | CD₃OD δ 7.92 (m, 1H, isomers A and B), 7.81 (m, 1H, isomers A and B), 7.63 (dd, 1H, isomers A and B), 7.50 (m, 1H, isomers A and B), 7.35 (m, 1H, isomers A and B), 7.20 (d, 0.6H, isomer A), 7.10 (d, 0.4H, isomer B), 3.00 (m, 2H, isomers A and B), 2.50 (q, 0.8H, isomer B), 2.39 (q, 1.2H, isomer A), 2.22 (m, 3H, isomers A and B), 1.85 (m, 2H, isomers A and B), 1.70 (m, 1H, isomers A and B), 1.10 (m, 3H, isomers A and B) |

TABLE A-continued

| Compound Number | Structure | ¹H NMR (CDCl₃ unless stated) or other physical data |
|---|---|---|
| T38 | 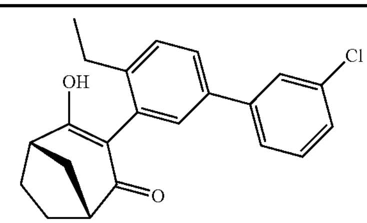 | CD$_3$OD δ 7.59 (m, 1H, isomers A and B), 7.50 (m, 2H, isomers A and B), 7.39 (m, 1H, isomers A and B), 7.30 (m, 2H, isomers A and B), 7.18 (d, 0.6H, isomer A), 7.08 (d, 0.4H, isomer B), 3.00 (m, 2H, isomers A and B), 2.50 (q, 0.8H, isomer B), 2.39 (q, 1.2H, isomer A), 2.22 (m, 3H, isomers A and B), 1.85 (m, 2H, isomers A and B), 1.70 (m, 1H, isomers A and B), 1.12 (m, 3H, isomers A and B) |
| T39 | 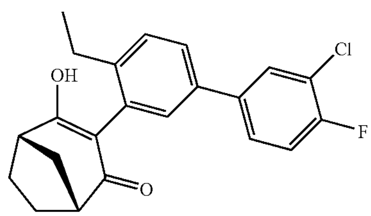 [SMILES: CCc1ccc(-c2ccc(F)c(Cl)c2)cc1C1=C(O)[C@H]2CC[C@H](C2)C1=O] | CD$_3$OD δ 7.68 (m, 1H, isomers A and B), 7.52 (m, 1H, isomers A and B), 7.42 (m, 1H, isomers A and B), 7.30 (m, 2H, isomers A and B), 7.14 (d, 0.6H, isomer A), 7.04 (d, 0.4H, isomer B), 3.00 (m, 2H, isomers A and B), 2.50 (q, 0.8H, isomer B), 2.38 (q, 1.2H, isomer A), 2.20 (m, 3H, isomers A and B), 1.85 (m, 2H, isomers A and B), 1.70 (m, 1H, isomers A and B), 1.10 (m, 3H, isomers A and B) |
| T40 | 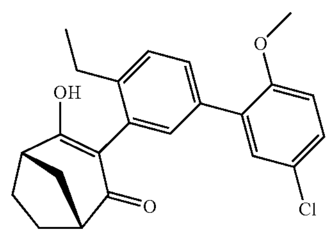 [SMILES: CCc1ccc(-c2cc(Cl)ccc2OC)cc1C1=C(O)[C@H]2CC[C@H](C2)C1=O] | CD$_3$OD δ 7.50 (m, 1H, isomers A and B), 7.28 (m, 3H, isomers A and B), 7.05 (m, 1.6H, isomers A and B), 6.93 (d, 0.4H, isomer B), 3.80 (m, 3H, isomers A and B), 3.02 (m, 2H, isomers A and B), 2.52 (q, 0.8H, isomer B), 2.40 (q, 1.2H, isomer A), 2.25 (m, 3H, isomers A and B), 1.88 (app. d, 2H, isomers A and B), 1.73 (m, 1H, isomers A and B), 1.15 (m, 3H, isomers A and B) |
| T41 | 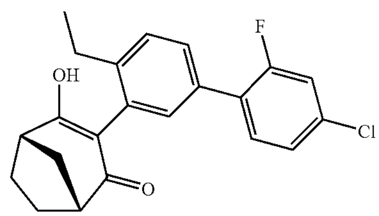 [SMILES: CCc1ccc(-c2ccc(Cl)cc2F)cc1C1=C(O)[C@H]2CC[C@H](C2)C1=O] | CD$_3$OD δ 7.45 (m, 1H, isomers A and B), 7.40 (m, 1H, isomers A and B), 7.30 (m, 1H, isomers A and B), 7.22 (m, 2H, isomers A and B), 7.10 (m, 0.6H, isomer A), 7.00 (m, 0.4H, isomer B), 3.00 (m, 2H, isomers A and B), 2.50 (q, 0.8H, isomer B), 2.38 (q, 1.2H, isomer A), 2.22 (m, 3H, isomers A and B), 1.85 (app. d, 2H, isomers A and B), 1.70 (m, 1H, isomers A and B), 1.10 (m, 3H, isomers A and B) |
| T42 | 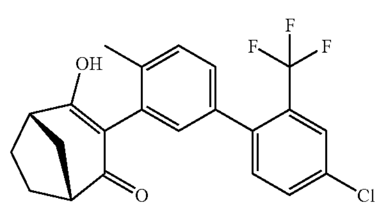 [SMILES: Cc1ccc(-c2ccc(Cl)cc2C(F)(F)F)cc1C1=C(O)[C@H]2CC[C@H](C2)C1=O] | CD$_3$OD δ 7.79 (m, 1H, isomers A and B), 7.67 (m 1H, isomers A and B), 7.42 (d, 1H, isomers A and B), 7.27 (m, 1H, isomers A and B), 7.12 (m, 1H, isomers A and B), 6.93 (d, 0.6H, isomer A), 6.88 (d, 0.4H, isomer B), 3.02 (m, 2H, isomers A and B), 2.25 (m, 3H, isomers A and B), 2.21 (s, 1.2H, isomer B), 2.11 (s, 1.8H, isomer A), 1.86 (m, 2H, isomers A and B), 1.74 (m, 1H, isomers A and B). |
| T43 | 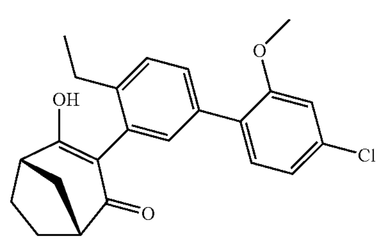 [SMILES: CCc1ccc(-c2ccc(Cl)cc2OC)cc1C1=C(O)[C@H]2CC[C@H](C2)C1=O] | CD$_3$OD δ 7.32 (m, 1H, isomers A and B), 7.22 (m, 2H, isomers A and B), 7.10 (m, 1H, isomers A and B), 7.00 (m, 2H, isomers A and B), 3.29 (m, 3H, isomers A and B), 3.00 (m, 2H, isomers A and B), 2.50 (q, 0.8H, isomer B), 2.35 (q, 1.2H, isomer A), 2.21 (m, 3H, isomers A and B), 1.85 (m, 2H, isomers A and B), 1.70 (m, 1H, isomers A and B), 1.10 (m, 3H, isomers A and B) |
| T44 | 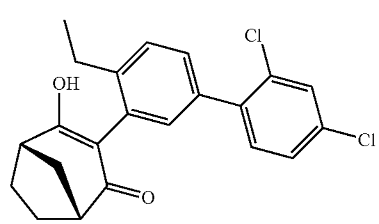 | CD$_3$OD δ 7.51 (s, 1H, isomers A and B), 7.36 (s, 2H, isomers A and B), 7.30 (s, 2H, isomers A and B), 6.99 (s, 0.6H, isomer A), 6.84 (0.4H, isomer B), 3.00 (m, 2H, isomers A and B), 2.50 (q, 0.8H, isomer B), 2.40 (q, 1.2H, isomer A), 2.21 (m, 3H, isomers A and B), 1.85 (m, 2H, isomers A and B), 1.70 (m, 1H, isomers A and B), 1.12 (m, 3H, isomers A and B) |

TABLE A-continued

| Compound Number | Structure | ¹H NMR (CDCl₃ unless stated) or other physical data |
|---|---|---|
| T45 | 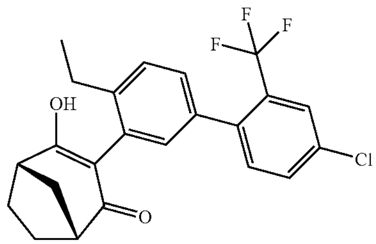 [SMILES: CCc1ccc(-c2ccc(Cl)cc2C(F)(F)F)cc1C1=C(O)[C@H]2CC[C@H](C2)C1=O] | CD₃OD δ 7.72 (s, 1H, isomers A and B), 7.62 (d, 1H, isomers A and B), 7.39 (d, 1H, isomers A and B), 7.29 (m, 2H, isomers A and B), 6.88 (s, 0.6H, isomer A), 6.79 (0.4H, isomer B), 3.00 (m, 2H, isomers A and B), 2.50 (q, 0.8H, isomer B), 2.40 (q, 1.2H, isomer A), 2.20 (m, 3H, isomers A and B), 1.85 (m, 2H, isomers A and B), 1.70 (m, 1H, isomers A and B), 1.15 (m, 3H, isomers A and B) |
| T46 | 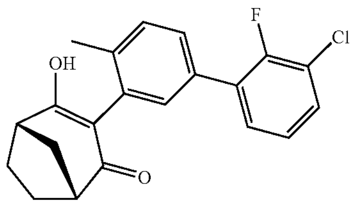 [SMILES: Cc1ccc(-c2cccc(Cl)c2F)cc1C1=C(O)[C@H]2CC[C@H](C2)C1=O] | CD₃OD δ 7.39 (m, 3H, isomers A and B), 7.30 (m, 1H, isomers A and B), 7.20 (m, 1H, isomers A and B), 7.11 (d, 0.6H, isomer A), 7.05 (d, 0.4H, isomer B), 3.00 (m, 2H, isomers A and B), 2.22 (m, 3H, isomers A and B), 2.18 (s, 1.2H, isomer B), 2.08 (s, 1.8H, isomer A), 1.85 (m, 2H, isomers A and B), 1.70 (m, 1H, isomers A and B). |
| T47 | 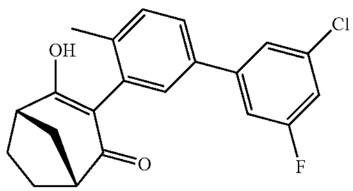 [SMILES: Cc1ccc(-c2cc(F)cc(Cl)c2)cc1C1=C(O)[C@H]2CC[C@H](C2)C1=O] | CD₃OD δ 7.39 (m, 2H, isomers A and B), 7.24 (m, 2H, isomers A and B), 7.18 (d, 0.6H, isomer A), 7.09 (m, 1.4H, isomers A and B), 3.00 (m, 2H, isomers A and B), 2.20 (m, 3H, isomers A and B), 2.13 (s, 1.2H, isomer B), 2.02 (s, 1.8H, isomer A), 1.85 (m, 2H, isomers A and B), 1.69 (m, 1H, isomers A and B). |
| T48 | 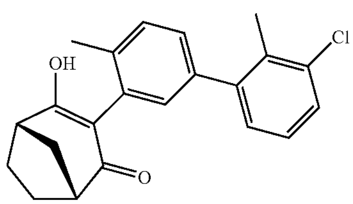 [SMILES: Cc1ccc(-c2cccc(Cl)c2C)cc1C1=C(O)[C@H]2CC[C@H](C2)C1=O] | CD₃OD δ 7.31 (dd, 1H, isomers A and B), 7.23 (m, 1H, isomers A and B), 7.13 (m, 2H, isomers A and B), 7.08 (m, 1H, isomers A and B), 6.86 (d, 0.6H, isomer A), 6.80 (m, 0.4H, isomer B), 3.00 (m, 2H, isomers A and B), 2.28 (app. d, 3H, isomers A and B), 2.21 (m, 3H, isomers A and B), 2.17 (s, 1.2H, isomer B), 2.06 (s, 1.8H, isomer A), 1.85 (m, 2H, isomers A and B), 1.69 (m, 1H, isomers A and B). |
| T49 | 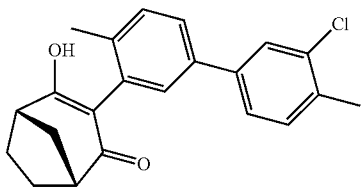 [SMILES: Cc1ccc(-c2ccc(C)c(C3=C(O)[C@H]4CC[C@H](C4)C3=O)c2)cc1Cl] | CD₃OD δ 7.51 (dd, 1H, isomers A and B), 7.38 (m, 2H, isomers A and B), 7.28 (d, 1H, isomers A and B), 7.22 (t, 1H, isomers A and B), 7.12 (d, 0.6H, isomer A), 7.08 (d, 0.4H, isomer B), 3.00 (m, 2H, isomers A and B), 2.35 (s, 3H, isomers A and B), 2.21 (m, 3H, isomers A and B), 2.12 (s, 1.2H, isomer B), 2.01 (s, 1.8H, isomer A), 1.85 (m, 2H, isomers A and B), 1.69 (m, 1H, isomers A and B). |
| T50 | 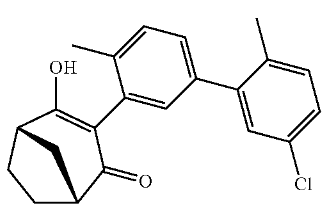 [SMILES: Cc1ccc(-c2cc(Cl)ccc2C)cc1C1=C(O)[C@H]2CC[C@H](C2)C1=O] | CD₃OD δ 7.26 (m, 1H, isomers A and B), 7.20 (m, 3H, isomers A and B), 7.10 (m, 1H, isomers A and B), 6.89 (d, 0.6H, isomer A), 6.80 (d, 0.4H, isomer B), 3.00 (m, 2H, isomers A and B), 2.23 (app. d, 3H, isomers A and B), 2.22 (m, 3H, isomers A and B), 2.18 (s, 1.2H, isomer B), 2.08 (s, 1.8H, isomer A), 1.85 (m, 2H, isomers A and B), 1.70 (m, 1H, isomers A and B). |
| T51 | 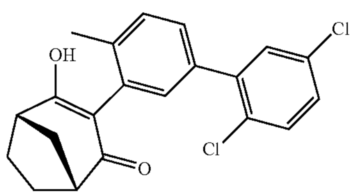 [SMILES: Cc1ccc(-c2cc(Cl)ccc2Cl)cc1C1=C(O)[C@H]2CC[C@H](C2)C1=O] | CD₃OD δ 7.45 (m, 1H, isomers A and B), 7.40 (d, 1H, isomers A and B), 7.30 (dd, 1H, isomers A and B), 7.28 (s, 2H, isomers A and B), 7.01 (d, 0.6H, isomer A), 6.92 (d, 0.4H, isomer B), 3.02 (m, 2H, isomers A and B), 2.22 (m, 3H, isomers A and B), 2.20 (s, 1.2H, isomer B), 2.09 (s, 1.8H, isomer A), 1.85 (m, 2H, isomers A and B), 1.70 (m, 1H, isomers A and B). |

TABLE A-continued

| Compound Number | Structure | ¹H NMR (CDCl₃ unless stated) or other physical data |
|---|---|---|
| T52 | 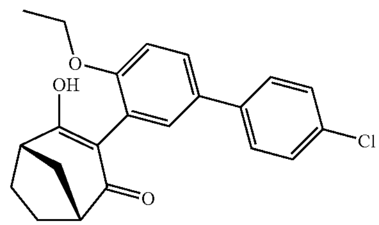 [SMILES: CCOc1ccc(-c2ccc(Cl)cc2)cc1C1=C(O)[C@H]2CC[C@H](C2)C1=O] | CD₃OD δ 7.55 (d, 2H), 7.50 (dd, 1H), 7.38 (d, 2H), 7.20 (s, 1H), 6.99 (d, 1H), 4.00 (q, 2H), 2.99 (br. s, 2H), 2.20 (m, 3H), 1.85 (d, 2H), 1.70 (m, 1H), 1.31 (t, 3H). |
| T53 | 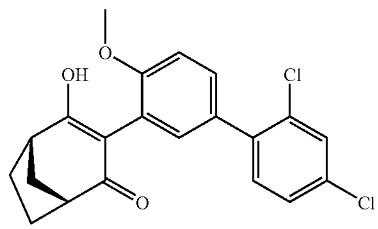 [SMILES: COc1ccc(-c2ccc(Cl)cc2Cl)cc1C1=C(O)[C@H]2CC[C@H](C2)C1=O] | CD₃OD δ 7.49 (d, 1H), 7.35-7.30 (m, 3H), 7.0 (d, 2H), 3.76 (s, 3H), 2.95 (m, 2H), 2.16 (m, 3H), 1.83 (br. d, 2H), 1.65 (m, 2H). |
| T54 | 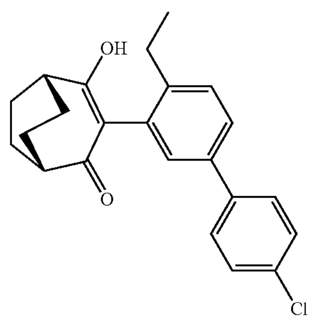 [SMILES: CCc1ccc(-c2ccc(Cl)cc2)cc1C1=C(O)[C@H]2CC[C@H](CC2)C1=O] | δ 7.55-7.47 (m, 3H), 7.43-7.35 (m, 3H), 7.23 (dd, 1H), 5.51 (s, 1H), 2.97 (m, 2H), 2.48 (m, 2H), 2.02-1.84 (m, 8H), 1.15 (t, 3H). |
| T55 | 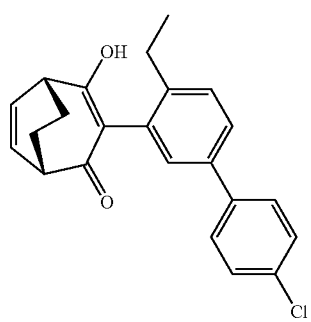 [SMILES: CCc1ccc(-c2ccc(Cl)cc2)cc1C1=C(O)[C@H]2C=C[C@H](CC2)C1=O] | δ 7.51-7.44 (m, 3H), 7.41-7.35 (m, 3H), 7.17 (d, 1H), 6.53 (m, 1H), 6.34 (m, 1H), 5.45 (br. d, 1H), 3.73 (t, 1H), 3.57 (m, 1H), 2.52-1.88 (m, 6H), 1.14 (t, 1.8H, isomer A), 1.08 (t, 1.2H, isomer B). |
| T56 | 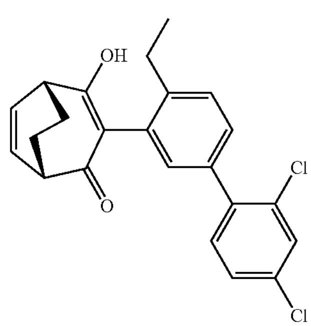 | δ 7.47 (m, 1H), 7.40-7.35 (m, 2H), 7.28 (m, 2H), 7.07 (m, 1H), 6.53 (m, 1H), 6.32 (m, 1H), 5.49 (d, 1H), 3.71 (t, 1H), 3.57 (m, 1H), 2.53-1.86 (m, 6H), 1.13 (m, 3H). |

TABLE A-continued

| Compound Number | Structure | $^1$H NMR (CDCl$_3$ unless stated) or other physical data |
|---|---|---|
| T57 | 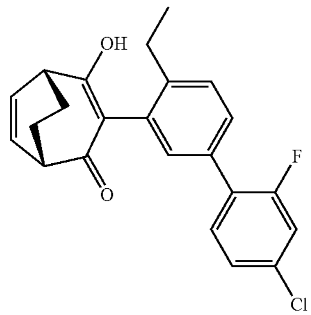 [SMILES: CCc1ccc(-c2ccc(Cl)cc2F)cc1C1=C(O)[C@H]2C=C[C@H](CC2)C1=O] | δ 7.52 (m, 1H), 7.47-7.35 (m, 2H), 7.26-7.15 (m, 3H), 6.57 (q, 1H), 6.37 (q, 1H), 5.49 (d, 1H), 3.76 (t, 1H), 3.61 (broad m, 1H), 2.58-1.91 (m, 6H), 1.19 (t, 1.8H, isomer A), 1.13 (t, 1.2H, isomer B). |
| T58 | 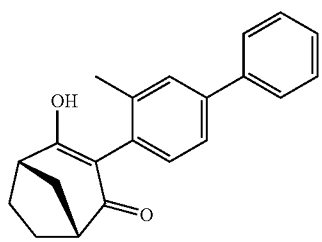 [SMILES: Cc1cc(-c2ccccc2)ccc1C1=C(O)[C@H]2CC[C@H](C2)C1=O] | δ 7.6-7.3 (m, 7H, isomers A and B), 7.13 (d, 0.59H, isomer B), 7.05 (d, 0.41H, isomer A), 5.64 (s, 0.41H, isomer A) 5.56 (s, 0.59H, isomer B), 3.1-3.0 (m, 2H, isomers A and B), 2.3-2.0 (m, 7H, isomers A and B), 1.9-1.6 (m, 2H, isomers A and B). |
| T59 | 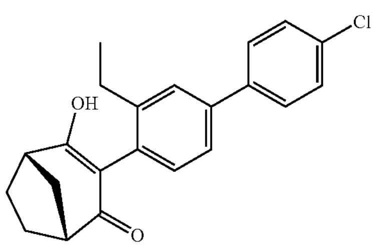 [SMILES: CCc1cc(-c2ccc(Cl)cc2)ccc1C1=C(O)[C@H]2CC[C@H](C2)C1=O] | δ 7.55-7.39 (m, 6H, isomers A and B), 7.12 (d, 0.53H, isomer B), 7.03 (d, 0.47H, isomer A), 5.7 (br s, 0.53H, isomer B) 5.6 (br s, 0.47H, isomer A), 3.1-3.0 (m, 2H, isomers A and B), 2.6-2.3 (m, 2H, isomers A and B), 2.3-2.1 (m, 3H, isomers A and B), 2.05-1.95 (m, 1H, isomers A and B), 1.85-1.75 (m, 1H, isomers A and B), 1.75-1.65 (m, 1H, isomers A and B), 1.16 (t, 1.41H, isomer A), 1.11 (m, 1.59H, isomer B). |
| T60 | 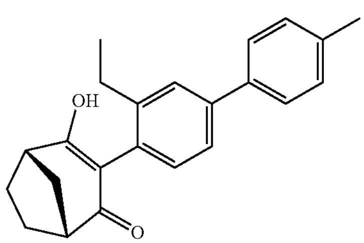 [SMILES: CCc1cc(-c2ccc(C)cc2)ccc1C1=C(O)[C@H]2CC[C@H](C2)C1=O] | δ 7.55-7.4 (m, 4H, isomers A and B), 7.3-7.2 (m, 2H, isomers A and B), 7.1 (d, 0.52H, isomer B), 7.0 (d, 0.47H, isomer A), 5.6 (s, 0.47H, isomer A), 5.55 (s, 0.52H, isomer B), 3.1-3.0 (m, 2H, isomers A and B), 2.6-2.3 (m, 4H, isomers A and B), 2.3-2.1 (m, 4H, isomers A and B), 2.05-1.95 (m, 1H, isomers A and B) 1.85-1.75 (m, 1H, isomers A and B), 1.75-1.65 (m, 1H, isomers A and B), 1.14 (t, 1.41H, isomer A), 1.11 (m, 1.56H, isomer B). |
| T61 | 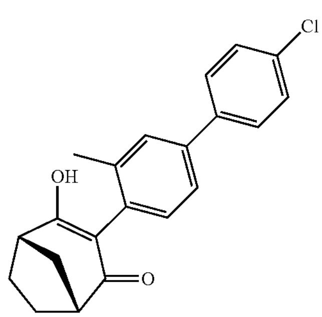 [SMILES: Cc1cc(-c2ccc(Cl)cc2)ccc1C1=C(O)[C@H]2CC[C@H](C2)C1=O] | δ (d$_6$-DMSO) 10.79 (br s, 1H, isomer A and B), 7.77-7.72 (m, 2H, isomers A and B), 7.59-7.55 (m, 2H, isomers A and B), 7.52-7.49 (m, 1H, isomers A and B), 7.45-7.41 (m, 2H, isomers A and B), 7.03 (d, 0.58H, isomer B), 7.0 (d, 0.42H, isomer A), 3.1 (m, 2H, isomers A and B), 2.17 (s, 3H, isomers A and B), 2.1-1.6 (m, 6H, isomers A and B). |

TABLE A-continued

| Compound Number | Structure | ¹H NMR (CDCl₃ unless stated) or other physical data |
|---|---|---|
| T62 | 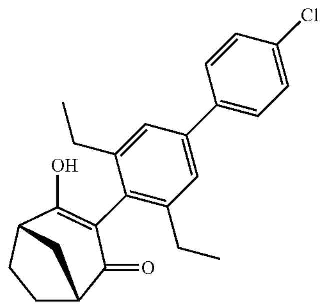 [SMILES: CCc1cc(-c2ccc(Cl)cc2)cc(CC)c1C1=C(O)[C@H]2CC[C@H](C2)C1=O] | δ 7.5 (dd, 2H), 7.4 (dd, 2H), 7.32-7.30 (m, 2H), 5.46 (s, 1H), 3.13-3.06 (m, 2H), 2.6-2.1 (m, 7H), 2.05-2.0 (m, 1H), 1.9-1.8 (m, 1H) 1.88-1.7 (m, 1H), 1.2-1.0 (m, 6H). |
| T63 | 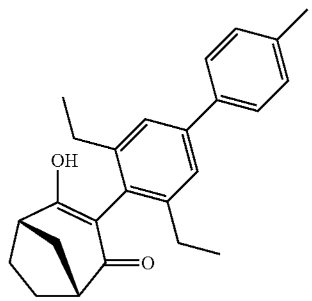 [SMILES: CCc1cc(-c2ccc(C)cc2)cc(CC)c1C1=C(O)[C@H]2CC[C@H](C2)C1=O] | δ 7.48 (m, 2H), 7.34 (m, 2H), 7.2 (m, 2H), 5.54 (s, 1H), 3.13-3.06 (m, 2H), 2.6-2.1 (m, 10H), 2.05-1.95 (m, 1H), 1.9-1.8 (m, 1H), 1.88-1.7 (m, 1H), 1.2-1.0 (m, 6H). |
| T64 | 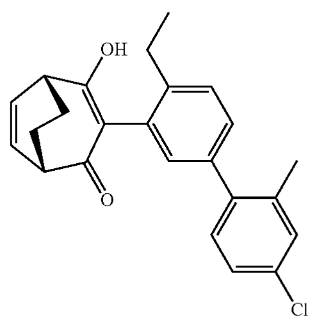 [SMILES: CCc1ccc(-c2ccc(Cl)cc2C)cc1C1=C(O)[C@H]2C=C[C@H](CC2)C1=O] | δ 7.36 (m, 1H), 7.30-7.09 (m, 4H), 6.92 (dd, 1H), 6.60-6.27 (br. d, 2H), 5.80-4.90 (br. s, 1H), 3.85-3.50 (broad d, 2H), 2.53-1.84 (br. m, 9H), 1.16 (t, 1.8H, isomer A), 1.10 (t, 1.2H, isomer B). |
| T65 | 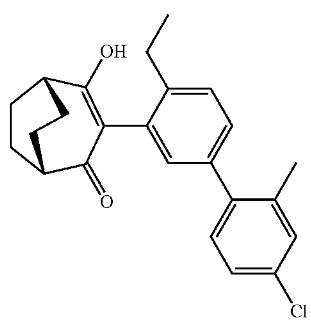 [SMILES: CCc1ccc(-c2ccc(Cl)cc2C)cc1C1=C(O)[C@H]2CC[C@H](CC2)C1=O] | δ 7.38 (dd, 1H), 7.30-7.13 (m, 4H), 6.98 (dd, 1H), 5.51 (s, 1H), 2.95 (m, 2H), 2.50 (m, 2H), 2.27 (s, 3H), 1.98-1.84 (m, 8H), 1.17 (t, 3H). |
| T66 | 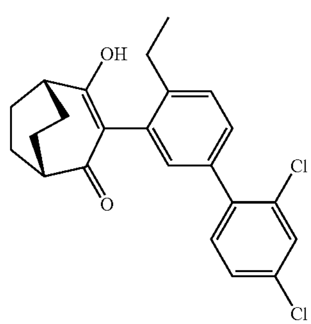 [SMILES: CCc1ccc(-c2ccc(Cl)cc2Cl)cc1C1=C(O)[C@H]2CC[C@H](CC2)C1=O] | δ 7.47 (m, 1H), 7.44-7.27 (m, 4H), 7.12 (dd, 1H), 5.59 (s, 1H), 2.97 (m, 2H), 2.50 (m, 2H), 1.99-1.84 (m, 8H), 1.17 (t, 3H). |

TABLE A-continued

| Compound Number | Structure | ¹H NMR (CDCl₃ unless stated) or other physical data |
|---|---|---|
| T67 | 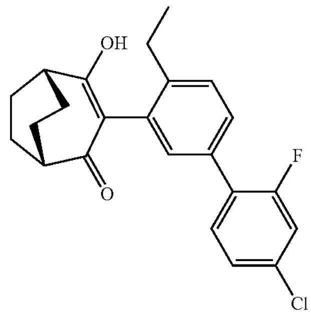 [SMILES: CCc1ccc(-c2ccc(Cl)cc2F)cc1C1=C(O)[C@H]2CC[C@H](CC2)C1=O] | δ 7.49 (dd, 1H), 7.34-7.45 (m, 2H), 7.21-7.14 (m, 3H), 5.56 (s, 1H), 2.97 (m, 2H), 2.49 (m, 2H), 2.01-1.85 (m, 8H), 1.15 (t, 3H). |
| T68 | 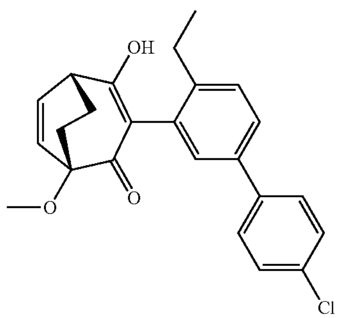 [SMILES: CCc1ccc(-c2ccc(Cl)cc2)cc1C1=C(O)[C@H]2C=C[C@](OC)(CC2)C1=O] | Method A: LCMS (ES⁺) 395 (MH+); HPLC retention time 1.78 minutes. |
| T69 | 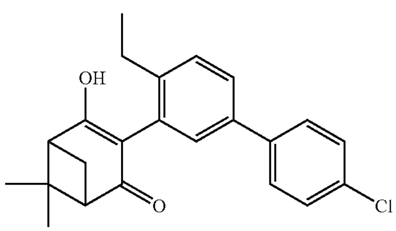 [SMILES: CCc1ccc(-c2ccc(Cl)cc2)cc1C1=C(O)C2CC(C1=O)C2(C)C] | Method A: LC-MS (ES+) 367 (MH+); HPLC retention time 1.74 minutes. |
| T70 | 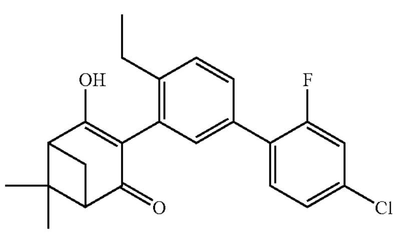 [SMILES: CCc1ccc(-c2ccc(Cl)cc2F)cc1C1=C(O)C2CC(C1=O)C2(C)C] | Method A: LC-MS (ES+) 385 (MH+); HPLC retention time 1.79 minutes. |
| T71 | 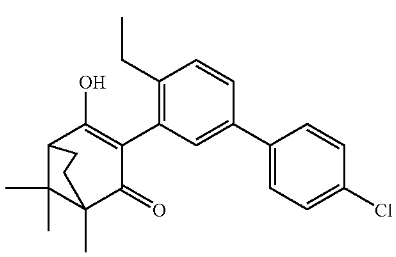 [SMILES: CCc1ccc(-c2ccc(Cl)cc2)cc1C1=C(O)C2CCC(C)(C1=O)C2(C)C] | Method A: LC-MS (ES+) 395 (MH+); HPLC retention time 1.91 minutes |
| T72 | 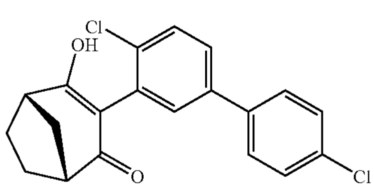 [SMILES: O=C1C(c2cc(-c3ccc(Cl)cc3)ccc2Cl)=C(O)[C@H]2CC[C@@H]1C2] | δ 7.56-7.38 (m, 6H), 7.36-7.33 (m, 0.6 H), 7.28-7.24 (m, 0.4 H), 3.16-3.04 (m, 2H), 2.35-2.08 (m, 3H), 2.07-1.85 (m, 2H), 1.75-1.63 (m, 1H). |

TABLE A-continued

| Compound Number | Structure | ¹H NMR (CDCl₃ unless stated) or other physical data |
|---|---|---|
| T73 | 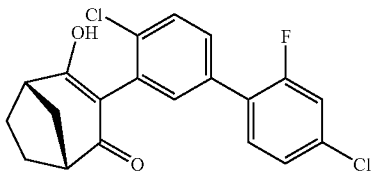 [SMILES: O=C1C(c2cc(-c3ccc(Cl)cc3F)ccc2Cl)=C(O)[C@H]2CC[C@@H]1C2] | δ 7.52-7.46 (m, 1H), 7.44-7.38 (m, 1H), 7.35-7.27 (m, 2H), 7.22-7.14 (m, 2H), 3.08-3.01 (m, 2H), 2.32-2.11 (m, 3H), 2.02-1.75 (m, 2H), 1.71-1.62 (m, 1H). |
| T74 | 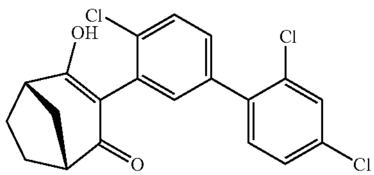 [SMILES: O=C1C(c2cc(-c3ccc(Cl)cc3Cl)ccc2Cl)=C(O)[C@H]2CC[C@@H]1C2] | δ 7.52-7.45 (m, 2H), 7.32 (dd, 1H), 7.29-7.20 (m, 2H), 7.19 (d, 0.6H), 7.12 (d, 0.4 H), 3.08-3.00 (m, 2H), 2.32-2.07 (m, 3H), 2.03-1.74 (m, 2H), 1.70-1.61 (m, 1H). |
| T75 | 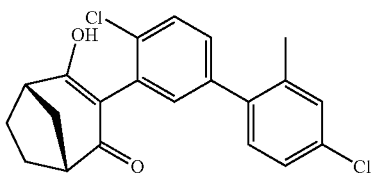 [SMILES: Cc1cc(Cl)ccc1-c1ccc(Cl)c(C2=C(O)[C@H]3CC[C@H](C3)C2=O)c1] | δ 7.49-7.43 (m, 1H), 7.25-7.22 (m, 1H), 7.21-7.15 (m, 2H), 7.12-7.09 (m, 1H), 7.09-7.06 (m, 1H), 3.08-3.00 (m, 2H), 2.33-2.05 (m, 3H), 2.23 (s, 3H), 2.05-1.70 (m, 2H), 1.70-1.62 (m, 1H). |
| T76 | 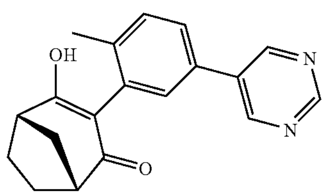 [SMILES: Cc1ccc(-c2cncnc2)cc1C1=C(O)[C@H]2CC[C@H](C2)C1=O] | CD₃OD δ 9.11 (s, 1H, isomers A and B), 9.06 (app. d, 2H, isomers A and B), 7.55 (m, 1H, isomers A and B), 7.40 (m, 1H, isomers A and B), 7.33 (d, 0.6H, isomer A), 7.27 (d, 0.4H, isomer B), 3.04 (m, 2H, isomers A and B), 2.28 (m, 3H, isomers A and B), 2.23 (s, 1.2H, isomer B), 2.12 (s, 1.8H, isomer A), 1.90 (m, 2H, isomers A and B), 1.75 (m, 1H, isomers A and B). |
| T77 | 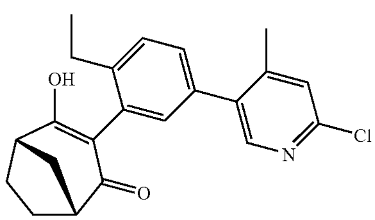 [SMILES: CCc1ccc(-c2cnc(Cl)cc2C)cc1C1=C(O)[C@H]2CC[C@H](C2)C1=O] | CD₃OD δ 8.13 (m, 1H, isomers A and B), 7.32 (m, 2H, isomers A and B), 7.20 (m, 1H, isomers A and B), 6.90 (d, 0.6H, isomer A), 6.81 (d, 0.4H, isomer B), 3.00 (m, 2H, isomers A and B), 2.52 (q, 0.8H, isomer B), 2.40 (q, 1.2H, isomer A), 2.32 (app. d, 3H, isomers A and B), 2.21 (m, 3H, isomers A and B), 1.85 (m, 2H, isomers A and B), 1.70 (m, 1H, isomers A and B), 1.10 (m, 3H, isomers A and B). |
| T78 | 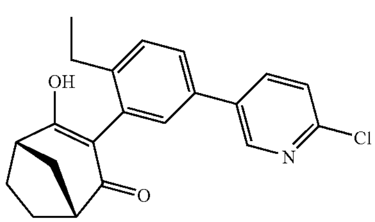 [SMILES: CCc1ccc(-c2ccc(Cl)nc2)cc1C1=C(O)[C@H]2CC[C@H](C2)C1=O] | CD₃OD δ 8.58 (m, 1H, isomers A and B), 8.02 (m, 1H, isomers A and B), 7.50 (m, 2H, isomers A and B), 7.35 (m, 1H, isomers A and B), 7.20 (m, 0.6H, isomer A), 7.07 (d, 0.4H, isomer B), 3.00 (m, 2H, isomers A and B), 2.50 (q, 0.8H, isomer B), 2.39 (q, 1.2H, isomer A), 2.22 (m, 3H, isomers A and B), 1.85 (m, 2H, isomers A and B), 1.71 (m, 1H, isomers A and B), 1.10 (m, 3H, isomers A and B) |
| T79 | 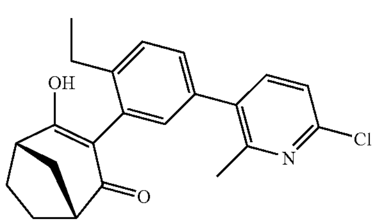 [SMILES: CCc1ccc(-c2ccc(Cl)nc2C)cc1C1=C(O)[C@H]2CC[C@H](C2)C1=O] | CD₃OD δ 7.62 (dd, 1H, isomers A and B), 7.31 (m, 2H, isomers A and B), 7.20 (m, 1H, isomers A and B), 6.90 (d, 0.6H, isomer A), 6.80 (d, 0.4H, isomer B), 3.00 (m, 2H, isomers A and B), 2.51 (q, 0.8H, isomer B), 2.46 (app. d, 3H, isomers A and B), 2.39 (q, 1.2H, isomer A), 2.20 (m, 3H, isomers A and B), 1.85 (m, 2H, isomers A and B), 1.69 (m, 1H, isomers A and B), 1.12 (m, 3H, isomers A and B). |

TABLE A-continued

| Compound Number | Structure | ¹H NMR (CDCl₃ unless stated) or other physical data |
|---|---|---|
| T80 | 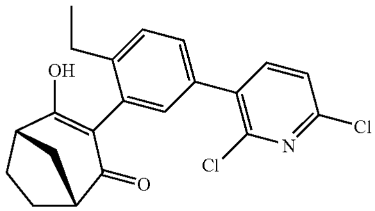 [SMILES: CCc1ccc(-c2ccc(Cl)nc2Cl)cc1C1=C(O)[C@H]2CC[C@H](C2)C1=O] | CD₃OD δ 7.80 (dd, 1H, isomers A and B), 7.46 (dd, 1H, isomers A and B), 7.32 (m, 2H, isomers A and B), 7.01 (d, 0.6H, isomer A), 6.91 (d, 0.4H, isomer B), 3.00 (m, 2H, isomers A and B), 2.50 (q, 0.8H, isomer B), 2.39 (q, 1.2H, isomer A), 2.20 (m, 3H, isomers A and B), 1.84 (m, 2H, isomers A and B), 1.70 (m, 1H, isomers A and B), 1.12 (m, 3H, isomers A and B). |
| T81 | 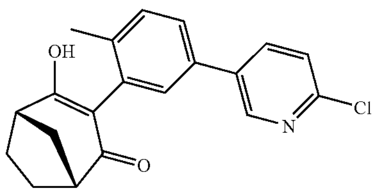 [SMILES: Cc1ccc(-c2ccc(Cl)nc2)cc1C1=C(O)[C@H]2CC[C@H](C2)C1=O] | CD₃OD δ 8.52 (m, 1H, isomers A and B), 8.00 (m 1H, isomers A and B), 7.46 (m, 1H, isomers A and B), 7.41 (m, 1H, isomers A and B), 7.29 (m, 1H, isomers A and B), 7.20 (d, 0.6H, isomer A), 7.12 (d, 0.4H, isomer B), 2.96 (m, 2H, isomers A and B), 2.20 (m, 3H, isomers A and B), 2.15 (s, 1.2H, isomer B), 2.05 (s, 1.8H, isomer A), 1.85 (m, 2H, isomers A and B), 1.69 (m, 1H, isomers A and B). |
| T82 | 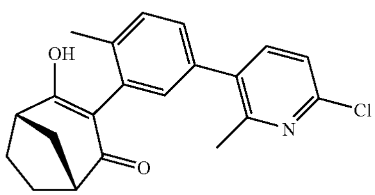 [SMILES: Cc1ccc(-c2ccc(Cl)nc2C)cc1C1=C(O)[C@H]2CC[C@H](C2)C1=O] | CD₃OD δ 7.62 (dd, 1H, isomers A and B), 7.30 (m, 2H, isomers A and B), 7.13 (m, 1H, isomers A and B), 6.93 (d, 0.6H, isomer A), 6.88 (d, 0.4H, isomer B), 3.06 (m, 2H, isomers A and B), 2.46 (app. d, 3H, isomers A and B), 2.20 (m, 3H, isomers A and B), 2.19 (s, 1.2H, isomer B), 2.09 (s, 1.8H, isomer A), 1.85 (m, 2H, isomers A and B), 1.70 (m, 1H, isomers A and B). |
| T83 | 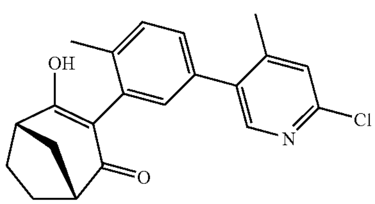 [SMILES: Cc1ccc(-c2cnc(Cl)cc2C)cc1C1=C(O)[C@H]2CC[C@H](C2)C1=O] | CD₃OD δ 8.14 (d, 1H, isomers A and B), 7.40 (d, 1H, isomers A and B), 7.31 (m, 1H, isomers A and B), 7.15 (m, 1H, isomers A and B), 6.94 (d, 0.6H, isomer A), 6.87 (d, 0.4H, isomer B), 3.00 (m, 2H, isomers A and B), 2.32 (app. d, 3H, isomers A and B), 2.22 (m, 3H, isomers A and B), 2.20 (s, 1.2H, isomer B), 2.10 (s, 1.8H, isomer A), 1.85 (m, 2H, isomers A and B), 1.70 (m, 1H, isomers A and B). |
| T84 | 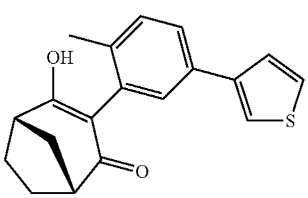 [SMILES: Cc1ccc(-c2ccsc2)cc1C1=C(O)[C@H]2CC[C@H](C2)C1=O] | CD₃OD δ 7.49 (m, 1H, isomers A and B), 7.42 (m, 1H, isomers A and B), 7.37 (m, 2H, isomers A and B), 7.20 (m, 2H, isomers A and B), 2.98 (m, 2H, isomers A and B), 2.20 (m, 3H, isomers A and B), 2.11 (s, 1.2H, isomer B), 2.00 (s, 1.8H, isomer A), 1.85 (m, 2H, isomers A and B), 1.68 (m, 1H, isomers A and B). |
| T85 | 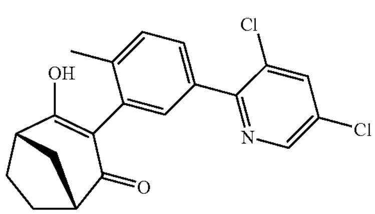 [SMILES: Cc1ccc(-c2ncc(Cl)cc2Cl)cc1C1=C(O)[C@H]2CC[C@H](C2)C1=O] | CD₃OD δ 8.52 (m, 1H, isomers A and B), 8.08 (m, 1H, isomers A and B), 7.51 (dd 1H, isomers A and B) 7.30 (m, 1.6H, isomers A and B), 7.21 (d, 0.4H, isomer B), 3.00 (m, 2H, isomers A and B), 2.22 (m, 3H, isomers A and B), 2.20 (s, 1.2H, isomer B), 2.10 (s, 1.8H, isomer A), 1.85 (m, 2H, isomers A and B), 1.70 (m, 1H, isomers A and B). |
| T86 | 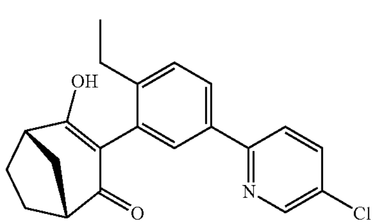 [SMILES: CCc1ccc(-c2ccc(Cl)cn2)cc1C1=C(O)[C@H]2CC[C@H](C2)C1=O] | CD₃OD δ 8.56 (m, 1H, isomers A and B), 7.88 (m, 1H, isomers A and B), 7.85 (m, 2H, isomers A and B), 7.57 (d, 0.6H, isomer A), 7.50 (d, 0.4H, isomer B), 7.36 (t, 1H, isomers A and B), 3.02 (m, 2H, isomers A and B), 2.52 (q, 0.8H, isomer B), 2.40 (q, 1.2H, isomer A), 2.25 (m, 3H, isomers A and B), 1.85 (m, 2H, isomers A and B), 1.70 (m, 1H, isomers A and B), 1.13 (m, 3H, isomers A and B). |

TABLE A-continued

| Compound Number | Structure | $^1$H NMR (CDCl$_3$ unless stated) or other physical data |
|---|---|---|
| T87 | 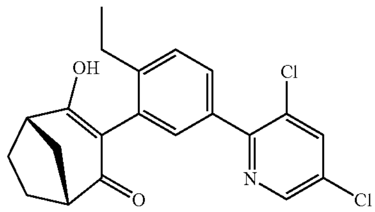 [SMILES: CCc1ccc(-c2ncc(Cl)cc2Cl)cc1C1=C(O)[C@H]2CC[C@H](C2)C1=O] | CD$_3$OD δ 8.53 (m, 1H, isomers A and B), 8.07 (d, 1H, isomers A and B), 7.60 (d, 1H, isomers A and B), 7.35 (m, 1H, isomers A and B) 7.30 (d, 0.6H, isomer A), 7.20 (d, 0.4H, isomer B), 3.00 (m, 2H, isomers A and B), 2.54 (q, 0.8H, isomer B), 2.42 (q, 1.2H, isomer A), 2.22 (m, 3H, isomers A and B), 1.85 (m, 2H, isomers A and B), 1.72 (m, 1H, isomers A and B), 1.16 (t, 1.2H, isomer B), 1.11 (t, 1.8H, isomer A). |
| T88 | 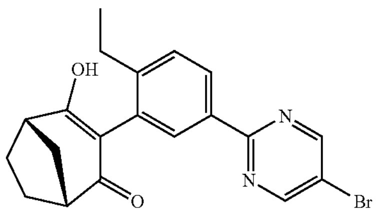 [SMILES: CCc1ccc(-c2ncc(Br)cn2)cc1C1=C(O)[C@H]2CC[C@H](C2)C1=O] | CD$_3$OD δ 8.88 (d, 2H, isomers A and B), 8.27 (d, 1H, isomers A and B), 8.00 (d, 0.6H, isomer A), 7.92 (d, 0.4H, isomer B), 7.36 (t, 1H, isomers A and B), 3.02 (m, 2H, isomers A and B), 2.53 (q, 0.8H, isomer B), 2.40 (q, 1.2H, isomer A), 2.25 (m, 3H, isomers A and B), 1.85 (m, 2H, isomers A and B), 1.72 (m, 1H, isomers A and B), 1.15 (t, 1.2H, isomer B), 1.10 (t, 1.8H, isomer A) |
| T89 | 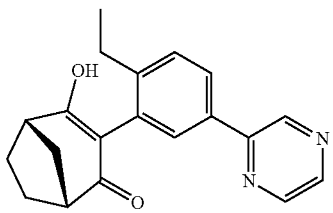 [SMILES: CCc1ccc(-c2cnccn2)cc1C1=C(O)[C@H]2CC[C@H](C2)C1=O] | CD$_3$OD δ 9.05 (m, 1H, isomers A and B), 8.62 (m, 1H, isomers A and B), 8.47 (m, 1H, isomers A and B), 7.93 (m, 1H, isomers A and B), 7.66 (d, 0.6H, isomer A), 7.58 (d, 0.4H, isomer B), 7.40 (m, 1H, isomers A and B), 3.02 (m, 2H, isomers A and B), 2.54 (q, 0.8H, isomer B), 2.40 (q, 1.2H, isomer A), 2.26 (m, 3H, isomers A and B), 1.86 (m, 2H, isomers A and B), 1.74 (m, 1H, isomers A and B), 1.14 (m, 3H, isomers A and B) |
| T90 | 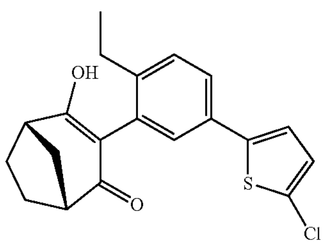 [SMILES: CCc1ccc(-c2ccc(Cl)s2)cc1C1=C(O)[C@H]2CC[C@H](C2)C1=O] | CD$_3$OD δ 7.42 (m, 1H, isomers A and B), 7.26 (m, 1H, isomers A and B), 7.11 (m, 1.6H, isomers A and B), 7.02 (d, 0.4H, isomer B), 6.91 (m, 1H, isomers A and B), 3.00 (m, 2H, isomers A and B), 2.46 (q, 0.8H, isomer B), 2.34 (q, 1.2H, isomer A), 2.23 (m, 3H, isomers A and B), 1.85 (m, 2H, isomers A and B), 1.70 (m, 1H, isomers A and B), 1.05 (m, 3H, isomers A and B) |
| T91 | 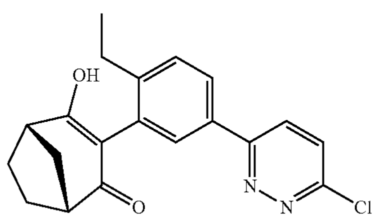 [SMILES: CCc1ccc(-c2ccc(Cl)nn2)cc1C1=C(O)[C@H]2CC[C@H](C2)C1=O] | CD$_3$OD δ 8.13 (dd, 1H, isomers A and B), 7.93 (m, 1H, isomers A and B), 7.80 (m, 1H, isomers A and B), 7.67 (d, 0.6H, isomer A), 7.60 (d, 0.4H, isomer B), 7.42 (m, 1H, isomers A and B), 3.02 (m, 2H, isomers A and B), 2.55 (q, 0.8H, isomer B), 2.42 (q, 1.2H, isomer A), 2.25 (m, 3H, isomers A and B), 1.85 (m, 2H, isomers A and B), 1.72 (m, 1H, isomers A and B), 1.15 (m, 3H, isomers A and B) |
| T92 | 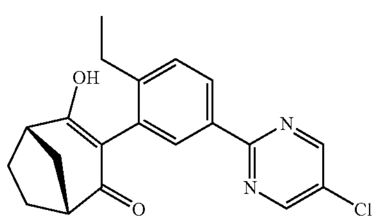 [SMILES: CCc1ccc(-c2ncc(Cl)cn2)cc1C1=C(O)[C@H]2CC[C@H](C2)C1=O] | CD$_3$OD δ 8.79 (d, 2H, isomers A and B), 8.26 (dd, 1H, isomers A and B), 7.99 (d, 0.6H, isomer A), 7.91 (d, 0.4H, isomer B), 7.35 (m, 1H, isomers A and B), 3.01 (m, 2H, isomers A and B), 2.53 (q, 0.8H, isomer B), 2.38 (q, 1.2H, isomer A), 2.24 (m, 3H, isomers A and B), 1.85 (m, 2H, isomers A and B), 1.74 (m, 1H, isomers A and B), 1.12 (m, 3H, isomers A and B). |
| T93 | 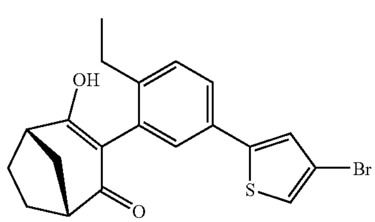 [SMILES: CCc1ccc(-c2cc(Br)cs2)cc1C1=C(O)[C@H]2CC[C@H](C2)C1=O] | CD$_3$OD δ 7.47 (m, 1H, isomers A and B), 7.25 (m, 3H, isomers A and B), 7.17 (d, 0.6H, isomer A), 7.08 (d, 0.4H, isomer B), 3.00 (m, 2H, isomers A and B), 2.46 (q, 0.8H, isomer B), 2.34 (q, 1.2H, isomer A), 2.22 (m, 3H, isomers A and B), 1.85 (m, 2H, isomers A and B), 1.72 (m, 1H, isomers A and B), 1.07 (m, 3H, isomers A and B) |

TABLE A-continued

| Compound Number | Structure | ¹H NMR (CDCl₃ unless stated) or other physical data |
|---|---|---|
| T94 | 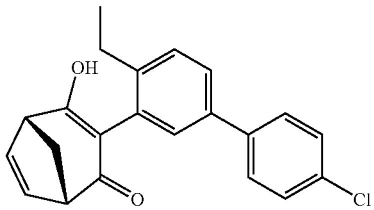 [SMILES: CCc1ccc(-c2ccc(Cl)cc2)cc1C1=C(O)[C@H]2C=C[C@H](C2)C1=O] | CD₃OD δ 7.56 (m, 2H, isomers A and B), 7.48 (m, 1H, isomers A and B), 7.41 (m, 2H, isomers A and B), 7.32 (d, 0.4H, isomer B), 7.28 (d, 0.6H, isomer A), 7.22 (d, 0.6H, isomer A), 7.01 (d, 0.4H, isomer B), 6.68 (s, 2H, isomers A and B), 3.41 (m, 2H, isomers A and B), 2.82 (m, 1H, isomers A and B), 2.63 (m, 1H, isomers A and B), 2.53 (q, 0.8H, isomer B), 2.31 (q, 1.2H, isomer A), 1.17 (t, 1.2H, isomer B), 1.04 (t, 1.8H, isomer A) |
| T95 | 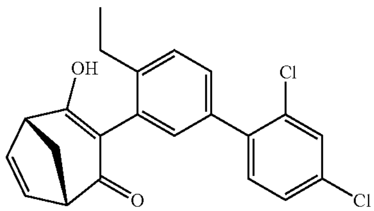 [SMILES: CCc1ccc(-c2ccc(Cl)cc2Cl)cc1C1=C(O)[C@H]2C=C[C@H](C2)C1=O] | CD₃OD δ 7.52 (d, 1H, isomers A and B), 7.35 (m, 2H, isomers A and B), 7.30 (m, 2H, isomers A and B), 7.00 (s, 0.6H, isomer A), 6.80 (s, 0.4H, isomer B), 6.65 (app. d, 2H, isomers A and B), 3.38 (m, 2H, isomers A and B), 2.78 (m, 1H, isomers A and B), 2.55 (m, 1.8H, isomers A and B), 2.30 (q, 1.2H, isomer A), 1.16 (t, 1.2H, isomer B), 1.03 (t, 1.8H, isomer A) |
| T96 | 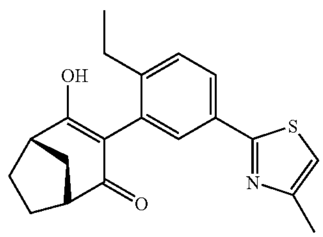 | (CD₃OD) δ 7.75 (t, 1H); 7.52 (s, 0.6H, isomer A); 7.46 (s, 0.4H, isomer B); 7.37 (t, 1H); 7.22 (s, 1H); 3.03 (bs, 2H); 2.52 (q, 0.8H, isomer B); 2.47 (s, 3H); 2.39 (q, 1.2H, isomer A); 2.28-2.17 (m, 3H); 1.89-1.82 (m, 2H); 1.74-1.70 (m, 1H); 1.14 (t, 1.2H, isomer B); 1.09 (t, 1.8H, isomer A) |
| T97 | 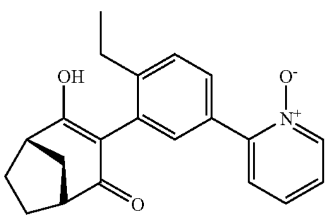 | (CD₃OD) δ 8.48-8.44 (m, 1H); 7.81-7.76 (m, 1H); 7.75-7.69 (m, 1H); 7.62 (t, 1H); 7.54 (t, 1H); 7.38 (t, 1H); 7.36 (s, 0.6H, isomer A); 7.26 (s, 0.4H, isomer B); 3.01 (bs, 2H); 2.55 (q, 0.8H, isomer B); 2.42 (q, 1.2H, isomer A); 2.28-2.16 (m, 3H); 1.88-1.81 (m, 2H); 1.74-1.67 (m, 1H); 1.16 (t, 1.2H, isomer B); 1.11 (t, 1.8H, isomer A) |
| T98 | 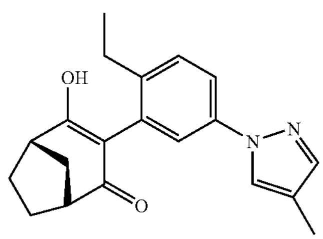 | (CD₃OD) δ 7.87 (s, 1H); 7.48-7.41 (m, 2H); 7.26 (t, 1H); 7.20 (s, 0.6H, isomer A); 7.13 (s, 0.4H, isomer B); 2.98-2.92 (m, 2H); 2.44 (q, 1.2H, isomer A); 2.31 (q, 0.8H, isomer B); 2.21-2.13 (m, 3H); 2.09 (s, 3H); 1.86-1.76 (m, 2H); 1.69-1.63 (m, 1H); 1.07 (t, 1.2H, isomer B); 1.03 (t, 1.8H, isomer A) |
| T99 | | Method B: LC-MS (ES+) 343 (MH+); HPLC retention time 1.21 minutes |
| | | |

TABLE A-continued

| Compound Number | Structure | $^1$H NMR (CDCl$_3$ unless stated) or other physical data |
| --- | --- | --- |
| T100 | 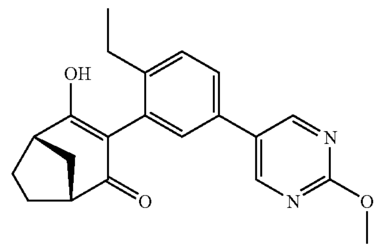 [SMILES: CCc1ccc(-c2cnc(OC)nc2)cc1C1=C(O)[C@H]2CC[C@H](C2)C1=O] | Method B: LC-MS (ES+) 351 (MH+); HPLC retention time 1.39 minutes. |
| T101 | 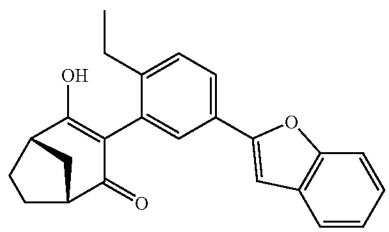 [SMILES: CCc1ccc(-c2cc3ccccc3o2)cc1C1=C(O)[C@H]2CC[C@H](C2)C1=O] | Method B: LC-MS (ES+) 359 (MH+); HPLC retention time 1.59 minutes |
| T102 | 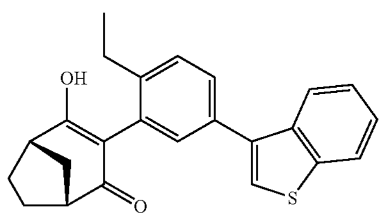 [SMILES: CCc1ccc(-c2csc3ccccc23)cc1C1=C(O)[C@H]2CC[C@H](C2)C1=O] | Method B: LC-MS (ES+) 375 (MH+); HPLC retention time 1.64 minutes |
| T103 | 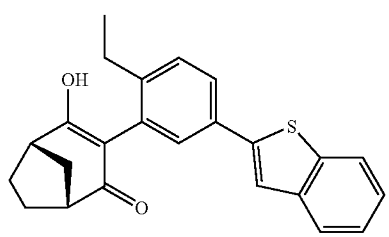 | Method B: LC-MS (ES+) 375 (MH+); HPLC retention time 1.65 minutes |
| T104 | 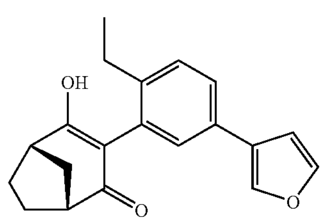 [SMILES: CCc1ccc(-c2ccoc2)cc1C1=C(O)[C@H]2CC[C@H](C2)C1=O] | Method B: LC-MS (ES+) 309 (MH+); HPLC retention time 1.39 minutes |
| T105 | 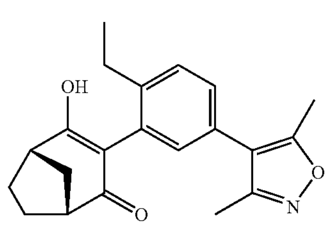 [SMILES: CCc1ccc(-c2c(C)noc2C)cc1C1=C(O)[C@H]2CC[C@H](C2)C1=O] | Method B: LC-MS (ES+) 338 (MH+); HPLC retention time 1.32 minutes |

TABLE A-continued

| Compound Number | Structure | ¹H NMR (CDCl₃ unless stated) or other physical data |
|---|---|---|
| T106 | 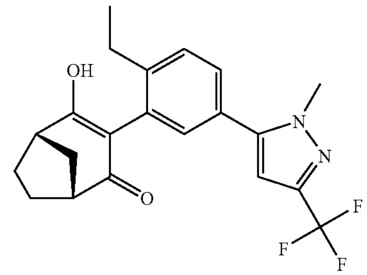 [SMILES: CCc1ccc(-c2cc(C(F)(F)F)nn2C)cc1C1=C(O)[C@H]2CC[C@H](C2)C1=O] | Method B: LC-MS (ES+) 391 (MH+); HPLC retention time 1.48 minutes |
| T107 | 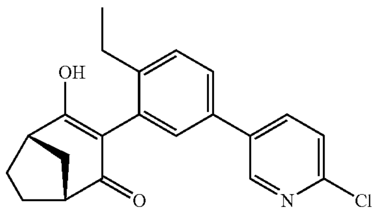 [SMILES: CCc1ccc(-c2ccc(Cl)nc2)cc1C1=C(O)[C@H]2CC[C@H](C2)C1=O] | Method B: LC-MS (ES+) 354 (MH+); HPLC retention time 1.39 minutes |
| T108 | 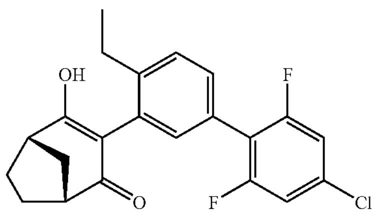 [SMILES: CCc1ccc(-c2c(F)cc(Cl)cc2F)cc1C1=C(O)[C@H]2CC[C@H](C2)C1=O] | Method B: LC-MS (ES+) 389 (MH+); HPLC retention time 1.65 minutes |
| T109 | 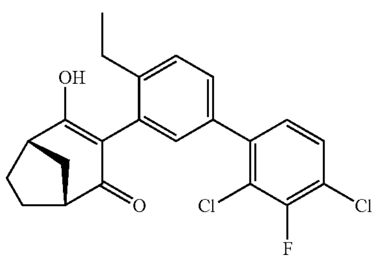 [SMILES: CCc1ccc(-c2ccc(Cl)c(F)c2Cl)cc1C1=C(O)[C@H]2CC[C@H](C2)C1=O] | Method B: LC-MS (ES+) 405 (MH+); HPLC retention time 1.70 minutes |
| T110 | 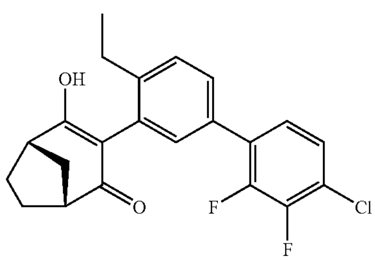 [SMILES: CCc1ccc(-c2ccc(Cl)c(F)c2F)cc1C1=C(O)[C@H]2CC[C@H](C2)C1=O] | Method B: LC-MS (ES+) 389 (MH+); HPLC retention time 1.66 minutes |
| T111 | 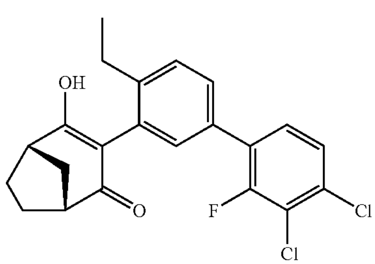 [SMILES: CCc1ccc(-c2ccc(Cl)c(Cl)c2F)cc1C1=C(O)[C@H]2CC[C@H](C2)C1=O] | Method B: LC-MS (ES+) 405 (MH+); HPLC retention time 1.72 minutes |

TABLE A-continued

| Compound Number | Structure | $^1$H NMR (CDCl$_3$ unless stated) or other physical data |
|---|---|---|
| T112 | 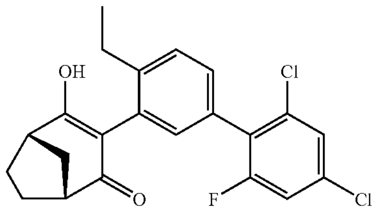 [SMILES: CCc1ccc(-c2c(F)cc(Cl)cc2Cl)cc1C1=C(O)[C@H]2CC[C@H](C2)C1=O] | Method B: LC-MS (ES+) 405 (MH+); HPLC retention time 1.70 minutes |
| T113 | 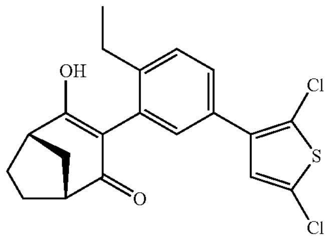 [SMILES: CCc1ccc(-c2cc(Cl)sc2Cl)cc1C1=C(O)[C@H]2CC[C@H](C2)C1=O] | Method B: LC-MS (ES+) 393 (MH+); HPLC retention time 1.73 minutes |

Specific examples of the compounds of the invention include those compounds detailed in Tables 1 to 35

TABLE 1

This table covers 202 compounds of the formula I:

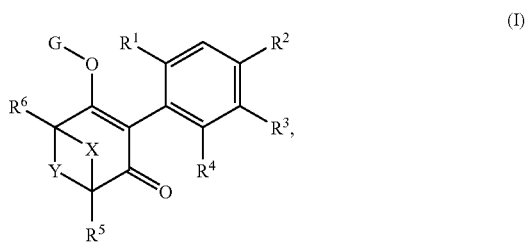

(I)

wherein X is CH$_2$, Y is CH$_2$, R$^1$ is methyl, R$^4$, R$^5$ and R$^6$ are hydrogen, G is hydrogen and R$^2$ and R$^3$ are as defined below:

| Compound Number | R$^2$ | R$^3$ |
|---|---|---|
| 1.001 | phenyl | H |
| 1.002 | 2-fluorophenyl | H |
| 1.003 | 3-fluorophenyl | H |
| 1.004 | 4-fluorophenyl | H |
| 1.005 | 2-chlorophenyl | H |
| 1.006 | 3-chlorophenyl | H |
| 1.007 | 4-chlorophenyl | H |
| 1.008 | 2-bromophenyl | H |
| 1.009 | 3-bromophenyl | H |
| 1.010 | 4-bromophenyl | H |
| 1.011 | 2-methylphenyl | H |
| 1.012 | 3-methylphenyl | H |
| 1.013 | 4-methylphenyl | H |
| 1.014 | 2-cyanophenyl | H |
| 1.015 | 3-cyanophenyl | H |
| 1.016 | 4-cyanophenyl | H |
| 1.017 | 2-methoxyphenyl | H |
| 1.018 | 3-methoxyphenyl | H |
| 1.019 | 4-methoxyphenyl | H |
| 1.020 | 2-trifluoromethylphenyl | H |
| 1.021 | 3-trifluoromethylphenyl | H |
| 1.022 | 4-trifluoromethylphenyl | H |
| 1.023 | 4-trifluoromethoxyphenyl | H |
| 1.024 | 4-difluoromethoxyphenyl | H |
| 1.025 | 4-methylthiophenyl | H |
| 1.026 | 4-methylsulfinylphenyl | H |

TABLE 1-continued

This table covers 202 compounds of the formula I:

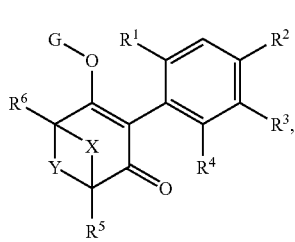

(I)

wherein X is CH$_2$, Y is CH$_2$, R$^1$ is methyl,
R$^4$, R$^5$ and R$^6$ are hydrogen, G is hydrogen
and R$^2$ and R$^3$ are as defined below:

| Compound Number | R$^2$ | R$^3$ |
|---|---|---|
| 1.027 | 4-methylsulfonylphenyl | H |
| 1.028 | 4-trifluoromethylthiophenyl | H |
| 1.029 | 4-trifluoromethylsulfinylphenyl | H |
| 1.030 | 4-trifluoromethylsulfonylphenyl | H |
| 1.031 | 2,3-difluorophenyl | H |
| 1.032 | 2,4-difluorophenyl | H |
| 1.033 | 2,5-difluorophenyl | H |
| 1.034 | 2,6-difluorophenyl | H |
| 1.035 | 3,4-difluorophenyl | H |
| 1.036 | 3,5-difluorophenyl | H |
| 1.037 | 2,3-dichlorophenyl | H |
| 1.038 | 2,4-dichlorophenyl | H |
| 1.039 | 2,5-dichlorophenyl | H |
| 1.040 | 2,6-dichlorophenyl | H |
| 1.041 | 3,4-dichlorophenyl | H |
| 1.042 | 3,5-dichlorophenyl | H |
| 1.043 | 2,3,4-trichlorophenyl | H |
| 1.044 | 2,3,5-trichlorophenyl | H |
| 1.045 | 2,3,6-trichlorophenyl | H |
| 1.046 | 2,4,5-trichlorophenyl | H |
| 1.047 | 2,4,6-trichlorophenyl | H |
| 1.048 | 3,4,5-trichlorophenyl | H |
| 1.049 | 4-chloro-2-fluorophenyl | H |
| 1.050 | 4-chloro-3-fluorophenyl | H |
| 1.051 | 4-chloro-2-methylphenyl | H |
| 1.052 | 4-chloro-3-methylphenyl | H |
| 1.053 | 4-chloro-2-trifluoromethylphenyl | H |
| 1.054 | 4-chloro-3-trifluoromethylphenyl | H |
| 1.055 | 4-chloro-2-cyanophenyl | H |
| 1.056 | 4-chloro-3-cyanophenyl | H |
| 1.057 | 4-chloro-2-methoxyphenyl | H |
| 1.058 | 4-chloro-3-methoxyphenyl | H |
| 1.059 | 4-fluoro-2-chlorophenyl | H |
| 1.060 | 4-fluoro-3-chlorophenyl | H |
| 1.061 | 4-fluoro-2-methylphenyl | H |
| 1.062 | 4-fluoro-3-methylphenyl | H |
| 1.063 | 4-fluoro-2-trifluoromethylphenyl | H |
| 1.064 | 4-fluoro-3-trifluoromethylphenyl | H |
| 1.065 | 2-fluoro-4-trifluoromethylphenyl | H |
| 1.066 | 3-fluoro-4-trifluoromethylphenyl | H |
| 1.067 | 3,4-methylenedioxyphenyl | H |
| 1.068 | benzo[1,3]diox-5-yl | H |
| 1.069 | 2,3-dihydrobenzo[1,4]dioxin-6-yl | H |
| 1.070 | 2-pyridyl | H |
| 1.071 | 3-pyridyl | H |
| 1.072 | 4-pyridyl | H |
| 1.073 | 3-chloropyridin-2-yl | H |
| 1.074 | 4-chloropyridin-2-yl | H |
| 1.075 | 5-chloropyridin-2-yl | H |
| 1.076 | 6-chloropyridin-2-yl | H |
| 1.077 | 2-chloropyridin-3-yl | H |
| 1.078 | 4-chloropyridin-3-yl | H |
| 1.079 | 2-chloropyridin-4-yl | H |
| 1.080 | 3-chloropyridin-4-yl | H |
| 1.081 | 2-chloropyridin-5-yl | H |
| 1.082 | 3-chloropyridin-5-yl | H |
| 1.083 | 3-methylpyridin-2-yl | H |
| 1.084 | 4-methylpyridin-2-yl | H |
| 1.085 | 5-methylpyridin-2-yl | H |

TABLE 1-continued

This table covers 202 compounds of the formula I:

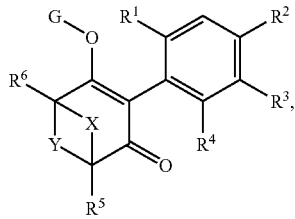

(I)

wherein X is $CH_2$, Y is $CH_2$, $R^1$ is methyl,
$R^4$, $R^5$ and $R^6$ are hydrogen, G is hydrogen
and $R^2$ and $R^3$ are as defined below:

| Compound Number | $R^2$ | $R^3$ |
|---|---|---|
| 1.086 | 6-methylpyridin-2-yl | H |
| 1.087 | 2-methylpyridin-3-yl | H |
| 1.088 | 4-methylpyridin-3-yl | H |
| 1.089 | 2-methylpyridin-4-yl | H |
| 1.090 | 3-methylpyridin-4-yl | H |
| 1.091 | 2-methylpyridin-5-yl | H |
| 1.092 | 3-methylpyridinyl-5-yl | H |
| 1.093 | 2-trifluoromethylpyridin-5-yl | H |
| 1.094 | 3-trifluoromethylpyridin-5-yl | H |
| 1.095 | 2,6-dichloropyridin-3-yl | H |
| 1.096 | 2-chloro-4-methylpyridin-5-yl | H |
| 1.097 | 6-chloro-2-methylpyridin-3-yl | H |
| 1.098 | 5-chlorothiophen-2-yl | H |
| 1.099 | 2-chlorothiophen-3-yl | H |
| 1.100 | 1-methylpyrazol-4-yl | H |
| 1.101 | 4-chloropyrazol-1-yl | H |
| 1.102 | H | phenyl |
| 1.103 | H | 2-fluorophenyl |
| 1.104 | H | 3-fluorophenyl |
| 1.105 | H | 4-fluorophenyl |
| 1.106 | H | 2-chlorophenyl |
| 1.107 | H | 3-chlorophenyl |
| 1.108 | H | 4-chlorophenyl |
| 1.109 | H | 2-bromophenyl |
| 1.110 | H | 3-bromophenyl |
| 1.111 | H | 4-bromophenyl |
| 1.112 | H | 2-methylphenyl |
| 1.113 | H | 3-methylphenyl |
| 1.114 | H | 4-methylphenyl |
| 1.115 | H | 2-cyanophenyl |
| 1.116 | H | 3-cyanophenyl |
| 1.117 | H | 4-cyanophenyl |
| 1.118 | H | 2-methoxyphenyl |
| 1.119 | H | 3-methoxyphenyl |
| 1.120 | H | 4-methoxyphenyl |
| 1.121 | H | 2-trifluoromethylphenyl |
| 1.122 | H | 3-trifluoromethylphenyl |
| 1.123 | H | 4-trifluoromethylphenyl |
| 1.124 | H | 4-trifluoromethoxyphenyl |
| 1.125 | H | 4-difluoromethoxyphenyl |
| 1.126 | H | 4-methylthiophenyl |
| 1.127 | H | 4-methylsulfinylphenyl |
| 1.128 | H | 4-methylsulfonylphenyl |
| 1.129 | H | 4-trifluoromethylthiophenyl |
| 1.130 | H | 4-trifluoromethylsulfinylphenyl |
| 1.131 | H | 4-trifluoromethylsulfonylphenyl |
| 1.132 | H | 2,3-difluorophenyl |
| 1.133 | H | 2,4-difluorophenyl |
| 1.134 | H | 2,5-difluorophenyl |
| 1.135 | H | 2,6-difluorophenyl |
| 1.136 | H | 3,4-difluorophenyl |
| 1.137 | H | 3,5-difluorophenyl |
| 1.138 | H | 2,3-dichlorophenyl |
| 1.139 | H | 2,4-dichlorophenyl |
| 1.140 | H | 2,5-dichlorophenyl |
| 1.141 | H | 2,6-dichlorophenyl |
| 1.142 | H | 3,4-dichlorophenyl |
| 1.143 | H | 3,5-dichlorophenyl |
| 1.144 | H | 2,3,4-trichlorophenyl |

TABLE 1-continued

This table covers 202 compounds of the formula I:

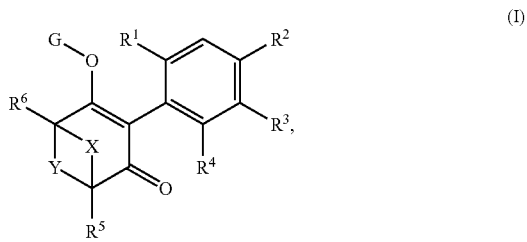

(I)

wherein X is CH$_2$, Y is CH$_2$, R$^1$ is methyl,
R$^4$, R$^5$ and R$^6$ are hydrogen, G is hydrogen
and R$^2$ and R$^3$ are as defined below:

| Compound Number | R$^2$ | R$^3$ |
|---|---|---|
| 1.145 | H | 2,3,5-trichlorophenyl |
| 1.146 | H | 2,3,6-trichlorophenyl |
| 1.147 | H | 2,4,5-trichlorophenyl |
| 1.148 | H | 2 4,6-trichlorophenyl |
| 1.149 | H | 3,4,5-trichlorophenyl |
| 1.150 | H | 4-chloro-2-fluorophenyl |
| 1.151 | H | 4-chloro-3-fluorophenyl |
| 1.152 | H | 4-chloro-2-methylphenyl |
| 1.153 | H | 4-chloro-3-methylphenyl |
| 1.154 | H | 4-chloro-2-trifluoromethylphenyl |
| 1.155 | H | 4-chloro-3-trifluoromethylphenyl |
| 1.156 | H | 4-chloro-2-cyanophenyl |
| 1.157 | H | 4-chloro-3-cyanophenyl |
| 1.158 | H | 4-chloro-2-methoxyphenyl |
| 1.159 | H | 4-chloro-3-methoxyphenyl |
| 1.160 | H | 4-fluoro-2-chlorophenyl |
| 1.161 | H | 4-fluoro-3-chlorophenyl |
| 1.162 | H | 4-fluoro-2-methylphenyl |
| 1.163 | H | 4-fluoro-3-methylphenyl |
| 1.164 | H | 4-fluoro-2-trifluoromethylphenyl |
| 1.165 | H | 4-fluoro-3-trifluoromethylphenyl |
| 1.166 | H | 2-fluoro-4-trifluoromethylphenyl |
| 1.167 | H | 3-fluoro-4-trifluoromethylphenyl |
| 1.168 | H | 3,4-methylenedioxyphenyl |
| 1.169 | H | benzo[1,3]diox-5-yl |
| 1.170 | H | 2,3-dihydrobenzo[1,4]dioxin-6-yl |
| 1.171 | H | 2-pyridyl |
| 1.172 | H | 3-pyridyl |
| 1.173 | H | 4-pyridyl |
| 1.174 | H | 3-chloropyridin-2-yl |
| 1.175 | H | 4-chloropyridin-2-yl |
| 1.176 | H | 5-chloropyridin-2-yl |
| 1.177 | H | 6-chloropyridin-2-yl |
| 1.178 | H | 2-chloropyridin-3-yl |
| 1.179 | H | 4-chloropyridin-3-yl |
| 1.180 | H | 2-chloropyridin-4-yl |
| 1.181 | H | 3-chloropyridin-4-yl |
| 1.182 | H | 2-chloropyridin-5-yl |
| 1.183 | H | 3-chloropyridin-5-yl |
| 1.184 | H | 3-methylpyridin-2-yl |
| 1.185 | H | 4-methylpyridin-2-yl |
| 1.186 | H | 5-methylpyridin-2-yl |
| 1.187 | H | 6-methylpyridin-2-yl |
| 1.188 | H | 2-methylpyridin-3-yl |
| 1.189 | H | 4-methylpyridin-3-yl |
| 1.190 | H | 2-methylpyridin-4-yl |
| 1.191 | H | 3-methylpyridin-4-yl |
| 1.192 | H | 2-methylpyridin-5-yl |
| 1.193 | H | 3-methylpyridinyl-5-yl |
| 1.194 | H | 2-trifluoromethylpyridin-5-yl |
| 1.195 | H | 3-trifluoromethylpyridin-5-yl |
| 1.196 | H | 2,6-dichloropyridin-3-yl |
| 1.197 | H | 2-chloro-4-methylpyridin-5-yl |
| 1.198 | H | 6-chloro-2-methylpyridin-3-yl |
| 1.199 | H | 5-chlorothiophen-2-yl |
| 1.200 | H | 2-chlorothiophen-3-yl |
| 1.201 | H | 1-methylpyrazol-4-yl |
| 1.202 | H | 4-chloropyrazol-1-yl |

Table 2:
This table covers 202 compounds of formula I, wherein X is $CH_2$, Y is $CH_2$, $R^1$ is ethyl, $R^4$, $R^5$ and $R^6$ are hydrogen, G is hydrogen and $R^2$ and $R^3$ are as defined in Table 1.

Table 3:
This table covers 202 compounds of formula I, wherein X is $CH_2$, Y is $CH_2$, $R^1$ and $R^4$ are methyl, $R^5$ and $R^6$ are hydrogen, G is hydrogen and $R^2$ and $R^3$ are as defined in Table 1.

Table 4:
This table covers 202 compounds of formula I, wherein X is $CH_2$, Y is $CH_2$, $R^1$ is ethyl, $R^4$ is methyl, $R^5$ and $R^6$ are hydrogen, G is hydrogen and $R^2$ and $R^3$ are as defined in Table 1.

Table 5:
This table covers 202 compounds of formula I, wherein X is $CH_2$, Y is $CH_2$, $R^1$ and $R^4$ are ethyl, $R^5$ and $R^6$ are hydrogen, G is hydrogen and $R^2$ and $R^3$ are as defined in Table 1.

Table 6:
This table covers 202 compounds of formula I, wherein X is $CH_2$, Y is $C(CH_3)_2$, $R^1$ is methyl, $R^4$, $R^5$ and $R^6$ are hydrogen, G is hydrogen and $R^2$ and $R^3$ are as defined in Table 1.

Table 7:
This table covers 202 compounds of formula I, wherein X is $CH_2$, Y is $C(CH_3)_2$, $R^1$ is ethyl, $R^4$, $R^5$ and $R^6$ are hydrogen, G is hydrogen and $R^2$ and $R^3$ are as defined in Table 1.

Table 8:
This table covers 202 compounds of formula I, wherein X is $CH_2$, Y is $C(CH_3)_2$, $R^1$ and $R^4$ are methyl, $R^5$ and $R^6$ are hydrogen, G is hydrogen and $R^2$ and $R^3$ are as defined in Table 1.

Table 9:
This table covers 202 compounds of formula I, wherein X is $CH_2$, Y is $C(CH_3)_2$, $R^1$ is ethyl, $R^4$ is methyl, $R^5$ and $R^6$ are hydrogen, G is hydrogen and $R^2$ and $R^3$ are as defined in Table 1.

Table 10:
This table covers 202 compounds of formula I, wherein X is $CH_2$, Y is $C(CH_3)_2$, $R^1$ and $R^4$ are ethyl, $R^5$ and $R^6$ are hydrogen, G is hydrogen and $R^2$ and $R^3$ are as defined in Table 1.

Table 11:
This table covers 202 compounds of formula I, wherein X is $CH_2$, Y is $CH{=}CH$, $R^1$ is methyl, $R^4$, $R^5$ and $R^6$ are hydrogen, G is hydrogen and $R^2$ and $R^3$ are as defined in Table 1.

Table 12:
This table covers 202 compounds of formula I, wherein X is $CH_2$, Y is $CH{=}CH$, $R^1$ is ethyl, $R^4$, $R^5$ and $R^6$ are hydrogen, G is hydrogen and $R^2$ and $R^3$ are as defined in Table 1.

Table 13:
This table covers 202 compounds of formula I, wherein X is $CH_2$, Y is $CH{=}CH$, $R^1$ and $R^4$ are methyl, $R^5$ and $R^6$ are hydrogen, G is hydrogen and $R^2$ and $R^3$ are as defined in Table 1.

Table 14:
This table covers 202 compounds of formula I, wherein X is $CH_2$, Y is $CH{=}CH$, $R^1$ is ethyl, $R^4$ is methyl, $R^5$ and $R^6$ are hydrogen, G is hydrogen and $R^2$ and $R^3$ are as defined in Table 1.

Table 15:
This table covers 202 compounds of formula I, wherein X is $CH_2$, Y is $CH{=}CH$, $R^1$ and $R^4$ are ethyl, $R^5$ and $R^6$ are hydrogen, G is hydrogen and $R^2$ and $R^3$ are as defined in Table 1.

Table 16:
This table covers 202 compounds of formula I, wherein X is $CH_2$, Y is $CH_2$—$CH_2$, $R^1$ is methyl, $R^4$, $R^5$ and $R^6$ are hydrogen, G is hydrogen and $R^2$ and $R^3$ are as defined in Table 1.

Table 17:
This table covers 202 compounds of formula I, wherein X is $CH_2$, Y is $CH_2$—$CH_2$, $R^1$ is ethyl, $R^4$, $R^5$ and $R^6$ are hydrogen, G is hydrogen and $R^2$ and $R^3$ are as defined in Table 1.

Table 18:
This table covers 202 compounds of formula I, wherein X is $CH_2$, Y is $CH_2$—$CH_2$, $R^1$ and $R^4$ are methyl, $R^5$ and $R^6$ are hydrogen, G is hydrogen and $R^2$ and $R^3$ are as defined in Table 1.

Table 19:
This table covers 202 compounds of formula I, wherein X is $CH_2$, Y is $CH_2$—$CH_2$, $R^1$ is ethyl, $R^4$ is methyl, $R^5$ and $R^6$ are hydrogen, G is hydrogen and $R^2$ and $R^3$ are as defined in Table 1.

Table 20:
This table covers 202 compounds of formula I, wherein X is $CH_2$, Y is $CH_2$—$CH_2$, $R^1$ and $R^4$ are ethyl, $R^5$ and $R^6$ are hydrogen, G is hydrogen and $R^2$ and $R^3$ are as defined in Table 1.

Table 21:
This table covers 202 compounds of formula I, wherein X is $CH_2$—$CH_2$, Y is $CH{=}CH$, $R^1$ is methyl, $R^4$, $R^5$ and $R^6$ are hydrogen, G is hydrogen and $R^2$ and $R^3$ are as defined in Table 1.

Table 22:
This table covers 202 compounds of formula I, wherein X is $CH_2$—$CH_2$, Y is $CH{=}CH$, $R^1$ is ethyl, $R^4$, $R^5$ and $R^6$ are hydrogen, G is hydrogen and $R^2$ and $R^3$ are as defined in Table 1.

Table 23:
This table covers 202 compounds of formula I, wherein X is $CH_2$—$CH_2$, Y is $CH{=}CH$, $R^1$ and $R^4$ are methyl, $R^5$ and $R^6$ are hydrogen, G is hydrogen and $R^2$ and $R^3$ are as defined in Table 1.

Table 24:
This table covers 202 compounds of formula I, wherein X is $CH_2$—$CH_2$, Y is $CH{=}CH$, $R^1$ is ethyl, $R^4$ is methyl, $R^5$ and $R^6$ are hydrogen, G is hydrogen and $R^2$ and $R^3$ are as defined in Table 1.

Table 25:
This table covers 202 compounds of formula I, wherein X is $CH_2$—$CH_2$, Y is $CH{=}CH$, $R^1$ and $R^4$ are ethyl, $R^5$ and $R^6$ are hydrogen, G is hydrogen and $R^2$ and $R^3$ are as defined in Table 1.

Table 26:
This table covers 202 compounds of formula I, wherein X is $CH_2$—$CH_2$, Y is $CH_2$—$CH_2$, $R^1$ is methyl, $R^4$, $R^5$ and $R^6$ are hydrogen, G is hydrogen and $R^2$ and $R^3$ are as defined in Table 1.

Table 27:
This table covers 202 compounds of formula I, wherein X is $CH_2$—$CH_2$, Y is $CH_2$—$CH_2$, $R^1$ is ethyl, $R^4$, $R^5$ and $R^6$ are hydrogen, G is hydrogen and $R^2$ and $R^3$ are as defined in Table 1.

Table 28:
This table covers 202 compounds of formula I, wherein X is $CH_2$—$CH_2$, Y is $CH_2$—$CH_2$, $R^1$ and $R^4$ are methyl, $R^5$ and $R^6$ are hydrogen, G is hydrogen and $R^2$ and $R^3$ are as defined in Table 1.

Table 29:
This table covers 202 compounds of formula I, wherein X is $CH_2$—$CH_2$, Y is $CH_2$—$CH_2$, $R^1$ is ethyl, $R^4$ is methyl, $R^5$ and $R^6$ are hydrogen, G is hydrogen and $R^2$ and $R^3$ are as defined in Table 1.

Table 30:
This table covers 202 compounds of formula I, wherein X is $CH_2$—$CH_2$, Y is $CH_2$—$CH_2$, $R^1$ and $R^4$ are ethyl, $R^5$ and $R^6$ are hydrogen, G is hydrogen and $R^2$ and $R^3$ are as defined in Table 1.

Table 31:
This table covers 202 compounds of formula I, wherein X is $CH_2$—$CH_2$, Y is $C(CH_3)_2$, $R^1$ is methyl, $R^4$ and $R^5$ are hydrogen, $R^6$ is methyl, G is hydrogen and $R^2$ and $R^3$ are as defined in Table 1.

Table 32:
This table covers 202 compounds of formula I, wherein X is $CH_2$—$CH_2$, Y is $C(CH_3)_2$, $R^1$ is ethyl, $R^4$ and $R^5$ are hydrogen, $R^6$ is methyl, G is hydrogen and $R^2$ and $R^3$ are as defined in Table 1.

Table 33:
This table covers 202 compounds of formula I, wherein X is $CH_2$—$CH_2$, Y is $C(CH_3)_2$, $R^1$ and $R^4$ are methyl, $R^5$ is hydrogen, $R^6$ is methyl, G is hydrogen and $R^2$ and $R^3$ are as defined in Table 1.

Table 34:
This table covers 202 compounds of formula I, wherein X is $CH_2$—$CH_2$, Y is $C(CH_3)_2$, $R^1$ is ethyl, $R^4$ is methyl, $R^5$ is hydrogen, $R^6$ is methyl, G is hydrogen and $R^2$ and $R^3$ are as defined in Table 1.

Table 35:
This table covers 202 compounds of formula I, wherein X is $CH_2$—$CH_2$, Y is $C(CH_3)_2$, $R^1$ and $R^4$ are ethyl, $R^5$ is hydrogen, $R^6$ is methyl, G is hydrogen and $R^2$ and $R^3$ are as defined in Table 1.

Example 23

Preparation of 3-(3,5-dimethylbiphen-4-yl)-4-oxo-bicyclo[3.2.1]oct-2-en-2-yl 2,2-dimethylpropionate

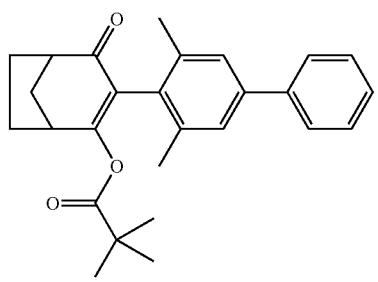 [SMILES: Cc1cc(-c2ccccc2)cc(C)c1C1=C(OC(=O)C(C)(C)C)C2CCC(C2)C1=O]

Pivaloyl chloride (248 μl, 2 mmol) is added to a solution of 3-(3,5-dimethylbiphen-4-yl)bicyclo[3.2.1]octane-2,4-dione (148 mg, 0.46 mmol) in dichloromethane (10 ml) and triethylamine (280 μl, 2 mmol) at room temperature. The reaction mixture is stirred at room temperature overnight. The reaction mixture is evaporated under reduced pressure and the residue is purified by column chromatography on silica gel to afford 3-(3,5-dimethylbiphen-4-yl)-4-oxo-bicyclo[3.2.1]oct-2-en-2-yl 2,2-dimethylpropionate.

Example 24

Preparation of carbonic acid 3-(2',4'-dichloro-4-ethylbiphen-3-yl)-4-oxo-bicyclo[3.2.1]oct-2-en-2-yl ester methyl ester To a solution of 3-(2',4'-dichloro-4-ethylbiphen-3-yl)-bicyclo[3.2.1]octane-2,4-dione (0.133 g, 0.34 mmol) in dichloromethane (2 ml) is added triethylamine (0.24 ml, 1.72 mmol) followed by stirring at room temperature for 5 minutes. To this solution is added methyl chloroformate (0.132 ml, 1.72 mmol) dropwise, then the mixture is left to stand overnight. The reaction mixture is concentrated in vacuo to afford a crude solid which is purified by flash column chromatography on silica gel (100% to 70% hexane/ethyl acetate eluant ratio) to afford carbonic acid 3-(2',4'-dichloro-4-ethylbiphen-3-yl)-4-oxo-bicyclo[3.2.1]oct-2-en-2-yl ester methyl ester.

Additional compounds in Table T2 below were prepared by similar methods using appropriate starting materials.

TABLE T2

| Compound Number | Structure | $^1$H NMR (CDCl$_3$ unless stated) or other physical data |
|---|---|---|
| P1 | 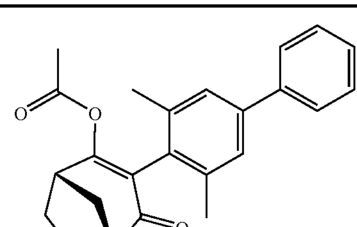 | δ 7.58 (d, 2H), 7.41 (dd, 2H), 7.31 (m, 1H); 7.24 (s, 2H), 3.19 (m, 1H), 3.08 (m, 1H), 2.41 (d, 1H), 2.31-2.10 (m, 3H), 2.15 (s, 3H), 2.07 (s, 3H), 1.93 (s, 3H), 1.87-1.73 (m, 2H) |

TABLE T2-continued

| Compound Number | Structure | ¹H NMR (CDCl₃ unless stated) or other physical data |
|---|---|---|
| P2 | 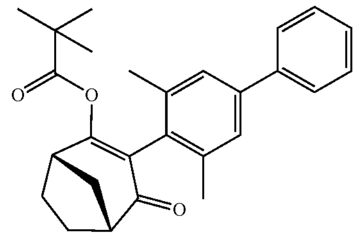 [SMILES: Cc1cc(-c2ccccc2)cc(C)c1C1=C(OC(=O)C(C)(C)C)[C@H]2CC[C@H](C2)C1=O] | δ 7.54 (d, 2H), 7.40 (dd, 2H), 7.31 (m, 1H); 7.22 (s, 2H), 3.19 (m, 1H), 3.05 (m, 1H), 2.42 (d, 1H), 2.31-2.10 (m, 3H), 2.15 (s, 3H), 2.08 (s, 3H), 1.86-1.73 (m, 2H), 1.23 (s, 9H) |
| P3 | 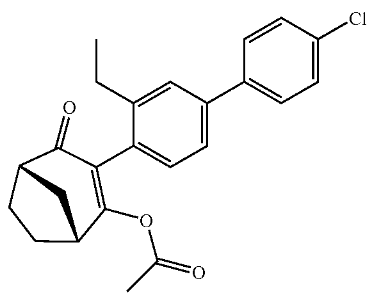 [SMILES: CCc1cc(-c2ccc(Cl)cc2)ccc1C1=C(OC(C)=O)[C@@H]2CC[C@@H](C2)C1=O] | δ 7.52-7.50 (m, 2H), 7.4-7.37 (m, 3H), 7.34-7.3 (m, 1H), 7.0-6.92 (m, 1H), 3.17-3.04 (m, 2H), 2.6-2.0 (m, 6H), 1.9 (s, 3H), 1.9-1.7 (m, 2H), 1.2-1.0 (m, 3H). |
| P4 | 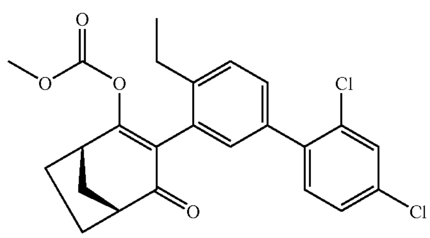 [SMILES: CCc1ccc(-c2ccc(Cl)cc2Cl)cc1C1=C(OC(=O)OC)[C@H]2CC[C@H](C2)C1=O] | δ 7.44 (m, 1H), 7.31 (m, 2H), 7.26 (m, 2H), 7.0 (s, 0.6H, isomer A), 6.94 (s, 0.4H, isomer B), 3.72 (s, 1.8H, isomer A), 3.69 (s, 1.2H, isomer B), 3.15 (m, 2H), 2.57-2.05 (m, 6H), 1.77 (m, 2H), 1.16 (m, 3H). |
| P7 | 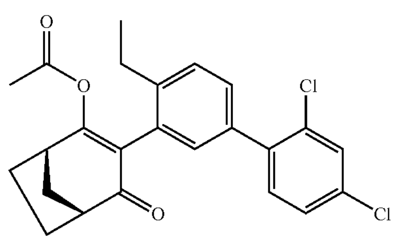 [SMILES: CCc1ccc(-c2ccc(Cl)cc2Cl)cc1C1=C(OC(C)=O)[C@H]2CC[C@H](C2)C1=O] | δ 7.45 (m, 1H), 7.3 (s, 2H), 7.26 (m, 2H), 6.96 (s, 0.6H, isomer A), 6.91 (s, 0.4H, isomer B), 3.15 (m, 1H), 3.04 (m, 1H), 2.46-2.00 (m, 6H), 1.94 (s, 1.8H, isomer A), 1.93 (s, 1.2H, isomer B), 1.70-1.87 (m, 2H), 1.17 (m, 3H). |
| P8 | 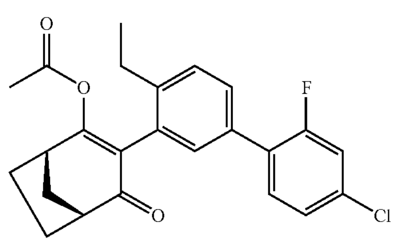 [SMILES: CCc1ccc(-c2ccc(Cl)cc2F)cc1C1=C(OC(C)=O)[C@H]2CC[C@H](C2)C1=O] | δ 7.41-7.39 (m, 1H); 7.34-7.3 (m, 2H); 7.18-7.13 (m, 2H); 7.07 (s, 0.6H, Isomer B); 7.02 (s, 0.4H, Isomer A); 3.16-3.14 (m, 1H); 3.06-3.04 (m, 1H); 2.53-2.33 (m, 2H), 2.31-2.21 (m, 2H); 2.14-2.09 (m, 2H); 1.96 (s, 1.8H, Isomer B); 1.94 (s, 1.2H, Isomer A); 1.82-1.71 (m, 2H); 1.18-1.12 (m, 3H). |
| P9 | 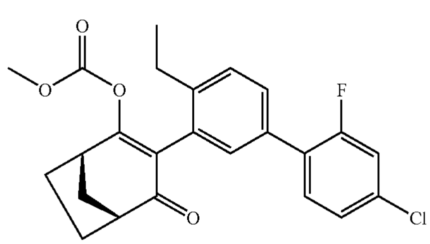 | δ 7.42-7.40 (m, 1H); 7.37-7.31 (m, 2H); 7.18-7.12 (m, 2H); 7.10 (s, 0.6H, Isomer A); 7.03 (s, 0.4H, Isomer B); 3.74 (s, 1.8H, Isomer A); 3.7 (s, 1.2H, Isomer B); 3.18-3.14 (m, 2H); 2.53-2.22 (m, 4H); 2.17-2.12 (m, 2H); 1.85-1.74 (m, 2H); 1.18-1.12 (m, 3H). |

TABLE T2-continued

| Compound Number | Structure | $^1$H NMR (CDCl$_3$ unless stated) or other physical data |
|---|---|---|
| P10 | 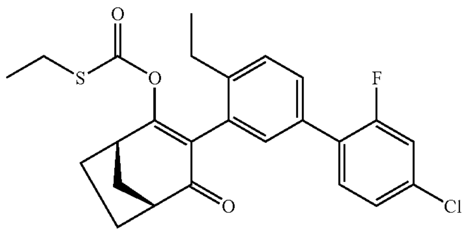 [SMILES: CCSC(=O)OC1=C(c2cc(-c3ccc(Cl)cc3F)ccc2CC)C(=O)[C@@H]2CC[C@H]1C2] | δ 7.43-7.41 (m, 1H); 7.37-7.30 (m, 2H); 7.17-7.13 (m, 2H); 7.08 (s, 0.6H, Isomer A); 7.0 (s, 0.4H, Isomer B); 3.18-3.12 (m, 2H); 2.77-2.68 (m, 2H); 2.53-2.23 (m, 4H); 2.16-2.09 (m, 2H); 1.82-1.72 (m, 2H); 1.18-1.10 (m, 6H). |
| P11 | 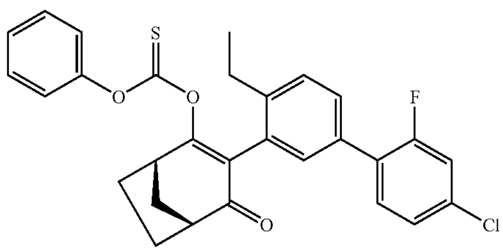 [SMILES: CCc1ccc(-c2ccc(Cl)cc2F)cc1C1=C(OC(=S)Oc2ccccc2)[C@H]2CC[C@H](C2)C1=O] | δ 7.52-7.49 (m, 1H); 7.39-7.23 (m, 6H); 7.18-7.15 (m, 2H); 6.80-6.76 (m, 2H); 3.37-3.34 (m, 1H); 3.21-3.18 (m, 1H); 2.58-2.28 (m, 4H); 2.19-2.15 (m, 2H); 1.88-1.80 (m, 2H); 1.20 (t, 1.2H, Isomer B); 1.13 (1.8H, t, Isomer A). |
| P12 | 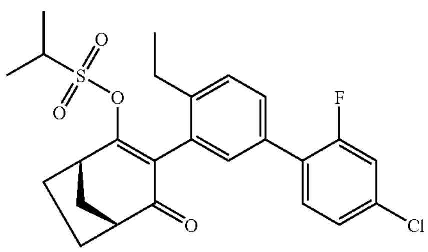 [SMILES: CCc1ccc(-c2ccc(Cl)cc2F)cc1C1=C(OS(=O)(=O)C(C)C)[C@H]2CC[C@H](C2)C1=O] | δ 7.43-7.41 (m, 1H); 7.36-7.31 (m, 2H); 7.19 (s, 0.6H, Isomer A); 7.17-7.14 (m, 2H); 7.05 (s, 0.4H, Isomer B); 3.56-3.51 (m, 1H); 3.18-3.15 (m, 1H); 2.92-2.84 (m, 1H); 2.53-2.46 (m, 1H); 2.40-2.18 (m, 5H); 1.81-1.74 (m, 2H); 1.19 (t, 1.2H, Isomer B); 1.14 (t, 1.8H, Isomer A); 1.09-0.95 (m, 6H). |
| P13 | 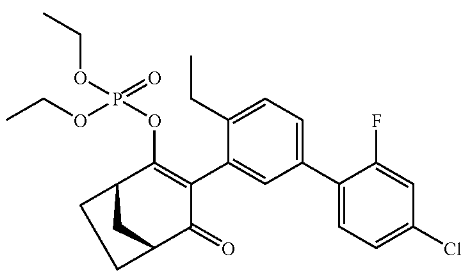 [SMILES: CCOP(=O)(OCC)OC1=C(c2cc(-c3ccc(Cl)cc3F)ccc2CC)C(=O)[C@@H]2CC[C@H]1C2] | δ 7.44-7.43 (m, 2H); 7.32-7.24 (m, 1H); 7.23 (s, 0.6H, Isomer A); 7.13-7.19 (m, 2H); 7.08 (s, 0.4H, Isomer B); 4.05-3.98 (m, 2H); 3.96-3.51 (m, 4H); 3.15-3.13 (m, 1H); 2.57-2.53 (q, 0.8H, Isomer B); 2.43-2.14 (m, 5.2H (1.2H Isomer A)); 1.84-1.70 (m, 2H); 1.27-1.11 (m, 6H); 1.03 (t, 1.2H, Isomer B); 0.94 (t, 1.8H, Isomer A). |

BIOLOGICAL EXAMPLES

Example A

Seeds of a variety of test species were sown in standard soil in pots. After cultivation for one day (pre-emergence) or after 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions in a glasshouse (at 24/16° C., day/night; 14 hours light; 65% humidity) and watered twice daily. After 13 days for pre and post-emergence, the test was evaluated (100=total damage to plant; 0=no damage to plant).

Test Plants:
*Alopecurus myosuroides* (ALOMY), *Avena fatua* (AVEFA), *Setaria faberi* (SETFA), *Echinochloa crus-galli* (ECHCG), *Solanum nigrum* (SOLNI) and *Amaranthus retroflexus* (AMARE)

Pre-Emergence Data:

| Compound Number | Rate g/ha | SOLNI | AMARE | SETFA | ALOMY | ECHCG | AVEFA |
|---|---|---|---|---|---|---|---|
| T1 | 250 | 0 | 0 | 90 | 50 | 90 | 40 |
| T4 | 250 | 0 | 0 | 90 | 50 | 100 | 50 |
| T9 | 250 | — | 0 | 50 | 0 | 0 | 0 |
| T13 | 250 | 0 | 0 | 0 | 0 | 0 | 0 |
| T14 | 250 | 0 | 0 | 0 | 0 | 0 | 0 |

-continued

| Compound Number | Rate g/ha | SOLNI | AMARE | SETFA | ALOMY | ECHCG | AVEFA |
|---|---|---|---|---|---|---|---|
| T15 | 250 | — | 0 | 0 | 0 | — | 0 |
| T16 | 250 | 0 | 0 | 0 | 0 | 0 | 0 |
| T17 | 250 | 0 | 0 | 80 | 0 | 50 | 10 |
| T18 | 250 | — | 0 | 0 | 0 | 0 | 0 |
| T19 | 250 | — | 0 | 0 | 0 | 0 | 0 |
| T20 | 250 | — | 0 | 0 | 10 | 40 | 0 |
| T21 | 250 | — | 0 | 0 | 0 | 0 | 0 |
| T22 | 250 | — | 0 | 10 | 0 | 20 | 0 |
| T23 | 250 | — | 0 | 100 | 50 | 90 | 0 |
| T32 | 250 | — | 0 | 20 | 30 | 100 | 40 |
| T33 | 250 | — | 0 | 90 | 60 | 90 | 20 |
| T34 | 250 | — | 0 | 100 | 60 | 70 | 0 |
| T35 | 250 | — | 0 | 90 | 20 | 90 | 20 |
| T36 | 250 | — | 0 | 100 | 70 | 100 | 50 |
| T37 | 250 | — | 0 | 90 | 50 | 90 | 0 |
| T38 | 250 | — | 0 | 0 | 0 | 60 | 0 |
| T39 | 250 | — | 20 | 100 | 50 | 100 | 30 |
| T40 | 250 | — | 0 | 0 | 0 | 0 | 0 |
| T41 | 250 | — | 0 | 100 | 60 | 90 | 100 |
| T42 | 250 | — | 0 | 0 | 0 | 0 | 0 |
| T43 | 250 | — | 0 | 30 | 0 | 90 | 0 |
| T44 | 250 | — | 0 | 100 | 50 | 90 | 20 |
| T45 | 250 | — | 0 | 0 | 0 | 0 | 0 |
| T46 | 250 | — | 0 | 0 | 0 | 0 | 0 |
| T47 | 250 | — | 0 | 0 | 0 | 0 | 0 |
| T48 | 250 | — | 0 | 0 | 0 | 0 | 0 |
| T49 | 250 | — | 0 | 0 | 0 | 30 | 0 |
| T50 | 250 | — | 0 | 0 | 0 | 0 | 0 |
| T51 | 250 | — | 0 | 0 | 0 | 0 | 0 |
| T52 | 250 | — | 0 | 0 | 0 | 0 | 0 |
| T53 | 250 | — | 0 | 0 | 0 | 0 | 0 |
| T54 | 250 | — | 40 | 100 | 90 | 100 | 90 |
| T55 | 250 | — | 0 | 90 | 0 | 70 | 0 |
| T56 | 250 | — | 60 | 50 | 10 | 30 | 0 |
| T57 | 250 | — | 0 | 90 | 0 | 50 | 0 |
| T58 | 250 | — | 30 | 20 | 10 | 40 | 0 |
| T59 | 250 | — | 0 | 100 | 70 | 100 | 70 |
| T60 | 250 | — | 0 | 100 | 60 | 100 | 30 |
| T61 | 250 | — | 0 | 90 | 40 | 80 | 30 |
| T62 | 250 | — | 20 | 100 | 80 | 100 | 80 |
| T63 | 250 | — | 0 | 100 | 50 | 90 | 30 |
| T69 | 250 | — | 0 | 90 | 20 | 100 | 0 |
| T77 | 250 | — | 0 | 30 | 0 | 0 | 0 |
| T78 | 250 | — | 0 | 90 | 40 | 60 | 30 |
| T79 | 250 | — | 0 | 70 | 0 | 0 | 0 |
| T80 | 250 | — | 0 | 100 | 30 | 90 | 50 |
| T81 | 250 | — | 20 | 70 | 30 | 50 | 40 |
| P3 | 250 | — | 0 | 80 | 60 | 70 | 40 |
| P4 | 250 | — | 40 | 100 | 80 | 90 | 50 |
| P5 | 250 | — | 0 | 100 | 90 | 100 | 90 |
| P6 | 250 | — | 0 | 100 | 90 | 100 | 100 |
| P7 | 250 | — | 0 | 100 | 40 | 100 | 90 |

Post-Emergence Data:

| Compound Number | Rate g/ha | SOLNI | AMARE | SETFA | ALOMY | ECHCG | AVEFA |
|---|---|---|---|---|---|---|---|
| T1 | 250 | 20 | 50 | 100 | 80 | 100 | 90 |
| T4 | 250 | 0 | 0 | 100 | 90 | 100 | 100 |
| T9 | 250 | — | 0 | 80 | 10 | 70 | 40 |
| T13 | 250 | 0 | 0 | 0 | 0 | 10 | 0 |
| T14 | 250 | 0 | 0 | 70 | 0 | 30 | 0 |
| T15 | 250 | 0 | 0 | 0 | — | — | — |
| T16 | 250 | 0 | 0 | 0 | 0 | 0 | 0 |
| T17 | 250 | 0 | 0 | 80 | 10 | 70 | 0 |
| T18 | 250 | — | 0 | 0 | 0 | 0 | 0 |
| T19 | 250 | — | 20 | 50 | 0 | 40 | 0 |
| T20 | 250 | — | 0 | 50 | 20 | 60 | 0 |
| T21 | 250 | — | 0 | 20 | 0 | 0 | 0 |
| T22 | 250 | — | 0 | 50 | 0 | 20 | 0 |
| T23 | 250 | — | 0 | 100 | 60 | 90 | 60 |
| T32 | 250 | — | 0 | 90 | 60 | 100 | 0 |

-continued

| Compound Number | Rate g/ha | SOLNI | AMARE | SETFA | ALOMY | ECHCG | AVEFA |
|---|---|---|---|---|---|---|---|
| T33 | 250 | — | 0 | 100 | 60 | 100 | 60 |
| T34 | 250 | — | 0 | 90 | 70 | 100 | 70 |
| T35 | 250 | — | 0 | 100 | 40 | 100 | 50 |
| T36 | 250 | — | 0 | 100 | 90 | 100 | 100 |
| T37 | 250 | — | 20 | 100 | 90 | 100 | 90 |
| T38 | 250 | — | 0 | 40 | 20 | 70 | 0 |
| T39 | 250 | — | 0 | 100 | 60 | 100 | 30 |
| T40 | 250 | — | 0 | 0 | 0 | 0 | 0 |
| T41 | 250 | — | 0 | 100 | 60 | 100 | 100 |
| T42 | 250 | — | 0 | 0 | 0 | 0 | 0 |
| T43 | 250 | — | 0 | 80 | 50 | 90 | 40 |
| T44 | 250 | — | 0 | 100 | 90 | 100 | 90 |
| T45 | 250 | — | 0 | 70 | 30 | 60 | 0 |
| T46 | 250 | — | 0 | 0 | 0 | 0 | 0 |
| T47 | 250 | — | 0 | 0 | 0 | 30 | 0 |
| T48 | 250 | — | 0 | 40 | 0 | 40 | 20 |
| T49 | 250 | — | 0 | 30 | 0 | 30 | 0 |
| T50 | 250 | — | 0 | 0 | 0 | 30 | 0 |
| T51 | 250 | — | 0 | 0 | 0 | 0 | 0 |
| T52 | 250 | — | 0 | 90 | 40 | 80 | 0 |
| T53 | 250 | — | 0 | 80 | 0 | 30 | 0 |
| T54 | 250 | — | 0 | 100 | 100 | 100 | 100 |
| T55 | 250 | — | 0 | 100 | 50 | 100 | 20 |
| T56 | 250 | — | 10 | 100 | 60 | 100 | 70 |
| T57 | 250 | — | 0 | 100 | 30 | 100 | 40 |
| T58 | 250 | — | 0 | 100 | 60 | 70 | 0 |
| T59 | 250 | — | 30 | 100 | 100 | 100 | 90 |
| T60 | 250 | — | 0 | 100 | 90 | 100 | 50 |
| T61 | 250 | — | 20 | 100 | 100 | 100 | 60 |
| T62 | 250 | — | 0 | 100 | 100 | 100 | 90 |
| T63 | 250 | — | 0 | 100 | 70 | 100 | 50 |
| T69 | 250 | — | 0 | 100 | 70 | 100 | 80 |
| T77 | 250 | — | 0 | 90 | 30 | 80 | 0 |
| T78 | 250 | — | 0 | 100 | 70 | 100 | 60 |
| T79 | 250 | — | 0 | 100 | 40 | 90 | 20 |
| T80 | 250 | — | 0 | 100 | 70 | 90 | 70 |
| T81 | 250 | — | 0 | 90 | 50 | 80 | 70 |
| P3 | 250 | — | 0 | 100 | 90 | 100 | 80 |
| P4 | 250 | — | 0 | 100 | 100 | 100 | 90 |
| P5 | 250 | — | 0 | 100 | 100 | 100 | 90 |
| P6 | 250 | — | 0 | 100 | 90 | 100 | 100 |
| P7 | 250 | — | 0 | 100 | 90 | 100 | 100 |

Example B

Seeds of a variety of test species were sown in standard soil in pots. After cultivation for one day (pre-emergence) or after 10 days cultivation (post-emergence) under controlled conditions in a glasshouse, the plants were sprayed with an aqueous spray solution derived from the formulation of the technical active ingredient in 0.6 ml acetone and 45 ml formulation solution containing 10.6% Emulsogen EL (Registry number 61791-12-6), 42.2% N-methylpyrrolidone, 42.2% dipropylene glycol monomethyl ether (Registry number 34590-94-8) and 0.2% X-77 (Registry number 11097-66-8). The test plants were then grown in a greenhouse under optimum conditions until, 15 days later for post-emergence and 20 days for pre-emergence, the test was evaluated (100=total damage to plant; 0=no damage to plant).

Test Plants:

Alopecurus myosuroides (ALOMY), Avena fatua (AVEFA), Lolium perenne (LOLPE), Setaria faberi (SETFA), Digitaria sanguinalis (DIGSA), Echinochloa crus-galli (ECHCG)

Pre-Emergence Data:

| Compound Number | Rate g/ha | ALOMY | AVEFA | LOLPE | SETFA | DIGSA | ECHCG |
|---|---|---|---|---|---|---|---|
| T1 | 250 | 80 | 30 | 100 | 100 | 50 | 100 |
| T2 | 250 | 0 | 20 | 10 | 0 | 0 | 100 |
| T3 | 250 | 50 | 60 | 70 | 100 | 80 | 100 |
| T4 | 250 | 100 | 80 | 100 | 100 | 100 | 100 |
| T5 | 250 | 0 | 10 | 0 | 0 | 10 | 100 |
| T6 | 250 | 60 | 0 | 50 | 80 | 100 | 90 |
| T7 | 250 | 0 | 10 | 0 | 10 | 20 | 0 |
| T8 | 250 | 50 | 30 | 50 | 70 | 70 | 100 |
| T10 | 250 | 50 | 0 | 20 | 80 | 30 | 50 |
| T11 | 250 | 10 | 0 | 10 | 10 | 0 | 10 |
| T12 | 250 | 30 | 40 | 70 | 60 | 100 | 40 |
| T24 | 250 | 40 | 0 | 10 | 20 | 70 | 80 |
| T25 | 250 | 0 | 0 | 20 | 80 | 80 | 50 |

-continued

| Compound Number | Rate g/ha | ALOMY | AVEFA | LOLPE | SETFA | DIGSA | ECHCG |
|---|---|---|---|---|---|---|---|
| T26 | 250 | 0 | 0 | 20 | 50 | 0 | 30 |
| T27 | 250 | 60 | 50 | 70 | 100 | 80 | 80 |
| T28 | 250 | 0 | 10 | 20 | 0 | 0 | 0 |
| T29 | 250 | 10 | 0 | 20 | 70 | 0 | 20 |
| T30 | 250 | 0 | 0 | 0 | 0 | 0 | 0 |
| T31 | 250 | 70 | 40 | 30 | 100 | 70 | 80 |
| T32 | 250 | 90 | 10 | 90 | 60 | 100 | 100 |
| T33 | 250 | 60 | 20 | 70 | 70 | 70 | 70 |
| T34 | 250 | 40 | 40 | 40 | 90 | 90 | 90 |
| T35 | 250 | 10 | 30 | 20 | 40 | 70 | 50 |
| T36 | 250 | 70 | 60 | 90 | 90 | 100 | 100 |
| T37 | 250 | 70 | 60 | 40 | 100 | 90 | 100 |
| T39 | 250 | 70 | 40 | 90 | 90 | 90 | 90 |
| T41 | 250 | 90 | 60 | 100 | 100 | 100 | 100 |
| T43 | 250 | 0 | 60 | 0 | 20 | 60 | 40 |
| T44 | 250 | 0 | 10 | 10 | 70 | 80 | 50 |
| T54 | 250 | 70 | 50 | 100 | 90 | 100 | 100 |
| T55 | 250 | 10 | 30 | 60 | 10 | 30 | 50 |
| T59 | 250 | 80 | 70 | 80 | 100 | 90 | 100 |
| T61 | 250 | 100 | 40 | 90 | 100 | 100 | 90 |
| T62 | 250 | 100 | 50 | 100 | 100 | 100 | 100 |
| T63 | 250 | 80 | 20 | 100 | 70 | 90 | 60 |
| P1 | 250 | 30 | 30 | 60 | 70 | 70 | 100 |
| P2 | 250 | 30 | 40 | 30 | 70 | 70 | 50 |
| P3 | 250 | 30 | 10 | 50 | 60 | 70 | 50 |
| P4 | 250 | 90 | 70 | 90 | 100 | 100 | 100 |
| P5 | 250 | 80 | 80 | 100 | 100 | 80 | 100 |
| P6 | 250 | 70 | 50 | 50 | 80 | 70 | 0 |
| P7 | 250 | 70 | 30 | 70 | 80 | 80 | 50 |

Post-Emergence Data:

| Compound Number | Rate g/ha | ALOMY | AVEFA | LOLPE | SETFA | DIGSA | ECHCG |
|---|---|---|---|---|---|---|---|
| T1 | 125 | 50 | 30 | 50 | 90 | 90 | 90 |
| T2 | 125 | 10 | 0 | 0 | 30 | 0 | 60 |
| T3 | 125 | 50 | 30 | 0 | 90 | 80 | 90 |
| T4 | 125 | 80 | 100 | 100 | 100 | 100 | 100 |
| T5 | 125 | 0 | 0 | 0 | 70 | 50 | 80 |
| T6 | 125 | 20 | 10 | 10 | 0 | 10 | 30 |
| T7 | 125 | 0 | 0 | 0 | 0 | 0 | 0 |
| T8 | 125 | 10 | 0 | 0 | 30 | 30 | 0 |
| T10 | 125 | 10 | 10 | 20 | 0 | 0 | 0 |
| T11 | 125 | 20 | 20 | 0 | 10 | 0 | 20 |
| T12 | 125 | 0 | 10 | 0 | 80 | 60 | 70 |
| T24 | 125 | — | — | — | 0 | 0 | 30 |
| T25 | 125 | 20 | 0 | 0 | 30 | 80 | 0 |
| T26 | 125 | 20 | 0 | 10 | 60 | 10 | 60 |
| T27 | 125 | 30 | 70 | 30 | 90 | 70 | 80 |
| T28 | 125 | 20 | 10 | 0 | 10 | 0 | 0 |
| T29 | 125 | 30 | 0 | 0 | 60 | 10 | 50 |
| T30 | 125 | 10 | 10 | 10 | 0 | 0 | 0 |
| T31 | 125 | 30 | 0 | 20 | 80 | 70 | 70 |
| T32 | 125 | 30 | 10 | 0 | 30 | 70 | 100 |
| T33 | 125 | 60 | 70 | 20 | 100 | 60 | 100 |
| T34 | 125 | 0 | 10 | 0 | 40 | 40 | 80 |
| T35 | 125 | 0 | 10 | 20 | 70 | 70 | 80 |
| T36 | 125 | 80 | 100 | 30 | 100 | 100 | 100 |
| T37 | 125 | 70 | 90 | 30 | 100 | 100 | 100 |
| T39 | 125 | 0 | 20 | 10 | 70 | 80 | 80 |
| T41 | 125 | 80 | 100 | 70 | 100 | 100 | 100 |
| T43 | 125 | 0 | 0 | 30 | 60 | 50 | 70 |
| T44 | 125 | 60 | 90 | 30 | 100 | 100 | 100 |
| T54 | 125 | 90 | 70 | 60 | 100 | 100 | 100 |
| T55 | 125 | 60 | 70 | 80 | 100 | 100 | 100 |
| T59 | 125 | 90 | 30 | 80 | 100 | 100 | 100 |
| T61 | 125 | 60 | 30 | 30 | 90 | 100 | 80 |
| T62 | 125 | 60 | 60 | 50 | 100 | 100 | 100 |
| T63 | 125 | 0 | 20 | 10 | 50 | 60 | 50 |
| P1 | 125 | 20 | 0 | 20 | 70 | 60 | 60 |
| P2 | 125 | 30 | 0 | 10 | 40 | 40 | 60 |
| P3 | 125 | 90 | 80 | 80 | 80 | 90 | 80 |

| Compound Number | Rate g/ha | ALOMY | AVEFA | LOLPE | SETFA | DIGSA | ECHCG |
|---|---|---|---|---|---|---|---|
| P4 | 125 | 100 | 80 | 90 | 100 | 100 | 100 |
| P5 | 125 | 80 | 90 | 80 | 100 | 100 | 100 |
| P6 | 125 | 30 | 80 | 60 | 100 | 100 | 100 |
| P7 | 125 | 60 | 80 | 70 | 100 | 90 | 100 |

The invention claimed is:

1. A compound of formula I

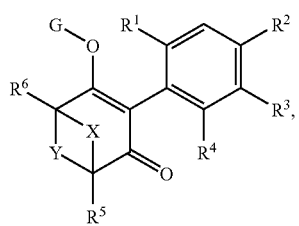

wherein
$R^1$ is methyl, ethyl, n-propyl, iso-propyl, cyclopropyl, halomethyl, haloethyl, halogen, vinyl, ethynyl, methoxy, ethoxy, halomethoxy or haloethoxy;

$R^2$ and $R^3$ are independently hydrogen, halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$haloalkenyl, $C_2$-$C_6$alkynyl, $C_3$-$C_6$alkenyloxy, $C_3$-$C_6$haloalkenyloxy, $C_3$-$C_6$alkynyloxy, $C_3$-$C_6$cycloalkyl, $C_1$-$C_6$alkylthio, $C_1$-$C_6$alkylsulfinyl, $C_1$-$C_6$alkylsulfonyl, $C_1$-$C_6$alkylsulfonyloxy, $C_1$-$C_6$haloalkylsulfonyloxy, cyano, nitro, optionally substituted phenyl or optionally substituted heteroaryl;

wherein at least one of $R^2$ and $R^3$ is optionally substituted phenyl or optionally substituted heteroaryl, in which the heteroaryl and the phenyl are optionally substituted by one or more substituents selected from $C_1$-$C_4$alkyl, $C_2$-$C_4$alkenyl, $C_2$-$C_4$alkynyl, $C_1$-$C_4$haloalkyl, $C_3$-$C_7$cycloalkyl, $C_5$-$C_7$cycloalkenyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$haloalkylsulfinyl, $C_1$-$C_4$alkylsulfonyl, $C_1$-$C_4$haloalkylsulfonyl, fluoro, chloro, bromo, iodo, cyano, nitro, hydroxy-$C_1$-$C_4$alkyl, formyl, carboxy, $C_1$-$C_4$alkylcarbonyl, $C_1$-$C_4$alkoxycarbonyl, amidocarbonyl, $C_1$-$C_4$alkylaminocarbonyl, di-$C_1$-$C_4$alkylaminocarbonyl, amino, $C_1$-$C_4$alkylcarbonylamino, $C_1$-$C_4$alkoxycarbonylamino, $C_1$-$C_4$alkylaminocarbonylamino, di$C_1$-$C_4$alkylaminocarbonylamino, $C_1$-$C_4$alkylsulfonylamino, $C_1$-$C_4$haloalkylsulfonylamino, $C_1$-$C_4$alkylsulfonyloxy and $C_1$-$C_4$haloalkylsulfonyloxy;

$R^4$ is hydrogen, methyl, ethyl, n-propyl, iso-propyl, halomethyl, haloethyl, halogen, vinyl, ethynyl, methoxy, ethoxy, halomethoxy or haloethoxy;

$R^5$ and $R^6$ are independently hydrogen, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_1$-$C_6$alkoxy, $C_3$-$C_6$alkenyloxy, $C_3$-$C_6$haloalkenyloxy, $C_3$-$C_6$alkynyloxy, $C_1$-$C_4$alkoxy$C_1$-$C_4$alkyl, $C_1$-$C_4$alkoxy$C_1$-$C_4$alkoxy, $C_1$-$C_4$alkoxy$C_1$-$C_4$alkoxy$C_1$-$C_4$alkyl, $C_1$-$C_6$alkylthio, $C_1$-$C_4$alkylthio$C_1$-$C_4$alkyl, $C_1$-$C_4$alkylsulfinyl, $C_1$-$C_4$alkylsulfinyl$C_1$-$C_4$alkyl, $C_1$-$C_4$alkylsulfonyl, $C_1$-$C_4$alkylsulfonyl$C_1$-$C_4$alkyl, hydroxy-$C_1$-$C_4$alkyl, $C_1$-$C_6$haloalkoxy$C_1$-$C_4$alkyl, $C_3$-$C_6$alkenyloxy$C_1$-$C_4$alkyl, $C_3$-$C_6$haloalkenyloxy$C_1$-$C_4$alkyl, $C_3$-$C_6$alkynyloxy$C_1$-$C_4$alkyl, $C_1$-$C_6$cyanoalkyl, $C_1$-$C_6$cyanoalkoxy, $C_1$-$C_4$cyanoalkoxy$C_1$-$C_4$alkyl, hydroxy, $C_1$-$C_6$alkylcarbonyl, carboxy, $C_1$-$C_6$alkoxycarbonyl, $C_1$-$C_6$alkylaminocarbonyl, di-$C_1$-$C_6$alkylcarbonyl, tri($C_1$-$C_4$alkyl)silyl or tri($C_1$-$C_4$alkyl)silyloxy;

X is optionally substituted $C_1$-$C_3$alkylene; and

Y is optionally substituted $C_1$-$C_3$alkylene or optionally substituted $C_2$-$C_3$alkenylene;

wherein the $C_1$-$C_3$alkylene and $C_2$-$C_3$alkenylene groups X and Y are unsubstituted, or are substituted once or twice by $C_1$-$C_4$alkyl, $C_1$-$C_4$alkoxy, $C_1$-$C_4$alkoxy$C_1$-$C_4$alkyl, halogen or hydroxy; and G is hydrogen, an alkali metal, alkaline earth metal, sulfonium, ammonium, $C_1$-$C_6$ alkyl, $C_3$-$C_6$ alkenyl, $C_3$-$C_6$alkynyl, or a latentiating group;

and wherein, when G is a latentiating group, then G is phenyl$C_1$alkyl (wherein the phenyl is optionally substituted $C_1$-$C_3$alkyl, $C_1$-$C_3$haloalkyl, $C_1$-$C_3$alkoxy, $C_1$-$C_3$haloalkoxy, $C_1$-$C_3$alkythio, $C_1$-$C_3$alkylsulfinyl, $C_1$-$C_3$ alkylsulfonyl, halogen, cyano or by nitro), heteroaryl$C_1$alkyl wherein the heteroaryl is optionally substituted $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro, $C_3$ alkenyl, $C_3$ haloalkenyl, $C_3$ alkynyl, $C(X^a)$—$R^a$, $C(X^b)$—$X^c$—$R^b$, $C(X^d)$—$N(R^c)$—$R^d$, —$SO_2$—$R^e$, —$P(X^e)$($R^f$)—$R^g$ or $CH_2$—$X^f$—$R^h$ wherein $X^a$, $X^b$, $X^c$, $X^d$, $X^e$ and $X^f$ are independently of each other oxygen or sulfer;

and wherein $R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro, heteroaryl$C_1$-$C_5$alkyl wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro, $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro;

$R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro, heteroaryl$C_1$-$C_5$alkyl wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro, $C_3$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro, heteroaryl$C_1$-$C_5$alkyl wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro, $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; or amino, $C_1$-$C_3$alkylamino, $C_1$-$C_3$dialkylamino, $C_1$-$C_3$alkoxy, $C_3$-$C_7$cycloalkylamino, di-$C_3$-$C_7$cycloalkylamino or $C_3$-$C_7$cycloalkoxy;

or $R^c$ and $R^d$ are joined together to form a 3-7 membered ring, optionally containing one heteroatom selected from O or S and optionally substituted by 1 or 2 $C_1$-$C_3$alkyl groups; and $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_{1\text{-}C5}$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro, heteroaryl$C_1$-$C_5$alkyl wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro, $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano, amino or by nitro; heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano, or nitro; amino; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di$C_3$-$C_7$cycloalkylamino, $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino;

$R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro, heteroaryl$C_1$-$C_5$alkyl wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro, $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; amino; hydroxyl; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di$C_3$-$C_7$cycloalkylamino, $C_3$-$C_7$cycloalkoxy, $C_1$-$C_{10}$haloalkoxy, $C_1$-$C_5$alkylamino or $C_2$-$C_8$dialkylamino; or benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro, heteroaryl$C_1$-$C_5$alkyl wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro, phenoxy$C_1$-$C_5$alkyl wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro, heteroaryloxy$C_1$-$C_5$alkyl wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro, $C_3$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro; or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro;

and wherein "heteroaryl" means thienyl, furyl, pyrrolyl, isoxazolyl, oxazolyl, isothiazolyl, thiazolyl, pyrazolyl, imidazolyl, triazolyl, tetrazolyl, pyridyl, pyrimidinyl, pyrazinyl, pyridazinyl, triazinyl, oxadiazolyl or thiadiazolyl, or, where appropriate, an N-oxide or a salt thereof.

2. A compound according to claim 1, wherein $R^1$ is methyl, ethyl, halogen, halomethyl, vinyl, ethynyl or halomethoxy.

3. A compound according to claim 2, wherein $R^1$ is methyl or ethyl.

4. A compound according to claim 3, wherein $R^1$ is ethyl.

5. A compound according to claim 2, wherein $R^1$ is —OCHF$_2$ or —OCF$_3$.

6. A compound according to claim 1, wherein $R^2$ and $R^3$ are independently hydrogen, optionally substituted phenyl or optionally substituted heteroaryl.

7. A compound according to claim 6, wherein $R^2$ and $R^3$ are independently hydrogen; phenyl or phenyl substituted by $C_1$-$C_2$alkyl, $C_1$-$C_2$alkoxy, $C_1$-$C_2$haloalkyl, $C_1$-$C_2$haloalkoxy, fluoro, chloro, bromo or cyano; or heteroaryl or heteroaryl substituted by $C_1$-$C_2$alkyl, $C_1$-$C_2$alkoxy, $C_1$-$C_2$haloalkyl, $C_1$-$C_2$haloalkoxy, fluoro, chloro, bromo or cyano.

8. A compound according to claim 7, wherein $R^2$ is hydrogen and $R^3$ is phenyl or phenyl substituted by $C_1$-$C_2$alkyl, $C_1$-$C_2$alkoxy, $C_1$-$C_2$haloalkyl, $C_1$-$C_2$haloalkoxy, fluoro, chloro, bromo or cyano.

9. A compound according to claim 1, wherein $R^4$ is hydrogen, methyl, ethyl, vinyl or ethynyl.

10. A compound according to claim 9, wherein $R^4$ is hydrogen, methyl or ethyl.

11. A compound according to claim 1, wherein $R^5$ is hydrogen, $C_1$-$C_4$ alkyl, $C_1$-$C_4$alkoxy or $C_1$-$C_4$alkoxy$C_1$-$C_4$alkyl.

12. A compound according to claim 11, wherein $R^5$ is hydrogen or methyl.

13. A compound according to claim 1, wherein $R^6$ is hydrogen or methyl.

14. A compound according to claim 13, wherein $R^6$ is hydrogen.

15. A compound according to claim 1, wherein X is optionally substituted $C_1$-$C_2$alkylene.

16. A compound according to claim 15, wherein X is methylene, ethylene, methylene substituted by $C_1$-$C_3$ alkyl, $C_1$-$C_3$alkoxy or $C_1$-$C_3$alkoxy$C_1$-$C_3$alkyl or ethylene substituted by $C_1$-$C_3$ alkyl, $C_1$-$C_3$alkoxy or $C_1$-$C_3$alkoxy$C_1$-$C_3$alkyl.

17. A compound according to claim 16, wherein X is methylene or ethylene.

18. A compound according to claim 1, wherein Y is optionally substituted $C_1$-$C_2$alkylene or optionally substituted $C_2$alkenylene.

19. A compound according to claim 18, wherein Y is $C_1$-$C_2$alkylene or $C_1$-$C_2$alkylene substituted by halogen, hydroxyl, $C_1$-$C_3$alkyl, $C_1$-$C_3$alkoxy or $C_1$-$C_3$alkoxy$C_1$-$C_3$alkyl, $C_2$alkenylene or $C_2$alkenylene substituted by halogen, hydroxyl, $C_1$-$C_3$alkyl, $C_1$-$C_3$alkoxy or $C_1$-$C_3$alkoxy$C_1$-$C_3$alkyl.

20. A compound according to claim 19, wherein Y is ethylene or ethenylene.

21. A compound according to claim 1, wherein $R^1$ is methyl or ethyl, $R^2$ is hydrogen, $R^3$ is phenyl or phenyl substituted by $C_1$-$C_2$alkyl, $C_1$-$C_2$alkoxy, $C_1$-$C_2$haloalkyl, $C_1$-$C_2$haloalkoxy, fluoro, chloro, bromo or cyano, $R^4$ is hydrogen, $R^5$ is hydrogen, $R^6$ is hydrogen, X is methylene, Y is ethylene and G is hydrogen.

22. A process for the preparation of a compound of formula I according to claim 1, wherein G is hydrogen, which comprises reacting a compound of the formula (J)

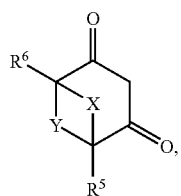

wherein X, Y, $R^5$ and $R^6$ are as defined in claim 1, with a compound of formula (M)

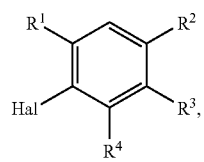

wherein $R^1$, $R^2$, $R^3$ and $R^4$ are as defined in claim 1 and Hal represents chlorine, bromine or iodine in the presence of a catalyst, a ligand, a base and a solvent.

23. A process for the preparation of a compound of formula I according to claim 1 which comprises reacting a compound of the formula (T)

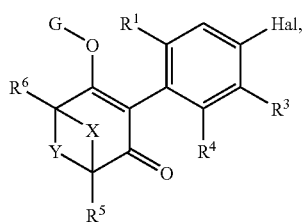

wherein Hal represents chlorine, bromine or iodine and X, Y, $R^1$, $R^3$, $R^4$, $R^5$, $R^6$ and G are as defined in claim 1, with a compound of the formula $R^2$—B(OH)$_2$, or an ester or salt thereof, wherein $R^2$ is optionally substituted phenyl or optionally substituted heteroaryl, in the presence of a catalyst, a ligand, a base and a solvent.

24. A process for the preparation of a compound of formula I according to claim 1 which comprises reacting a compound of the formula ($T_1$)

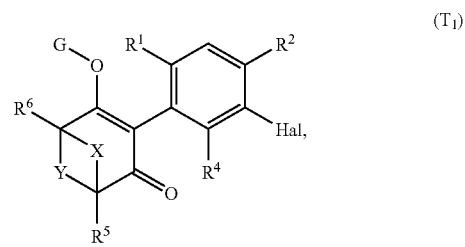

wherein Hal represents chlorine, bromine or iodine and X, Y, $R^1$, $R^2$, $R^4$, $R^5$, $R^6$ and G are as defined in claim 1, with a compound of the formula $R^3$—B(OH)$_2$, or an ester or salt thereof, wherein $R^3$ is optionally substituted phenyl or optionally substituted heteroaryl, in the presence of a catalyst, a ligand, a base and a solvent.

25. A process for the preparation of a compound of formula I according to claim 1 which comprises reacting a compound of the formula (Y)

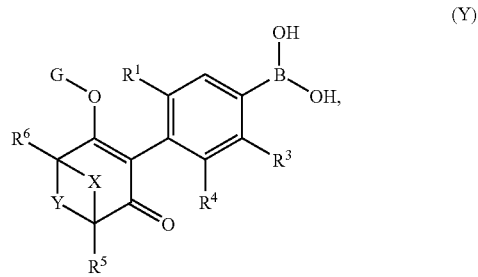

wherein $R^1$, $R^3$, $R^4$, $R^5$, $R^6$, and X, Y and G are as defined in claim 1, or an ester or salt thereof, with a compound of the formula $R^2$-Hal, wherein $R^2$ is optionally substituted phenyl or optionally substituted heteroaryl and Hal is chlorine, bromine or iodine, in the presence of a catalyst, a ligand, a base and a solvent.

26. A process for the preparation of a compound of formula I according to claim 1 which comprises reacting a compound of the formula ($Y_1$)

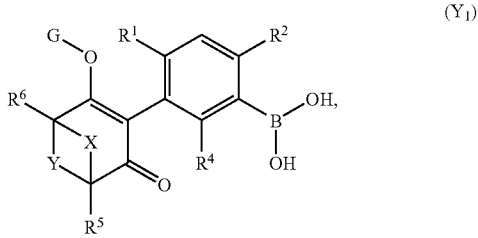

wherein $R^1$, $R^2$, $R^4$, $R^5$, $R^6$ and X, Y and G are as defined in claim 1, or an ester or salt thereof, with an aryl- or heteroaryl halide of formula $R^3$-Hal, wherein $R^3$ is as defined in claim 1 and Hal is chlorine, bromine or iodine, in the presence of a catalyst, a ligand, a base and a solvent.

27. Compounds of the formula (T) and (T₁)

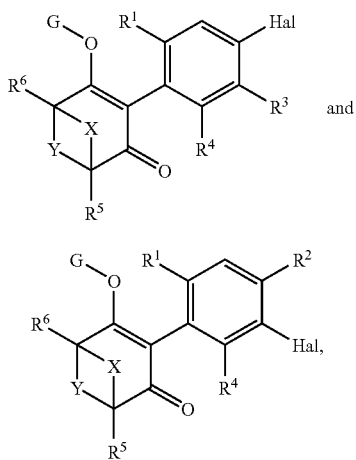

wherein R¹, R², R³, R⁴, R⁵, R⁶, X, Y and G are as defined in claim 1 and Hal is chlorine, bromine or iodine.

28. Compounds of the formulae (Y) and (Y₁)

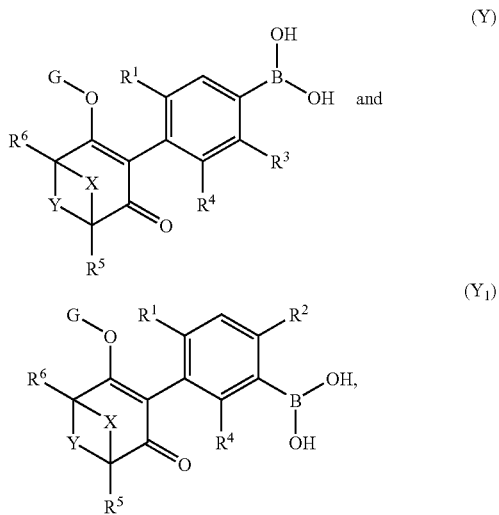

wherein R¹, R², R³, R⁴ R⁵, R⁶, X, Y and G are as defined in claim 1.

29. A method of controlling grasses and weeds in crops of useful plants, which comprises applying a herbicidally effective amount of a compound of formula I as defined in claim 1, or of a composition comprising such a compound, to the plants or to the locus thereof.

30. A herbicidal composition, which, in addition to comprising formulation adjuvants, comprises a herbicidally effective amount of a compound of formula I as defined in claim 1.

31. A composition according to claim 30, which, in addition to comprising the compound of formula I, comprises a further herbicide as mixing partner.

32. A composition according to claim 30, which, in addition to comprising the compound of formula I, comprises a safener.

33. A composition according to claim 30, which, in addition to comprising the compound of formula I, comprises a further herbicide as mixing partner and a safener.

34. A method according to claim 29, which comprises applying a herbicidally effective amount of a composition comprising the compound of formula I to the plants or to the locus thereof, and wherein the crops of useful plants are cereals, cotton, soybeans, sugar beet, sugar cane, rape, maize or rice.

35. A compound according to claim 1, wherein, when G is a latentiating group, then G is a group —C($X^a$)—$R^a$ or —C($X^b$)—$X^C$—$R^b$, and the meanings of $X^a$, $R^a$, $X^b$, $X^C$ and $R^b$ are as defined in claim 1.

36. A compound according to claim 1, wherein G is hydrogen.

37. A compound according to claim 1, wherein R² is phenyl or phenyl substituted by $C_1$-$C_2$alkyl, $C_1$-$C_2$alkoxy, $C_1$-$C_2$haloalkyl, $C_1$-$C_2$haloalkoxy, fluoro, chloro, bromo or cyano; or heteroaryl or heteroaryl substituted by $C_1$-$C_2$alkyl, $C_1$-$C_2$alkoxy, $C_1$-$C_2$haloalkyl, $C_1$-$C_2$haloalkoxy, fluoro, chloro, bromo or cyano; and R³ is hydrogen.

38. A compound according to claim 1, wherein "heteroaryl" means thienyl, pyridyl, pyrimidinyl, pyrazolyl or thiazolyl.

39. A compound according to claim 37, wherein "heteroaryl" means thienyl, pyridyl, pyrimidinyl, pyrazolyl or thiazolyl.

40. A compound of formula I according to claim 1,

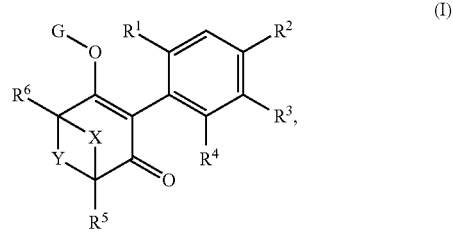

wherein:
X is $CH_2$,
Y is $CH_2$-$CH_2$,
R¹ and R⁴ are methyl,
R⁵ and R⁶ are hydrogen,
G is hydrogen,
R³ is H, and
R² is phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-cyanophenyl, 3-cyanophenyl, 4-cyanophenyl, 4-methoxyphenyl, 2-trifluoromethylphenyl, 3-trifluoromethylphenyl, 4-trifluoromethylphenyl, 4-trifluoromethoxyphenyl, 4-difluoromethoxyphenyl, 4-methylthiophenyl, 4-methylsulfinylphenyl, 4-methylsulfonylphenyl, 4-trifluoromethylthiophenyl, 4-trifluoromethylsulfinylphenyl, 4-trifluoromethylsulfonylphenyl, 2,3-difluorophenyl, 2,4-difluorophenyl, 2,5-difluorophenyl, 2,6-difluorophenyl, 3,4-difluorophenyl, 3,5-difluorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,3,4-trichlorophenyl, 2,3,5-trichlorophenyl, 2,3,6-trichlorophenyl, 2,4,5-trichlorophenyl, 2,4,6-trichlorophenyl, 3,4,5-trichlorophenyl, 4-chloro-2-fluorophenyl, 4-chloro-3-fluorophenyl, 4-chloro-2-methylphenyl, 4-chloro-3-methylphenyl, 4-chloro-2-trifluoromethylphenyl, 4-chloro-3-trifluoromethylphenyl, 4-chloro-2-cyanophenyl, 4-chloro-3-cyanophenyl, 4-chloro-2-methoxyphenyl, 4-chloro-3-methoxyphenyl, 4-fluoro-2-chlorophenyl, 4-fluoro-3-chlorophenyl, 4-fluoro-2-methylphenyl, 4-fluoro-3-methylphenyl, 4-fluoro-3-trifluoromethylphenyl, 4-fluoro-3-trifluoromethylphenyl, 2-fluoro-4-trifluoromethylphenyl, 3-fluoro-4-trifluoromethylphenyl, 3,4-methylenedioxyphenyl, 2,3-dihydrobenzo[1,4]dioxin-6-yl, 2-pyridyl, 3-pyridyl, 4-pyridyl, 3-chloropyridin-2-yl, 4-chloropyridin-2-yl, 5-chloropyridin-2-yl, 6-chloropyridin-2-yl, 2-chloropyridin-3-yl, 4-chloropyridin-3-yl, 2-chloropyridin-4-yl, 3-chloropyridin-4-yl, 2-chloropyridin-5-yl, 3-chloropyridin-5-yl, 3-methylpyridin-2-yl, 4-methylpyridin-2-yl, 5-methylpyridin-2-yl, 6-methylpyridin-2-yl, 2-methylpyridin-3-yl, 4-methylpyridin-3-yl, 2-methylpyridin-4-yl, 3-methylpyridin-4-yl, 2-methylpyridin-5-yl, 3-methylpyridinyl-5-yl, 2-trifluoromethylpyridin-5-yl, 3-trifluoromethylpyridin-5-yl, 2,6-dichloropyridin-3-yl, 2-chloro-4-methylpyridin-5-yl, 6-chloro-2-methylpyridin-3-yl, 5-chlorothiophen-2-yl, 2-chlorothiophen-3-yl, 1-methylpyrazol-4-yl, or 4-chloropyrazol-1-yl.

41. A compound of formula I according to claim 1,

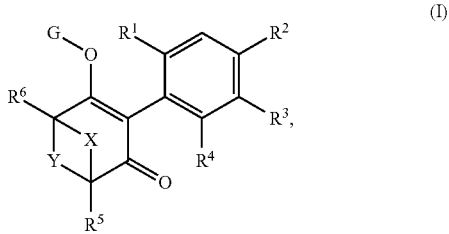

(I)

wherein:
X is $CH_2$,
Y is $CH_2$-$CH_2$,
$R^1$ is methyl,
$R^4$, $R^5$ and $R^6$ are hydrogen,
G is hydrogen,
$R^3$ is H, and
$R^2$ is as defined in claim 40.

42. A compound of formula I according to claim 1, wherein:
X is $CH_2$, Y is $CH_2$-$CH_2$, $R^1$ and $R^4$ are methyl, $R^5$ and $R^6$ are hydrogen, G is hydrogen, $R^3$ is H, and
$R^2$ is 4-fluorophenyl.

43. A compound of formula I according to claim 1, wherein:
X is $CH_2$, Y is $CH_2$-$CH_2$, $R^1$ and $R^4$ are methyl, $R^5$ and $R^6$ are hydrogen, G is hydrogen, $R^3$ is H, and
$R^2$ is 4-chlorophenyl.

44. A compound of formula I according to claim 1, wherein:
X is $CH_2$, Y is $CH_2$-$CH_2$, $R^1$ and $R^4$ are methyl, $R^5$ and $R^6$ are hydrogen, G is hydrogen, $R^3$ is H, and
$R^2$ is 4-chloropyridin-2-yl.

45. A compound of formula I according to claim 1, wherein:
X is $CH_2$, Y is $CH_2$-$CH_2$, $R^1$ and $R^4$ are methyl, $R^5$ and $R^6$ are hydrogen, G is hydrogen, $R^3$ is H, and
$R^2$ is 5-chloropyridin-2-yl.

46. A compound of formula I according to claim 1, wherein:
X is $CH_2$, Y is $CH_2$-$CH_2$, $R^1$ and $R^4$ are methyl, $R^5$ and $R^6$ are hydrogen, G is hydrogen, $R^3$ is H, and
$R^2$ is 6-chloropyridin-2-yl.

47. A compound of formula I according to claim 1, wherein:
X is $CH_2$, Y is $CH_2$-$CH_2$, $R^1$ and $R^4$ are methyl, $R^5$ and $R^6$ are hydrogen, G is hydrogen, $R^3$ is H, and
$R^2$ is 2-chloropyridin-5-yl.

48. A compound of formula I according to claim 1, wherein:
X is $CH_2$, Y is $CH_2$-$CH_2$, $R^1$ and $R^4$ are methyl, $R^5$ and $R^6$ are hydrogen, G is hydrogen, $R^3$ is H, and
$R^2$ is 3-chloropyridin-5-yl.

49. A compound of formula I according to claim 1, wherein:
X is $CH_2$, Y is $CH_2$-$CH_2$, $R^1$ is methyl, $R^4$, $R^5$ and $R^6$ are hydrogen, G is hydrogen, $R^3$ is H, and $R^2$ is 4-chloropyridin-2-yl.

50. A compound of formula I according to claim 1, wherein:
X is $CH_2$, Y is $CH_2$-$CH_2$, $R^1$ is methyl, $R^4$, $R^5$ and $R^6$ are hydrogen, G is hydrogen, $R^3$ is H, and $R^2$ is 5-chloropyridin-2-yl.

51. A compound of formula I according to claim 1, wherein:
X is $CH_2$, Y is $CH_2$-$CH_2$, $R^1$ is methyl, $R^4$, $R^5$ and $R^6$ are hydrogen, G is hydrogen, $R^3$ is H, and $R^2$ is 6-chloropyridin-2-yl.

52. A compound of formula I according to claim 1, wherein:
X is $CH_2$, Y is $CH_2$-$CH_2$, $R^1$ is methyl, $R^4$, $R^5$ and $R^6$ are hydrogen, G is hydrogen, $R^3$ is H, and $R^2$ is 2-chloropyridin-5-yl.

53. A compound of formula I according to claim 1, wherein:
X is $CH_2$, Y is $CH_2$-$CH_2$, $R^1$ is methyl, $R^4$, $R^5$ and $R^6$ are hydrogen, G is hydrogen, $R^3$ is H, and $R^2$ is 3-chloropyridin-5-yl.

* * * * *